US007074904B2

(12) United States Patent
Wong et al.

(10) Patent No.: US 7,074,904 B2
(45) Date of Patent: Jul. 11, 2006

(54) MHC COMPLEXES AND USES THEREOF

(75) Inventors: Hing C. Wong, Fort Lauderdale, FL (US); Peter R. Rhode, Miami, FL (US); Jon A. Weidanz, Miami, FL (US); Susan Grammer, Coral Gables, FL (US); Ana C. Edwards, Miami, FL (US); Pierre-Andre Chavaillaz, Cooper City, FL (US); Jin-An Jiao, Fort Lauderdale, FL (US)

(73) Assignee: Altor Bioscience Corporation, Miramar, FL (US)

( * ) Notice: Subject to any disclaimer, the term of this patent is extended or adjusted under 35 U.S.C. 154(b) by 532 days.

(21) Appl. No.: 09/900,379

(22) Filed: Jul. 6, 2001

(65) Prior Publication Data

US 2002/0198144 A1    Dec. 26, 2002

Related U.S. Application Data

(63) Continuation of application No. 08/776,084, filed on Jan. 17, 1997, now abandoned, which is a continuation-in-part of application No. 08/382,454, filed on Feb. 1, 1995, now abandoned, which is a continuation-in-part of application No. 08/283,302, filed on Jul. 29, 1994, now abandoned.

(51) Int. Cl.
*C07K 7/00* (2006.01)
*C07K 14/74* (2006.01)
*C07K 17/02* (2006.01)

(52) U.S. Cl. ............... 530/395; 530/324; 530/325; 530/326; 530/327; 530/328; 530/391.1; 530/391.7; 530/402; 530/868

(58) Field of Classification Search ............. 530/387.3, 530/388.1, 350, 395, 402, 868, 391.1, 391.7, 530/324, 325, 326, 327, 328
See application file for complete search history.

(56) References Cited

U.S. PATENT DOCUMENTS

| 5,130,297 | A |   | 7/1992  | Sharma et al.   |
|-----------|---|---|---------|-----------------|
| 5,194,425 | A |   | 3/1993  | Sharma et al.   |
| 5,260,422 | A |   | 11/1993 | Clark et al.    |
| 5,284,935 | A |   | 2/1994  | Clark et al.    |
| 5,338,532 | A | * | 8/1994  | Tomalia et al.  |
| 6,015,884 | A | * | 1/2000  | Schneck et al.  |
| 6,083,708 | A | * | 7/2000  | Singh et al.    |

FOREIGN PATENT DOCUMENTS

| WO | WO 89/12458 | 12/1989 |
| WO | WO 92/18150 | 10/1992 |
| WO | WO 93/10220 | 3/1993  |
| WO | WO 93/09810 | 5/1993  |
| WO | WO 94/18998 | 9/1994  |
| WO | WO 94/25054 | 11/1994 |
| WO | WO 95/23814 | 9/1995  |
| WO | WO 96 40944 A | 12/1996 |

OTHER PUBLICATIONS

McCluskey et al. J. Immunol. (1988) 141: 1451-1455.*
Lehninger, A.L. "Principals of Biochemistry." Anderon and Fox, editors. Worth Publishers, New York. pp. 111-112.*
H. Kozono et al., *Nature*, 369:151-154 (1994).
J. Altman et al., *Proc. Natl. Acad. Sci. USA*, 90:10330-10334 (1993).
L. Stern et al., *Nature*, 368:215-221 (1994).
S. Sharma et al., *Proc. Natl. Acad. Sci, USA*, 88:11465-11469 (1991).
J. Guery et al., *Critical Reviews in Immunology*, 13 (3/4):195-206 (1993).
M. Nicolle et al., *J. Clin. Invest*, 93:1361-1369 (1994).
D. Harlan et al., *Proc. Natl. Acad. Sci USA*, 91:3139-3141 (1994).
B. Evavold et al., *Immunology Today*, 14(12):602-609 (1993).
R. Chicz et al., *Immunology Today*, 15(4):155-160 (1994).
R. Tisch et al., *Proc. Natl. Acad. Sci. USA*, 91:437-438 (1994).
*Science*, 259: 1691-1692 (1993).
J. Ulmer et al., *Science*, 259:1745-1749 (1993).
H. Ploegh et al., *Nature*, 364:16-17 (1993).
J. Brown et al., *Nature*, 364:33-39 (1993).
D. O'Sullivan, et al., *Journal of Immunology*, 147:2663(1991).
J. Hammer, et al., *J. Exp. Med.*, 176:1007 (1992).
L. Stern, et al., *Cell*, 68:465 (1992).
K. Webber, et al., *Molecular Immunology*, 32:249 (1995).
Y. Reiter, et al., *Molecular Immunology*, 32:249 (1995).
K. O'Neil, et al., *Science*, 249:774 (1990).
F. Godeau, et al., *Journal of Biological Chemistry*, 267:24223 (1992).
Wong, Ph.D., Shan S., "Reactive Groups Of Proteins And Their Modifying Agents", Chemistry of Protein Conjugation and Cross-Linking, CRC Press, Inc., 1991, 44 pages.
Leszek Ignatowicz, et al, "Cell Surface Expression Of Class II MHC Proteins Bound By A Single Peptide", Journal Of Immunology, vol. 154, No. 8, Apr. 15, 1995, pp. 3852-3862.

* cited by examiner

*Primary Examiner*—Christina Chan
*Assistant Examiner*—F. Pierre VanderVegt
(74) *Attorney, Agent, or Firm*—Robert L. Buchanan; Peter F. Corless; Edwards Angell Palmer & Dodge, LLP

(57) ABSTRACT

The present invention relates to novel complexes of major histocompatibility complex (MHC) molecules and uses of such complexes. In particular, the invention relates to MHC fusion complexes that contain a MHC molecule with a peptide-binding groove and a presenting peptide covalently linked to the MHC protein. Fusion complexes of the invention are useful for a variety of applications including in vitro screens for identification and isolation of peptides that modulate activity of selected T cells, including peptides that are T cell receptor antagonists and partial agonists, methods of suppressing an immune response of a mammal and methods for inducing an immune response in a mammal.

10 Claims, 64 Drawing Sheets

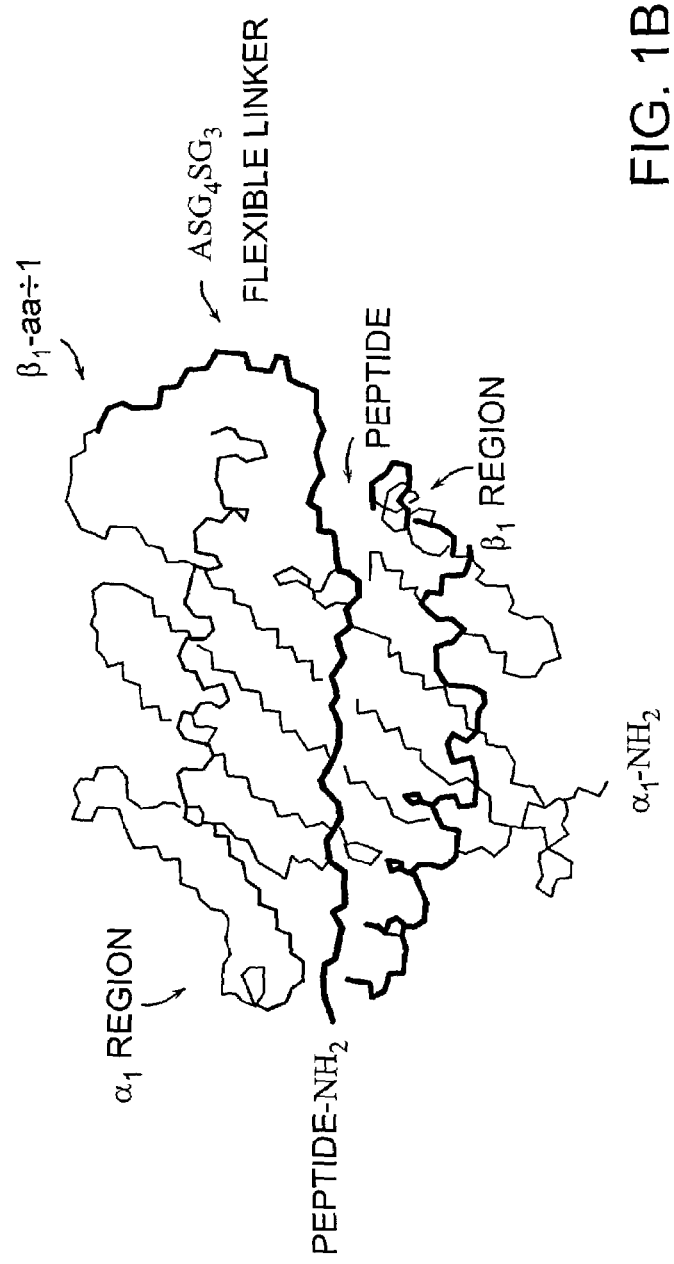
FIG. 1A
FIG. 1B

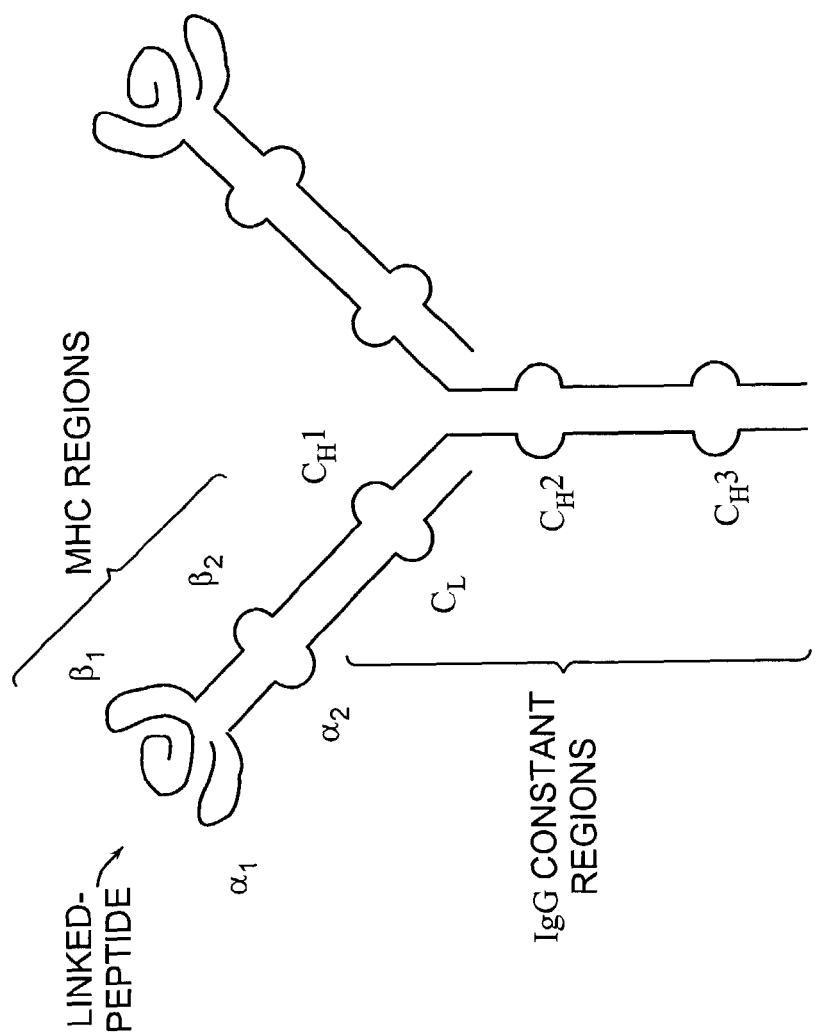

I-A$^d$ α CHAIN CLONING SCHEME
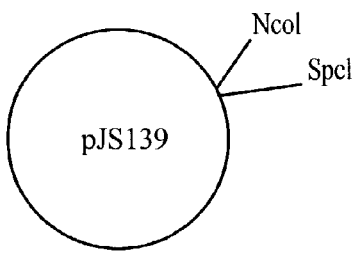
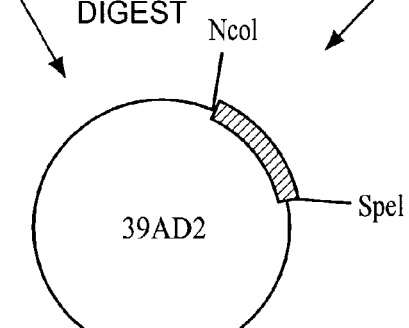
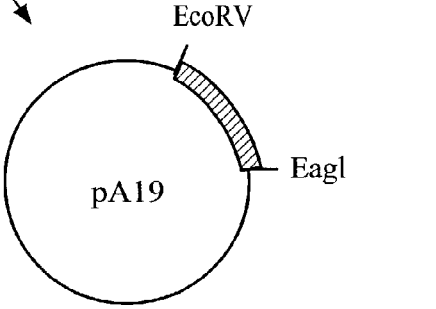
FIG. 2

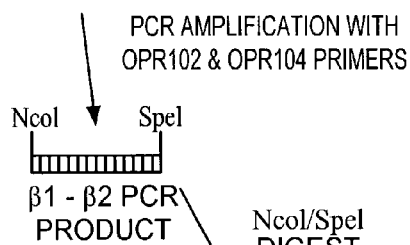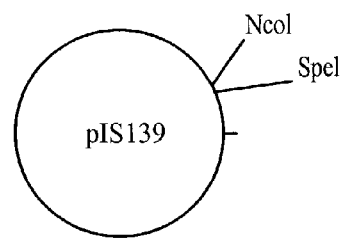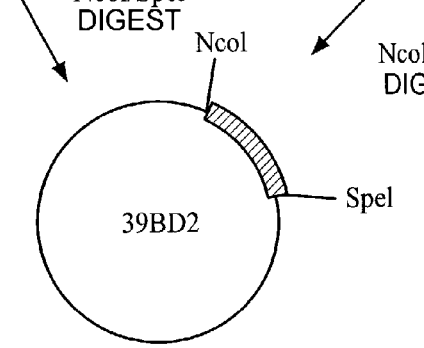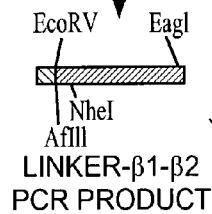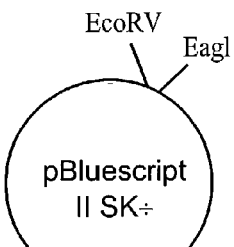
FIG. 3A

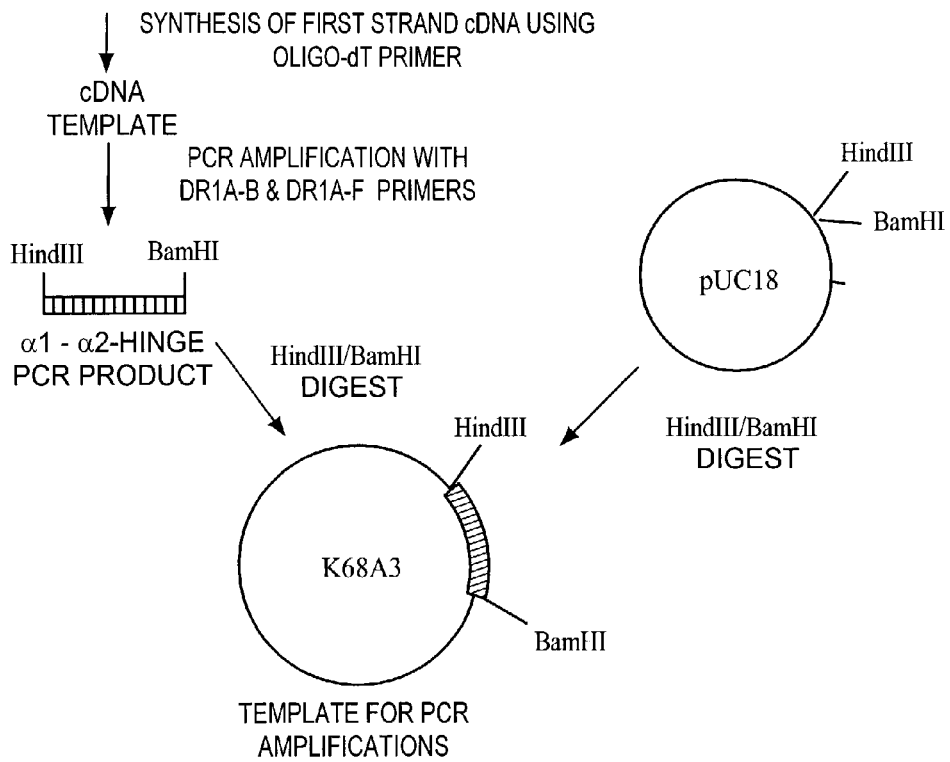
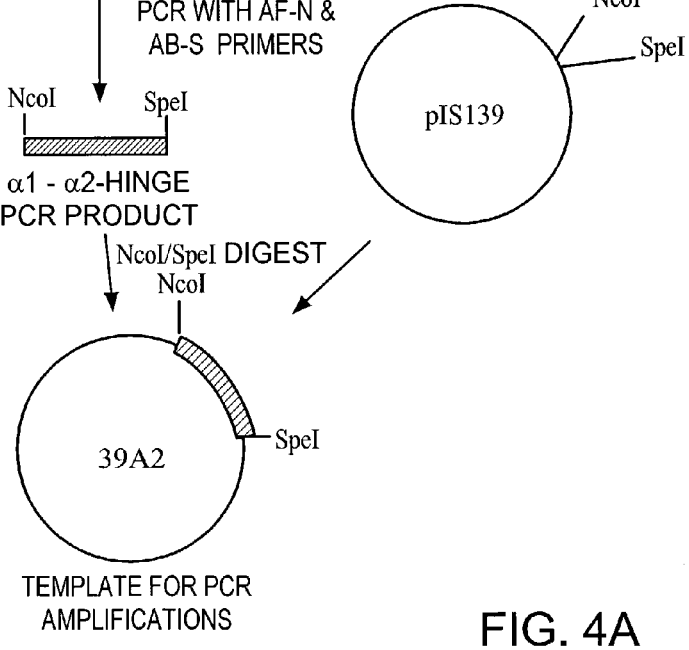
FIG. 4A

HLA-DRI β CHAIN CLONING SCHEME

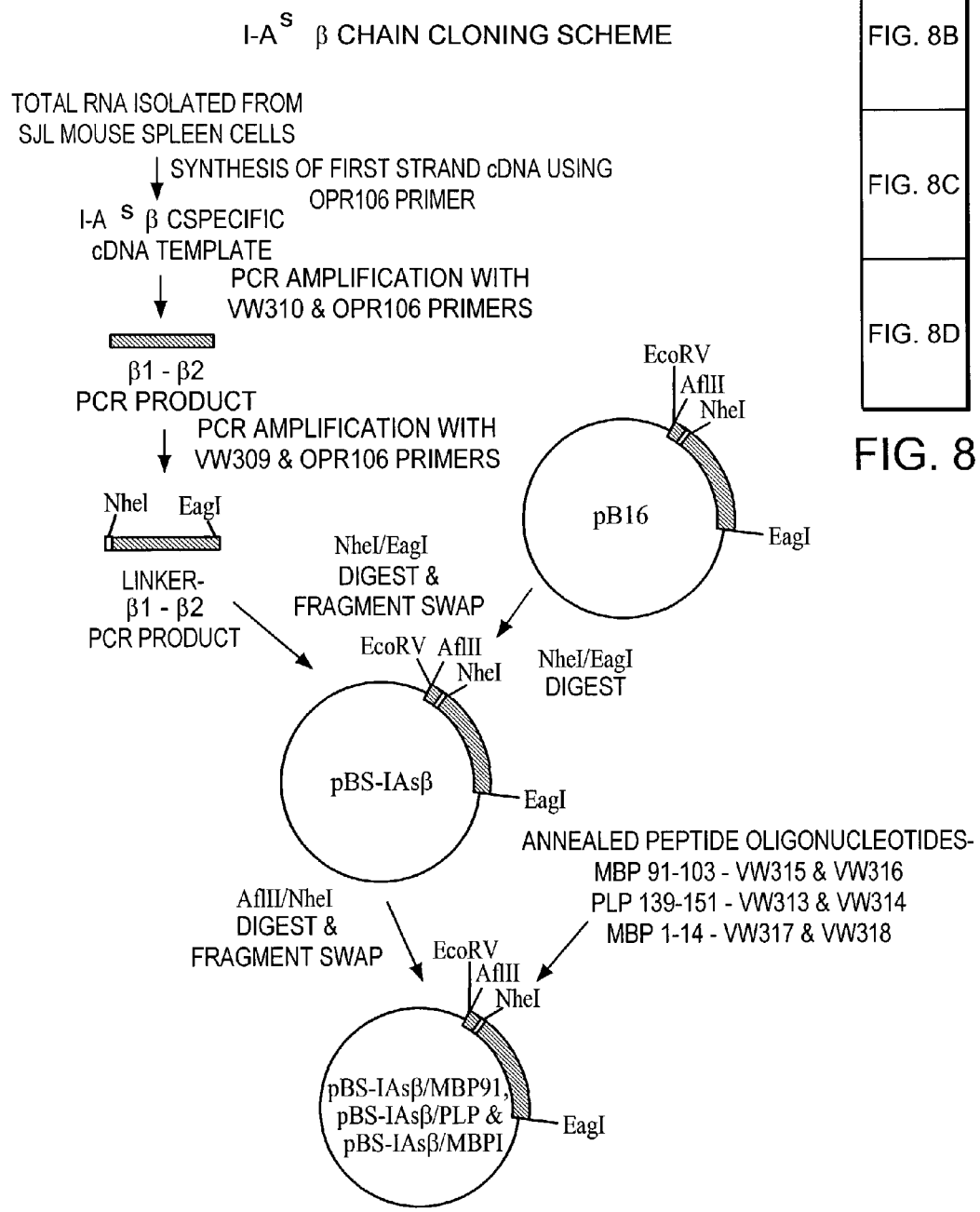
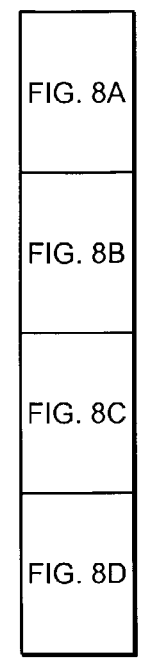
FIG. 8
FIG. 7

OLIGONUCLEOTIDES USED IN CONSTRUCTING MHC VECTORS

I-A$^d$/I-A$^s$ PCR PRIMERS AND CLONING OLIGENUCLEOTIDES
(RESTRICTION SITES ARE UNDERLINED)

OPR100
5'-GGG GGG GCC ATG GCC GAA GAC GAC ATT GAG GCC GAC-3'

OPR101
5'-GGG GGG ACT AGT CCA GTG TTT CAG AAC CGG CTC-3'

OPR107
5'-CCC CCC GAT ATC TCA GCT TCC AGC AGT GGA GAC GAC ATT GAG GCC G-3'

OPR108
5'-CCC CCC CGG CCG CTA CTT ACG TTT CCA GTG TTT CAG AAC CGG C-3'

OPR102
5'-GGG GGG GCC ATG GCC GGA AAC TCC GAA AGG CAT TTC G-3'

OPR104
5'-GCG GCG ACT AGT CCA CTC CAC AGT GAT GGG GC-3'

OPR106
5'-CCC CCC CGG CCG TAC CTG AGG ACC ACT CCA CAG TGA TGG-3'

OPR112
5'-CCC CCC GAT ATC ACA GGT GTC TTA AGT GCT AGC GGA GGG GGC GGA AGC GGC GGA GGG GGA AAC TCC GAA AGG CAT TTC-3'

OPR119
5'-AGC TTG ATA TCA CAG GTG TCT TAA GTG GAG-3'

OPR120-2
5'-CTA GCT CCA CTT AAG ACA CCT GTG ATA TCA-3'

VW310
5'-TCC GGA GGC GGC GGA GAC TCC GAA AGG CAT TTC G-3'

VW309
5'-CGA TCG CTA GCG GCG GTG GTG GTT CCG GTG GCG GCG GAG-3'

OPR136
5'-CCC CCC AGG CTT CCC GGG CCA CCA TGC CGT GCA GCA GAG CTC TG-3'

OPR139
5'-CCC CCC GAG CTC GAA TTC TCA TAA AGG CCC TGG GTG TCT G-3'

FIG. 8A

OPR132
5'-CCC CCC AAG CTT CCC GGG CGA CCA TGG CTC TGC AGA TCC CCA GC-3'

OPR133
5'-CCC CCC ACT TAA GGT CCT TGG GCT GCT CAG CAC C-3'

OPR134
5'-CCC CCC CCA TCA CTG TGG AGT GGA GGG-3'

OPR135
5'-CCC CCC GAG CTC GAA TTC TCA CTG CAG GAG CCC TGC TGG-3'

HLA-DR1 PCR PRIMERS AND CLONING OLIGONUCLEOTIDES

DR1A-F
5'-GGG GGG AAG CTT ATG ATC AAA GAA GAA CAT GTG ATC ATC-3'

DR1A-B
5'-GCG GCG GGA TCC GTT CTC TGT AGT CTC TGG GAG AGG-3'

DR1B-F
5'-GGG GGG AAG CTT ATG GGG GAC ACC CGA CCA CGT TTC TTG TGG CAG C-3'

AF-N
5'-GGG GGG GCC ATG GCC ATC AAA GAA GAA CAT GTG ATC ATC-3'

AB-S
5'-GCG GCG ACT AGT GTT CTC TGT AGT CTC TGG GAG AGG-3'

OPR124
5'-GGG GGG AAG CTT GAT ATC TCA GCT TCC AGC AGT AGT ATC AAA GAA GAA CAT GTG ATC-3'

OPR125
5'-GGG GGG CGG CCG CTA CTT ACG TTT CTC TGG GAG AGG GCT TGG AGC-3'

DR1B-B
5'-GCG GCG GGA TCC CTT GCT CTG TGC AGA TTC AGA CC-3'

BF-NN
5'-GGG GGG GCC ATG GCC GGA TCC GCT AGC GGG GAC ACC CGA CCA CGT TTC TTG-3'

BB-5
5'-GCG GCG ACT AGT CTT GCT CTG TGC AGA TTC AGA CCG-3'

FIG. 8B

OPR121
5'-GTT GTC TTA AGT GGA GCT AGC GGA GGG GGC GGG TCC GGA GGT GGT GGG GAC ACC CG-3'

OPR122
5'-GAA ATG ACA TTC AAA CTT CAG CTG CCA CAA GAA ACG TGG TCG GGT GTC CCC ACC ACC-3'

OPR123
5'-GGG GGG CGG CCG TAC CTG AGG ACT TGC TCT GTG CAG ATT CAG-3'

PEPTIDE OLIGONUCLEOTIDES.

Ova 323-339
OPR110
5'-TTA AGT ATC TCT CAG GCT GTT CAC GCT GCT CAC GCT GAA ATC AAC GAA GCT GGT CGT G-3'

OPR111
5'-CTA GCA CGA CCA GCT TCG TTG ATT TCA GCC TGA GCA GCG TGA ACA GCC TGA GAG ATA C-3'

Ova H331R
OPR115
5'-TTA AGT ATC TCT CAG GCT GTT CAC GCT GCT CGG GCT GAA ATC AAC GAA GCT GGT CGT G-3'

OPR116
5'-CTA GCA CGA CCA GCT TCG TTG ATT TCA GCC CGA GCA GCG TGA ACA GCC TGA GAG ATA C-3'

Ova A332Y
OPR117
5'-TTA AGT ATC TCT CAG GCT GTT CAC GCT GCT CAC TAC GAA ATC AAC GAA GCT GGT CGT G-3'

OPR116
5'-CTA GCA CGA CCA GCT TCG TTG ATT TCA TAG TGA GCA GCG TGA ACA GCC TGA GAG ATA C-3'

HEL 74-86
OPR140
5'-TTA AGT AAC CTG TGC AAC ATC CCC TGC AGC GCC CTG CTG AGC TCC G-3'

OPR141
5'-CTA GCG GAG CTC AGC AGG GCG CTG CAGBGGG ATG TTG CAC AGG TTA C-3'

FIG. 8C

NP 404-415
OPR129
5'-<u>TTA AGT</u> CAG ATC AGC GTG CAG CCC GCC TTC AGC GTG CAG <u>G</u>-3'

OPR129
5'-<u>CTA GCC</u> TGC ACG CTG AAG GCG GGC TEA ACG CTG ATC TGA <u>C</u>-3'

HA 307-319
OPR130
5'-<u>TTA AGT</u> CCC AAG TAC GTG AAG CAG AAC ACC CTG AAG CTG GCC ACC <u>G</u>-3'

OPR131
5'-<u>CTA GCG</u> GTG GCC AGC TTC AGG GTG TTC TGC TTC ACG TAC TTG GGA <u>C</u>-3'

MBP 91-103
VW315
5'-<u>TTA AGT</u> CAC TAT GGC TCC CTG CCG CAG AAG TCC CAG CAC GGG CGC <u>G</u>-3'

VW316
5'-<u>CTA GCG</u> CGC CCG TGC TGG GAC TTC TGC GGC AGG GAG CCA TAG TGA <u>C</u>-3'

PLP 139-151
VW313
5'-<u>TTA CAC</u> CAC TCC CTG GGC AAG TGG CTG GGC CAC CCG GAC AAG TTC <u>G</u>-3'

VW314
5'-<u>CTA GCG</u> AAC TTG TTC GGG TGG CCC AGC CAC TTG CCC AGG GAG TGA <u>C</u>-3'

MBP 1-14
VW317
5'-<u>TTA AGT</u> ATG GCA TCC CAG AAG CGC CCG TCC CAG CGC TCC AAG TAC CTG <u>G</u>-3'

VW316
5'-<u>CTA GCC</u> AGG TAC TTG AGC GCT GGG ACG GGC GCT TCT GGG ATG CCA TA<u>C</u>-3'

FIG. 8D

SOLUBLE I-A^d α CHAIN CONSTRUCT

```
EcoRV        10              20              30              40              50                          550              560              570              580      XbaI
GATATCTCAGCT TCC AGC AGT GAA GAC GAC ATT GAG GCC GAC CAC //  CCG GTT CTG AAA CAC TGG AAA CGT AAGTAGGGCCG
CTATAGAGTCGA AGG TCG TCA CTT CTG CTG TAA CTC CGG CTG GTG //  GGC CAA GAC TTT GTG ACC TTT GCA TTCATCGGCCGGC
              S   S   S   E   D   D   I   E   A   D   H  //   P   V   L   K   H   W   K   R
                                                -1                                         aa192
  IgG < CHAIN        SIGNAL PEPTIDE                            I-A^α α CHAIN                    IgG < CHAIN
    INTRON           CLEAVAGE SITE                                                               INTRON
```

FIG. 9A

SOLUBLE I-A^d β CHAIN CONSTRUCT

RESTRICTION SITES FOR INSERTION OF
OLIGONUCLEOTIDES ENCODING PEPTIDES OF INTEREST

```
EcoRV        10           AflII    20              NheI   30                   40                       50                        60                       70
GATATCACAGGT GTC TTA AGT TCA AGT GGA GCT AGC CCT CGA CCT GGA GGG GGC GGA AGC GGC GGA AGC GGT GGA AAC TCC GAA AGG CAT //
CTATAGTGTCCA CAG AAT TCA AGT TCA CCT CGA TCG GGA GCT GGA CCT CCC CCG CCT TCG CCG CCT TCG CCA CCT TTG AGG CTT TCC GTA //
              V   L   S   S   S   G   A   S   P   R   P   G   G   G   G   S   G   G   S   G   G   N   S   E   R   H
                           ↑                                             |+1|
                   SIGNAL PEPTIDE                                    LINKER REGION                       I-A^α β CHAIN
                   CLEAVAGE SITE 610             620             630
ATC ACT GTG GAG TGG TCC TCA GGT ACGGGCCGCC
TAG TGA CAC CTC ACC AGG AGT CCA TGCCCGGGGG
  I   T   V   E   W   S   S
                          aaL89
    I-A^α β CHAIN                                IgG H CHAIN
                                                  INTRON
```

FIG. 9B

ORIGINAL MAMMALIAN CELL EXPRESSION VECTORS

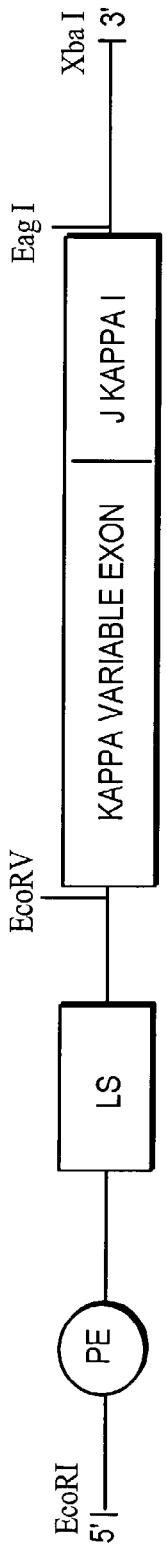
FIG. 11A
FIG. 11B
THE 2.7 Kb KAPPA AND THE 1.7 Kb HEAVY CHAIN EcoR V AND Eag I. MUTATED CONSTRUCTS PRIMERS USED FOR SEQUENCING MUTATED 2.7Kb FRAGMENT

| PRIMER LIST | SEQUENCE |
|---|---|
| PMC-33 | (5'GCTCAGCTGTCTCTTGTTTCAGTACTGATC3') |
| PMC-77 | (5'GTAAGTAGCGGGCCG3') |
| PMC-111 | (5'GGTATGTAAAATAAACATCACAG3') |
| PMC-114 | (5'GCTTTGCTTACGGAGTTACTC3') |

FIG. 14

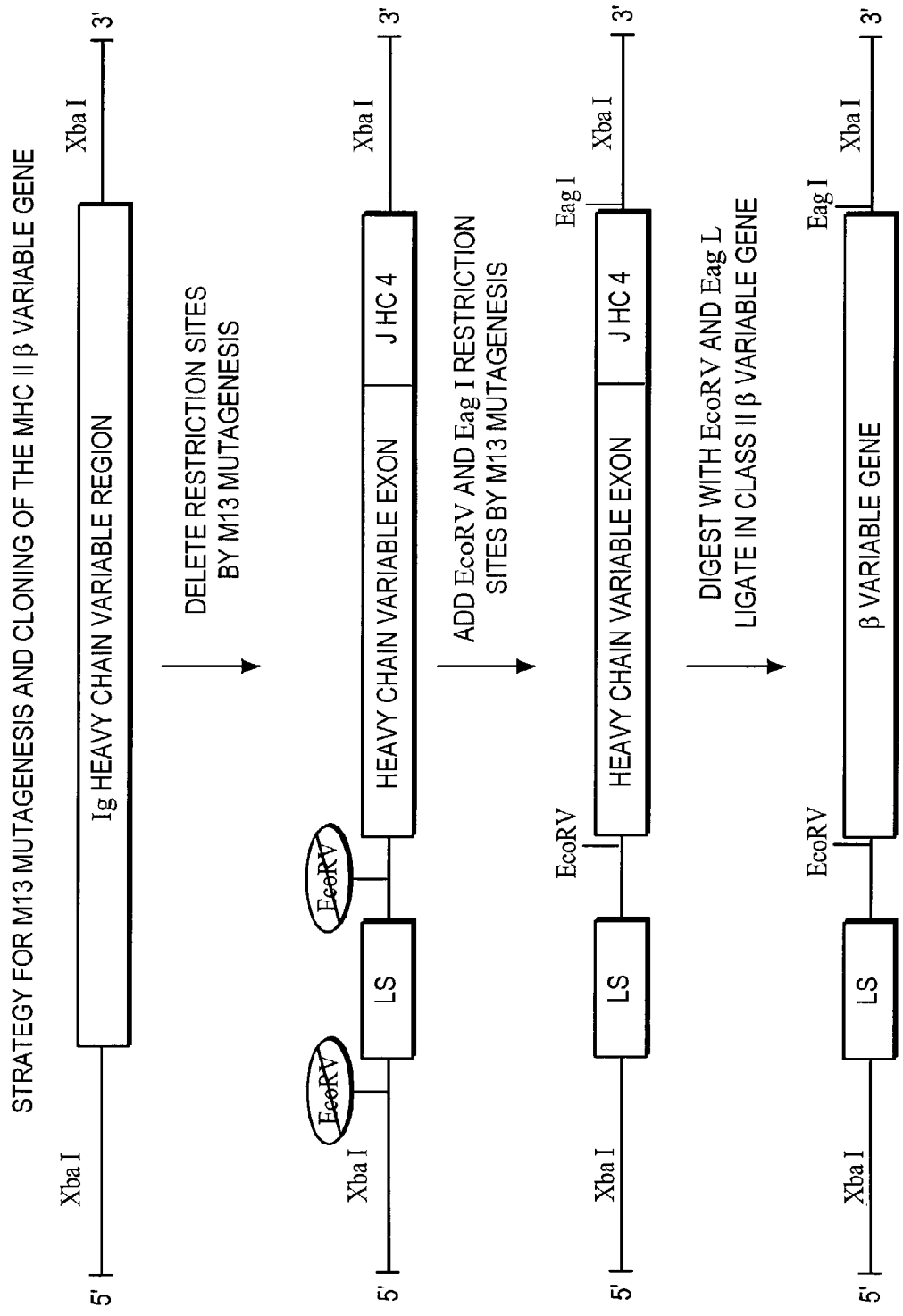

FINAL VECTORS FOR EXPRESSING MHC II/Ig CHIMERIC PROTEINS

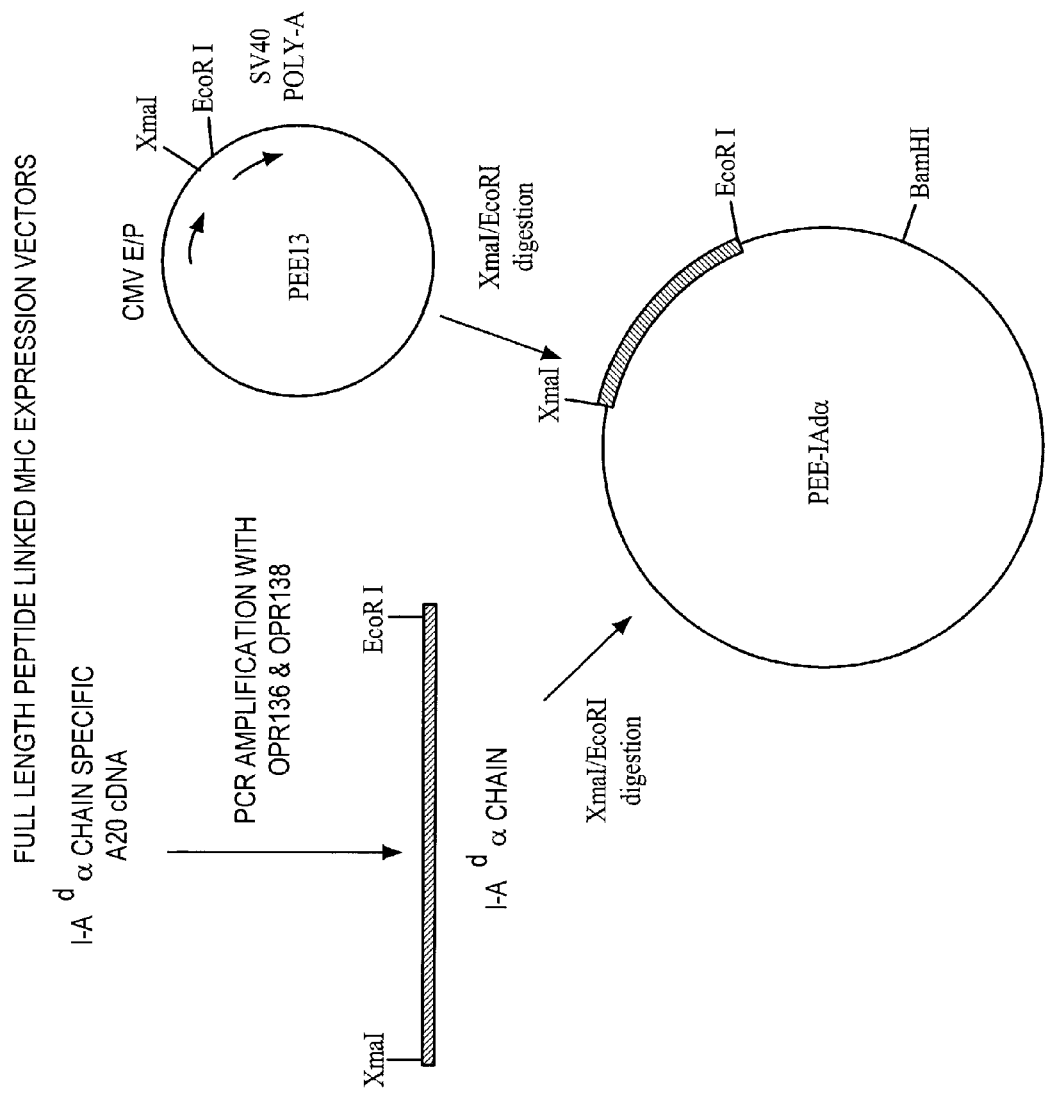
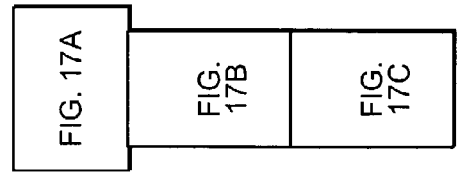
FIG. 17A

FULL LENGTH I-A$^d$ α CHAIN INSERT

```
     Xhaf
             10          20          30          40          50
     ─────
     CCCGGGCCAC C ATG CCG TGC AGC AGA GCT CTG ATT CTG GGG GTC CTC GCC
     GGGCCCGGTG G TAC GGC ACG TCG TCT CGA GAC TAA GAC CCC CAG GAG CGG
                  M   P   C   S   R   A   L   I   L   G   V   L   A
                  └─────────────────────────────────────────────────
       KOZAK              I-A$^d$ α CHAIN SIGNAL PEPTIDE
     CONSENSUS
```

```
             60          70          80          90
     CTG AAC ACC ATG CTC AGC CTC TGC GGA GGT GAA GAC GAC ATT GAG //
     GAC TTG TGG TAC GAG TCG GAG ACG CCT CCA CTT CTG CTG TAA CTC //
      L   N   T   M   L   S   L   C   G   G↑  E   D   D   I   E  //
     ──────────────────────────────────────┘│└ -1
                                                                ─//
     I-A$^d$ α CHAIN SIGNAL PEPTIDE         SIGNAL PEPTIDE
                                            CLEAVAGE SITE
```

```
                                                       EcorI
            750         760         770         780   ─────
     CGA TCA GGT GCC ACC TCC AGA CAC CCA GGG CCT TTA TGA GAATTC
     GCT AGT CCA CGG TGG AGG TCT GTG GGT CCC GGA AAT ACT CTTAAG
      R   S   G   G   T   S   R   H   P   G   P   L   -
                                                     stop
     ──────────────────────────────────────────────────────
                  I-A$^d$ α CHAIN
```

FIG. 18A

FULL LENGTH I-A$^d$ β CHAIN INSERT

```
HindIII Xhaf
         10         20         30         40         50
AAGCTTCCCG GGCCACC ATG GCT CTG CAG ATC CCC AGC CTC CTC CTC TCA GCT
TTCGAAGGGC CCGGTGG TAC CGA GAC GTC TAG GGG TCG GAG GAG GAG AGT CGA
                    M   A   L   Q   I   P   S   L   L   L   S   A
```

KOZAK            I-A$^d$ β CHAIN SIGNAL PEPTIDE
CONSENSUS

```
                                             AflII
         60         70         80         90        100
GCT GTG GTG GTG CTG ATG GTG CTG AGC AGC CCA AGG ACC TTA AGT ATC
CGA CAC CAC CAC GAC TAC CAC GAC TCG TCG GGT CCT TCC TGG AAT TCA TAG
 A   V   V   V   L   M   V   L   S   S   P   R   T   L   S   I
```

I-A$^d$ β CHAIN SIGNAL PEPTIDE     SIGNAL PEPTIDE CLEAVAGE SITE

```
        110        120        130        140
TCT CAG GCT GTT CAC GCT GCT CAC GCT GAA ATC AAC GAA GCT GGT CGT
AGA GTC CGA CAA GTG CGA CGA GTG CGA CTT TAG TTG CTT CGA CCA GCA
 S   Q   A   V   H   A   A   H   A   E   I   N   E   A   G   R
```

OVE PEPTIDE

```
NbeI
150        160        170        180        190
GCT AGC GGA GGG GGC GGA AGC GGC GGA GGG GGA AAC TCC GAA AGG //
CGA TCG CCT CCC CCG CCT TCG CCG CCT CCC CCT TTG AGG CTT TCC //
 A   S   G   G   G   G   S   G   G   G   G   N   S   E   R  //
```

LINKER REGION       -1  I-A$^d$ β CHAIN

```
                                    EcoRI    SacI
870        880        890        900
CCT CCT CCA GCA GGG CTC CTG CAG TGA GAAT TCCAGCTC
GGA GGA GGT CGT CCC GAG GAC GTC ACT CTTA AGCTCGAG
 P   P   P   A   G   L   L   Q   —
                                 stop
```

I-A$^d$ β CHAIN

FIG. 18B

OLIGONUCLEOTIDES USED IN CLONING

OPR132

I-A$^d$ β SIGNAL PEPTIDE FRONT PRIMER WITH KOZAK CONSENSUS FOR CellTech VECTOR- HindIII/XmaI SITES
5' -CCC CCC AAG CTT CCC GGG CCA CCA TGG CTC TGC AGA TCC CCA GC-3'

OPR133

I-A$^d$ β SIGNAL PEPTIDE BACK PRIMER WITH KOZAK CONSENSUS FOR CellTech VECTOR- AflII SITE
5' -CCC CCC ACT TAA GGT CCT TGG GCT GCT CAG CAC C-3'

OPR134

I-A$^d$ β TRANSMEMBRANE FRONT PRIMER FOR CellTech VECTOR- BstXI SITES
5' -CCC CCC CCA TCA CTG TGG AGT GGA GGG-3'

OPR135

I-A$^d$ β TRANSMEMBRANE BACK PRIMER FOR CellTech VECTOR- SstI, EcoRI SITES
5' -CCC CCC GAG CTC GAA TCC TCA CTG CAG GAG CCC TGC TGG-3'

OPR136

I-A$^d$ α SIGNAL PEPTIDE FRONT PRIMER WITH KOZAK CONSENSUS FOR CellTech VECTOR- HindIII/XmaI SITES
5' -CCC CCC AAG CTT CCC GGG CCA CCA TGC CGT GCA GCA GAG CTC TG-3'

OPR139

I-A$^d$ α TRANSMEMBRANE PRIMER FOR CellTech VECTOR- SstI/EcoRI SITES
5' -CCC CCC GAG CTC GAA TCC TCA TAA AGG CCC TGG GTG TCT G-3'

B7-1-2F
MURINE B7-1 FRONT PRIMER WITH KOZAK CONSENSUS FOR CellTech VECTOR- NotI SITES
5' -CCC CCC CCG CGG CCG CCC CAC CAT GGG ACT GAG TAA CAT CTC C-3'

B7-1-2B
MURINE B7-1 BACK PRIMER FOR CellTech VECTOR- NotI SITE
5' -CCC CCC GCG GCC GCT TTA AAA ACA TGT ATC ACT TTT-3'

FIG. 20

JLA-005

5'-CCCCCCGCCATGGCCGCTAGCGGAGGGGGCGGAAGC-3'

JLA-007

5'-CCCGGGGCCTCGAGTGAAGACGACATTGAGGCCGAC-3'

JLA-009

5'-CCCCCCACTAGTCCACTCCACAGTGATGGGGCT-3'

JLA-010

5'-CCCCCCCCCGGGACCAGTGTTTCAGAACCGGCTCCTC-3'

JLA-301

5'-TCGAGGAACCGCCACCGCCAGAACCGCCGCCACCGGA-
    ACCACCACCGCCGCTGCCACCGCCACCA-3'

JLA-302

5'-CTAGTGGTGGCGGTGGCAGCGGCGGTGGTGGTTCCGG-
    TGGCGGCGGTTCTGGCGGTGGCGGTTCC-3'

OPR-142

5'-CTTGGGAATCTTGACTAAGAGG-3'

JS-305

5'-CAGGTCGAATTCTCATTCCATCGGCATGTACTCTTCTT-
    CCTCCCAGTGTTTCAGAACCGG-3'

```
          10         20         30         40         50
           *          *          *          *          *
CCACC ATG GCT CTG CAG ATC CCC AGC CTC CTC CTC TCA GCT GCT GTG GTG
GGTGG TAC CGA GAC GTC TAG GGG TCG GAG GAG GAG AGT CGA CGA CAC CAC
       M   A   L   Q   I   P   S   L   L   L   S   A   A   V   V>
      <------------------ I-Ad β CHAIN LEADER ------------------
```

```
         60         70         80         90
          *          *          *          *
GTG CTG ATG GTG CTG AGC AGC CCA AGG ACC TTA AGT ATC TCT CAG GCT
CAC GAC TAC CAC GAC TCG TCG GGT TCC TGG AAT TCA TAG AGA GTC CGA
 V   L   M   V   L   S   S   P   R   T   L   S   I   S   Q   A>
-------------------------------------------------->< ---------
```

```
100        110        120        130        140
  *          *          *          *          *
GTT CAC GCT GCT CAC GCT GAA ATC AAC GAA GCT GGT CGT GCT AGC GGA
CAA GTG CGA CGA GTG CGA CTT TAG TTG CTT CGA CCA GCA CGA TCG CCT
 V   H   A   A   H   A   E   I   N   E   A   G   R   A   S   G>
--------- OVA 323-339 -------------------------------->< ------
```

```
        150        160        170        180        190
         *          *          *          *          *
GGG GGC GGA AGC GGC GGA GGG GGA AAC TCC GAA AGG CAT TTC GTG GTC
CCC CCG CCT TCG CCG CCT CCC CCT TTG AGG CTT TCC GTA AAG CAC CAG
 G   G   G   S   G   G   G   G   N   S   E   R   H   F   V   V>
-- 10 AMINO ACID LINKER -->< --------- I-Ad β-1 DOMAIN ---------
```

```
       200        210        220        230        240
        *          *          *          *          *
CAG TTC AAG GGC GAG TGC TAC TAC ACC AAC GGG ACG CAG CGC ATA CGG
GTC AAG TTC CCG CTC ACG ATG ATG TGG TTG CCC TGC GTC GCG TAT GCC
 Q   F   K   G   E   C   Y   Y   T   N   G   T   Q   R   I   R>
-----------------------------------------------------------------
```

```
       250        260        270        280        290
        *          *          *          *          *
CTC GTG ACC AGA TAC ATC TAC AAC CGG GAG GAG TAC GTG CGC TAC GAC
GAG CAC TGG TCT ATG TAG ATG TTG GCC CTC CTC ATG CAC GCG ATG CTG
 L   V   T   R   Y   I   Y   N   R   E   E   Y   V   R   Y   D>
-----------------------------------------------------------------
```

```
       300        310        320        330
        *          *          *          *
AGC GAC GTG GGC GAG TAC CGC GCG GTG ACC GAG CTG GGG CGG CCA GAC
TCG CTG CAC CCG CTC ATG GCG CGC CAC TGG CTC GAC CCC GCC GGT CTG
 S   D   V   G   E   Y   R   A   V   T   E   L   G   R   P   D>
-----------------------------------------------------------------
```

```
340        350        360        370        380
  *          *          *          *          *
GCC GAG TAC TGG AAC AGC CAG CCC GAG ATC CTG GAG CGA ACG CGG GCC
CGG CTC ATG ACC TTG TCG GTC GGG CTC TAG GAC CTC GCT TGC GCC CGG
 A   E   Y   W   N   S   Q   P   E   I   L   E   R   T   R   A>
-----------------------------------------------------------------
```

FIG. 27B

```
         390         400         410         420         430
          *           *           *           *           *
GAG GTG GAC ACG GCG TGC AGA CAC AAC TAC GAG GGG CCG GAG ACC AGC
CTC CAC CTG TGC CGC ACG TCT GTG TTG ATG CTC CCC GGC CTC TGG TCG
 E   V   D   T   A   C   R   H   N   Y   E   G   P   E   T   S>
-----------------------------------------------------------------

440         450         460         470         480
          *           *           *           *           *
ACC TCC CTG CGG CGG CTT GAA CAG CCC AAT GTC GCC ATC TCC CTG TCC
TGG AGG GAC GCC GCC GAA CTT GTC GGG TTA CAG CGG TAG AGG GAC AGG
 T   S   L   R   R   L   E   Q   P   N   V   A   I   S   L   S>
----- I-Ad β-1 DOMAIN --------><------------ I-Ad β-2 DOMAIN -----------

490         500         510         520         530
          *           *           *           *           *
AGG ACA GAG GCC CTC AAC CAC CAC AAC ACT CTG GTC TGT TCG GTG ACA
TCC TGT CTC CGG GAG TTG GTG GTG TTG TGA GAC CAG ACA AGC CAC TGT
 R   T   E   A   L   N   H   H   N   T   L   V   C   S   V   T>
-----------------------------------------------------------------

540         550         560         570
          *           *           *           *
GAT TTC TAC CCA GCC AAG ATC AAA GTG CGC TGG TTC AGG AAT GGC CAG
CTA AAG ATG GGT CGG TTC TAG TTT CAC GCG ACC AAG TCC TTA CCG GTC
 D   F   Y   P   A   K   I   K   V   R   W   F   R   N   G   Q>
-----------------------------------------------------------------

580         590         600         610         620
  *           *           *           *           *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
-----------------------------------------------------------------

630         640         650         660         670
          *           *           *           *           *
TGG ACC TTC CAG GTC CTG GTC ATG CTG GAG ATG ACC CCT CAT CAG GGA
ACC TGG AAG GTC CAG GAC CAG TAC GAC CTC TAC TGG GGA GTA GTC CCT
 W   T   F   Q   V   L   V   M   L   E   N   T   P   H   Q   G>
-----------------------------------------------------------------

680         690         700         710         720
          *           *           *           *           *
GAG GTC TAC ACC TGC CAT GTG GAG CAT CCC AGC CTG AAG AGC CCC ATC
CTC CAG ATG TGG ACG GTA CAC CTC GTA GGG TCG GAC TTC TCG GGG TAG
 E   V   V   T   C   H   V   E   H   P   S   L   K   S   P   I>
---------------------------------------------------- I-Ad β-2 DOMAIN ----------------

730         740         750         760         770
          *           *           *           *           *
ACT GTG GAG TGG ACT AGT GGT GGC GGT GGC AGC GGC GGT GGT GGT TCC
TCA CAC CTC ACC TGA TCA CCA CCG CCA CCG TCG CCG CCA CCA CCA AGG
 T   V   E   W   T   S   G   G   G   G   S   G   G   G   G   S>
-------------------------------------------- 24 AMINO ACID LINKER ------------
```

FIG. 27C

```
                 780              790              800              810
                  *                *                *                *
        GGT GGC GGC GGT TCT GGC GGT GGC GGT TCC TCC ACT GAA GAC GAC ATT
        CCA CCG CCG CCA AGA CCG CCA CCG CCA AGG AGC TCA CTT CTG CTG TAA
         G   G   G   G   S   G   G   G   G   S   S   E   D   D   I>
        -----------------------------------------------------------><---------------

820              830              840              850              860
      *                *                *                *                *
    GAG GCC GAC CAC GTA GGC TTC TAT GGT ACA ACT GTT TAT CAG TCT CCT
    CTC CGG CTG GTG CAT CCG AAG ATA CCA TGT TGA CAA ATA GTC AGA GGA
     E   A   D   H   V   G   F   Y   G   T   T   V   Y   Q   S   P>
    -------- I-Ad α-1 DOMAIN -----------------------------------------

870              880              890              900              910
          *                *                *                *                *
        GGA GAC ATT GGC CAG TAC ACA CAT GAA TTT GAT GGT GAT GAG TTC TTC
        CCT CTG TAA CCG GTC ATG TGT GTA CTT AAA CTA CCA CTA CTC AAC AAG
         G   D   I   G   Q   Y   T   H   E   F   D   G   D   E   L   F>
        ----------------------------------------------------------------

920              930              940              950              960
          *                *                *                *                *
        TAT GTG GAC TTG GAT AAG AAG AAA ACT GTC TGG AGG CTT CCT GAG TTT
        ATA CAC CTG AAC CTA TTC TTC TTT TGA CAG ACC TCC GAA GGA CTC AAA
         Y   V   D   L   D   K   K   K   T   V   W   R   L   P   E   F>
        ----------------------------------------------------------------

970              980              990             1000             1010
          *                *                *                *                *
        GGC CAA TTG ATA CTC TTT GAG CCC CAA GGT GGA CTG CAA AAC ATA GCT
        CCG GTT AAC TAT GAG AAA CTC GGG GTT CCA CCT GAC GTT TTG TAT CGA
         G   Q   L   I   L   F   E   P   Q   G   G   L   Q   N   I   A>
        ----------------------------------------------------------------

1020             1030             1040             1050
                *                *                *                *
        GCA GAA AAA CAC AAC TTG GGA ATC TTG ACT AAG AGG TCA AAT TTC ACC
        CGT CTT TTT GTG TTG AAC CCT TAG AAC TGA TTC TCC AGT TTA AAG TGG
         A   E   K   H   N   L   G   I   L   T   K   R   S   N   F   T>
        --------------------------------- I-Ad α-1 DOMAIN -----------------

1060             1070             1080             1090             1100
      *                *                *                *                *
    CCA GCT ACC AAT GAG GCT CCT CAA GCG ACT GTG TTC CCC AAG TCC CCT
    GGT CGA TGG TTA CTC CGA GGA GTT CGC TGA CAC AAG GGG TTC AGG GGA
     P   A   T   N   E   A   P   Q   A   T   V   F   P   K   S   P>
    ----------------------><---------- I-Ad α-2 DOMAIN -----------------

1110             1120             1130             1140             1150
           *                *                *                *                *
        GTG CTG CTG GGT CAG CCC AAC ACC CTT ATC TGC TTT GTG GAC AAC ATC
        CAC GAC GAC CCA GTC GGG TTG TGG GAA TAG ACG AAA CAC CTG TTG TAG
         V   L   L   G   Q   P   N   T   L   I   C   F   V   D   N   T>
        ----------------------------------------------------------------
```

```
      1160              1170              1180              1190              1200
        *                 *                 *                 *                 *
TTC CCA GCT GTG ATC AAC ATC ACA TGG CTC AGA AAT AGC AAG TCA GTC
AAG GGT CGA CAC TAG TTG TAG TGT ACC GAG TCT TTA TCG TTC AGT CAG
 F   P   P   V   I   N   I   T   W   L   R   N   S   K   S   V>
---------------------------------------------------------------------

1210              1220              1230              1240              1250
        *                 *                 *                 *                 *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H   S>
---------------------------------------------------------------------

1260              1270              1280              1290
              *                 *                 *                 *
TTC CAC AAG CTG TCT TAT CTC ACC TTC ATC CCT TCT GAT GAT GAC ATT
AAG GTG TTC GAC AGA ATA GAG TGG AAG TAG GGA AGA CTA CTA CTG TAA
 F   H   K   L   S   Y   L   T   F   I   P   S   D   D   D   I>
---------------------------------------------------------------------

1300              1310              1320              1330              1340
  *                 *                 *                 *                 *
TAT GAC TGC AAG GTG GAG CAC TGG GGC CTG GAG GAG CCG GTT CTG AAA
ATA CTG ACG TTC CAC CTC GTG ACC CCG GAC CTC CTC GGC CAA GAC TTT
 Y   D   C   K   V   E   H   W   G   L   E   E   P   V   L   K>
------------------------------------- I-Ad α-2 DOMAIN -----------------
        1350              1360              1370              1380
          *                 *                 *                 *
CAC TGG TCC CGG GCT AGT CAC CAT CAC CAT CAT CAC TAG
GTG ACC AGG GCC CGA TCA GTG GTA GTG GTA GTA GTG ATC
 H   W   S   R   A   S   H   H   H   H   H   H   *>
----------><-------------- 6 X HIS TAG------->
```

```
              10           20           30           40           50
               *            *            *            *            *
     CCACC ATG GCT CTG CAG ATC CCC AGC CTC CTC CTC TGA GCT GCT GTG GTG
     GGTGG TAC CGA GAC GTC TAG GGG TCG GAG GAG GAG AGT CGA CGA CAC CAC
            M   A   L   Q   I   P   S   L   L   L   S   A   A   V   V>
           <------------------------ I-Ad β CHAIN LEADER ---------------------------

60           70           80           90
               *            *            *            *
     GTG CTG ATG GTG CTG AGC AGC CCA AGG ACC TTA AGT ATC TCT CAG GCT
     CAC GAC TAC CAC GAC TCG TCG GGT TCC TGG AAT TCA TAG AGA GTC CGA
      V   L   M   V   L   S   S   P   R   T   L   S   I   S   Q   A>
     ----------------------------------------------------------><---------------------

100          110          120          130          140
      *            *            *            *            *
     GTT CAC GCT GCT CAC GCT GAA ATC AAC GAA GCT GGT CGT GCT AGC GGA
     CAA GTG CGA CGA GTG CGA CTT TAG TTG CTT CGA CCA GCA CGA TCG CCT
      V   H   A   A   H   A   E   I   N   E   A   G   R   A   S   G>
     -------------- OVA 323-339 -----------------------------------><-------------

150          160          170          180          190
      *            *            *            *            *
     GGG GGC GGA AGC GGC GGA GGG GGA AAC TCC GAA AGG CAT TTC GTG GTC
     CCC CCG CCT TCG CCG CCT CCC CCT TTG AGG CTT TCC GTA AAG CAC CAG
      G   G   G   S   G   G   G   G   N   S   E   R   H   F   V   V>
     ---10 AMINO ACID LINKER--><-------------- I-Ad β-1 DOMAIN -----------------

200          210          220          230          240
      *            *            *            *            *
     CAG TTC AAG GGC GAG TGC TAC TAC ACC AAC GGG ACG CAG CGC ATA CGG
     GTC AAG TTC CCG CTC ACG ATG ATG TGG TTG CCC TGC GTC GCG TAT GCC
      Q   F   L   G   E   C   Y   Y   T   N   G   T   Q   R   I   R>
     ------------------------------------------------------------------------------

250          260          270          280          290
      *            *            *            *            *
     CTC GTG ACC AGA TAC ATC TAC AAC CGG GAG GAG TAC GTG CGC TAC GAC
     GAG CAC TGG TCT ATG TAG ATG TTG GCC CTC CTC ATG CAC GCG ATG CTG
      L   V   T   R   Y   I   Y   N   R   E   E   Y   V   R   Y   D>
     ------------------------------------------------------------------------------

300          310          320          330
               *            *            *            *
     AGC GAC GTG GGC GAG TAC CGC GCG GTG ACC GAG CTG GGG CGG CCA GAC
     TCG CTG CAC CCG CTC ATG GCG CGC CAC TGG CTC GAC CCC GCC GGT CTG
      S   D   V   G   E   Y   R   A   V   T   E   L   G   R   P   D>
     ------------------------------------------------------------------------------

340          350          360          370          380
      *            *            *            *            *
     GCC GAG TAC TGG AAC AGC CAG CCG GAG ATC CTG GAG CGA ACG CGG GCC
     CGG CTC ATG ACC TTG TCG GTC GGC CTC TAG GAC CTC GCT TGC GCC CGG
      A   E   Y   W   N   S   Q   P   E   I   L   E   R   T   R   A>
     ------------------------------------------------------------------------------
```

FIG. 28B

```
         390            400            410            420            430
          *              *              *              *              *
    GAG GTG GAC ACG GCG TGC AGA CAC AAC TAC GAG GGG CCG GAG ACC AGC
    CTC CAC CTG TGC CGC ACG TCT GTG TTG ATG CTC CCC GGC CTC TGG TCG
     E   V   D   T   A   C   R   H   N   Y   E   G   P   E   T   S>
    ----------------------------------------------------------------

440            450            460            470            480
          *              *              *              *              *
    ACC TCC CTG CGG CGG CTT GAA CAG CCC AAT GTC GCC ATC TCC CTG TCC
    TGG AGG GAC GCC GCC GAA CTT GTC GGG TTA CAG CGG TAG AGG GAC AGG
     T   S   L   R   R   L   E   Q   P   N   V   A   I   S   L   S>
    ---- I-Ad β-1 DOMAIN ---------><----------- I-Ad β-2 DOMAIN ------

490            500            510            520            530
          *              *              *              *              *
    AGG ACA GAG GCC CTC AAG CAC CAC AAC ACT CTG GTC TGT TCG GTG ACA
    TCC TGT CTC CGG GAG TTG GTG GTG TTG TGA GAC CAG ACA AGC CAC TGT
     R   T   E   A   L   N   H   H   N   T   L   V   C   S   V   T>
    ----------------------------------------------------------------

540            550            560            570
              *              *              *              *
        GAT TTC TAC CCA GCC AAG ATC AAA GTG CGC TGG TTC AGG AAT GGC CAG
        CTA AAG ATG GGT CGG TTC TAG TTT CAC GCG ACC AAG TCC TTA CCG GTC
         D   F   Y   P   A   K   I   K   V   R   W   F   R   N   G   Q>
        ------------------------------------------------------------

580            590            600            610            620
    *              *              *              *              *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
----------------------------------------------------------------

630            640            650            660            670
          *              *              *              *              *
    TGG ACC TTC CAG GTC CTG GTC ATG CTG GAG ATG ACC CCT CAT CAG GGA
    ACC TGG AAG GTC CAG GAC CAG TAC GAC CTC TAC TGG GGA GTA GTC CCT
     W   T   F   Q   V   L   V   M   L   E   M   T   P   H   Q   G>
    ----------------------------------------------------------------

680            690            700            710            720
          *              *              *              *              *
    GAG GTC TAC ACC TGC CAT GTG GAG CAT CCC AGC CTG AAG AGC CCC ATC
    CTC CAG ATG TGG ACG GTA CAC CTC GTA GGG TCG GAC TTC TCG GGG TAG
     E   V   Y   T   C   H   V   E   H   P   S   L   K   S   P   I>
    -------------------------------------------- I-Ad β-2 DOMAIN ----

730            740            750            760            770
          *              *              *              *              *
    ACT GTG GAG TGG ACT AGT GGT GGC GGT GGC AGC GGC GGT GGT GGT TCC
    TGA CAC CTC ACC TGA TCA CCA CCG CCA CCG TCG CCG CCA CCA CCA AGG
     T   V   E   W   T   S   G   G   G   G   S   G   G   G   G   S>
    ---------------------------------------- 24 AMINO ACID LINKER----
```

FIG. 28C

```
              780            790           800           810
               *              *             *             *
       GGT GGC GGC GGT TCT GGC GGT GGC GGT TCC TCG AGT GAA GAC GAC ATT
       CCA CCG CCG CCA AGA CCG CCA CCG CCA AGG AGC TCA CTT CTG CTG TAA
        G   G   G   G   S   G   G   G   G   S   S   S   E   D   D  I>
       ---------------------------------------------------------><-----------------------

820            830           840           850           860
        *              *             *             *             *
       GAG GCC GAC CAC GTA GGC TTC TAT GGT ACA ACT GTT TAT CAG TCT CCT
       CTC CGG CTG GTG CAT CCG AAG ATA CCA TGT TGA CAA ATA GTC AGA GGA
        E   A   D   H   V   G   F   Y   G   T   T   V   Y   Q   S   P>
       -------- I-Ad α-1 DOMAIN -----------------------------------------

870           880           890           900           910
               *             *             *             *             *
       GGA GAC ATT GGC CAG TAC ACA CAT GAA TTT GAT GGT GAT GAG TTG TTC
       CCT CTG TAA CCG GTC ATG TGT GTA CTT AAA CTA CCA CTA CTC AAC AAG
        G   D   I   G   Q   Y   T   H   E   F   D   G   D   E   L   F>
       ----------------------------------------------------------------------

920           930           940           950           960
               *             *             *             *             *
       TAT GTG GAC TTG GAT AAG AAG AAA ACT GTC TGG AGG CTT CCT GAG TTT
       ATA CAC CTG AAC CTA TTC TTC TTT TGA CAG ACC TCC GAA GGA CTC AAA
        Y   V   D   L   D   K   K   K   T   V   W   R   L   P   E   F>
       ----------------------------------------------------------------------

970           980           990          1000          1010
               *             *             *             *             *
       GGC CAA TTG ATA CTC TTT GAG CCC CAA GGT GGA CTG CAA AAC ATA GCT
       CCG GTT AAC TAT GAG AAA CTC GGG GTT CCA CCT GAC GTT TTG TAT CGA
        G   Q   L   I   L   F   E   P   Q   G   G   L   Q   N   I   A>
       ----------------------------------------------------------------------

1020          1030          1040          1050
               *             *             *             *
       GCA GAA AAA CAC AAC TTG GGA ATC TTG ACT AAG AGG TCA AAT TTC ACC
       CGT CTT TTT GTG TTG AAC CCT TAG AAC TGA TTC TCC AGT TTA AAG TGG
        A   E   K   H   N   L   G   I   L   T   K   R   S   N   F   T>
                                        ----------- I-Ad α-1 DOMAIN ---------

1060          1070          1080          1090          1100
         *             *             *             *             *
       CCA GCT ACC AAT GAG GCT CCT CAA GCG ACT GTG TTC CCC AAG TCC CCT
       GGT CGA TGG TTA CTC CGA GGA GTT CGC TGA CAC AAG GGG TTC AGG GGA
        P   A   T   N   E   A   P   Q   A   T   V   F   P   K   S   P>
       -----------------------><-------- I-Ad α-2 DOMAIN -------------------

1110          1120          1130          1140          1150
                *             *             *             *             *
       GTG CTG CTG GGT CAG CCC AAC ACC CTT ATC TGC TTT GTG GAC AAC ATC
       CAC GAC GAC CCA GTC GGG TTG TGG GAA TAG ACG AAA CAC CTG TTG TAG
        V   L   L   G   Q   P   N   T   L   I   C   F   V   D   N   I>
       ----------------------------------------------------------------------
```

```
      1160           1170           1180           1190           1200
        *              *              *              *              *
TTC CCA CCT GTG ATC AAC ATC ACA TGG CTC AGA AAT AGC AAG TCA GTG
AAG GGT GGA CAC TAG TTG TAG TGT ACG GAG TCT TTA TCG TTC AGT CAG
 F   P   P   V   I   N   I   T   W   L   R   N   S   K   S   V>
-----------------------------------------------------------------

1210           1220           1230           1240           1250
           *              *              *              *              *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H   S>
-----------------------------------------------------------------

1260           1270           1280           1290
               *              *              *              *
TTC CAC AAG CTG TCT TAT CTC ACG TTC ATC CCT TCT GAT GAT GAC ATT
AAG GTG TTC GAC AGA ATA GAG TGC AAG TAG GGA AGA CTA CTA CTG TAA
 F   H   K   L   S   Y   L   T   F   I   P   S   D   D   D   I>
-----------------------------------------------------------------

1300           1310           1320           1330           1340
   *              *              *              *              *
TAT GAC TGC AAG GTG GAG CAC TGG GGC CTG GAG GAG CCG GTT CTG AAA
ATA CTG ACG TTC CAC CTC GTG ACC CCG GAC CTC CTC GGC CAA GAC TTT
 Y   D   C   K   V   E   H   W   G   L   E   E   P   V   L   X>
--------------------------------------------------- I-Ad α-2 DOMAIN ----------
    1350           1360           1370           1380           1390
      *              *              *              *              *
CAC TCG GAA CCT GAG ATT CCA GCC CCC ATG TCA GAG CTG ACA GAA ACT
GTG ACC CTT GGA CTC TAA GGT CGG GGG TAC AGT CTC GAC TGT CTT TGA
 H   N   E   P   E   I   P   A   P   M   S   E   L   T   E   T>
---------->< ------------- I-Ad α-TM DOMAIN -----------------------
       1400           1410           1420           1430           1440
         *              *              *              *              *
GTG GTG TGT GCC CTG GGG TTG TCT GTG GGC CTT GTG GGC ATC GTG GTG
CAC CAC ACA CGG GAC CCC AAC AGA CAC CCG GAA CAC CCG TAG CAC CAC
 V   V   C   A   L   G   L   S   V   G   L   V   G   I   V   V>
-----------------------------------------------------------------

1450           1460           1470           1480           1490
            *              *              *              *              *
GGC ACC ATC TTC ATC ATT CAA GGC CTG CGA TCA GGT GGC ACC TCC AGA
CCG TGG TAG AAG TAG TAA GTT CCG GAC GCT AGT CCA CCG TGG AGG TCT
 G   T   I   F   I   I   Q   G   L   R   S   G   G   T   S   R>
-----------------------------------------------------------------

1500
               *
CAC CCA GGG CCT TTA TGA
GTG GGT CCC GGA AAT ACT
 H   P   G   P   L   *>
-- I-Ad α-TM DOMAIN ->
```

```
               10               20              30              40             50
                *                *               *               *              *
          CCACC ATG GCT CTG CAG ATC CCC AGC CTC CTC CTC TCA GCT GCT GTG GTG
          GGTGG TAC CGA GAC GTC TAG GGG TCG GAG GAG GAG AGT CGA CGA CAC CAC
                M   A   L   Q   I   P   S   L   L   L   S   A   A   V   V>
                <----------------- I-Ad β CHAIN LEADER ----------------------

60              70              80              90
               *               *               *               *
          GTG CTG ATG GTG CTG AGC AGC CCA AGG ACC TTA AGT ATC TCT CAG GCT
          CAC GAC TAC CAC GAC TCG TCG GGT TCC TGG AAT TCA TAG AGA GTC CGA
           V   L   M   V   L   S   S   P   R   T   L   S   I   S   Q   A>
          -------------------------------------------------><------------

100             110             120             130             140
          *               *               *               *               *
         GTT CAC GCT GCT CAC GCT GAA ATC AAC GAA GCT GGT CGT GCT AGC GGA
         CAA GTG CGA CGA GTG CGA CTT TAG TTG CTT CGA CCA GCA CGA TCG CCT
          V   H   A   A   H   A   E   I   N   E   A   G   R   A   S   G>
         ---------- OVA 323-339 -------------------------------><--------

150             160             170             180             190
              *               *               *               *               *
         GGG GGC GGA AGC GGC GGA GGG GGA AAC TCC GAA AGG CAT TTC GTG GTC
         CCC CCG CCT TCG CCG CCT CCC CCT TTG AGG CTT TCC GTA AAG CAC CAG
          G   G   G   S   G   G   G   G   N   S   E   R   H   F   V   V>
         ---10 AMINO ACID LINKER--><------------ I-Ad β-1 DOMAIN -----------

200             210             220             230             240
              *               *               *               *               *
         CAG TTC AAG GGC GAG TGC TAC TAC ACC AAC GGG ACG CAG CGC ATA CGG
         GTC AAG TTC CCG CTC ACG ATG ATG TGG TTG CCC TGC GTC GCG TAT GCC
          Q   F   K   G   E   C   Y   Y   T   N   G   T   Q   R   I   R>
         ------------------------------------------------------------------

250             260             270             280             290
              *               *               *               *               *
         CTC GTG ACC AGA TAC ATC TAC AAC CGG GAG GAG TAC GTG CGC TAC GAC
         GAG CAC TGG TCT ATG TAG ATG TTG GCC CTC CTC ATG CAC GCG ATG CTG
          L   V   T   R   Y   I   Y   N   R   E   E   Y   V   R   Y   D>
         ------------------------------------------------------------------

300             310             320             330
               *               *               *               *
         AGC GAC GTG GGC GAG TAC CGC GCG GTG ACC GAG CTG GGG CGG CCA GAC
         TCG CTG CAC CCG CTC ATG GCG CGC CAC TGG CTC GAC CCC GCC GGT CTG
          S   D   V   G   E   Y   R   A   V   T   E   L   G   R   P   D>
         ------------------------------------------------------------------

340             350             360             370             380
          *               *               *               *               *
         GCC GAG TAC TGG AAC AGC CAG CCG GAG ATC CTG GAG CGA ACG CGG GCC
         CGG CTC ATG ACC TTG TCG GTC GGC CTC TAG GAC CTC GCT TGC GCC CGG
          A   E   Y   W   N   S   Q   P   E   I   L   E   R   T   R   A>
         ------------------------------------------------------------------
```

FIG. 29B

```
        390            400           410           420           430
         *              *             *             *             *
GAG GTG GAC ACG GCG TGC AGA CAC AAC TAC GAG GGG CCG GAG ACC AGC
CTC CAC CTG TGC CGC ACG TCT GTG TTG ATG CTC CCC GGC CTC TGG TCG
 E   V   D   T   A   C   R   H   N   Y   E   G   P   E   T   S>
-----------------------------------------------------------------

440            450           460           470           480
         *              *             *             *             *
ACC TCC CTG CGG CGG CTT GAA CAG CCC AAT GTC GCC ATC TCC CTG TCC
TGG AGG GAC GCC GCC GAA CTT GTC GGG TTA CAG CGG TAG AGG GAC AGG
 T   S   L   R   R   L   E   Q   P   N   V   A   I   S   L   S>
----- I-Ad β-1 DOMAIN ------><-------------- I-Ad β-2 DOMAIN ----------

490            500           510           520           530
         *              *             *             *             *
AGG ACA GAG GCC CTC AAC CAC CAC AAC ACT CTG GTC TGT TCG GTG ACA
TCC TGT CTC CGG GAG TTG GTG GTG TTG TGA GAC CAG ACA AGC CAC TGT
 R   T   E   A   L   N   H   H   N   T   L   V   C   S   V   T>
-----------------------------------------------------------------

540            550           560           570
         *              *             *             *
GAT TTC TAC CCA GCC AAG ATC AAA GTG CGC TGG TTC AGG AAT GGC CAG
CTA AAG ATG GGT CGG TTC TAG TTT CAC GCG ACC AAG TCC TTA CCG GTC
 D   F   Y   P   A   K   I   K   V   R   W   F   R   N   G   Q>
-----------------------------------------------------------------

580           590           600           610           620
  *             *             *             *             *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
-----------------------------------------------------------------

630            640           650           660           670
         *              *             *             *             *
TGG ACC TTC CAG GTC CTG GTC ATG CTG GAG ATG ACC CCT CAT CAG GGA
ACC TGG AAG GTC CAG GAC CAG TAC GAC CTC TAC TGG GGA GTA GTC CCT
 W   T   F   Q   V   L   V   M   L   E   M   T   P   H   Q   G>
-----------------------------------------------------------------

680            690           700           710           720
         *              *             *             *             *
GAG GTC TAC ACC TGC CAT GTG GAG CAT CCC AGC CTG AAG AGC CCC ATC
CTC CAG ATG TGG ACG GTA CAC CTC GTA GGG TCG GAC TTC TCG GGG TAG
 E   V   Y   T   C   H   V   E   H   P   S   L   K   S   P   I>
---------------------------------- I-Ad β-2 DOMAIN ----------------------

730            740           750           760           770
         *              *             *             *             *
ACT GTG GAG TGG ACT AGT GGT GGG GGT GGC AGC GGC GGT GGT GGT TCC
TGA CAC CTC ACC TGA TCA CCA CCC CCA CCG TCG CCG CCA CCA CCA AGG
 T   V   E   W   T   S   G   G   G   G   S   G   G   G   G   S>
----------------------><---------------- 24 AMINO ACID LINKER-----------
```

FIG. 29C

```
              780           790           800           810
               *             *             *             *
GGT GGC GGC GGT TCT GGC GGT GGC GGT TCC TCC AGT GAA GAC GAC ATT
CCA CCG CCG CCA AGA CCG CCA CCG CCA AGG AGC TCA CTT CTG CTG TAA
 G   G   G   G   S   G   G   G   G   S   S   S   E   D   D   I>
-------------------------------------------------------><----------------

820           830           840           850           860
 *             *             *             *             *
GAG GCC GAC CAC GTA GGC TTC TAT GGT ACA ACT GTT TAT CAG TCT CCT
CTC CGG CTG GTG CAT CCG AAG ATA CCA TGT TGA CAA ATA GTC AGA GGA
 E   A   D   H   V   G   F   Y   G   T   T   V   Y   Q   S   P>
------- I-Ad α-1 DOMAIN ----------------------------------------

870           880           890           900           910
               *             *             *             *             *
GGA GAC ATT GGC CAG TAC ACA CAT GAA TTT GAT GGT GAT GAG TTG TTC
CCT CTG TAA CCG GTC ATG TGT GTA CTT AAA CTA CCA CTA CTC AAC AAG
 G   D   I   G   Q   Y   T   H   E   F   D   G   D   E   L   F>
----------------------------------------------------------------

920           930           940           950           960
               *             *             *             *             *
TAT GTG GAC TTG GAT AAG AAG AAA ACT GTC TGG AGG CTT CCT GAG TTT
ATA CAC CTG AAC CTA TTC TTC TTT TGA CAG ACC TCC GAA GGA CTC AAA
 Y   V   D   L   D   K   K   K   T   V   W   R   L   P   E   F>
----------------------------------------------------------------

970           980           990          1000          1010
               *             *             *             *             *
GGC CAA TTG ATA CTC TTT GAG CCC CAA GGT GSA CTG CAA AAC ATA GCT
CCG GTT AAC TAT GAG AAA CTC GGG GTT CCA CCT GAC GTT TTG TAT CGA
 G   Q   L   I   L   F   E   P   Q   G   G   L   Q   N   I   A>
----------------------------------------------------------------

1020          1030          1040          1050
               *             *             *             *
GCA GAA AAA CAC AAC TTG GGA ATC TTG ACT AAG AGG TCA AAT TTC ACC
CGT CTT TTT GTG TTG AAC CCT TAG AAC TGA TTC TCC AGT TTA AAG TGG
 A   E   K   H   N   L   G   I   L   T   K   R   S   N   F   T>
---------------------------------------------- I-Ad α-1 DOMAIN --------------

1060          1070          1080          1090          1100
 *             *             *             *             *
CCA GCT ACC AAT GAG GCT CCT CAA GCG ACT GTG TTC CCC AAG TCC CCT
GGT CGA TGG TTA CTC CGA GGA GTT CGC TGA CAC AAG GGG TTC AGG GGA
 P   A   T   N   E   A   P   Q   A   T   V   F   P   K   S   P>
------------------><------ I-Ad α-2 DOMAIN ----------------------

1110          1120          1130          1140          1150
               *             *             *             *             *
GTG CTG CTG GGT CAG CCC AAC ACC CTT ATC TGC TTT GTG GAC AAC ATC
CAC GAC GAC CCA GTC GGG TTG TGG GAA TAG ACG AAA CAC CTG TTG TAG
 V   L   L   G   Q   P   N   T   L   I   C   F   V   D   N   I>
----------------------------------------------------------------
```

```
        1160           1170           1180           1190           1200
         *              *              *              *              *
TTC CCA CCT GTG ATC AAC ATC ACA TGG CTC AGA AAT AGC AAG TCA GTC
AAG GGT GGA CAC TAG TTG TAG TGT ACS GAG TCT TTA TCG TTC AGT CAG
 F   P   P   V   I   N   I   T   W   L   R   N   S   K   S   V>
-----------------------------------------------------------------

1210           1220           1230           1240           1250
         *              *              *              *              *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H   S>
-----------------------------------------------------------------

1260           1270           1280           1290
         *              *              *              *
TTC CAC AAG CTG TCT TAT CTC ACC TTC ATC CCT TCT GAT GAT GAC ATT
AAG GTG TTC GAC AGA ATA GAG TGG AAG TAG GGA AGA CTA CTA CTG TAA
 F   H   K   L   S   Y   L   T   F   I   P   S   D   D   D   I>
-----------------------------------------------------------------
1300           1310           1320           1330           1340
 *              *              *              *              *
TAT GAC TGC AAG GTG GAG CAC TGG GGC CTG GAG GAG CCG GTT CTG AAA
ATA CTG ACG TTC CAC CTC GTG ACC CSS GAC CTC CTC GGC CAA GAC TTT
 Y   D   C   K   V   E   H   W   G   L   E   E   P   V   L   K>
--------------------------------------------------------- I-Ad α-2 DOMAIN -------------
        1350           1360           1370           1380
         *              *              *              *
CAC TGG GAG GAA GAA GAG TAC ATG CCG ATG GAA TGA
GTG ACC CTC CTT CTT CTC ATG TAC GGC TAC CTT ACT
 H   W   E   E   E   E   Y   M   P   M   E   *>
----------><------------ EE TAG ---------------------->
```

FIG. 29D

MHC COMPLEXES AND USES THEREOF

CROSS-REFERENCE TO RELATED APPLICATIONS

The present application is a continuation of U.S. Ser. No. 08/776,084 as filed on Jan. 17, 1997 now abandoned which application is a continuation-in-part of U.S. Ser. No. 08/382,454 as filed Feb. 1, 1995 now abandoned which application is a continuation-in-part of U.S. Ser. No. 08/283,302 as filed on Jul. 29, 1994 now abandoned. The disclosures of the U.S. Ser. No. 08/776,084, U.S. Ser. No. 08/382,454, and U.S. Ser. No. 08/283,302 applications are each incorporated by reference.

BACKGROUND OF THE INVENTION

1. Field of the Invention

The present invention relates to novel complexes of major histocompatibility complex (MHC) molecules and uses of such complexes. More particularly, the invention relates to MHC fusion complexes that contain a MHC molecule with a peptide-binding groove and a presenting peptide covalently linked to the MHC protein. Fusion complexes of the invention are useful for a variety of applications including in vitro screens for identification and isolation of peptides that modulate activity of selected T cells, including peptides that are T cell receptor antagonists and partial agonists, methods of suppressing an immune response of a mammal and methods for inducing an immune response in a mammal.

2. Background

Antigen-specific T cell responses are invoked by antigenic peptides bound to the binding groove or cleft of major histocompatibility complex (MHC) glycoproteins as part of the mechanism of the immune system to identify and respond to foreign antigens. The bound antigenic peptides interact with T cell receptors and thereby modulate an immune response. The antigenic peptides are bound by non-covalent means to particular "binding pockets" comprised of polymorphic residues of the MHC protein's binding groove.

MHC class II molecules are heterodimeric glycoproteins consisting of $\alpha$ and $\beta$ chains. The $\alpha 1$ and $\beta 1$ domains of these molecules fold together to form a peptide binding grove. Antigenic peptides bind the MHC molecule through interaction between anchor amino acids on the peptide and the $\alpha 1$ and $\beta 1$ domains. Crystal structure of human class II HLA-DR1 complex with an influenza virus peptide indicate that the N- and C-terminal ends of the bound peptide extend out of the binding groove such that the C-terminus of the peptide is proximal to the N-terminus of the $\beta$ chain [Brown, J. H. et al. (1993) Nature 364: 33–39; Stern, L. J. et al. (1994) Nature 368: 215–221]. MHC class I molecules have different domain organizations than MHC class II molecules, but generally similar structure with a peptide binding site or groove that is distal to membrane domains [see, e.g., Rudensky, A. Y. et al., (1991) Nature 353:622–626]. See also U.S. Pat. Nos. 5,284,935; 5,260,422; 5,194,425; 5,130,297; and WO 92/18150 and WO 93/10220 for discussions of MHC molecules.

MHC molecules complexed with antigenic peptides can induce selective immunosuppression by several different mechanisms [see, e.g., Guery, J. et al. (1993) Critical Reviews in Immunology 13(3/4): 195–206].

More specifically, it has been reported that peptide-MHC complexes on the surface of antigen presenting cells will only induce clonal expansion of a T cell line specific for the MHC bound peptide if the antigen presenting cells also deliver co-stimulatory signals. One proposed approach takes advantage of this requirement for T cell activation and inhibits T cell development by interaction with the antigenic peptide bound to the MHC molecule in the absence of co-stimulatory signals. See Nicolle, M. et al., J. Clin. Invest. (1994) 93: 1361–1369; and Sharma, S., et al., Proc. Natl. Acad. Sci. USA (1991) 88: 11465–11469.

Another proposed approach inhibits T cell development with MHC molecules that contain a bound peptide that is an antagonist or partial agonist to a T cell receptor (TcR). See Evavold, B. et al., Immunology Today (1993) 14(12): 602–609.

Modifications of the antigenic peptides bound to T cell receptors have been attempted to examine residues responsible for specific T cell responses. Determination of such "activating" amino acids of the antigenic peptides could provide insight of suitable sequence of a TcR partial agonist or antagonist. See Evavold, B. et al., supra.

It also has been speculated that new vaccines might be developed based on determination of the nature of various antigenic peptides bound to MHC molecules. See Chicz, R., et al., Immunology Today (1994) 15(4): 155–160.

It thus would be desirable to have MHC molecules that contain an antigenic peptide for modulation of the activity of a T cell receptor. It also would be desirable to have a means for preparation of MHC molecules with virtually any desired peptide positioned in a binding groove for interaction with a T cell receptor. It would be further desirable to have a means to identify peptides that are capable of modulating the activity of a T cell receptor.

SUMMARY OF THE INVENTION

The present invention relates to novel complexes of major histocompatibility complex (MHC) molecules and uses of such complexes.

MHC fusion complexes of the invention comprise a presenting peptide covalently linked to the MHC molecule that contains a peptide-binding groove or cleft. As used herein, the term "presenting peptide" refers to a peptide that is capable of modulating the activity of a T cell receptor, either to induce T-cell proliferation or to inhibit or inactivate T cell development as determined by the assays disclosed below, including the assay that includes sequential steps of culturing T cells to proliferate same, and contacting the T cells with a MHC fusion complex of the invention and then evaluating whether the MHC fusion complex inhibits further development of the T cells.

Covalently linking the presenting peptide to the MHC peptide in accordance with the invention provides a number of significant advantages. Current practice requires the purification of MHC molecules that had been previously loaded with peptides from antigen presenting cells. The loaded peptides are tightly bound and can not be efficiently exchanged with the peptide of interest. MHC fusion complexes of the invention can be produced that contain a single antigenic peptide, including such a peptide of known structure. Analysis of interactions with T cell receptors will be facilitated by use of such MHC molecules. Additionally, a wide variety of peptides can be presented for interaction with T cells by virtue of the fact that only a small number (ca. 4 to 6) of amino acids in the presenting peptide are important for binding to a particular MHC molecule. That is, a library of different peptides constrained only by the MHC anchor residues can be covalently linked to the MHC molecule for presentation of T cells. Further, for therapeutic applications, rather than administration of an MHC molecule to a subject, a DNA expression vector coding for the MHC molecule linked to the presenting peptide can be administered for in vivo expression of the MHC fusion complex. Such an approach avoids costly purification steps typically associated with preparation of recombinant proteins and avoids the complexities of antigen uptake and processing associated with conventional approaches.

The MHC molecule of fusion complexes of the invention can be either MHC class I or class II, preferably class II. For a MHC fusion complex that contains a class II MHC molecule, preferably the presenting peptide is covalently linked to the N-terminus of the β chain of the MHC protein, although the presenting peptide also may be linked to the α chain of the MHC protein. In the case of a MHC class I molecule, preferably the presenting peptide is covalently linked to the N-terminus of the a chain of the MHC protein.

MHC fusion complexes may be truncated (particularly, not including a transmembrane portion), or may be "full-length" and include a transmembrane portion and/or cytoplasmic domain and/or other cellular membranes. As discussed below, for some approaches, an MHC fusion complex that does not include a transmembrane portion is suitably employed, while for other applications a MHC fusion complex is employed that contains a transmembrane portion and/or cytoplasmic portion and/or other such domains.

MHC fusion complexes of the invention preferably also include a flexible linker sequence interposed between the MHC protein and the presenting peptide. The linker sequence should allow effective positioning of the presenting peptide with respect to the MHC molecule binding groove so that the presenting peptide can modulate the activity of a T cell receptor, either to induce T-cell proliferation or to inhibit or inactivate T cell development as determined by the assays disclosed below, including the in vitro assays that includes sequential steps of culturing T cells to proliferate same, and contacting the T cells with a MHC fusion complex of the invention and then evaluating whether the MHC fusion complex inhibits further development of the T cells.

In a preferred aspect of the invention, a MHC fusion complex without a transmembrane portion (i.e., a "truncated" complex) is covalently linked to an immunoglobulin such as IgG, IgM, or IgA or fragment thereof (e.g., Fab, Fab', F(ab')$_2$). Suitably the MHC fusion complex is linked to constant regions of the immunoglobulin. Such linkage to an immunoglobulin can provide a number of advantages over expression of the MHC fusion complex alone including increased stability, easy affinity purification and flexibility in the number of binding domains presented, e.g., from one domain on Fab-like fragments to multivalent domains on IgG or IgM-like molecules.

In another preferred aspect, a MHC fusion complex of the invention is a single-chain fusion protein, i.e. in the case of an MHC class II complex, where the α and β chain subunits are linked as a single chain fusion protein. The presenting peptide is preferably linked to the β chain of the fusion protein. Such a linked single-chain complex can provide a number of advantages. In particular, in reducing the complex to a single molecule, yields and stability of the molecules may be enhanced. That can be especially important for soluble molecules which may not be produced efficiently in active form. The single chain MHC fusion complexes of the invention are useful for the methods disclosed herein, including in vitro identification of peptides recognized by a T cell receptor, methods for suppressing an immune response (e.g. treatment of individuals with immune disorders such as autoimmune disorders or allergies) and methods for inducing a desired immune response, and diagnostic methods such as HLA typing and in vivo diagnostic imaging. Direct administration of a DNA construct coding for a single-chain MHC fusion molecule (complex) of the invention is also preferred.

The invention also includes methods for in vitro identification of peptides recognized by a T cell receptor, including peptides that can induce T cell development as well as peptides that can antagonize T cell receptors, i.e. T cell receptor (TcR) antagonists or partial agonists.

Further provided are methods for suppressing an immune response of a mammal, particularly a human, that comprise administering to the mammal an effective amount of a MHC fusion complex of the invention. Those methods include treatment of a mammal that suffers from or is susceptible to an autoimmune disorder such as multiple sclerosis, insulin-dependent diabetes mellitus or rheumatoid arthritis or, alternatively, a mammal who is susceptible to undesired immune response(s) such as a subject with chronic allergies or a patient undergoing transplant surgery such as organ or skin transplant surgery.

An immune response may be suppressed in accordance with the invention by one or a combination of alternative strategies. Thus, one treatment method for suppression of an immune response by inducing anergy or apoptosis of specific T cells and provides for the administration of an effective amount of one or more MHC fusion complexes of the invention in the substantial absence of co-stimulatory signal(s). Typically a truncated MHC fusion complex of the invention is employed, i.e. a soluble MHC fusion complex that does not contain transmembrane and cytoplasmic domains of a full-length or intact MHC molecule. Another method of the invention for suppression of an immune response provides for administration of an effective amount of one or more MHC fusion complexes of the invention that each contain a covalently linked presenting peptide that is a T cell antagonist or partial agonist.

The MHC fusion complex containing the presenting peptide that is a T cell receptor antagonist or partial agonist can be administered as a soluble MHC fusion complex lacking co-stimulatory signals. Alternatively, administration can take the form of an effective amount of a DNA sequence comprising a vector coding for a "full-length" MHC fusion complex of the invention, i.e., a complex that contains full-length MHC proteins including the transmembrane portion and a presenting peptide with antagonist or partial agonist activity covalently linked to the MHC molecule.

In a further aspect the invention provides methods for inducing an immune response in a mammal that in general comprise administration of an effective amount of a DNA sequence that comprises a vector coding for a "full-length" MHC fusion complex of the invention, i.e. a complex that contains full-length MHC proteins including the transmembrane portion and a presenting peptide covalently linked to the MHC molecule. Preferably DNA that codes for a full length MHC fusion complex of the invention is administered to a mammal together with a DNA sequence coding for a T cell costimulatory factor such as a gene coding for B7 or B7-2. As used herein, the term "T cell co-stimulatory factor" refers to a peptide that is capable of providing a co-stimulatory signal to thereby activate T cell proliferation in the presence of one or more MHC fusion complexes of the invention. Such activation of T cell proliferation can be determined by the assays disclosed herein, including the assay as exemplified in Example 9 and discussed below. Further provided are diagnostic methods including HLA typing and in vivo diagnostic imaging using MHC fusion complexes of the invention, including MHC fusion complexes that contain a radioactive label (e.g., $^{125}$I, $^{32}$P or $^{99}$Tc) or other detectable tag.

Other aspects of the invention are discussed infra.

BRIEF DESCRIPTION OF THE DRAWINGS

FIGS. 1A and 1B each depict a MHC fusion complex of the invention that includes a linker sequence. FIG. 1C schematically shows a MHC fusion complex of the invention linked or fused to an immunoglobulin.

FIG. 2 shows the scheme for isolating the I-A$^d$ α1-α2 gene fragment and the cloning thereof. FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 7 shows the scheme for isolating the I-A$^s$ β1-β2 gene fragment, attaching the linker sequence and inserting the oligonucleotides encoding the antigenic peptides. FIG. 8 specifies the oligonucleotide primers used in the depicted procedure.

FIG. 8 (SEQ ID NOS: 26–74) shows the sequences of oligonucleotides used in constructing MHC fusion complexes of the invention.

FIGS. 11A and 11B shows DNA constructs of the invention which are described in Example 2 which follows. In FIGS. 11A and 11B (and FIGS. 15, 16A and 16B) the reference "PE" designates promoter and enhancer, the reference "LS" designates leader sequence exon and the reference "HC" designates heavy chain.

FIG. 14 (SEQ ID NOS: 99–102) shows primers used for sequencing mutated 2.7 kb fragment.

FIG. 15 shows the scheme for M13 mutagenesis and cloning of the MHC II β variable gene.

FIGS. 18A and 18B (SEQ ID NOS: 103–109) shows DNA and amino acid sequences of full length MHC fusion complexes of the invention.

FIG. 20 depicts oligonucleotide primers used in the depicted cloning scheme.

FIG. 20 (SEQ ID NOS: 110–112) depicts sequences of oligonucleotide primers used in constructing MHC fusion complexes of the invention.

FIG. 26 (SEQ ID NOS: 113–120) depicts sequences of oligonucleotide primers used in constructing MHC fusion complexes of the invention.

FIG. 27 (SEQ ID NO: 121) shows the DNA and amino acid sequences of the SSC1 single-chain gene.

DETAILED DESCRIPTION OF THE INVENTION

Figure 3B:
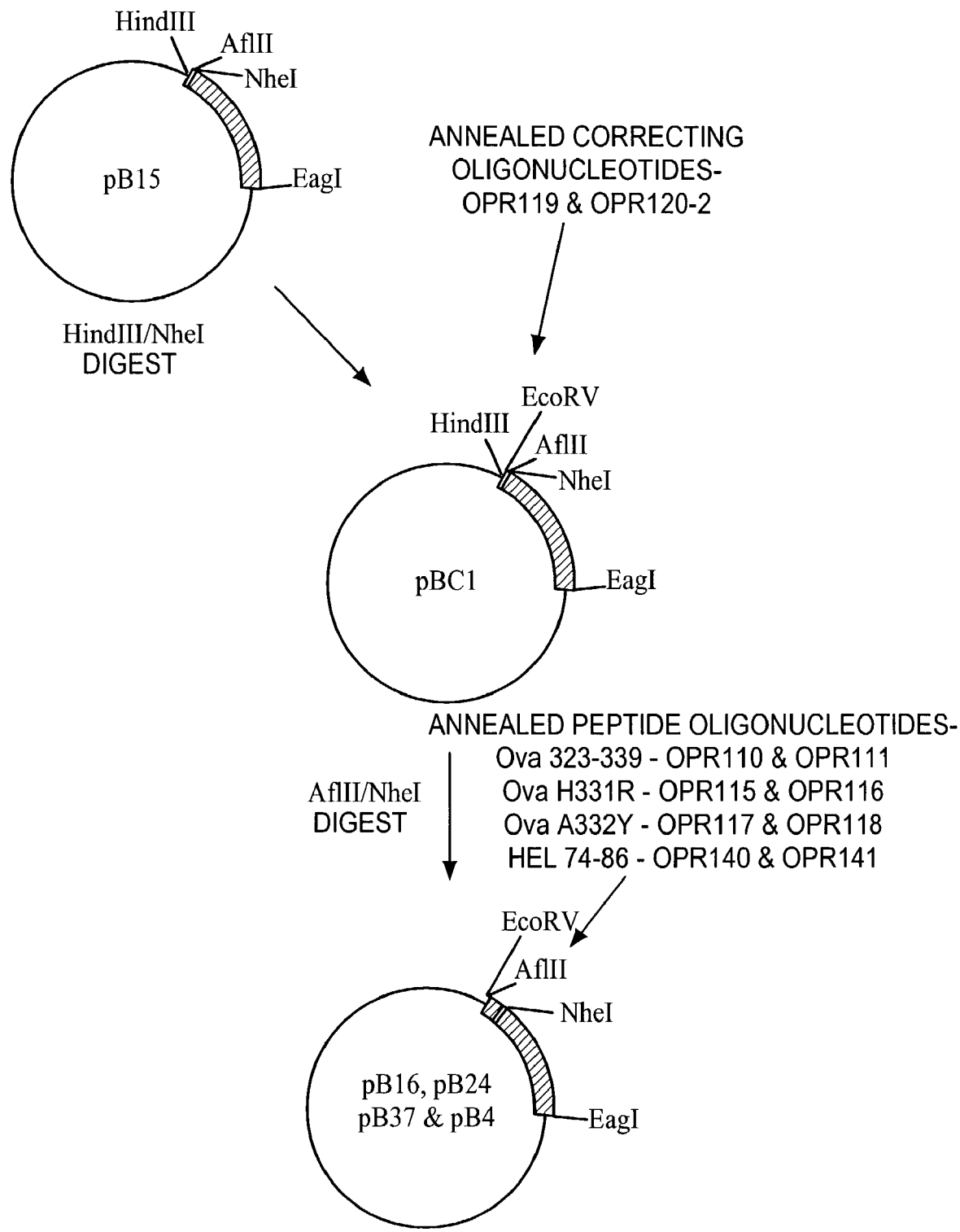
FIG. 3 shows the scheme for isolating the I-A$^d$ α1-α2 gene fragment, attaching the linker sequence and inserting the oligonucleotides encoding the antigenic peptides.

We have now discovered MHC fusion complexes, and expression vectors that encode such complexes, that comprise a MHC molecule covalently linked to a presenting peptide, and methods for use of such fusion complexes and expression vectors.

In general, preparation of MHC fusion complexes can be accomplished by procedures disclosed herein and by recognized recombinant DNA techniques, e.g. preparation of plasmid DNA, cleavage of DNA with restriction enzymes, ligation of DNA, transformation or transfection of a host, culturing of the host, and isolation and purification of the expressed fusion complex. Such procedures are generally known and disclosed e.g. in Sambrook, et al., Molecular Cloning (2d ed. 1989).

More specifically, DNA coding for a desired MHC protein is obtained from a suitable cell line as disclosed for instance in Example 1 which follows. Other sources of DNA coding for MHC protein are known, e.g. human lymphoblastoid cells. Once isolated, the gene coding for the MHC molecule can be amplified by the polymerase chain reaction (PCR) or other means known in the art. Suitable PCR primers to amplify the MHC peptide gene may add restriction sites to the PCR product. For example, for expression of a truncated fusion complex, specifically a soluble MHC fusion complex that does not contain transmembrane or cytoplasmic portions and is linked to an immunoglobulin such as IgG, the PCR product preferably includes IgG splice sites and leader sequences necessary for proper expression and secretion of the MHC-immunoglobulin fusion complex. The PCR product also preferably includes a sequence coding for the linker sequence, or a restriction enzyme site for ligation of such a sequence. Suitable primers, PCR conditions and expression vector construction techniques are e.g. disclosed in the examples which follow and the Drawings.

The linker sequence is preferably a nucleotide sequence that codes for a peptide that can effectively position the presenting peptide in the binding groove of the MHC molecule. As used herein, the phrase "presenting peptide is effectively positioned in the binding groove of an MHC molecule" or "MHC fusion complex capable of modulating the activity of a T cell", or other similar phrase, is intended to mean the presenting peptide linked to a MHC protein is positioned so that the presenting peptide and the fusion complex is capable of modulating the activity of a T cell receptor, either to induce T cell proliferation or to inhibit or inactivate T cell development as determined by an assay disclosed below, including the assay that includes sequential steps of culturing T cells to proliferate same, and contacting the T cells with a MHC fusion complex of the invention and then evaluating whether the MHC fusion complex inhibits further development of the T cells.

Preferably the linker sequence comprises from about 7 to 20 amino acids, more preferably from about 8 to 16 amino acids, still more preferably from about 8 to 12 amino acids. The linker sequence is preferably flexible so as not hold the presenting peptide in a single undesired conformation. The linker preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. Preferably the linker sequence does not contain any proline residues, which could inhibit flexibility. For a MHC fusion complex that contains a MHC class II molecule, the linker sequence is suitably linked to the β chain of the MHC molecule, although the linker sequence also could be attached to the α chain of the MHC molecule. For covalently linking a presenting peptide to a MHC class II β chain molecule, the amino sequence of the linker should be capable of spanning approximately 30 angstroms from the N-terminal residue of the MHC class II β chain to the C-terminal residue of the presenting peptide. See for example FIGS. 1A and 1B of the Drawings. When such a β+peptide chain is expressed along with the α chain, the linked presenting peptide should fold into the α1 and β1 binding groove resulting in a functional MHC molecule as generally depicted in FIG. 1C. One suitable linker sequence is ASGGGGSGGG (SEQ ID NO: 1) (i.e., Ala Ser Gly Gly Gly Gly Ser Gly Gly Gly), preferably linked to the first amino acid of the β1 domain of the MHC class II protein. Different linker sequences could be used including any of a number of flexible linker designs that have been used successfully to join antibody variable regions together, see Whitlow, M. et al., (1991) Methods: A Companion to Methods in Enzymology 2:97–105. Suitable linker sequences can be readily identified empirically. For example, a DNA construct coding for a MHC fusion complex that includes a linker sequence can be cloned and expressed, and the fusion complex tested to determine if the complex is capable of modulating the activity of a T cell receptor, either to induce T-cell proliferation or to inhibit or inactivate T cell development as determined by the assay disclosed below. Suitable size and sequences of linker sequences also can be determined by conventional computer modeling techniques based on the predicted size and shape of the MHC molecule.

Preferably restriction sites are engineered in the DNA construct comprising the fused nucleotide sequences coding for the linker sequence and MHC protein so that essentially any nucleotide sequence coding for a presenting peptide of interest (e.g. either an antigenic or an antagonist presenting peptide) can be attached to the construct. For example, in one preferred system exemplified in the examples which follow, suitable restriction sites (e.g., Af/II and NheI sites) are included between the end of the leader sequence and the beginning of the linker to facilitate insertion of a wide variety of presenting peptides to the β chain gene of the MHC molecule. See, for example, FIG. 3 of the Drawings. The nucleotide and amino acid sequences of specifically preferred leader sequences are depicted in FIGS. 18A and 18B of the Drawings.

The presenting peptide component of a MHC fusion complex of the invention should be capable of modulating the activity of a T cell as discussed above. For a MHC fusion complex that contains a class II MHC molecule, preferably the presenting peptide has from about 4 to 35 amino acids, more preferably about 6 to about 30 amino acids, still more preferably from about 8 to about 25 amino acids. For a MHC fusion complex that contains a class I MHC molecule, preferably the presenting peptide has from about 4 to 25 amino acids, more preferably about 6 to about 20 amino acids, still more preferably from about 6 to about 15 amino acids, even more preferably 8 to about 10 amino acids. Class I and class II MHC molecules show preferential binding toward different peptide sequences. Recently, anchor residues defining MHC allele-specific peptide motifs have been identified in class II binding peptides [Sinigaglia, F. et al. (1994) Curr. Opin. in Immun. 6:52–56]. For example, in human class II HLA-DR1 molecules, an aromatic amino acid (e.g., Tyr, Phe, or Trp) is usually found near the amino terminus of the peptide (position 1), a hydrophobic residue (e.g., Met or Leu) at position 4 and a small amino acid (e.g., Ala or Gly) at position 6. Other MHC molecules have different motifs, e.g., for class II molecules, see Sinigaglia., supra; for class I molecules, see Parker, K. C. et al. (1994) J. Immunol. 152:163–175. Preferred presenting peptides include the desired MHC binding motif in order to facilitate optimum MHC binding. Thus, for example, in human class II HLA-DR1 MHC molecules, an aromatic amino acid (e.g., Tyr, Phe, or Trp) is preferably located near the amino terminus of the presenting peptide (position 1), a hydrophobic residue (e.g., Met or Leu) is at position 4 of the presenting peptide, and a small amino acid (e.g., Ala or Gly) is at position 6 of the presenting peptide. For the immunosuppression methods of the invention (e.g., to treat autoimmune diseases or allergies, or otherwise suppress an unwanted T cell response), the presenting peptide preferably may be the same as or homologous to (e.g., at least greater than about 80 or 90% shared sequence) a peptide known or suspected to be responsible for activating T cells in the targeted disorder. Thus, for example, the MPB peptide 80–105 is recognized by over 30% of MPB-specific T cells isolated from multiple sclerosis patients [see E. Meinl et al., J. Clin. Invest. 92: 2633–2643 (1993)] and should be a suitable as a presenting peptide in MHC fusion complexes of the invention used for immunosuppression applications as disclosed herein. Additionally, the activity of a particular presenting peptide, i.e. antigenic or antagonist or partial agonist, can be readily determined empirically by the methods disclosed herein, including the in vivo assays disclosed below.

To make the vector coding for a MHC fusion complex, the sequence coding for the MHC molecule is linked to a sequence coding for the presenting peptide by use of suitable ligases. DNA coding for the presenting peptide can be obtained by isolating DNA from natural sources or by known synthetic methods, e.g. the phosphate triester method. See, e.g, Oligonucleotide Synthesis, IRL Press (M.

J. Gait, ed., 1984). Synthetic oligonucleotides also may be prepared using commercially available automated oligonucleotide synthesizers. A nucleotide sequence coding for a MHC molecule may be directly joined to a DNA sequence coding for the presenting peptide or, more typically, a DNA sequence coding for the linker sequence as discussed above may be interposed between the sequence coding for the MHC molecule and the sequence coding for the presenting peptide and joined using suitable ligases.

Other nucleotide sequences also can be included in the gene construct. For example, a promoter sequence, which controls expression of the sequence coding for the MHC peptide fused to the presenting peptide, or a leader sequence, which directs the MHC fusion complex to the cell surface or the culture medium, can be included in the construct or present in the expression vector into which the construct is inserted. An immunoglobulin or CMV promoter is particularly preferred. See the examples which follow. A strong translation initiation sequence also can be included in the construct to enhance efficiency of translational initiation. A preferred initiation sequence is the Kozak consensus sequence (CCACCATG) (SEQ ID NO: 2). See also FIGS. 18A and 18B of the Drawings.

Preferably a leader sequence included in a DNA construct of the invention contains an effectively positioned restriction site so that an oligonucleotide encoding a presenting peptide of interest can be attached to the MHC molecule. Suitably the restriction site can be incorporated into the 3-end of the leader sequence, sometimes referred to herein as a junction sequence, e.g. of about 2 to 10 codons in length, that is positioned before the coding region for the presenting peptide. A particularly preferred restriction site is the Af/II site, although other cleavage sites also can be incorporated before the presenting peptide coding region. As discussed above, use of such a restriction site in combination with a second restriction site, typically positioned at the beginning of the sequence coding for the linker, enables rapid and straightforward insertion of sequences coding for a wide variety of presenting peptides into the DNA construct for the MHC fusion complex. Preferred leader sequences contain a strong translation initiation site and a cap site at the 3'-end of their mRNA. Preferably a leader sequence is attached to the α domain of a class I MHC molecule, and preferably a leader sequence is attached to the β domain of a class II MHC molecule. Preferred leader sequences provides for secretory expression of the MHC fusion complex.

A number of strategies can be employed to express MHC fusion complexes of the invention. For example, the MHC gene fusion construct described above can be incorporated into a suitable vector by known means such as by use of restriction enzymes to make cuts in the vector for insertion of the construct followed by ligation. The vector containing the gene construct is then introduced into a suitable host for expression of the MHC fusion peptide or complex. See, generally, Sambrook et al., supra. Selection of suitable vectors can be made empirically based on factors relating to the cloning protocol. For example, the vector should be compatible with, and have the proper replicon for the host that is being employed. Further the vector must be able to accommodate the DNA sequence coding for the MHC fusion complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus,* etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a MHC fusion complex of the invention can be determined by known procedures. For example, expression of a MHC fusion complex linked to an immunoglobulin can be determined by an ELISA specific for the linked immunoglobulin and/or by immunoblotting.

In one preferred protocol for preparation of soluble MHC fusion complexes of the invention, DNA sequences encoding the presenting peptide and β1-β2 domains of the MHC molecule (class II) are arranged such that the C-terminal end of the presenting peptide is attached to an initial amino acid of the β1 domain, preferably the first amino acid of the β1 domain by a flexible linker sequence. Such a construct is depicted in FIGS. 1A and 1B of the Drawings. For a class I MHC molecule, preferably the DNA sequence encoding the presenting peptide is attached to the α domain of the MHC molecule, preferably such that the presenting peptide will be linked to the N-terminus end of that α chain. As discussed above, preferably restriction sites are engineered between the end of the leader sequence and the beginning of the linker so that essentially any oligonucleotide encoding a presenting peptide of interest (i.e. antigenic or antagonist) can be attached to the β chain gene. For soluble expression, the α1-α2 and peptide-linked β1-β2 domains are suitably fused to an immunoglobulin, preferably to the constant domains of the immunoglobulin kappa and heavy chains, respectively, as depicted in FIG. 1C. Preferred immunoglobulins for such fusion to α and β for soluble expression include, e.g., the light chain constant domains and CH2-CH3 domains of IgG2b.

An expressed MHC fusion complex can be isolated and purified by known methods. Typically the culture medium is centrifuged and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked MHC or immunoglobulin region thereof. For example, MHC fusion complexes containing human HLA-DR1 sequences can be purified by affinity chromatography on a monoclonal antibody L243-Sepharose column by procedures that are generally known and disclosed, e.g., see Harlow, E. et al., Antibodies, A Laboratory Manual (1988). The L243 monoclonal antibody is specific to a conformational epitope of the properly folded HLA-DR1 molecule [Gorga, J. C. et al. (1992) J. Biol. Chem. 262:16087–16094], and therefore would be preferred for purifying the biologically active MHC fusion complex. The MHC fusion complex also may contain a sequence to aid in purification; see, e.g., Example 17 which follows which discloses use of a 6×His tag.

Truncated MHC fusion complexes of the invention contain a MHC molecule that is sufficiently truncated so the MHC fusion complex can be secreted into culture medium (e.g. physiological conditions; in the substantial or complete absence of detergent or the like) after expression. Thus, a truncated MHC fusion complex will not include regions rich in hydrophobic residues, typically the transmembrane and cytoplasmic domains of the MHC molecule, although at least portions of those domains may be suitable present provided the MHC molecule can be secreted as discussed. Thus, for example, for a preferred truncated DR1 MHC molecule of the invention, preferably from about residues 199 to 237 of the β chain and from about residues 193 to 230 of the α chain of the MHC molecule are not included in the truncated MHC fusion complex. See the examples which follow. In addition to the sequences disclosed herein, sequences of domains of MHC class I and II molcules have been disclosed previously (see, e.g., the above mentioned publications). Truncated MHC fusion complexes of the invention of course also can be readily identified empirically, i.e. by examining if the MHC complex is secreted into culture medium after expression as discussed. Truncated MHC fusion complexes can be prepared by several means, e.g. expression of a soluble MHC molecule or enzymatic (e.g. papain) cleavage of at least portions of transmembrane and/or cytoplasmic domains of a full length MHC fusion complex.

Full length MHC molecules of the invention include a transmembrane portion and/or cytoplasmic domain and/or other cellular membranes or substantial portions thereof (e.g. greater than about 80 or 90 percent of such sequences. For a full length MHC class II molecule of the invention, generally both the α and β chains are linked to transmembrane and cytoplasmic domains, although only one of the α and β chains may be linked to transmembrane and cytoplasmic domains, particularly in the case of single chain MHC molecules of the invention. As discussed below, full length MHC molecules can be anchored to cell membranes through hydrophobic membrane spanning domains or alternatively through post-translational attachment of other anchor domains such as covalently linked glycosylated form of phosphatidylinositol.

Figure 24:
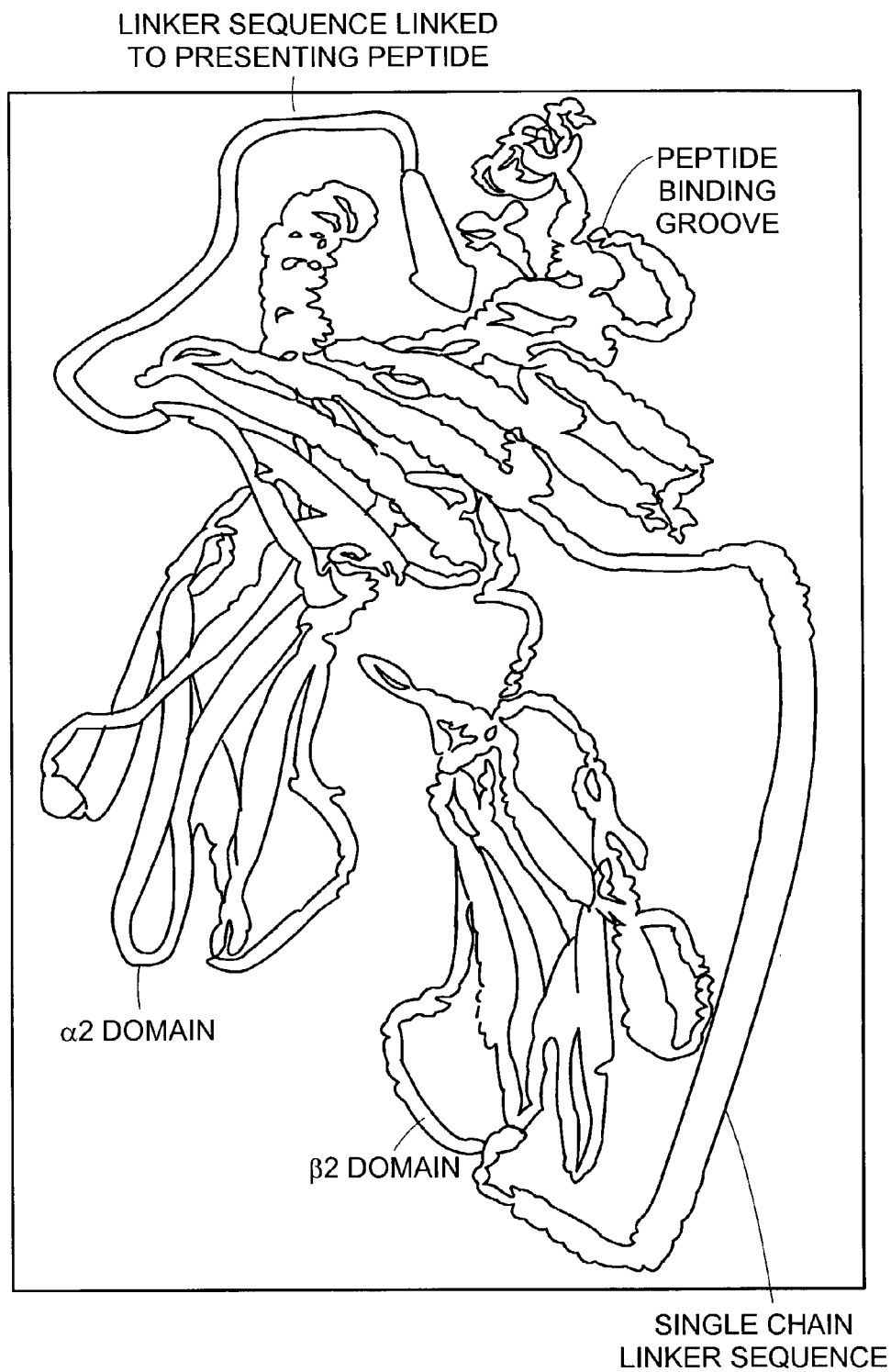
FIG. 24 depicts a single-chain MHC fusion complex of the invention.
Figure 25A:
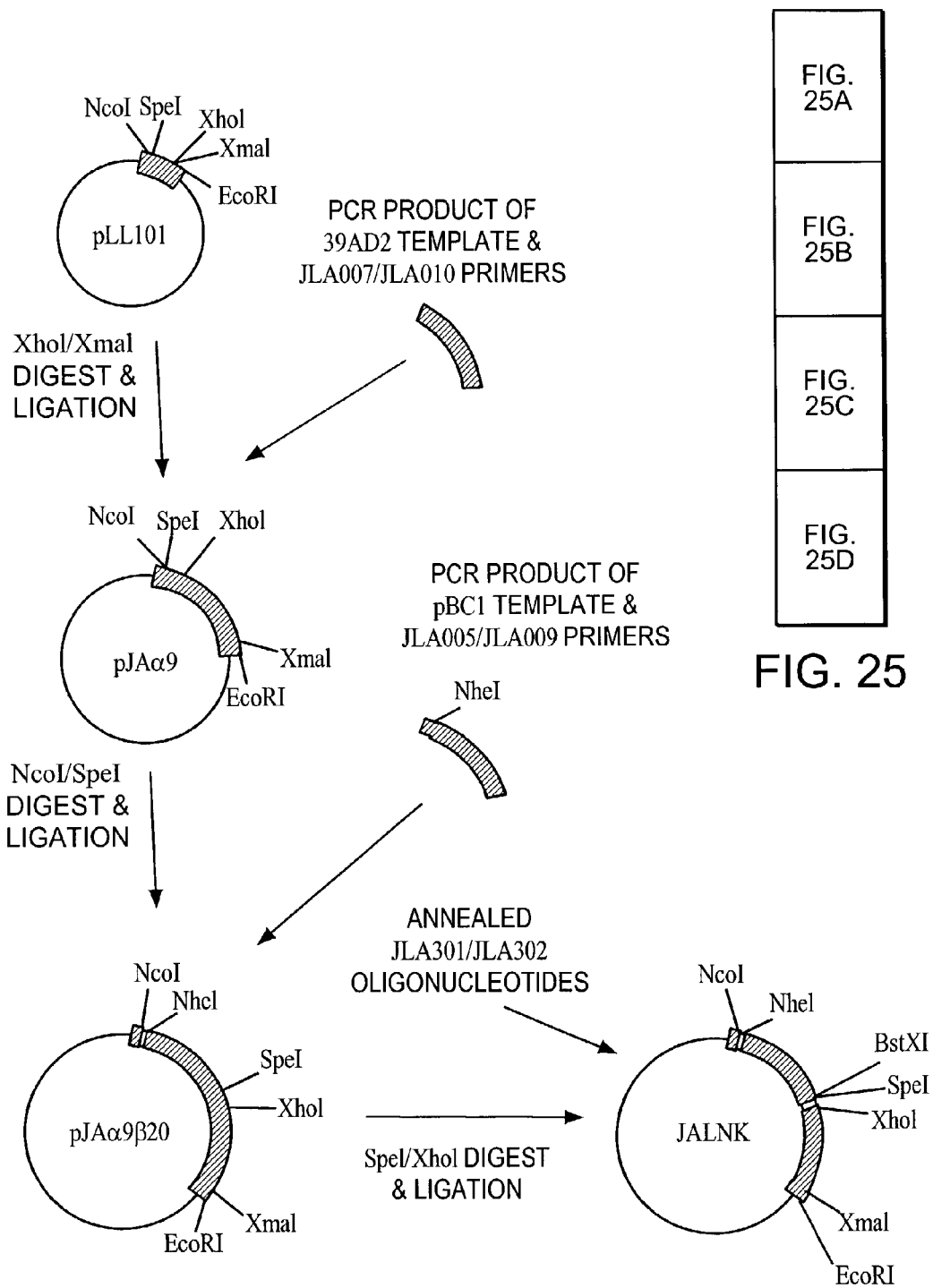
FIG. 25 (total of 3 sheets) shows the cloning scheme carried out in Example 17 which follows.
Figure 25B:
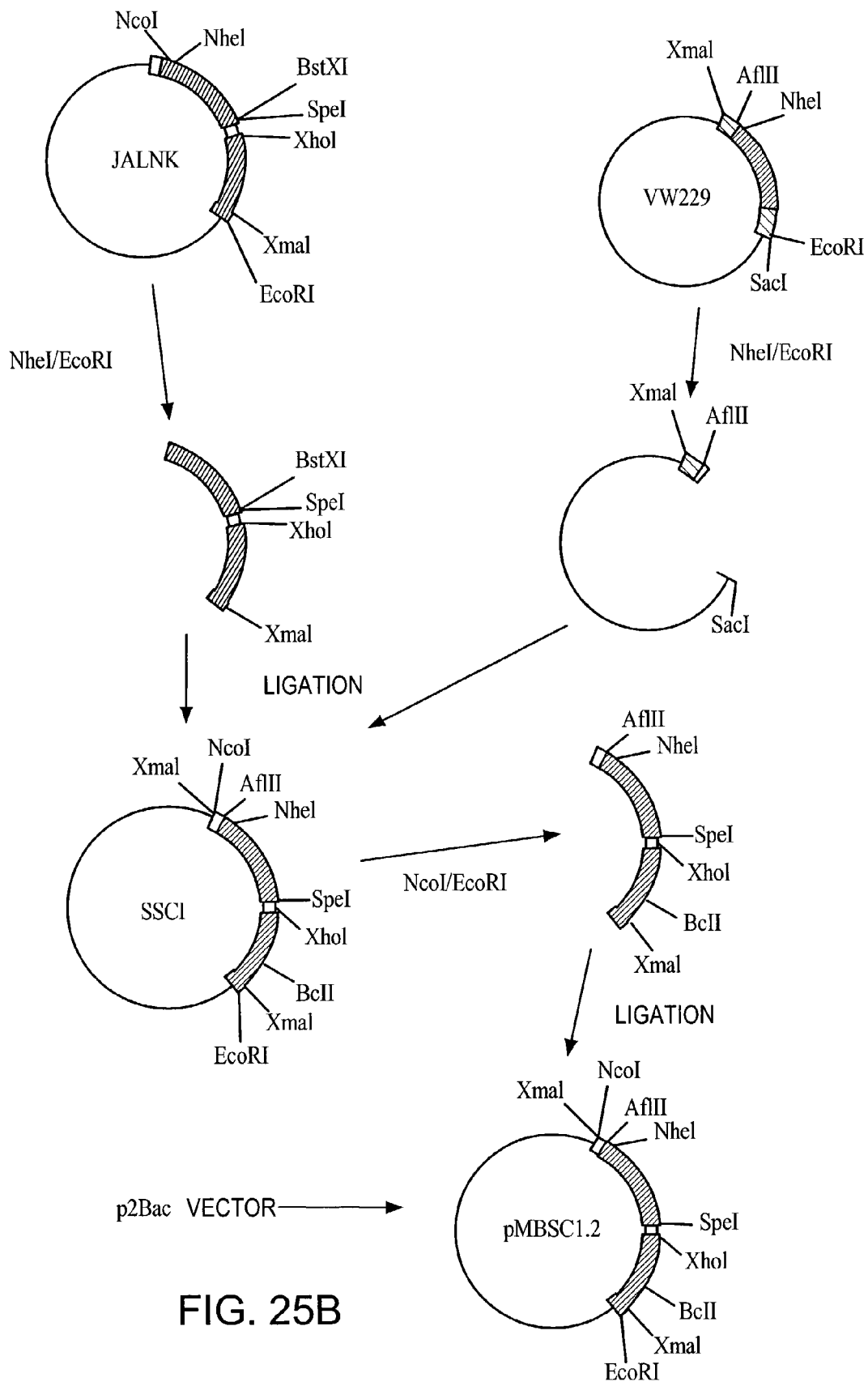
Figure 25C:
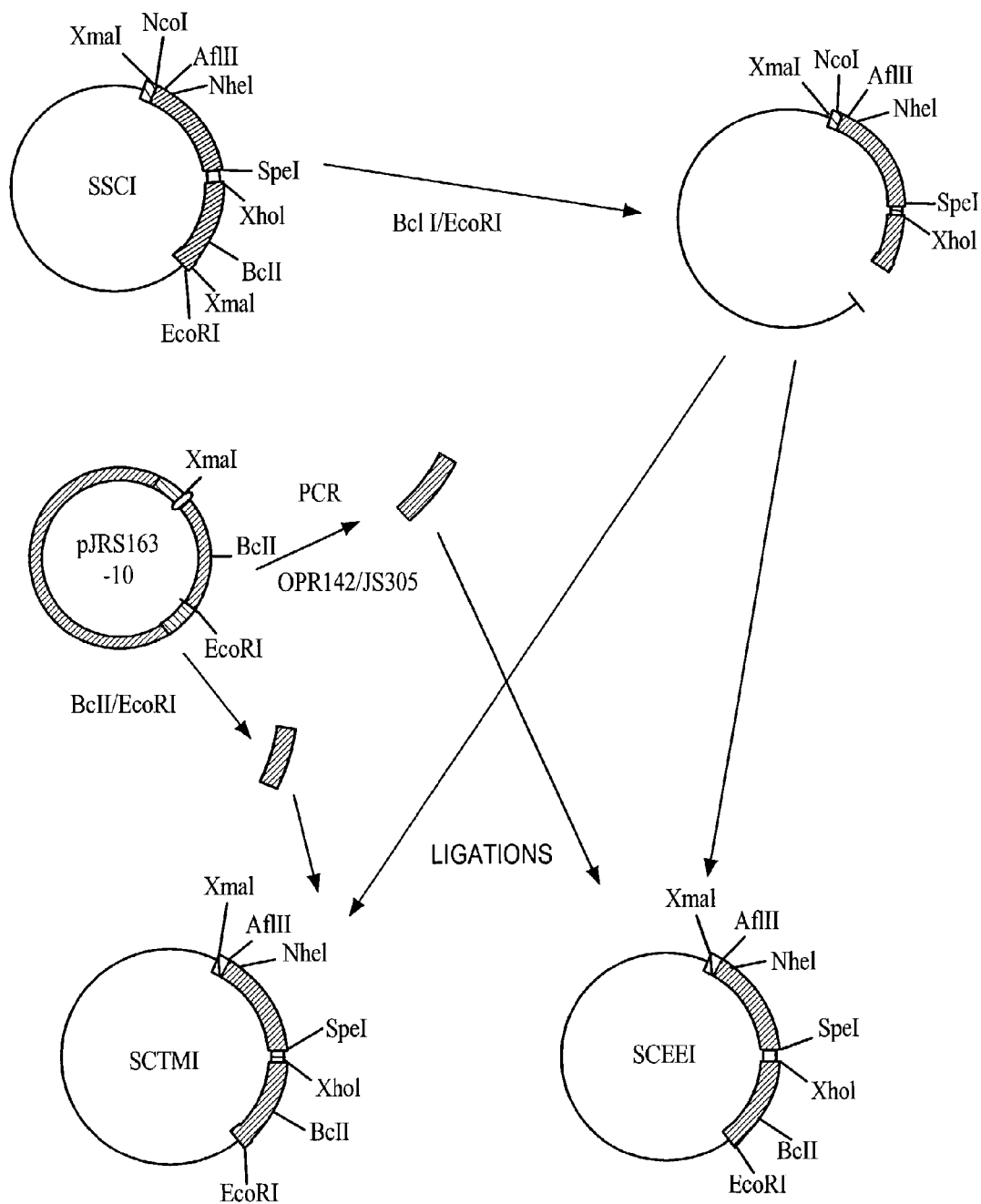
Figure 25D:
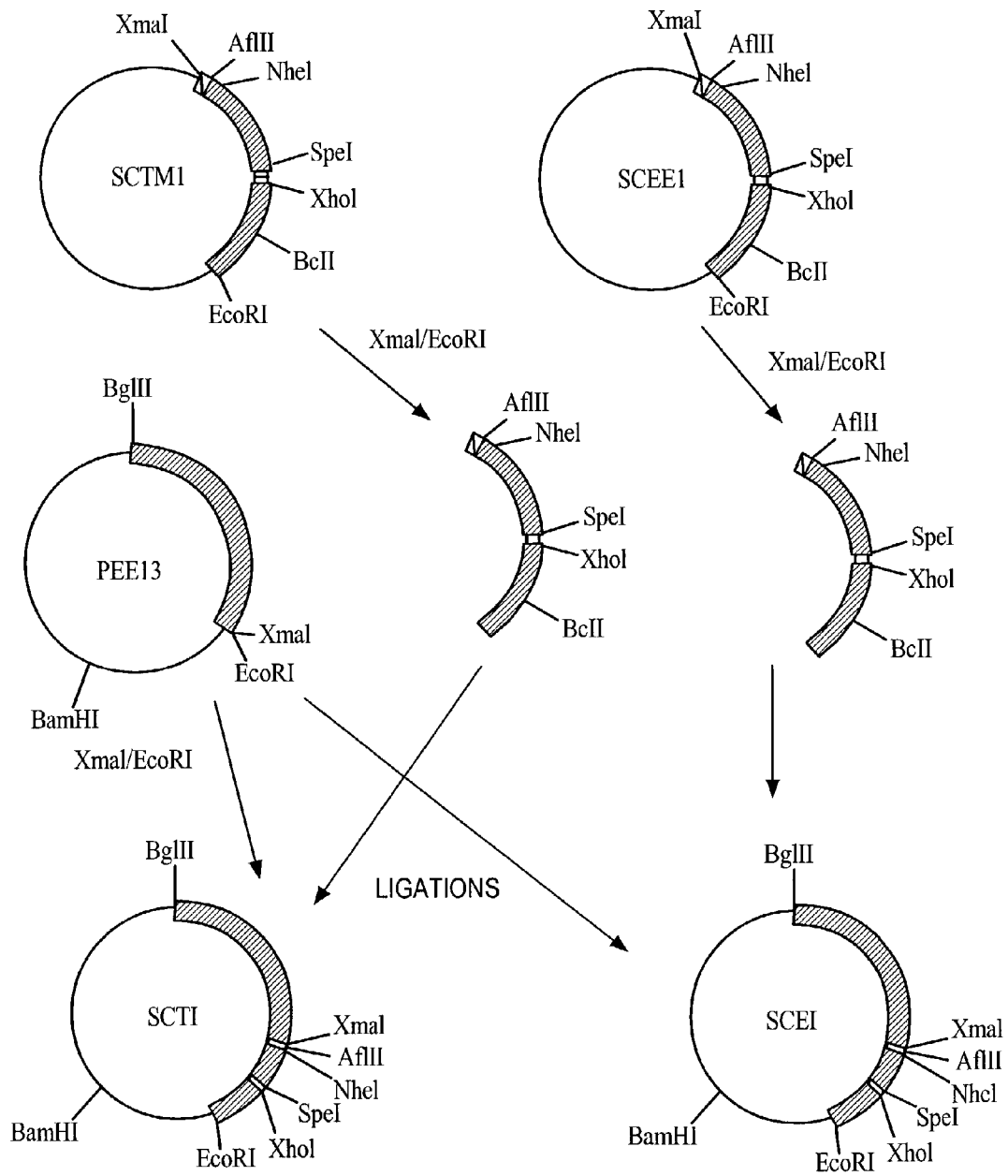

As discussed above, single chain MHC fusion complexes of the invention are also preferred, i.e. a fusion complex that consists of a single polypeptide rather than a multiple chain aggregate such the native heterotrimeric classII/peptide complex where α and β chains and a peptide are associated through non-covalent interactions. In the case of a single chain MHC class II complex, the α and β chain subunits are linked as a single chain fusion protein with the presenting peptide preferably linked to the β chain of the chain fusion protein. Such a preferred single chain MHC molecule is depicted in FIG. 24. Preferably a linker sequence is used to link the α and β chains. Such a linker sequence used to link domains of an MHC molecule is sometimes referred to herein as a "single chain linker sequence" and is thereby distinguished from the linker sequence discussed above that is interposed between and covalently links a presenting peptide and an MHC molecule.

Preferably a single chain MHC class II complex of the invention is linked between the carboxyl terminus of the β2 domain and the amino terminus of the α1 domain, although multiple domains of a MHC complex of the invention may be linked through other positions.

The single chain linker sequence should enable the linked MHC molecule to fold to an active form, i.e. a form where the MHC molecule can modulate the activity of a T cell. Such effective single chain linker sequences can be readily determined empirically. Thus, e.g., a DNA construct coding for a single chain MHC molecule of the invention where the α and β chains are linked by a linker sequence can be cloned and expressed, and the single chain MHC molecule tested to determine if the complex is capable of modulating the activity of a T cell receptor, either to induce T-cell proliferation or to inhibit T cell development as determined by the assays disclosed below.

Both length and composition of the single chain linker sequence can in general vary. For example, the length of a suitable single chain linker sequence may vary with the positions at which the linker sequence is linked to polypeptide chains of the MHC complex; in other words the length of the linker sequence may vary with the geometry of the "gap" between polypeptides which the linker sequence bridges.

The single chain linker sequence preferably also should be flexible to permit folding of the single chain molecule to an active form. The linker sequence thus preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. Preferably this linker sequence between the α and β chains does not contain any proline residues, which could inhibit flexibility. Preferably a linker sequence positioned between the carboxyl terminus of a β2 domain and the amino terminus of the α1 domain will comprise about 15 to 40 amino acids, more preferably about 15 to 30 amino acids. A particularly preferred linker sequence is disclosed in Example 17 which follows. Suitable size and sequence of single chain linker sequences also can be determined by conventional computer techniques; see Example 17 which follows.

Single chain MHC complexes of the invention can be prepared as discussed above as well as the examples which follow, including Examples 17–19. For example, DNA coding for a desired MHC protein can be obtained from a suitable cell line, and the isolated gene can be amplified by PCR or other means. In the case of a MHC class II molecule of the invention, an α1-α2 gene fragment can be cloned into a vector, followed by cloning of a gene fragment cloning for the β1-β2 domains with an interposed single chain linker sequence. The single vector is then expressed in a suitable host and the single chain molecule harvested and purified if desired. See the examples which follow, including Examples 17–19. See also U.S. Pat. No. 5,260,203 to Ladner et al., which discusses preparation of single chain antibodies, which methods can be generally employed to the single chain MHC fusion complexes of this invention.

In a preferred preparation method, coding regions of the α and β chains of the MHC class II molecules are obtained, particularly by isolating the coding regions by PCT from a B cell line or other MHC molecule source. A sequence encoding a single-chain β-α fusion MHC fusion molecule of the invention can be constructed by replacing sequences encoding the transmembrane spanning domain of the β chain gene with a single chain linker sequence as discussed above which joins the β chain gene to the mature α chain (particularly at the first codon of the α chain gene). The α chain gene may suitably contain its transmembrane region for membrane bound expression of the single chain fusion complex, or the α chain gene may be truncated at the end of the extracellular region for soluble expression of the single chain MHC fusion complex. A suitable restriction site and linker for the presenting peptide is preferably included between the β chain leader and the first codon of the β chain. The coding region of essentially any presenting peptide can then be introduced as an oligonucleotide into the created restriction site. The resulting construct is then suitably placed under the control of mammalian or bacterial promoters, including those specific promoters disclosed herein. One such preferred MHC class II single-chain construct of the invention contains linked nucleotide sequences encoding the sequence: β chain leader/presenting peptide/linker sequence/β1-β2 extracellular region/single chain linker sequence/α1-α2 extracellular region. The MHC single-chain DNA constructs of the invention are suitably introduced into bacterial, baculoviral-insect cell and mammalian expression systems, including those specific expression systems disclosed herein, then expressed and purified is desired.

The single chain MHC molecule may be either full length, i.e. the MHC molecule is associated with cellular domains and contains e.g. complete or substantial amounts (e.g. greater than 80% of the sequences) of transmembrane and/or cytoplasmic portions of an α or β chain, or be truncated as discussed above for soluble expression. Such truncated and full length single chain MHC molecules may be produced as described above and in the examples for multiple polypeptide MHC complexes of the invention. For an MHC class II molecule, a full length molecule may have only one of the α and β chains linked to transmembrane and cytoplasmic domains, preferably the α chain. A preferred full-length single chain fusion MHC class II complex comprises covalently linked in sequence: 1) the presenting peptide, 2) the class II β chain lacking transmembrane and cytoplasmic domains, 3) a single chain linker sequence, and 4) the class II α chain containing transmembrane and cytoplasmic domains or a membrane anchor domain. A preferred soluble single chain fusion MHC class II complex comprises covalently linked in sequence: 1) the presenting peptide, 2) the class II β chain lacking transmembrane and cytoplasmic domains, 3) a single chain linker sequence, and 4) the class II α chain lacking transmembrane and cytoplasmic domains.

With respect to the full length MHC complexes of the invention (both single chain and non-single chain molecules) the MHC proteins can be anchored to cell membranes through hydrophobic membrane spanning domains (transmembrane domains) as well as through post-translational attachment of the covalently linked glycosylated form of phosphatidylinositol (GPI membrane anchor). Typically for the α and β chains of the MHC class II molecule, the transmembrane domain consists of approximately 25 hydrophobic amino acids connected to the carboxy terminal side of the α2 and β2 domains. These residues allow the protein to span the membrane. The transmembrane region ends with about 10–15 residues comprising the cytoplasmic tail at the carboxy terminal end of each of these chains. It has been demonstrated that these transmembrane and cytoplasmic regions can be replaced with sequences signaling GPI linkage and that the chimeric GPI-anchored class II molecules are membrane bound (Wettstein, D. A., J. J. Boniface, P. A. Reay, H. Schild, and M. M. David, 1991, J. Exp. Med. 174:219–228). GPI-linked membrane anchor domains have been defined in a number of proteins including decay accelerating factor (DAF), CD59 and humans placental alkaline phosphatase (HPAP) (Wettstein, D. A., J. J. Boniface, P. A. Reay, H. Schild, and M. M. Davis, 1991, J. Exp. Med., 174:219–228; Kooyman, D. L., G. W. Byrne, S. McClellan, D. Nielsen, M. Tone, H. Waldmann, T. M. Coffman, K. R. McCurry, J. L. Plaft, and J. S. Logan). for example, the 38 carboxy terminal amino acids of HPAP are sufficient to act as a signal sequence for GPI linkage. If the DNA sequence encoding this domain is linked to a secreted molecule such as the soluble portion of the MHC class II α or β chain, a membrane bound chimeric molecule is formed (Wettstein, D. A., J. J. Boniface, P. A. Reay, H. Schild, and M. M. Davis, 1991, J. Exp. Med., 174:219–228), and such an approach can be employed to anchor peptide-linked single chain class II MHC molecules of the invention to a cell membrane.

Molecular weight of MHC fusion molecules of the invention will vary, particularly depending on whether the molecule is soluble or full length (membrane bound). A soluble MHC class II fusion complex generally will have a molecular weight of greater than about 45 kDa, and mature α and β chains without trans-membrane and cytoplasmic domains each will have a molecular weight of greater than about 20 kDa, more typically between about 21 to about 26 kDa. Typically, mature single-chain MHC class II molecules of the invention without trans-membrane and cytoplasmic domains will have a molecular weight of about 48 to about 50 kDa. For full length (membrane bound) molecules, mature α and β chains generally will have a molecuir weight of greater than about 25 kDa, preferably between about 26 and about 30 kDa. Typically, mature single-chain MHC class II fusion molecules of the invention with a single (linked to α or β chain) transmembrane or membrane anchor domain will have a molecular weight of greater than about 49 kDa, preferably between about 50 and 52 kDa. All of the above mentioned molecular weights are by a SDS-PAGE determination.

Multivalent MHC fusion complexes of the invention are preferred for a number of applications. The valence of a MHC-antigenic peptide complex influences the effect of the complex on T cell receptor(s). For example, activation of the 3DT52.5 T cell hybridomas requires a MHC-antigenic molecule that has been made multivalent. Monovalent, soluble MHC complexes are incapable of stimulating this T cell [McCluskey, J. et al. (1988) J. Immunology 141, 1451–1455]. Preferred multivalent MHC fusion complexes of the invention includes those linked to an immunoglobulin, e.g., IgG, IgM or Fab'$_2$. Chemically cross-linked MHC fusion complexes of the invention (for example cross-linked to dendrimers) are also suitable multivalent species. For example, the MHC fusion complex can be genetically modified by including sequences encoding amino acid residues with chemically reactive side chains such as Cys or His. Such amino acids with chemically reactive side chains may be positioned in a variety of positions of a MHC fusion complex, preferably distal to the presenting peptide and binding domain of the MHC fusion complex. For example, the C-terminus of the β chain of a MHC molecule distal from the presenting peptide suitably may contain such reactive amino acid(s). Suitable side chains can be used to chemically link two or more MHC fusion complexes to a suitable dendrimer particle to give a multivalent MHC fusion complex. Dendrimers are synthetic chemical polymers that can have any one of a number of different functional groups of their surface [Tomalia, D. A. (1993) Aldrichimica Acta 26:91:101]. Exemplary dendrimers for use in accordance with the present invention include e.g. E9 starburst polyamine dendrimer and E9 combburst polyamine dendrimer, which can link cysteine residues.

It may be preferable to construct a single expression vector that expresses both chains of an MHC fusion complex of the invention, i.e. sequences that code for both the α and β chains of an MHC fusion complex are each connected to a single expression vector, even if not a single chain molecule. Such an expression vector may provide better results than where separate vectors are used for each chain of a MHC fusion complex, particularly where selection is difficult for cells into which the vector has been introduced. It also may be preferred to construct a single expression vector that codes for both chains of a MHC fusion complex as well as other agents, particularly a T cell costimulatory factor such as B7 or B7-2, i.e. sequences that code for both chains of an MHC fusion complex and sequence(s) that code for a costimulatory factor are each connected to a single expression vector, to enable a single transformation procedure. Again, this approach would avoid potentially difficult selection for cells that have been transformed or transfected two or more times.

The MHC molecules of the fusion complexes of the invention suitably correspond in amino acid sequence to naturally occurring MHC molecules, e.g. MHC molecules of a human (class I or class II), mouse or other rodent, or other mammal. Preferably at least about 70 percent of the amino acid sequence of a MHC molecule of the fusion complex of the invention will be the same as the amino acid sequence of a naturally occurring MHC molecule such as those mentioned above, more preferably at least about 90 percent amino acid sequence of a MHC molecule of the fusion complex of the invention will be the same as the amino acid sequence of a naturally occurring MHC molecule, and even more preferably about 98 percent to all of the amino acid sequence of a MHC molecule of the fusion complex of the invention will be the same as the amino acid sequence of a naturally occurring MHC molecule.

The present invention also includes detection and characterization of recombinant peptides. For example, the invention includes a method that can be used to map an uncharacterized epitope for T cells as follows: sequences encoding either a library of random peptides or selected peptides can be cloned into the presenting peptide position of an expression vector system of the invention such as those identified above that contains a DNA sequence encoding a MHC molecule and, optionally, a DNA sequence coding for a linker sequence. Suitably restriction fragments of an appropriate cDNA or genomic DNA library (see Sambrook, et al., supra) are used as the source of the sequences inserted into the expression vector or, alternatively, selected oligonucleotides such as synthetic oligonucleotides of known sequence are used as the inserted sequences. Suitable hosts, such mammalian cells and others identified above, are transformed or transfected with the vector containing the gene fusion, i.e. the sequence coding for the MHC molecule linked to sequence coding for the additional peptide. Transformants are cultured under suitable conditions and the cells screened for expression of fusion complex of interest that reacts with T cell clones as determined by assays disclosed below. Reactive colonies can then be picked and the vectors isolated. Sequence analysis of the DNA insert would reveal which of the cloned peptide sequences corresponded to the epitope(s) recognized by the T cell clone.

The ability of a MHC fusion complex of the invention to modulate the activity of a T cell receptor (including inactivation of the T cell responses) can be readily determined by an in vitro assay. Typically T cells for the assays will be provided by transformed T cell lines such as T cell hybridomas or T cells which are isolated from a mammal, e.g., from a human or from a rodent such as a mouse. Suitable T cell hybridomas are publicly available or can be prepared by known methods. T cells can be isolated from a mammal by known methods. See, for example, Shimonkevitz, R., et al., (1983) J. Exp. Med. 158:303 and Examples 4 and 5 which follow.

A suitable assay to determine if a MHC fusion complex of the invention is capable of modulating the activity of T cells is conducted as follows, by the sequential steps 1–4 below. T cells suitably express a marker that can be assayed and that indicates T cell activation, or modulation of T cell activity after activation. Thus, e.g., as disclosed in Example 4 below, the murine T cell hybridoma DO 11.10 that express interleukine-2 (IL-2) upon activation can be employed. IL-2 concentrations can be measured to determine if a particular presenting peptide is capable of modulating activity of this T cell hybridoma. Such a suitable assay is conducted by the following sequential steps:

1. T cells carrying the T cell receptor specific to the peptide/MHC complex are obtained such as from a T cell hybridoma of interest or by isolating from a mammal.
2. The T cells are cultured under conditions that allow proliferation.
3. The proliferating T cells are contacted with a selected MHC fusion complex of the invention.
4. The T cell are contacted with the antigen presenting cells to provide signal necessary for activation and assayed for a marker, e.g. IL-2 production is measured. A decrease in IL-2 production, e.g., a 40 percent or greater decrease in IL-2 production after a period of 24 hrs., more typically a 50 percent or greater decrease in IL-2 production after a period of 24 hrs., indicates the MHC fusion complex modulates the activity of the T cells and can suppress an immune response. Example 4 which follows exemplifies such an assay. The assay is suitably employed for analysis of activity of soluble "truncated" MHC complexes of the invention that do not contain a transmembrane portion. In addition, the assay is suitably employed for identification of MHC fusion complexes of the invention that contain a covalently linked presenting peptide that functions as a T cell receptor antagonist or partial agonist.

The T cells employed in the assays are incubated under conditions suitable for proliferation. For example, a DO11.10 T cell hybridoma is suitably incubated at about 37° C. and 5% $CO_2$ in complete culture medium (RPMI 1640 supplemented with 10% FBS, penicillin/streptomycin, L-glutamine and $5 \times 10^{-5}$ M 2-mercaptoethanol). Serial dilutions of MHC fusion complex of the invention can be added to the T cell culture medium. Suitable concentrations of the MHC fusion complex added to the T cells typically will be in the range of from $10^{-12}$ to $10^{-6}$ M. T cell activation signals are provided by antigen presenting cells that have been loaded with the appropriate antigenic peptide. It is believed that use of antigen dose and APC numbers giving slightly submaximal T cell activation is preferred to detect inhibition of T cell responses with MHC fusion complexes of the invention. A decrease in production of IL-2 following contact with the MHC fusion complex indicates the fusion complex modulates activity of the T cells and can suppress immune response.

Alternatively, rather than measurement of an expressed protein such as IL-2, modulation of T cell activation can be suitably determined by changes in antigen-dependent T cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T cell proliferation. See Example 5 which follows, where such a procedure is specifically described. This assay is not suitable for T cells that do not require antigen presentation for growth, e.g., T cell hybridomas. It is suitable for measurement of modulation by the MHC fusion complexes of T cell activation for untransformed T cells isolated from mammals. A decrease in the level of T cell proliferation following contact with the MHC fusion complex indicates the fusion complex modulates activity of the T cells and can suppress immune response, e.g., see Example 5 which follows. The in vitro T cell proliferation assay is preferred for measuring the effects of MHC fusion complexes of the invention on antigen-specific changes in T cell clonal expansion in vivo. Such an assay is specifically described in Example 7 which follows.

These in vitro assays can be employed to select and identify peptide(s), coded by DNA from a random library or other oligonucleotides, that are capable of modulating the activity of T cell receptor (including activation or inhibition of T cell development). Specifically, DNA sequences encoding either a library of random peptides or selected peptides can be cloned into the presenting peptide position of an expression vector system of the invention such as those identified above that contains a DNA sequence encoding a MHC molecule and, optionally, a DNA sequence coding for a linker sequence. Suitably, restriction fragments of an appropriate cDNA of genomic DNA library (see Sambrook, et al., supra) are used as a source of the sequences inserted into the expression vector or, alternatively, selected oligonucleotides such as synthetic oligonucleotides of known sequence are used as the inserted sequence. Suitable hosts, such as a mammalian cells and others identified above, are transformed with the vector containing the gene fusion, e.g., the sequence coding for the MHC molecule linked to sequence coding for the presenting peptide. Transformants are cultured under suitable conditions and the cells are screened for expression of the MHC fusion complex of interest by contacting same with selected T cells. Assays described above, e.g., measurement of IL-2 production or T cell proliferation, are employed to determine if contact with the MHC fusion complex modulated T cell activation. For example, a decrease in IL-2 production of APC-stimulated T cells identifies those MHC fusion complexes that modulate activity of the T cells and suppress the immune responses. Alternatively, the in vitro assays can be employed to identify multivalent MHC fusion complexes of the invention described above, that contained presenting peptides that increase T cell responses.

In vivo assays also may be suitably employed to determine the ability of a MHC fusion complex of the invention to modulate the activity of T cells, including the ability to inhibit or inactivate T cell development. For example, an MHC fusion complex of the invention can be assayed for its ability to inhibit immunoglobulin class switching (i.e. IgM to IgG). See, e.g., Linsley, P. S. et al. (1992) Science 257:792–795. Such an assay is specifically described in Example 6 which follows.

Diagnostic methods using MHC fusion molecules of the invention are also provided including in vivo diagnostic imaging and HLA typing [see, e.g., A. K. Abbas, Cellular and Molecular Immunology, page 328 (W. B. Saunders Co. 1991)]. For in vivo imaging applications, a MHC fusion molecule of the invention that has a radioactive label (e.g., $^{125}$I, $^{32}$P, $^{99}$Tc) or other detectable tag can be administered to a mammal and the subject scanned by known procedures for binding of the MHC molecule. Such an analysis of the mammal could aid in the diagnosis and treatment of a number of disorders including e.g. undesired immune responses as disclosed herein.

Assays also may be employed to evaluate the potential use of a MHC complex of the invention for treatment of an immune disorder. For example, experimental allergic encephalomyelitis (EAE) is an autoimmune disease in mice and a recognized model for multiple sclerosis. A suitable mouse strain can be treated to develop EAE and then a MHC fusion complex of the invention administered and the animal evaluated to determine if EAE development is inhibited or prevented after administration of the MHC fusion complex. Such an assay is specifically described in Examples 8 and 11 which follow.

The ability of a MHC fusion complex of the invention to induce an immune response, including to provide vaccination against a targeted disorder, may be readily determined by an in vivo assay. For example, a MHC fusion complex of the invention, or DNA coding for a MHC fusion complex of the invention, can be administered to a mammal such as a mouse, blood samples obtained from the mammal at the time of initial administration and several times periodically thereafter (e.g. at 2, 5 and 8 weeks after administration of the fusion complex or DNA). Serum is collected from the blood samples and assayed for the presence of antibodies raised by the immunization. Antibody concentrations may be determined. Example 9 which follows specifically describes such an assay.

As discussed above, the invention includes direct administration of DNA construct coding for MHC fusion complex of the invention for expression of the fusion complex within cells of the subject. Preferably DNA carrying the coding regions of the MHC-presenting peptide fusion, suitably under the control of an appropriate promotor such as the CMV promoter, is injected directly to skeletal muscle of the subject. To ensure the display of the MHC fusion molecules will induce an immune response in the subject, DNA vectors that code for a co-stimulatory factor is preferably co-administered to the subject with the DNA coding for the MHC-presenting peptide fusion. Preferred co-administered DNA vectors include e.g. those that comprise either the coding region of B7-1 or B7-2 under the control of the CMV promoter. The expressed B7-1 and B7-2 protein can provide the co-stimulatory signal to assist the initiation of the immune response.

Such an approach for induction of an immune response in a subject such as a mammal offers significant advantages over prior approaches. The initial step in the presentation of a foreign protein antigen is the binding of the native antigen to an antigen presenting cell (APC). After binding to APCs, antigens enter the cells, either by phagocytosis, receptor-mediated endocytosis or pinocytosis. Such internalized antigens become localized in intracellular membrane-bound vesicles called endosomes. After endosome-lysosome fusion, the antigens are processed into small peptides by cellular proteases located in lysosomes. The peptides become associated with the α and β chains of MHC class II molecules within these lysosomes. These MHC class II molecules, previously synthesized in the rough endoplasmic reticulum, are sequentially transported to the Golgi complexes and then to the lysosomal compartment. The peptide-MHC complex is presented on the surface of APCs for T and B cell activation. Therefore, the accessibility of proteolytic processing sites within the antigen, the stability of the resultant peptides in the lysosome and the affinities of the peptides for MHC molecules are determining factors for the immunogenicity of a particular epitope. These factors can not be changed by administration of adjuvants. Direct expression of the MHC fusion complexes of the invention (i.e. MHC directly covalently linked to the presenting peptide), however, should bypass such complications and induce immune response against the epitope carried on the MHC fusion molecules.

Also, rather than directly administering DNA coding for an MHC fusion complex of the invention to a subject, host compatible antigen presenting cells into which such DNA has been introduced may be administered to the subject.

That is, DNA coding for one or more MHC fusion complexes of the invention may be introduced into host compatible antigen presenting cells and such transformed or transfected antigen presenting cells can be administered to the targeted host, and with the site targeted where the most efficient interaction with the appropriate T cell would take place. See, for instance, the Examples 13 and 14 which follow. Upon administration to a subject, such engineered cells can then express in vivo on the cell surface the MHC fusion complex coded for by the DNA. Such engineered cells can be administered to a subject to induce an immune response or alternatively to suppress an immune response, as disclosed herein, depending on the expression of other co-stimulatory signals of the cells. That is, if upon administration the cells can provide an MHC fusion complex in the absence of an effective amount of co-stimulatory signal(s), or provide a MHC fusion complex that contains a presenting peptide with antagonist or partial agonist activity, the cells can be administered to a host to suppress an immune response. Alternatively, if the cells can provide a MHC fusion complex in the presence of an effective amount of co-stimulatory signal(s), e.g. if a T cell co-stimulatory factor such as B7 or B7-2 is expressed on the surface of the cells, the cells can be administered to a mammalian host to induce an immune response in the mammal, as disclosed herein. It may be preferred to construct a single expression that codes for both chains of a MHC fusion complex as well as for a T-cell costimulatory factor if employed, as discussed above, and introduce that vector into a host compatible APC to prepare the cells for administration. As will be recognized by those in the art, the term "host compatible" antigen presenting cells means antigen presenting cells that are of the same haplotype as that of the subject or "host" to which the cells are administered. Preferably the transformed host compatible antigen presenting cells are those that can migrate to lymph nodes of the subject to which the cells have been administered and, at that site, express the MHC fusion complex.

As discussed above, MHC fusion complexes of the invention and DNA constructs that encode such fusion complexes have a number of therapeutic applications.

For example, MHC fusion complexes of the invention that do not contain a transmembrane portion (see, e.g., the soluble complex of Example 2 which follows) can be administered to suppress an immune response of a mammal, e.g., to treat a mammal including a human that suffers from or is susceptible to an autoimmune disorder such as e.g. multiple sclerosis, insulin-dependent diabetes mellitus, rheumatoid arthritis and the like. Also suitable for treatment are those subjects suffering or likely to suffer from an undesired immune response e.g. patients undergoing some type of transplant surgery such as transplant of heart, kidney, skin or other organs. In such situations, a treatment protocol may suitably be commenced in advance of the surgical procedure.

Preferably, to suppress an immune response, an MHC fusion complex is administered that is linked to an immunoglobulin, e.g., fused to the constant domains of an immunoglobulin molecule such as an IgG, IgM or IgA immunoglobulin or fragment. See FIG. 1C of the Drawings and the examples which follow.

A number of distinct approaches can be employed to suppress an immune response of a mammal in accordance with the invention.

Specifically, as discussed above, it has been shown that a MHC molecule will only induce clonal expansion of a T cell line specific if co-stimulatory signal(s) such as from antigen presenting cells are also In the absence of co-stimulatory signals, or at least in the absence delivery of an T cell proliferation effective amount of such T cell co-stimulatory signal(s), the T cells will be induced to a state of anergy or apoptosis resulting in clonal deletion.

Accordingly, one treatment method of the invention for suppression of an immune response provides for the administration of an effective amount of one or more MHC fusion complexes of the invention in the substantial absence of any costimulatory signal(s) to thereby induce anergy for specific T cells and effectively suppress an undesired immune response. Preferably, a "truncated" soluble MHC complex is administered, i.e. the MHC complex does not contain a transmembrane portion. The presenting peptide of the administered soluble MHC fusion complex can be selected that are specific for T cells of an undesired immune response to induce a state of anergy with respect to those T cells. Such presenting peptides can be readily identified and selected by the in vitro protocols identified above.

Soluble MHC fusion complexes of the invention suitably can be administered to a mammal by injection, e.g., intraperitoneal or intravenous injection. Topical administration, e.g., eye drops, and administration through nasal and lung inhalers also should be possible. A MHC fusion complex of the invention, at least those complexes used in therapeutic applications, should be produced in mammalian cells and purified prior to use so it is essentially or completely free of any bacterial or pyrogens. The optimal dose for a given therapeutic application can be determined by conventional means.

MHC fusion complexes of the invention may be suitably administered to a subject (particularly mammal such as human or livestock such as cattle) in treatment or pharmaceutical compositions which comprise the fusion complex. Such pharmaceutical compositions of the invention are prepared and used in accordance with procedures known in the art. For example, formulations containing a therapeutically effective amount of an MHC fusion complex of the invention may be presented in unit-dose or multi-dose containers, e.g., sealed ampules and vials, and may be stored in a freeze dried (lyophilized) condition requiring only the addition of the sterile liquid carrier, e.g. water for injections, immediately prior to use. Liposome formulations also may be preferred for many applications. Other compositions for parenteral administration also will be suitable and include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Another treatment method of the invention for suppression of an immune response provides for administration of a MHC fusion complex of the invention that contains a covalently linked presenting peptide that is a T cell receptor antagonist or partial agonist. See Sette, A., et al. (1994) Annu. Rev. Immunol. 12: 413–431. The MHC fusion complex may be a truncated form and be administered as a soluble protein as described above. Alternatively, the MHC fusion complex may be full length, i.e. will contain a transmembrane portion. Treatment with these complexes will comprise administration to a mammal an effective amount of a DNA sequence that comprises a DNA vector encoding the full length MHC fusion complex of the invention and a presenting peptide that is a TcR antagonist or partial agonist. See, e.g., the discussion above and Examples 3, 10 and 11 which follow for suitable means of preparation of such MHC fusion complexes and use of same for immunosuppressive therapy. Presenting peptides that are TcR antagonists or partial agonists can be readily identified and selected by the in vitro protocols identified above. A MHC fusion complex that contains a presenting peptide that is a T cell receptor antagonist or partial agonist is particularly preferred for treatment of allergies and autoimmune diseases such as multiple sclerosis, insulin-dependent diabetes mellitus and rheumatoid arthritis.

Further, as discussed above, host compatible antigen presenting cells into which DNA coding for an MHC fusion complex of the invention has been introduced may be administered to a subject to suppress an immune response. Upon administration the cells express a MHC fusion complex of the invention in the absence of an effective amount of T cell co-stimulatory signal(s), i.e. such that T cell anergy is induced, and/or the administered cells express an MHC fusion complex that contains a linked presenting peptide with antagonist or partial agonist activity.

Different immunosuppressive therapies of the invention also may be used in combination as well as with other known immunosuppressive agents such as anti-inflammatory drugs to provide a more effective treatment of a T cell-mediated disorder. For example, immunosuppressive MHC fusion complexes that can be used in combination with anti-inflammatory agents such as corticosteroids and nonsteroidal drugs for the treatment of autoimmune disorders and allergies.

The invention also provides methods for invoking an immune response in a mammal such as a human, including vaccinating a mammal such as a human against an infectious agent or a targeted disorder such as cancer, particularly a melanoma cancer, or other disorder such as malaria.

These methods comprise administering to a mammal an effective amount of a DNA sequence that comprises a DNA vector that codes for an MHC fusion complex of the invention that contains a transmembrane portion, and/or administration of such a MHC fusion complex that contains a transmembrane portion and/or administration of host compatible antigen presenting cells that contain such DNA that code for such MHC fusion complexes. Preparation of expression vectors of MHC fusion complexes is described above and in Examples 3 and 12 which follow. Methods for administration of plasmid DNA, uptake of that DNA by cells of the administered subject and expression of protein has been reported. See Ulmer, J. B., et al., Science (1993) 259: 1745–1749.

Preferably the DNA that codes for a full length MHC fusion complex of the invention is administered to a mammal together with a DNA sequence coding for a T cell costimulatory factor such as DNA coding for B7 or B7-2. The B7 gene and expression thereof is described in Harlan, D., et al., Proc. Natl. Acad. Sci. USA (1994) 91: 3137–3141. Upon uptake of that DNA by the cells of the subject, the T cell co-stimulatory factor will be expressed and can provide the co-stimulatory signal(s) and thereby assist in the initiation of the immune response. See Examples 3 and 12 which follow and disclose the construction of expression vectors containing B7 or B7-2 genes.

While administration of DNA coding for an MHC fusion complex of the invention to a mammal such as a human as discussed above is a preferred method for invoking an immune response in the subject, MHC fusion complexes also may be suitably administered by other routes. Thus, as discussed above, host compatible antigen presenting cells into which DNA coding for an MHC fusion complex of the invention has been introduced may be administered to a subject to induce an immune response. Upon administration the cells express an MHC fusion complex of the invention in the presence of an effective amount of T cell co-stimulatory signal(s) such as B7 or B7-2 genes to invoke an immune response, and/or the administered cells express a full length MHC fusion complex that is capable of invoking an immune response, e.g. as shown by an increase in T cell proliferation such as by procedures detailed in Examples which follow. Although typically less preferred than approaches discussed above, MHC fusion complexes of the invention that are capable of invoking an immune response also may be directly administered to a subject, e.g. a full length MHC fusion complex that contains a covalently linked antigenic presenting peptide which can stimulate or induce T cell proliferation.

Methods of the invention for inducing an immune response, including vaccinating a subject against a targeted disorder, may be used in combination with known methods for inducing an immune response. For example, a MHC fusion complex of the invention, or DNA construct coding for such MHC fusion complex, may be administered to a subject in coordination or combination with administration of a vaccine composition, in order to boost or prolong the desired effect of such vaccine composition.

DNA vectors that encode MHC fusion complexes of the invention are suitably administered to a mammal including a human preferably by intramuscular injection. Administration of cDNA to skeletal muscle of a mammal with subsequent uptake of administered expression vector by the muscle cells and expression of protein encoded by the DNA has been described by Ulmer et al. and represents an exemplary protocol [Ulmer, J. B., et al., Science 259: 1745–1749]. The optimal dose for a given therapeutic application can be determined by conventional means.

Additionally, MHC fusion complexes, DNA vectors that encode such complexes and host compatible antigen presenting cells that contain such DNA vectors of the inventions each suitably may be administered to a subject by a variety of other routes. For example, to induce an immune response, it may be preferable to administer DNA vectors that encode antigenic MHC fusion complexes of the inventions, alone or together with DNA coding for a co-stimulatory factor, intradermally to a subject, by procedures known to those skilled in the art. Such administration can result in transformation of intradermal antigen presenting cells (e.g, dendritic cells) and T cell proliferation. See the results of Example 16 which follows. MHC fusion complexes and DNA vectors encoding such fusion complexes also may be administered to a subject by other routes, e.g., orally or transdermally.

In addition to treatment of human disorders, MHC fusion complexes of the invention and DNA constructs of the invention that encode such fusion complexes will have significant use for veterinary applications, e.g., treatment of disorders of livestock such as cattle, sheep, etc. and pets such as dog and cats.

While MHC fusion complexes of the invention or DNA constructs coding for such fusion complexes may be administered alone to a subject, they also each may be used as part of a pharmaceutical composition. Pharmaceutical compositions of the invention in general comprise one or more MHC fusion complexes of the invention or DNA constructs coding for such fusion complexes together with one or more acceptable carriers. The carriers must be "acceptable" in the sense of being compatible with other ingredients of the formulation and not deleterious to the recipient thereof. For example, for parenteral administration such as by an injection formulation, a sterile solution or suspension with water may be prepared, or other pharmaceutically acceptable solutions. Such pharmaceutical compositions are suitably prepared by methods known in the art.

It will be appreciated that actual preferred amounts of a given MHC fusion complex of the invention or DNA construct coding for same used in a given therapy will vary to the particular active compound or compounds being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests conducted e.g. with regard to the foregoing guidelines and the assays disclosed herein.

All documents mentioned herein are incorporated herein by reference in their entirety.

The following non-limiting examples are illustrative of the invention.

EXAMPLES 1A–1F

Construction of Soluble MHC Fusion Complexes of the Invention

MHC class II-peptide fusion vectors for expressing soluble MHC class II molecules with covalently linked presenting peptides were prepared as described below in Examples 1A–1F. The MHC class II genes used to prepare the following MHC fusion complex constructs were isolated by PCR amplification of cDNA generated from the appropriate Antigen Presenting Cell (APC), as shown in FIGS. 2–8 of the Drawings.

EXAMPLE 1A

Figure 9C:
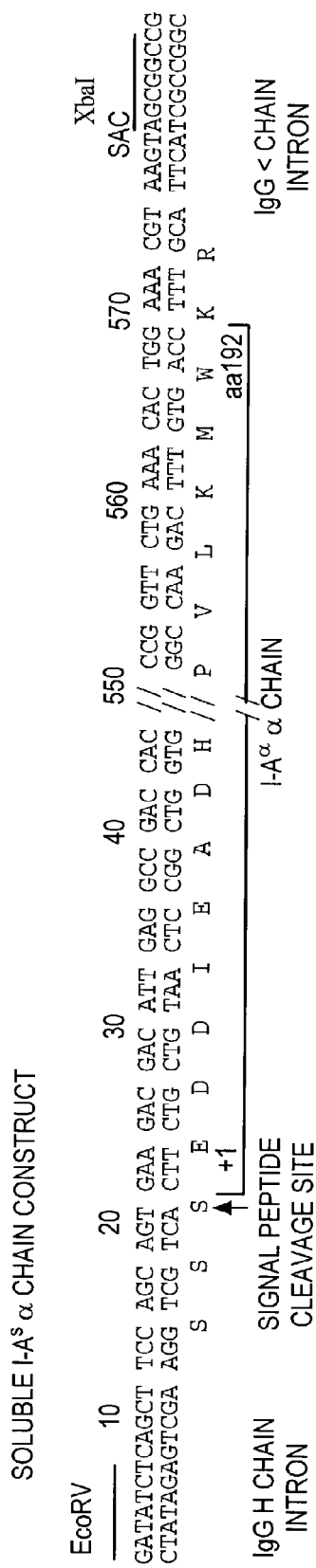
FIG. 9 (which includes FIGS. 9A–9F) (SEQ ID NOS: 75–98) shows nucleotide and amino acid sequences of soluble MHC fusion complexes of the invention.

For the I-A$^d$ genes, total RNA was isolated from the mouse B cell lymphoma A20 cell line. Briefly, 1×10$^8$ A20 cells (ATCC TIB 208) were homogenized in 6 ml of ice cold 4 M guanidinium thiocyanate, 0.1 M Tris-Hcl, Ph 7.5 using a Tissue Tearer homogenizer for 5 minutes. Following homogenization, sarcosyl was added to a final concentration of 0.5% and the solution was mixed thoroughly. The homogenate was centrifuged at 5000 g for 10 minutes and the supernatant was brought up to 10 mls with 4 M guanidinium thiocyanate, 0.1 M Tris-Hcl, Ph 7.5, 0.5% sarcosyl buffer. The supernatant was gently layered on top of a 3.5 ml cushion of 5.7 M CsCl, 0.01 M EDTA, pH 7.5 in an SW41 clear ultracentrifuge tube. The samples were centrifuged in an SW41 rotor at 32,000 rpm for 24 hours at 20° C. Following centrifugation, the supernatant was carefully removed and the RNA pellet was washed with 70% ethanol. The RNA was dissolved in 350 μl of DEPC-treated water containing 40 units of RNasin (Promega). The RNA was precipitated with 35 μl of 3 M sodium acetate and 970 μl of ethanol. This procedure yielded approximately 370 μg of total RNA. The RNA was resuspended to 5 μg/μl with DEPC-treated water and was used for RT-PCR cloning of the I-A$^d$ genes. FIG. 2 of the Drawings shows the strategy for isolating the I-A$^d$ α1-α2 gene fragment (encoding aa1 to 182) and FIG. 8 of the Drawings lists the oligonucleotides primers used. The A20 total RNA (5 μg) was converted to cDNA by using Superscript-MLV Reverse Transcriptase (GIBCO-BRL) and α2-specific priming according to manufacturer's procedures. Of the 20 μl of cDNA generated, 2 μl was used as template DNA for PCR. Typical PCR amplification reactions (100 μl) contained template DNA, 10 pmoles of the appropriate primers (OPR100 and OPR101), 2.5 units of Taq polymerase, 100 μM dNTP, 50 mM KCl, 10 mM Tris-HCL, pH 8.3, 1.5 mM MgCl$_2$, 0.01% gelatin. The template was denatured by an initial incubation at 96° C. for 5 minutes during which the Taq polymerase was added to hot-start the reaction. The desired products were amplified by 10 thermal cycles of 55° C. for 1 minute, 70° C. for 1 minute, then 96° C. for 1 minute followed by 25 step cycles of 70° C. for 1 minute, then 96° C. for 1 minute. The initial α1-α2 PCR product (approximately 550 bp) was designed to be cloned into the bacterial expression vector, pJRS139. The PCR products from 5 reactions were pooled, precipitated with 2 volumes of ethanol/0.3 M sodium acetate, and the resulting products (about 0.2 μg of DNA) were resuspended in water. The α1-α2 gene fragment was digested with NcoI and SpeI, resolved by agarose gel electrophoresis and purified by elution from the agarose gel. The purified digested PCR products were then ligated into NcoI/SpeI digested pJRS139. The α1-α2 gene fragment cloned in pJRS139 was designated 39AD2 and served as the template for PCR amplification to add the restriction sites and flanking sequences necessary for cloning and expression in the mammalian expression vectors. In these reactions, 0.5 ng of NcoI-digested 39AD2 was used as a template, OPR107 and OPR108 were the primers and the PCR conditions were 5 thermal cycles of 60° C. for 1 minute, 70° C. for 1 minute, and 96° C. for 1 minute followed by 20 step cycles of 70° C. for 1 minute and 96° C. for 1 minute. The α1-α2 PCR product (approximately 590 bp) contains a 5' EcoRV site and a 3' EagI site for cloning between the leader intron and J-region intron of the IgG kappa chain shuttle vector (see FIG. 9A of the Drawings). In addition, PCR product has the IgG splice sites and leader sequences necessary for proper expression of the MHC-IgG fusion protein. The PCR products were digested with EcoRV and EagI and gel-purified. The purified digested PCR products were then ligated into EcoRV/EagI digested pBlueScript II SK+ (Stratagene) resulting in the pA19 construct. This vector was digested with EcoRV and EagI and the resulting α1-α2 gene fragment was subcloned into the pJW003 IgG shuttle vector as described in Example 2 below.

EXAMPLE 1B

The following approach was employed to isolate the I-A$^d$ β1-β2 gene fragment (encoding aa1 to 189), attaching the linker sequence and inserting the oligonucleotides encoding the antigenic peptides. This approach also is depicted in FIG. 3 of the Drawings. The A20 total RNA (10 μg) was converted to cDNA by using Superscript-MLV Reverse Transcriptase (GIBCO-BRL) and oligo dT-specific priming according to manufacturer's procedures. Of the 20 μl of cDNA generated, 2 μl was used as template DNA for PCR. The reactions were carried out as described above except oligonucleotide primers were OPR102 and OPR104 (see FIG. 8 of the Drawings) and the PCR conditions were 10 thermal cycles of 60° C. for 1 minute, 70° C. for 1 minute, and 96° C. for 1 minute followed by 40 step cycles of 70° C. for 1 minute and 96° C. for 1 minute. The initial β1-β2 PCR product (approximately 570 bp) was designed to be cloned into the bacterial expression vector, pJRS139. The PCR products were digested with NcoI and SpeI and gel-purified in the same manner as described above. The purified digested PCR products were then ligated into NcoI/SpeI digested pJRS139. The β1-β2 gene fragment cloned in pJRS139 was designated 39BD2 and served as the template for PCR amplification to add the linker sequence and restriction sites and flanking sequences necessary for cloning and expression in the mammalian expression vectors. In these reactions, 0.5 ng of NcoI-digested 39AB2 was used as a template, OPR107 and OPR108 were the primers and the PCR conditions were 5 thermal cycles of 60° C. for 1 minute, 70° C. for 1 minute, and 96° C. for 1 minute followed by 20 step cycles of 70° C. for 1 minute and 96° C. for 1 minute. The linker-β1-β2 PCR product (approximately 640 bp) contains a 5' EcoRV site and a 3' EagI site for cloning between the leader intron and J-region intron of the IgG heavy chain shuttle vector (FIG. 9B). In addition, PCR product has the IgG splice sites and leader sequences necessary for proper expression of the MHC-IgG fusion protein. To allow for cloning of the antigenic peptide sequences, an Af/II site was engineered into the end of the signal sequence and an NheI site was present at the beginning of the linker. The PCR products were digested with EcoRV and EagI and gel-purified. The purified digested PCR products were then ligated into EcoRV/EagI digested pBlueScript II SK+ (Stratagene) resulting in the pB15 construct. Sequence and restriction analyses indicated that this construct contained a mutation in the EcoRV site. To correct this mutation, two oligonucleotides (OPR119 and OPR 120-2) were annealed and ligated into HindIII/NheI digested pB15, resulting in the vector, pBC1. To insert sequences encoding the class II I-A$^d$ binding peptides, oligonucleotides were annealed and ligated into Af/II/NheI digested pBC1. The Ova 323-339 peptide (SISQAVHAAHAEINEAGR) (SEQ ID NO: 3) was encoded by oligonucleotides OPR110 and OPR111, Ova:H331 R (SISQAVHAARAEINEAGR) (SEQ ID NO: 4) by OPR115 and OPR116, Ova A331Y (SISQAVHAAHYEINEAGR) (SEQ ID NO: 5) by OPR117 and OPR118, and HEL 74-86 (NLCNIPCSALLSS) (SEQ ID NO: 6) by OPR140 and OPR141. The respective constructs in the pBC1 backbone were designated pB16, pB24, pB37 and pB4. These vectors were digested with EcoRV and EagI and the resulting peptide-linker-β1-β2 gene fragment was subcloned into the pJW009 IgG shuttle vector as described in Example 2 which follows.

EXAMPLE 1C

Figure 4B:
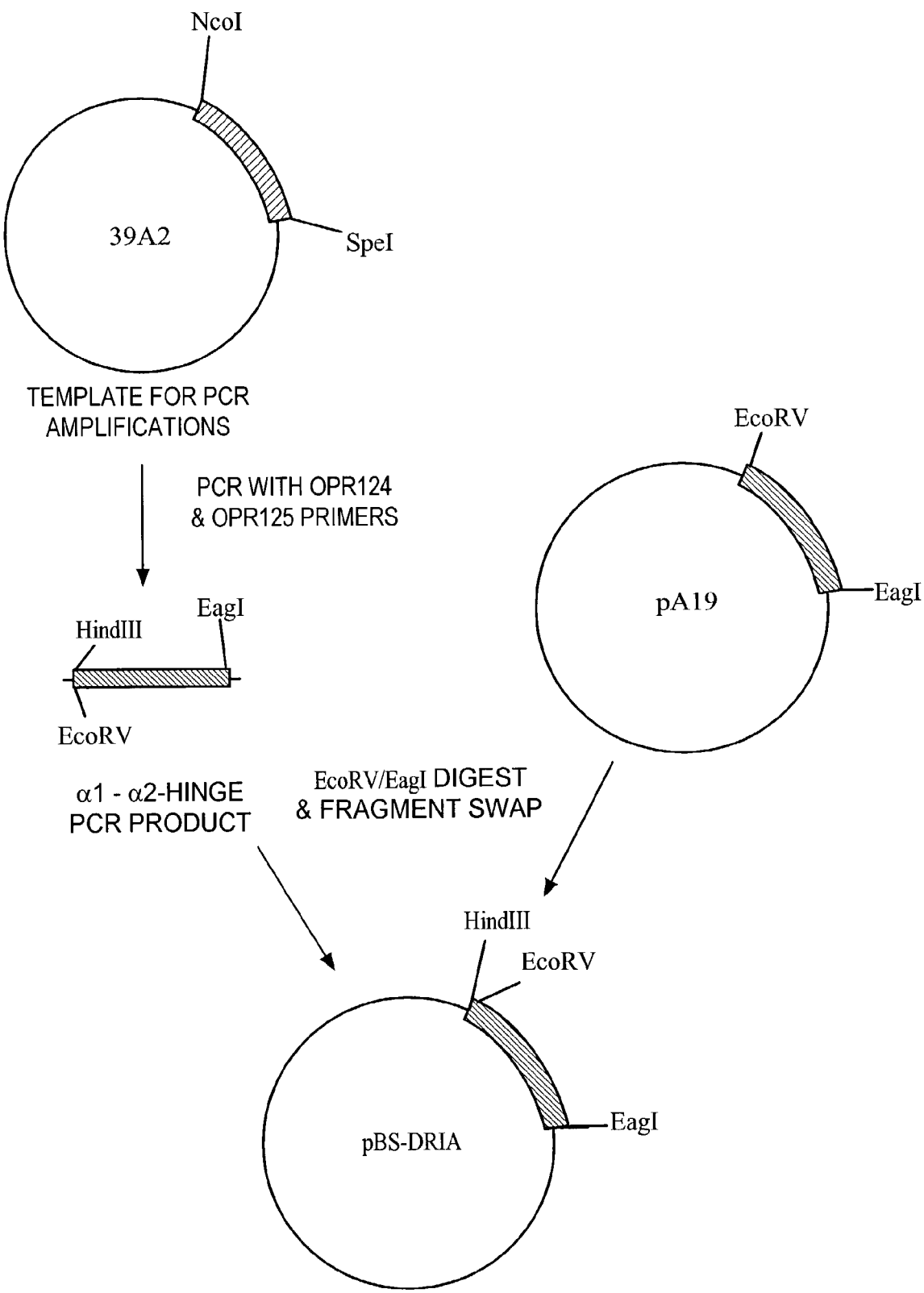
FIG. 4 shows the cloning scheme for human HLA-DR1 α1-α2.
Figure 9D:
Figure 9E:
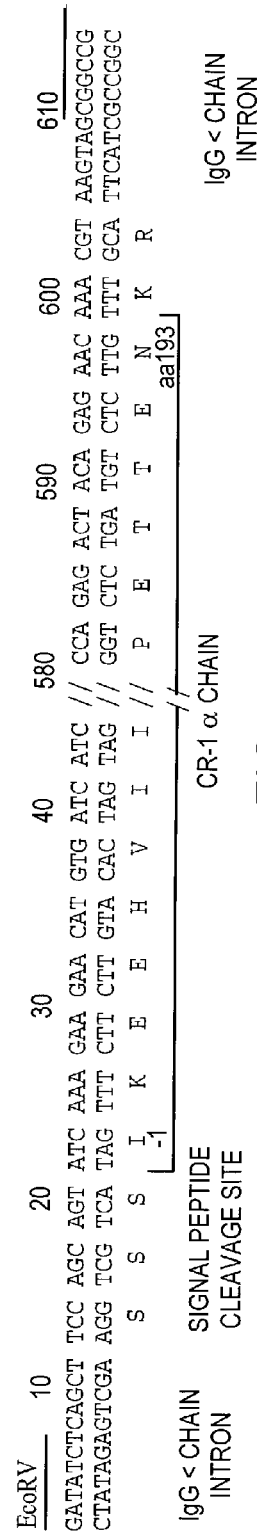

The following approach was employed to isolate the human HLA-DR1 α1-α2-hinge gene fragment (encoding aa1-192) and is depicted in FIG. 4 of the Drawings. Total cellular RNA was made by the procedure described above from 3×10⁶ BLCL-K68 cells obtained from a HLA-DR1 homozygous individual. Total RNA was converted to cDNA (20 μl) by using Superscript-MLV Reverse Transcriptase (GIBCO-BRL) and oligo dT-specific priming according to manufacturer's procedures. The initial PCR reactions were design to add restriction sites necessary for cloning the α1-α2-hinge gene fragment into bacterial expression vectors (for work that is not relevant to this application). PCRs were performed as described above except 5 μl of the template cDNA was used, the primers were DR1A-F and DR1A-B (FIG. 8) and the PCR conditions were 10 thermal cycles of 55° C. for 1 minute, 70° C. for 1 minute, and 96° C. for 1 minute followed by 20 step cycles of 70° C. for 1 minute and 96° C. for 1 minute. The α1-α2-hinge PCR product (approximately 570 bp) was digested with HindIII and BamHI, gel-purified and ligated into HindIII/BamHI digested pUC18, resulting in the K68A3 vector. This vector (0.5 ng) served as a template for further PCR amplifications using AF-N and AB-S oligonucleotides as primers. The resulting α1-α2-hinge PCR product was digested with NcoI and SpeI, gel-purified and ligated into NcoI/SpeI digested pJRS139, resulting in the 39A2 vector. This vector served as the template for PCR amplification to add the linker sequence and restriction sites and flanking sequences necessary for cloning and expression in the mammalian expression vectors. PCRs were performed as described above except 10 ng of the NcoI-digested 39A2 template DNA was used, the primers were OPR124 and OPR125 (sequences thereof set forth in FIG. 8 of the Drawings) and the PCR conditions were 5 thermal cycles of 50° C. for 1 minute, 70° C. for 1 minute, and 96° C. for 1 minute followed by 10 step cycles of 70° C. for 1 minute and 96° C. for 1 minute. The α1-α2-hinge PCR product (approximately 610 bp) contains a 5' EcoRV site and a 3' EagI site for cloning between the leader intron and J-region intron of the IgG kappa chain shuttle vector (see FIG. 9e of the Drawings). In addition, PCR product has the IgG splice sites and leader sequences necessary for proper expression of the MHC-IgG fusion protein. The PCR products were digested with EcoRV and EagI and gel-purified. The purified digested PCR products were then ligated into EcoRV/EagI digested pA19 resulting in the pBS-DR1A construct. This vector was digested with EcoRV and EagI and the resulting HLA-DR1 α1-α2-hinge gene fragment will be subcloned into the pJW003 IgG shuttle vector as described in Example 2 which follows.

EXAMPLE 1D

Figures 5, 5A:
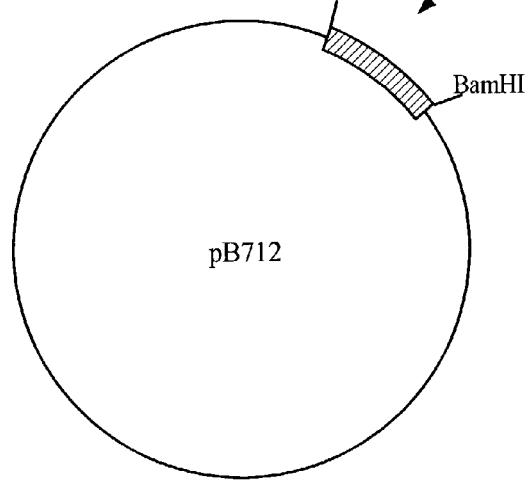
FIG. 5 shows the cloning scheme for human HLA-DR1 β1-β2 chain.
Figure 5B:
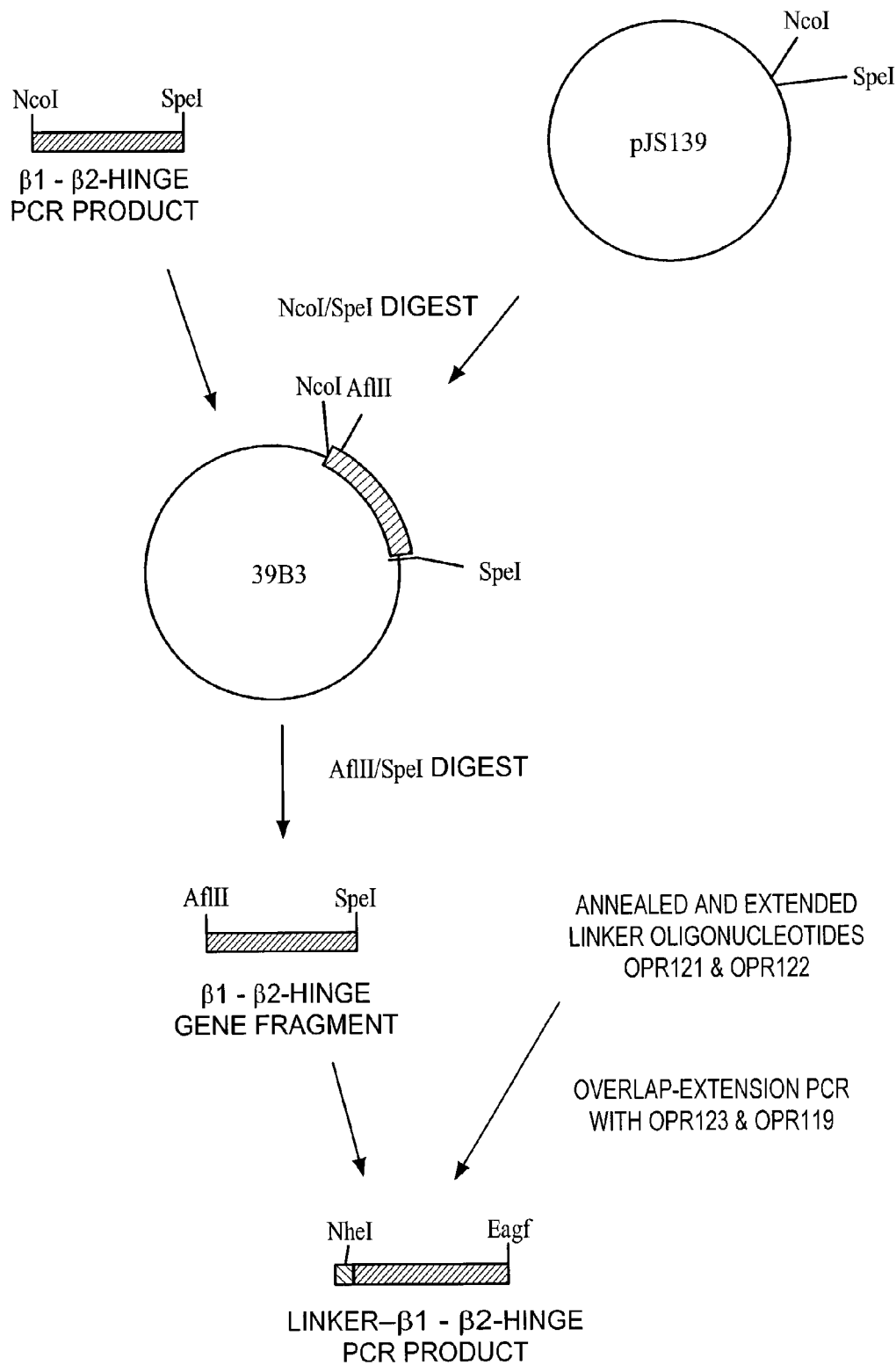
Figure 5C:
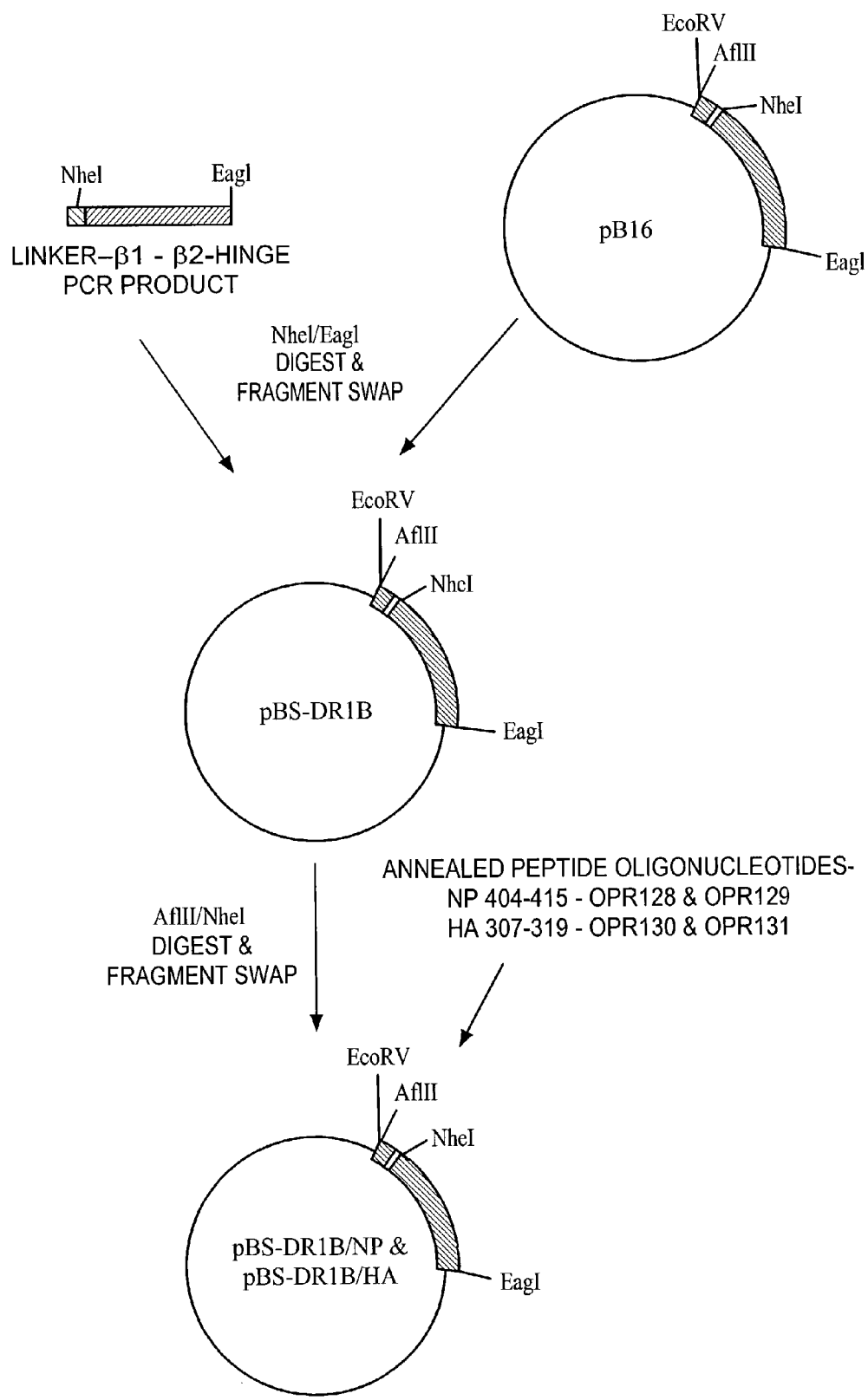
Figure 9F:
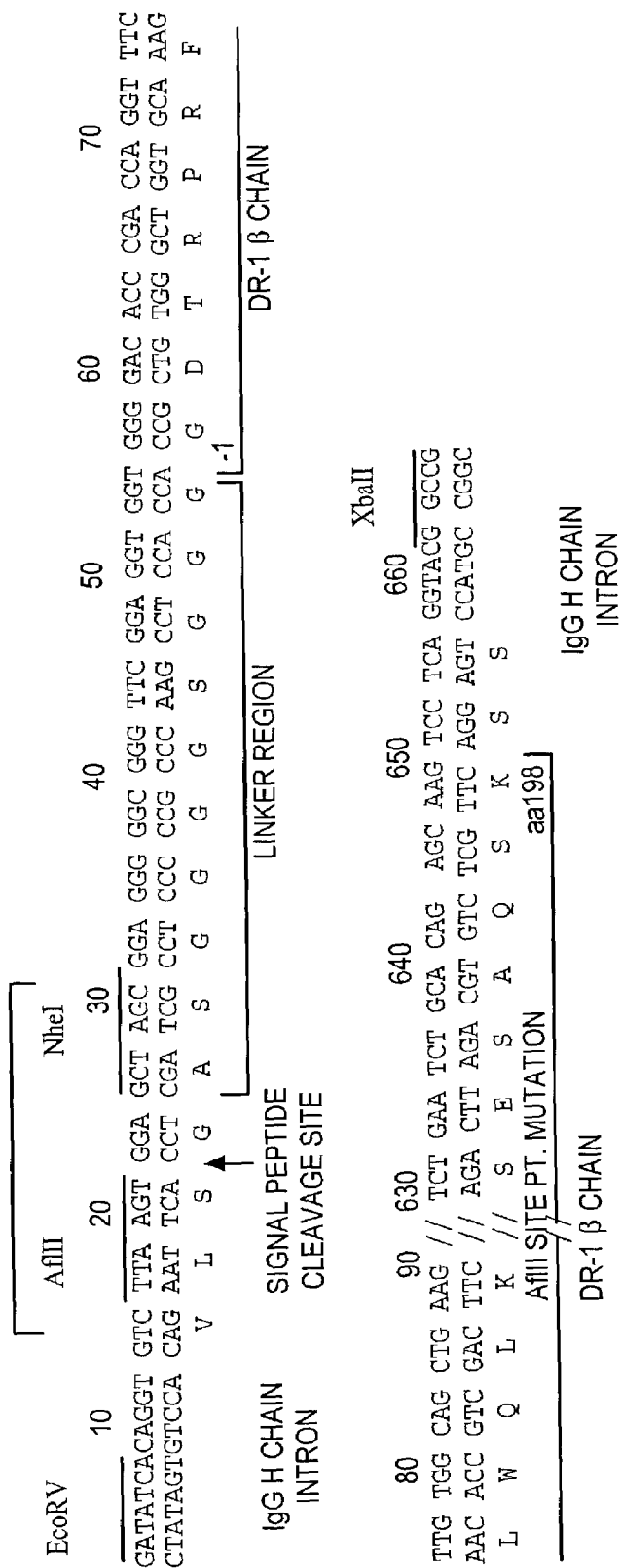

The following approach was employed to isolate the human HLA-DR1 β1-β2-hinge gene fragment (encoding aa1-198), attaching the linker sequence and inserting the oligonucleotides encoding the antigenic peptides. This approach also is depicted in FIG. 5 of the Drawings. Total cellular RNA was made by the procedure described above from 3×10⁶ BLCL-K68 cells obtained from a HLA-DR1 homozygous individual. Total RNA was converted to cDNA (20 μl) by using Superscript-MLV Reverse Transcriptase (GIBCO-BRL) and oligo dT-specific priming according to manufacturer's procedures. The initial PCR reactions were design to add restriction sites necessary for cloning the β1-β2-hinge gene fragment into bacterial expression vectors (for work that is not relevant to this application). PCRs were performed as described above except 5 μl of the template cDNA was used, the primers were DR1B-F and DR1B-B (sequences of those primers set forth in FIG. 8 of the Drawings) and the PCR conditions were 10 thermal cycles of 55° C. for 1 minute, 70° C. for 1 minute, and 96° C. for 1 minute followed by 25 step cycles of 70° C. for 1 minute and 96° C. for 1 minute. The β1-β2-hinge PCR product (approximately 610 bp) was digested with HindIII and BamHI, gel-purified and ligated into HindIII/BamHI digested JS143.3, resulting in the pB712 vector. This vector (0.5 ng) served as a template for further PCR amplifications using BF-NN and BB-S oligonucleotides as primers. The resulting β1-β2-hinge PCR product was digested with NcoI and SpeI, gel-purified and ligated into NcoI/SpeI digested pJRS139, resulting in the 39B3 vector. This vector served as the template for PCR amplification to add the linker sequence and restriction sites and flanking sequences necessary for cloning and expression in the mammalian expression vectors. Overlap-extension PCR was used to mutate an Af/II in the β1 region and add the linker sequence. The 39B3 vector was digested with Af/II and SpeI and the Af/II/SpeI β1-β2-hinge gene fragment was gel-purified. Two oligonucleotides coding for the linker and beginning of the β1 region (OPR121 and OPR122) were annealed, extended with Taq DNA polymerase resulting in a 78 bp fragment where the Af/II in the β1 region is mutated without changing the amino acid specified. This fragment (5 ng) was mixed with the Af/II/SpeI β1-β2-hinge gene fragment (5 ng) and overlap-extensions were carried out for 5 thermal cycles of 37° C. for 1 minute, 70° C. for 1 minute, and 96° C. for 1 minute. Following the addition of the PCR primers-OPR119 and OPR123, 5 additional thermal cycles of 37° C. for 1 minute, 70° C. for 1 minute, and 96° C. for 1 minute and 10 step cycles of 70° C. for 1 minute and 96° C. for 1 minute were carried out. The resulting linker-β1-β2-hinge PCR product (approximately 670 bp) contains a 5' EcoRV site and a 3' EagI site for cloning between the leader intron and J-region intron of the IgG heavy chain shuttle vector (see FIG. 9F of the Drawings). In addition, the PCR product has the IgG splice sites and leader sequences necessary for proper expression of the MHC-IgG fusion protein. To allow for cloning of the antigenic peptide sequences, an Af/II site was engineered into the end of the signal sequence and an NheI site was present at the beginning of the linker. The PCR products were digested with NheI and EagI, gel-purified, and ligated into NheI/EagI digested pB16 (see above), in order to swap the β chain gene fragments. The resulting vector was designated pBS-DR1β. To insert sequences encoding the class II HLA-DR1 binding peptides, oligonucleotides are annealed and ligated into Af/II/NheI digested pBS-DR1β. The NP 404-415 peptide having the sequence QISVQPAFSVQ (SEQ ID NO: 7) is encoded by oligonucleotides OPR128 and OPR129, and HA 307-319 having the sequence PKYVKQNTLKLAT (SEQ ID NO: 8) is encoded by OPR130 and OPR131. The sequences of OPR128, OPR129, OPR130 and OPR131 are set forth in FIG. 8 of the Drawings. The respective constructs in the pBS-DR1β backbone are designated pBS-DR1β/NP and pBS-DR1β/HA. These vectors are digested with EcoRV and EagI and the resulting peptide-linker-β1-β2-hinge gene fragment are subcloned into the pJW009 IgG shuttle vector as described in Example 2 which follows.

EXAMPLE 1E

Figure 6:
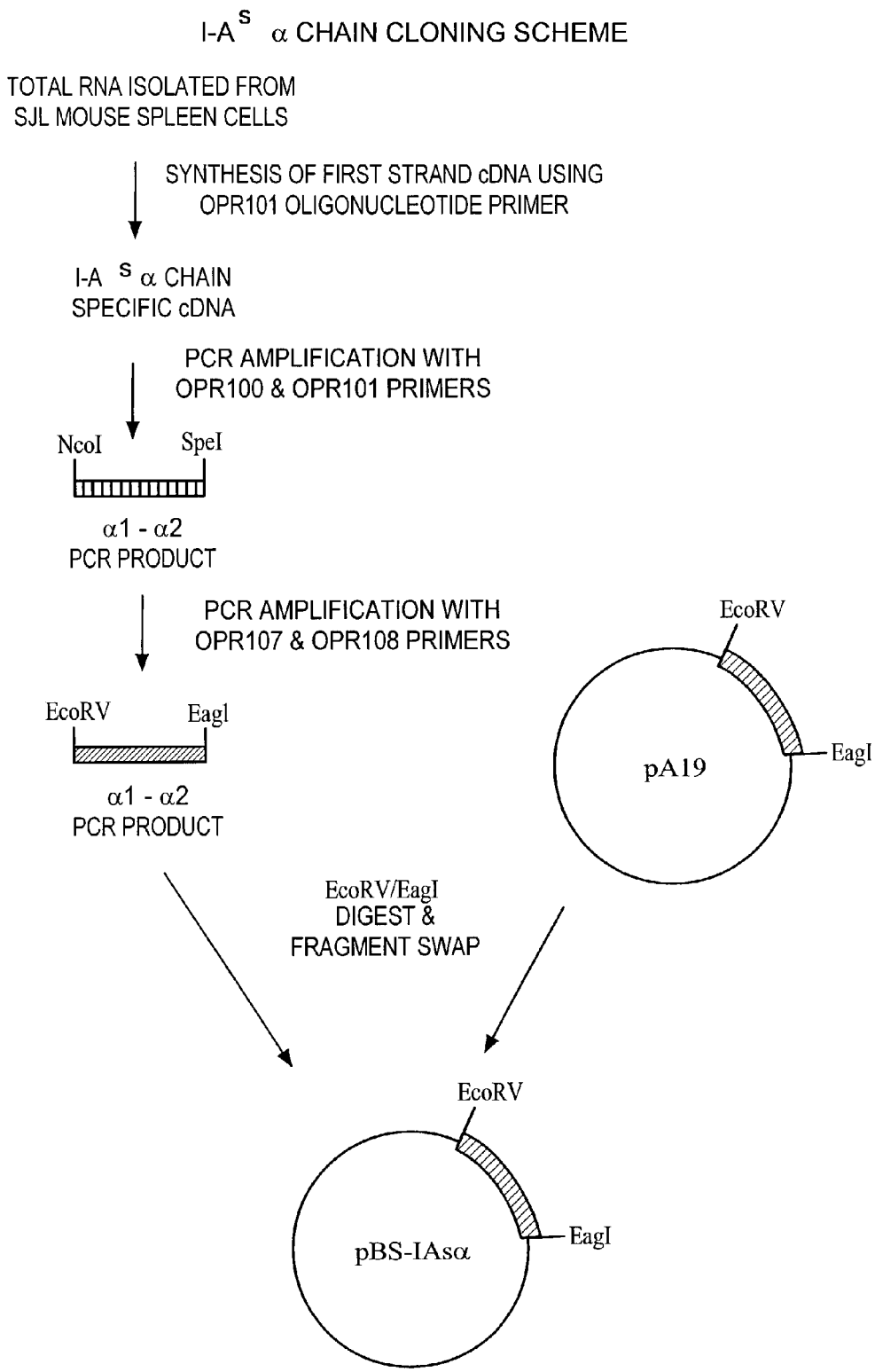
FIG. 6 shows the scheme for isolating the I-A$^s$ α1-α2 gene fragment and the cloning thereof.

The following approach is employed to isolate the I-A$^s$ α1-α2 gene fragment (encoding aa1 to 182). FIG. 8 lists the oligonucleotides primers used. FIG. 6 of the Drawings also depicts the protocol. The total RNA was prepared from the spleen of an SJL mouse by the same procedure used to prepare RNA from cell cultures. The RNA (10 μg) was converted to cDNA (50 μl) by using MLV Reverse Transcriptase (GIBCO-BRL) and α2-specific priming according to manufacturer's procedures. PCRs were performed as described above except 6 μl of the template cDNA was used, the primers were OPR100 and OPR101 (sequences thereof set forth in FIG. 8 of the Drawings) and the PCR conditions were 5 thermal cycles of 55° C. for 30 seconds, 72° C. for 30 seconds, and 96° C. for 1 minute followed by 20 step cycles of 72° C. for 1 minute and 96° C. for 1 minute. The initial α1-α2 PCR product (approximately 550 bp) was reamplified using the PCR primers OPR107 and OPR108 for 5 thermal cycles of 55° C. for 30 seconds, 72° C. for 30 seconds, and 96° C. for 1 minute followed by 10 to 15 step cycles of 72° C. for 1 minute and 96° C. for 1 minute. The resulting α1-α2 PCR product (approximately 590 bp) contains a 5' EcoRV site and a 3' EagI site for cloning between the leader intron and J-region intron of the IgG kappa chain shuttle vector (see FIG. 9C of the Drawings). In addition, the PCR product has the IgG splice sites and leader sequences necessary for proper expression of the MHC-IgG fusion protein. The PCR products were digested with EcoRV and EagI and gel-purified. The purified digested PCR products will be ligated into EcoRV/EagI digested pA19 (see above) in order to swap the α chain regions. The resulting vector, pBS-IASα is digested with EcoRV and EagI and the α1-α2 gene fragment is subcloned into the pJW003 IgG shuttle vector as described in Example 2 which follows.

EXAMPLE 1F

The following strategy is employed to isolate the I-A$^s$ β1-β2 gene fragment (encoding aa1 to 189), attaching the linker sequence and inserting the oligonucleotides encoding the antigenic peptides. This approach also is depicted in FIG. 7 of the Drawings. The SJL spleen total RNA (10 μg) was converted to cDNA by using MLV Reverse Transcriptase (GIBCO-BRL) and β2-specific priming according to manufacturer's procedures. Of the 50 μl of cDNA generated, 6 μl was used as template DNA for PCR. The reactions were carried out as described above except oligonucleotide primers were VW310 and OPR106 (FIG. 8) and the PCR conditions were 5 thermal cycles of 62° C. for 30 seconds, 72° C. for 30 seconds, and 96° C. for 1 minute followed by 21 step cycles of 72° C. for 1 minute and 96° C. for 1 minute. In order to add the linker sequences, the initial β1-β2 PCR product (approximately 570 bp) was reamplified using the PCR primers-VW309 and OPR106 for 3 thermal cycles of 50° C. for 30 seconds, 72° C. for 30 seconds, and 96° C. for 1 minute followed by 10 step cycles of 72° C. for 1 minute and 96° C. for 1 minute. See FIG. 8 for sequences of VW309 and OPR106 primers. The linker-β1-β2 PCR product (approximately 640 bp) was digested with NheI and EagI, gel-purified, and ligated into NheI/EagI digested pB16 (see above), in order to swap the β chain gene fragments. The resulting vector, designated pBS-IASβ, contains the EcoRV/ EagI linker-β1-β2 fragment needed for cloning between the leader intron and J-region intron of the IgG kappa chain shuttle vector (see FIG. 9D of the Drawings). To insert sequences encoding the class II I-A$^s$ binding peptides, oligonucleotides are annealed and ligated into Af/II/NheI digested pBS-IASβ. The MBP 91-103 peptide (HYGSLPQKSQHGR) (SEQ ID NO: 9) is encoded by oligonucleotides VW315 and VW316, PLP 139-151 (HSLGKWLGHPDKF) (SEQ ID NO: 10)) by VW313 and VW314 and MBP 1-14 (MASQKRPSQRSKYL) (SEQ ID NO: 11) by VW317 and VW318. Sequences of those oligonucleotides are set forth in FIG. 8 of the Drawings. The respective constructs in the pBS-IASβ backbone are designated pBS-IASβ/MBP91, pBS-IASβ/PLP and pBS-IASβ/ MBP1. These vectors are digested with EcoRV and EagI and the resulting peptide-linker-β1-β2 gene fragment is subcloned into the pJW009 IgG shuttle vector as described in Example 2 which follows.

EXAMPLE 2

Preparation of Expression Vector of MHC Fusion Complex of the Invention Linked to Immunoglobulin The following protocol includes expression of soluble peptide-linked MHC class II/immunoglobulin molecules as chimeric protein. The objective is to construct an antibody-like molecule that has kappa constant domain plus the MHC class II α chain region and the murine IgG2b constant domain joined with the MHC class II β chain covalently linked to peptides of interest. These constructs are then cloned into separate mammalian expression vectors and used to transfect lymphoid derived cell lines, i.e. J558.

Figure 10A:
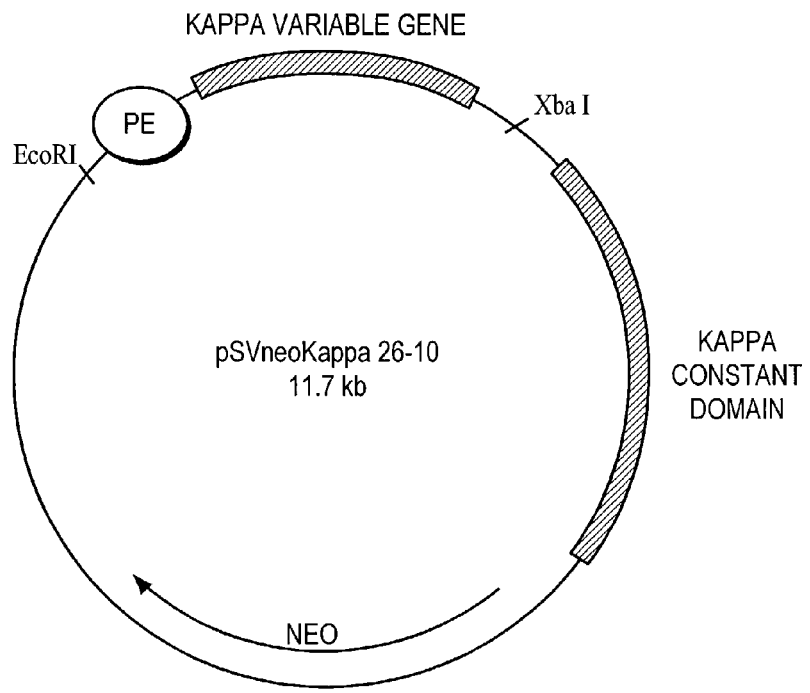
FIGS. 10A and 10B show mammalian cell expression vectors used in the Example 2 which follows.

Two commonly used mammalian expression vectors were modified so that the chimeric constructs could be cloned and expressed. The original vectors are described by Near et al., Molecular Immunology 27: 901–909 (1990). FIG. 10A of the Drawings shows the 11.7 Kb pSVneoKappa 26-10 light chain expression vector which contains pBR322 as backbone and the neomycin resistance gene. Furthermore, it has a 6.7 Kb piece of germline kappa DNA that was initially cloned as genomic DNA into lambda. A 2.7 Kb EcoRI-XbaI fragment contains the Ig kappa promoter and enhancer, the leader sequence and its intron, the variable region exon rearranged with JK1, the remaining JK exons and introns, and part of the major intron separating the variable region from kappa constant region as shown in FIG. 11A of the Drawings.

Figure 10B:
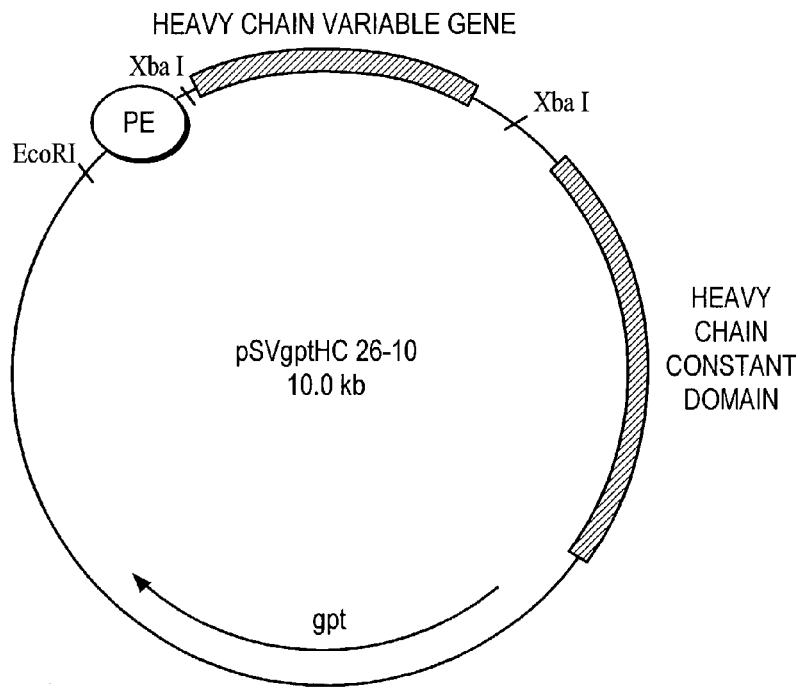

The peptide-linked β chain plus the IgG2b immunoglobulin constant region has been cloned into pSVgptHC 26-10 referred to as pJW010. This mammalian cell vector was originally described by Mulligan et al. (Science, 209:1422–1427, 1980); and later by Near et al., supra. Briefly, pSVgptHC 26-10, shown in FIG. 10B of the Drawings, is 10 Kb and contains the E. coli xanthine-guanine phosphoribosyl transferase gene (gpt) under the control of the SV40 early promoter. Germline murine IgG2b constant domain was cloned into pSVgpt as a BglII-XbaI fragment. Another change to the vector made by Near et al., supra, was cloning of a 0.7 Kb EcoRI-XbaI piece that contains the Ig heavy chain promoter/enhancer. These changes left the pSVgptHC 26-10 vector with an XbaI cloning site that was used to clone a 1.7 Kb XbaI fragment by Near et al. This 1.7 Kb insert contains an Ig heavy chain leader sequence and its intron, the variable exon linked to the JH4 domain, and part of the major intron residing between the V region and C region. Furthermore, the 1.7 Kb fragment is the target sequence DNA that has been mutated. In summary, to make cloning of the α and β chains possible several mutations to the 2.7 Kb and 1.7 Kb fragments had to be completed as described below.

Figure 12:
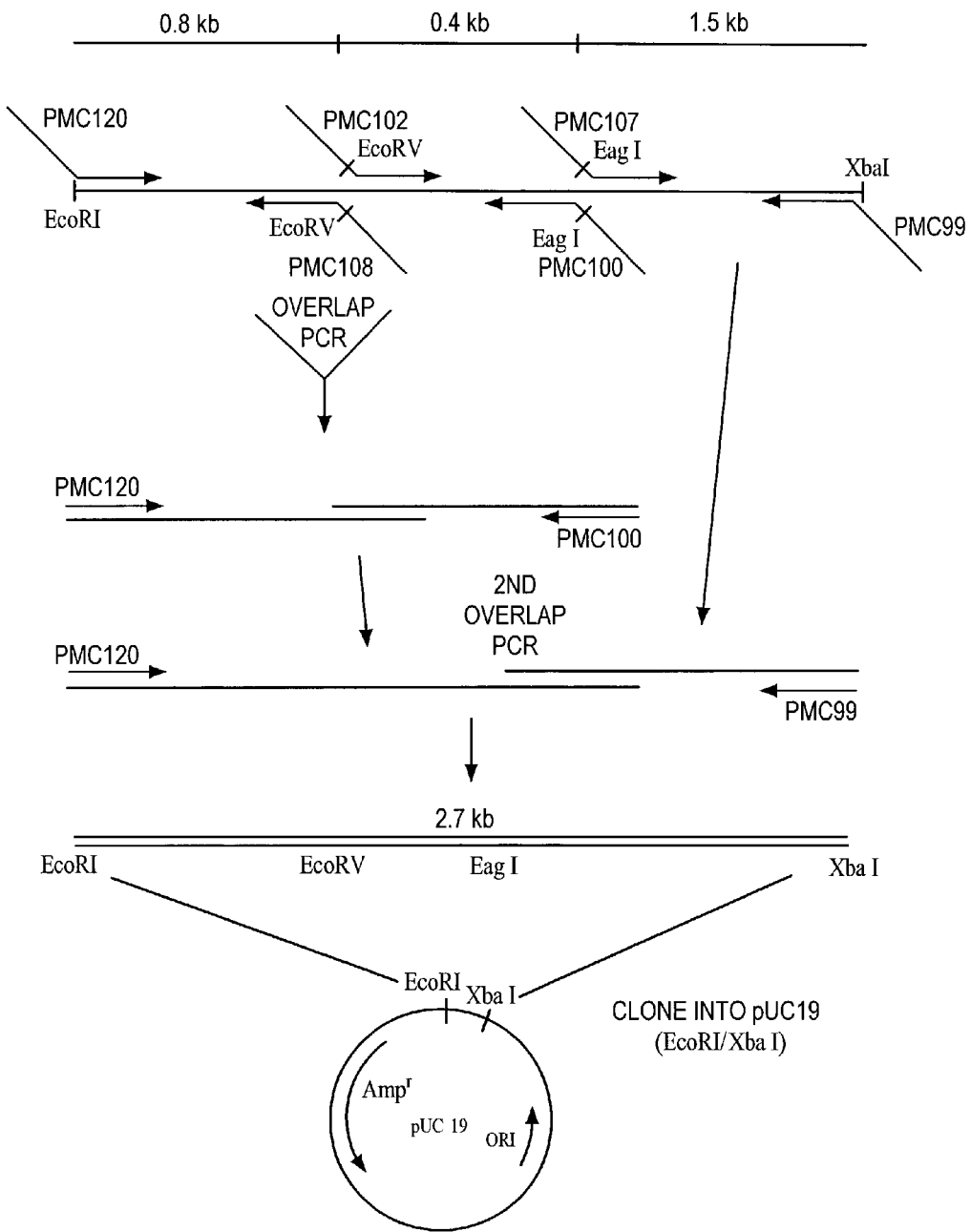
FIG. 12 shows the scheme for introducing restriction sites into the kappa chain 2.7 kb insert via PCR site directed mutagenesis.

The strategy for preparing the pJW004 vector for cloning and expression of the α chain gene was to make two site mutations within the 2.7 Kb insert is described in FIG. 11A. A sample of pJW004 has been deposited with the American Type Culture Collection (ATCC), Rockland, Md. USA and has received ATCC number 75832. An EcoRV site was created at eight nucleotides 5' of the kappa variable region while an EagI site was added at eight nucleotides 3' of the JK1 domain. These mutations would enable directional cloning of the MHC class II α gene into the vector for expression of the α chain/kappa constant region fusion molecule. Polymerase chain reaction (PCR) site directed mutagenesis was used to add these two restriction sites, and the primers and steps taken to make these changes are shown in FIG. 12 of the Drawings. The 2.7 Kb piece of DNA was cloned from pUC19 into M13 mp18 as an EcoRI-XbaI fragment that was linearized with EcoRI and used as template (5 ng/100 ul mixture) in the PCR reactions. The 2.7 Kb insert was divided into three PCR fragments by designing primers that would specifically amplify three different length PCR products, which included a 0.8 Kb EcoRI to EcoRV fragment, a 0.4 Kb EcoRV to EagI fragment, and a 1.5 Kb EagI to XbaI fragment. The PCR primers used to amplify each fragment are summarized and the underlined sequence corresponds to the restriction endonuclease site. Primers PMC 120 [5'GCAGAAGAATTCGAGCTCGG-CCCCCAG3'] (SEQ ID NO: 12) containing an EcoRI site and PMC108 [5'GATGATATCAGAGAGAAATAC-ATACTAACACAC3'] (SEQ ID NO: 13) containing an EcoRV site were used to amplify the 0.8 Kb product, while primers PMC 100 [5'CGGAAGAAAGAGACTT CGGCCGCTACTTAC3'] (SEQ ID NO: 14) containing an EagI site and PMC 102 [5'GTGTGTTAGTATG-TATTTCTCTCTGATATCTTCAGCTTCCAGCAGTG3'] (SEQ ID NO: 15) containing an EcoRV site were used to PCR the 0.4 Kb fragment. The final piece to be amplified was 1.5 Kb in length and was amplified using primers PMC 99 [5'TCTTCTAGAAGACCACGCTAC3'] (SEQ ID NO: 16) containing an XbaI site and PMC 107 [5'GATGATATC CGGCCGAAGTCTCTTTCTTCCGTTGTC3'] (SEQ ID NO: 17) containing an EagI site. Two overlapping PCR reactions were done with the three PCR products to construct the mutated 2.7 Kb insert. The first overlap PCR resulted in amplifying a 1.2 Kb product using primers PMC 100 and PMC 120 and the 0.8 Kb and 0.4 Kb fragments. A second overlapping PCR reaction was done using the gel purified 1.2 Kb DNA and the 1.5 Kb piece and primers PMC99 and 120. From this reaction, a 2.7 Kb fragment was produced that was later digested with EcoRI and XbaI and cloned into pUC19. DNA from ligation reaction mixtures was transformed into DG101 cells and 36 colonies were picked and screened by double digests using EcoRV-EagI and EcoRI-XbaI enzymes.

Figure 13:
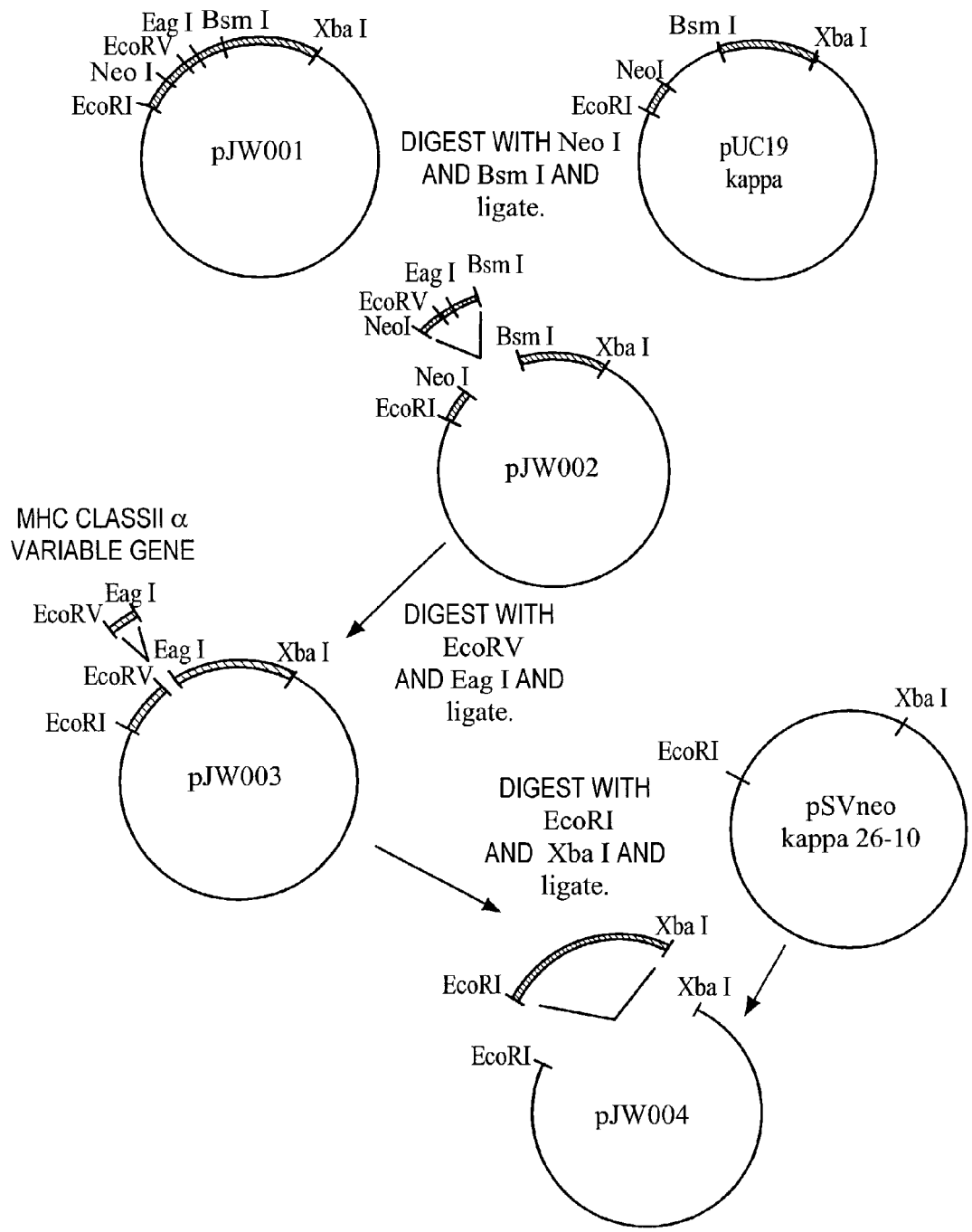
FIG. 13 shows the scheme for constructing a fusion gene encoding the MHC (class IIα)/kappa chain constant region in mammalian cell expression vector.

After detecting several positive clones by restriction mapping, three clones were chosen for sequencing. By using primers PMC-33, 77, 111, and 114 (sequences of those primers set forth in FIG. 14 of the Drawings), 900 bp of sequence data was obtained. The region where correct sequence was found to include 400 bp of DNA between the EcoRV and EagI sites and 300 bp 5' of the EcoRV site and 200 bp 3' of the EagI site. One clone, pJW001, had good sequence that was different from the consensus sequence at five bases. A disturbing observation made after restriction mapping and from reviewing sequence data generated using M13 universal primers was that insert DNA cloned into pUC19 and transformed into DG101 was deleted. These deleted sequences poised a problem since much of the transcriptional machinery was deleted along with the major intron located between the EagI site and XbaI. To salvage the piece of DNA that contained the mutated sites, EcoRV and EagI, clone #12 insert was digested with two unique cutters, NcoI and BsmI. The NcoI site is located about 300 bp 5' from the EcoRV site, and a BsmI site is present about 200 bp 3' of the EagI site. Therefore, as seen in FIG. 13 of the Drawings, the 0.9 Kb NcoI-BsmI piece was cut from pJW001 and cloned into pUC19/kappa 26-10 insert which did not have the EcoRV and EagI sites but did have the unique sites NcoI and BsmI. To confirm whether the correct size insert had been cloned into pJW002, an aliquot of pJW002 DNA was digested with three different pairs of restriction enzymes, EcoRI-XbaI, NcoI-BsmI, and EcoRV-EagI.

To prevent recombination events from occurring again, the strain of E. coli was changed from DG101 to XL1-B, a recA negative host. At this step, the insert DNA contained the two site mutations and cloning of the MHC class II α gene could proceed.

pJW002 DNA was digested with EcoRV and EagI, dephosphorylated with calf intestinal alkaline phosphatase (CIAP), and then gel purified. The isolated vector DNA was then used in ligations with the gel purified 577 bp EcoRV-EagI cut α chain I-A$^d$ gene. Ligation, transformation and screening of 10 colonies yielded a single positive clone which was digested with two pairs of enzymes, EcoRI-XbaI and EcoRV-EagI. The positive clone, pJW003 (pUC19 mutated kappa containing the α gene), was grown up and the DNA was Qiagen purified.

Figure 16A:
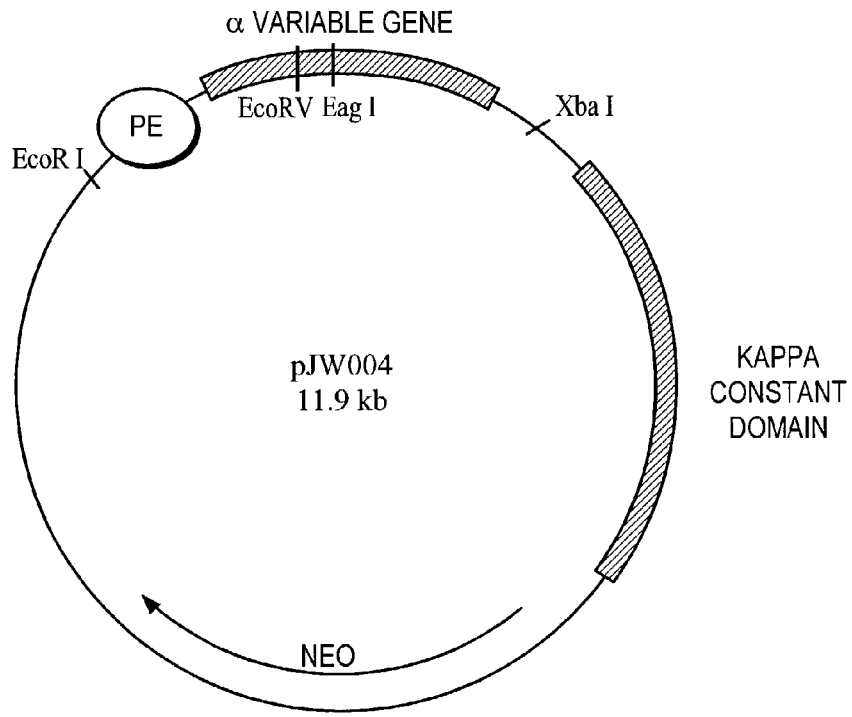
FIGS. 16A and 16B show vectors of the invention for expression of MHC II/Ig chimeric proteins.

A triple digest of pJW003 DNA was done using EcoRI, XbaI, and HindIII. The cut DNA was then treated with phenol chloroform, precipitated with ethanol, and washed with 70% ethanol after which the DNA was digested with ScaI and treated with CIAP. pUC19 DNA migrates at 2.7 Kb on an agarose gel which makes it difficult to separate pUC DNA from the desired insert DNA. However, pUC19 has a unique ScaI site that cuts and gives two smaller size fragments that can be separated on an agarose gel away from the 2.9 Kb insert DNA. After gel purification, the 2.9 Kb α I-A$^d$ gene insert was ligated in EcoRI-XbaI gel purified pSVneo vector to make pJW004 (FIG. 16A). Ligations were transformed into DG103. Qiagen maxi-preparations were done to isolate large amounts of vector DNA so that pJW004 could be transfected into mammalian cells.

The strategy for cloning the MHC β variable gene into the pSVgpt expression vector was to make four mutations within the 1.7 Kb XbaI piece described in FIG. 11B. The four mutations included two EcoRV site deletions, one situated 68 nucleotides 5' of the leader sequence exon and the other site located at 27 nucleotides 5' of the variable region. The other two mutations were site additions and involved an EcoRV site eight nucleotides 5' of the variable region and an EagI site eight nucleotides 3' of the JH4 domain. M13 site directed mutagenesis was used to make the mutations on the 1.7 Kb insert. The approach was to subclone the 1.7 Kb XbaI fragment from pSVgptHC26-10 and clone it into M13. Site directed mutagenesis was done using the BioRad Muta-Gene in vitro Mutagenesis Kit that is based on the highly efficient and simple method of Kunkel. This method employs a special *E. coli* strain that is deficient for dUTPase (dut) and uracil-N-glycosylase (ung). These deficiencies allow random uracil substitutions for thymine in the M13 ssDNA. When the double stranded DNA, or replicative form (RF), is transformed back into a wild type host strain the uracil-N-glycosylase degrades uracils present in the original template so that only the strand of DNA that carries the site specific mutation is replicated thereby generating a high efficiency of positive clones.

The steps taken in making the mutations are shown in FIG. 15. Briefly, primer PMC 26 [5'CAGGGTTATC AACACCCTGAAAAC3'] (SEQ ID NO: 18) was used to delete the EcoRV site located 68 nucleotides 5' of the leader sequence exon, and contained a single base change, indicated by the underlined nucleotide, from A to T. The deletion of the second EcoRV site at 27 nucleotides 5' of the variable region was done with primer PMC 28 [5'GTCACAG TTATCCACTCTGTC3'] (SEQ ID NO: 19) and again was a simple point mutation change from A to T. Primer PMC 96 [5'CCGTCTCCTCAGGTACGGCC GGCCTCTCCAGGTCTTCG3'] (SEQ ID NO: 20) contained the EagI site mutation, which consisted of four base changes indicated by the underlined nucleotides. Finally, primer PMC 97 [5'CACAGTTATCCACTCTGTCTTT GATATCACAGGTGTCCT3'] (SEQ ID NO: 21) was used to create the EcoRV site by changing four nucleotides as shown.

Figure 16B:
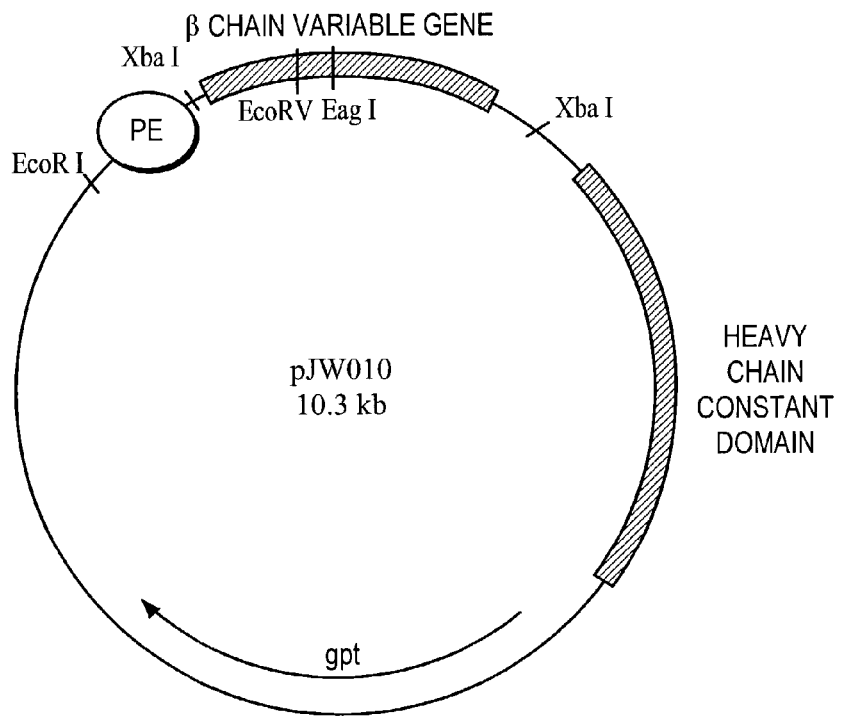

The mutated 1.7 Kb insert was then digested with EcoRV-EagI, CIAP treated, gel purified and used in ligations with the EcoRV-EagI cut, gel purified MHC class II β gene. Other variants, such as the Ova 323-339/I-A$^d$ β1-β2 gene fragment described in Example 1 above, were also cloned into the EcoRV -EagI site and grown up in M13. FIG. 15 of the Drawing describes the strategy for cloning the MHC class II β variable and variants into the vector pJW009. After cloning into pJW009, the DNA was digested with XbaI to drop out the XbaI fragments containing the various peptide-linked β variable gene and was subcloned into the mammalian expression vector pJW010 as shown in FIG. 16B. Since directional cloning was not possible, screening for positive clones was done by digesting with EcoRI-EcoRV. Positive clones containing the β genes and other peptide-linked β chain variants have been isolated and the DNA has been Qiagen purified. These have been designated pHB27, pHB310, pHB412 and pHB58 for the I-A$^d$ β chain construct containing no peptide, the Ova 323-339 peptide, the Ova: H331R peptide and the Ova:A331Y peptide, respectively (see Example 1B). Samples of pHB27, pHB310, pHB412 and pHB58 have been deposited with the American Type Culture Collection (ATCC), Rockville, Md. USA and have received ATCC numbers 75833, 75835, 75836 and 75834, respectively.

Transfection of lymphoid derived cells such as J558 and NS0 cells, can be done essentially as described by Near et al. 20 μg of both, pJW004 and pJW010, can be co-transfected into either J558 or NS0 cells by electroporation using the BioRad gene pulser. Stable cell lines are selected within 7 to 10 days. Expression of the chimeric MHC class II/Ig molecule of the invention is determined by an ELISA specific for detecting murine IgG2b constant region and/or a western blot analysis can be done. Finally, the expressed protein is purified by Protein-A or -G affinity chromatography.

EXAMPLE 3

Construction of the Full-length Peptide-linked MHC Expression Vectors of the Invention and Expression Vectors for Co-stimulatory Factors (B7-1 and B7-2)

Figure 17B:
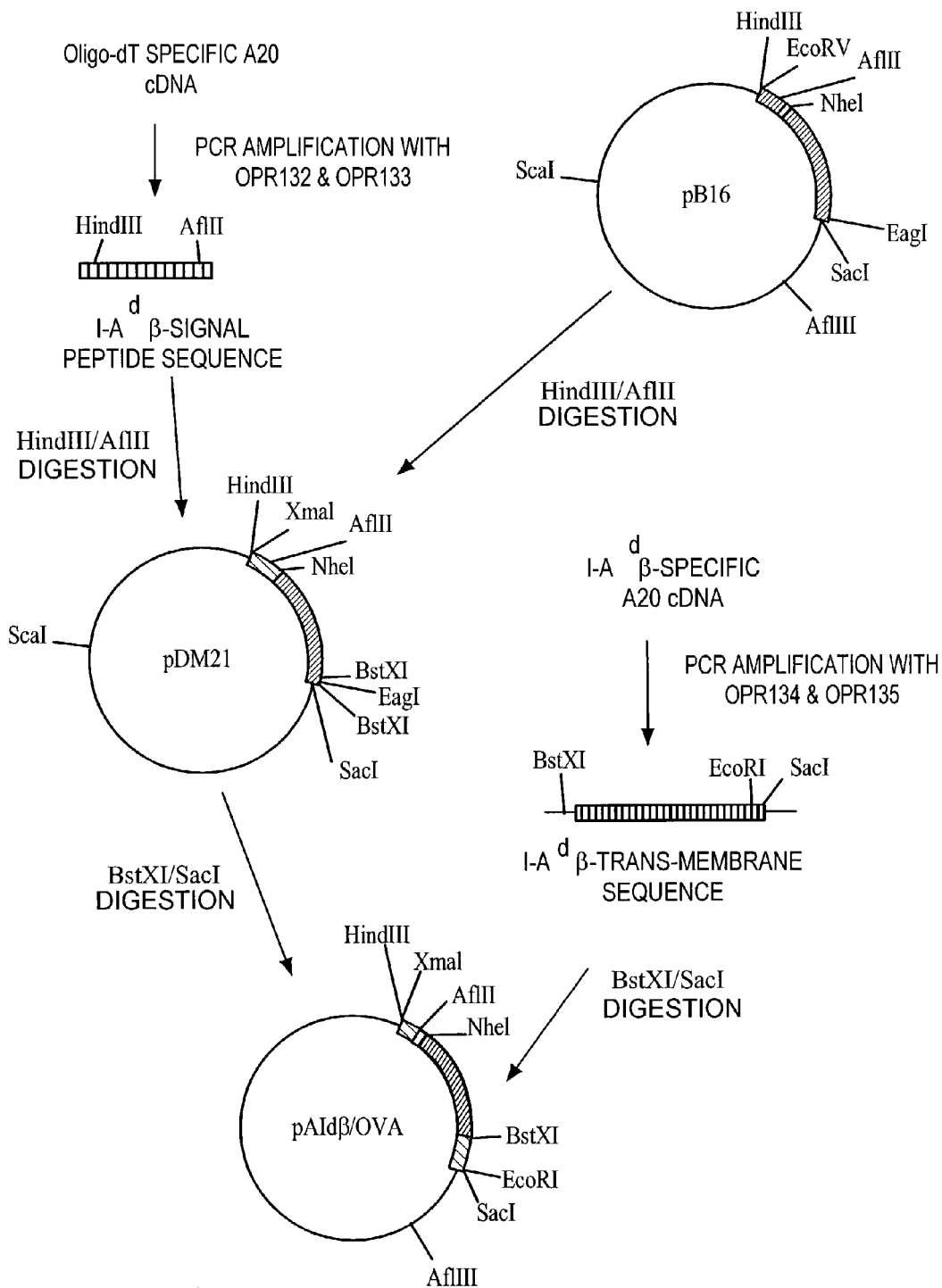
FIG. 17 shows the scheme for construction of a full length MHC fusion complex expression vector of the invention.
Figure 17C:
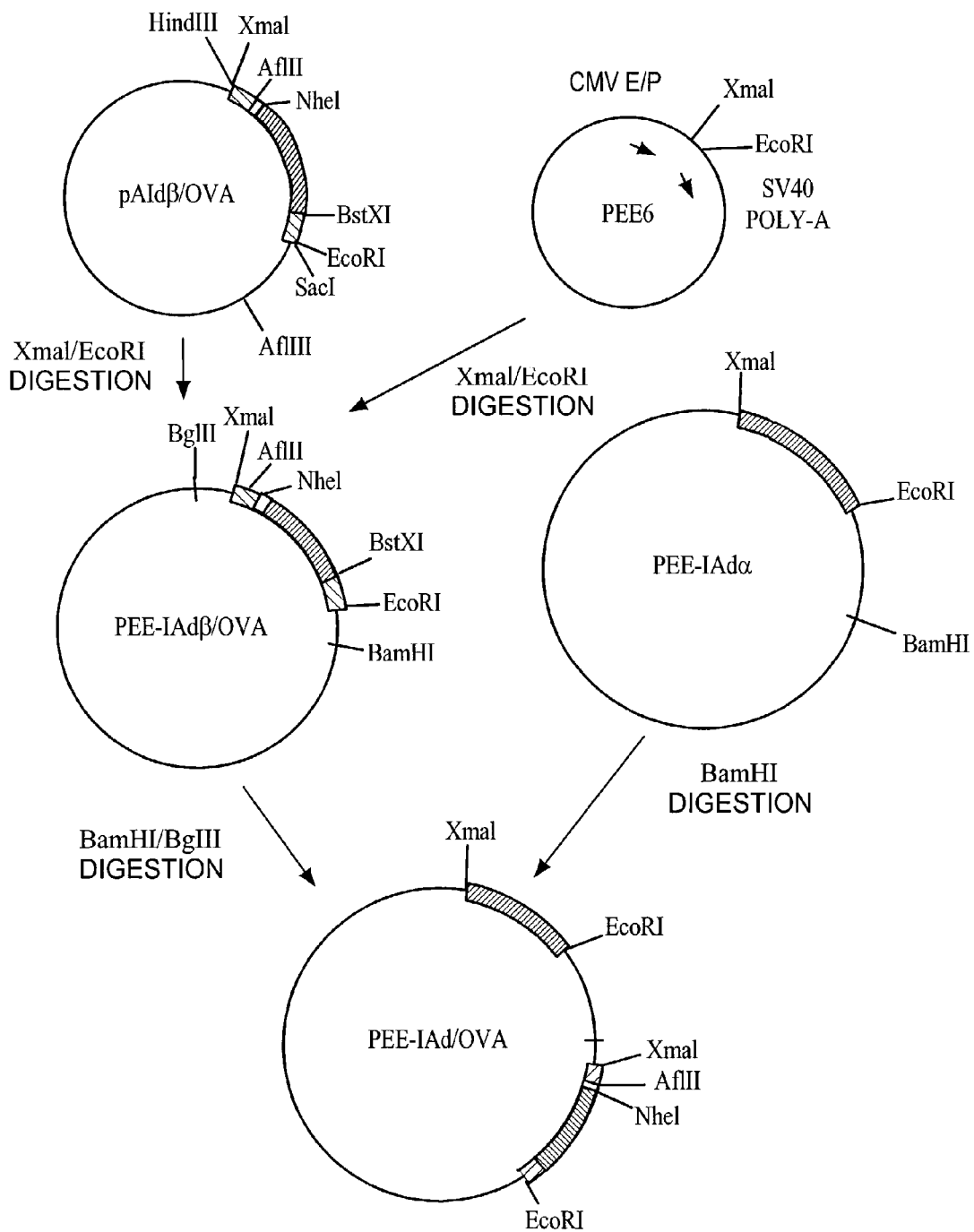

Vectors capable of co-expressing the full-length I-A$^d$ α chain and peptide-linked I-A$^d$ β chain molecules are suitably constructed by the procedures outlined in FIG. 17 of the Drawings. In order to isolate the full-length I-A$^d$ α chain, A20 total RNA (5 μg) was converted to cDNA by using Superscript-MLV Reverse Transcriptase (GIBCO-BRL) and α chain TM-specific priming according to manufacturer's procedures. This cDNA was used as the template for PCR amplification using an a chain leader-specific primer OPR136 (sequence of that primer set forth in FIG. 8) and an a chain TM-specific primer OPR139 (sequence of that primer set forth in FIG. 8) by the PCR conditions described in Example 1 above. The resulting PCR product has about 800 bp and contains a 5' XmaI site and a 3' EcoRI site for cloning between the CMV promoter and SV40 poly-A sites of the PEE13 mammalian expression vector (Celltech). In addition, this fragment carries a Kozak consensus sequence for efficient translational initiation (see FIG. 18A of the Drawings). The PCR product was digested with XmaI and EcoRI, gel-purified and ligated into XmaI/EcoRI digested PEE13, to give the PEE-IA$^d$α vector. The full-length peptide-linked β chain fragment was constructed by inserting the leader and TM sequences into the Ova 323-339 and the HEL 74-86 peptide-linker-β1-β2 vectors (pB16 and pB4, respectively) described in Example 1 above. A20 total RNA (5 μg) was converted to cDNA by using Superscript-MLV Reverse Transcriptase (GIBCO-BRL) and either oligo dT-specific or β chain TM-specific priming according to manufacturer's procedures. These cDNAs were used as the template for PCR amplifications using either a pair of β chain leader-specific primers (OPR132/OPR133) (sequences of those primers set forth in FIG. 8 of the Drawings) or a pair of β chain TM-specific primers (OPR134/OPR135) (sequences of those primers set forth in FIG. 8 of the Drawings). The 110 bp β leader PCR product contains 5' HindIII and XmaI sites and a 3' Af/II site for cloning into the pBC1 and pB16 peptide-linker-β1-β2 vectors. The inclusion of the Af/II site changes the last two amino acids of the I-$A^d$ β chain leader to those found in the IgG leader. The β leader PCR product was digested with HindIII and XmaI, gel-purified and ligated into HindIII/Af/II digested pB16, to give pDM21. The 180 bp β TM PCR product contains a 5' BstXI and sites and 3' XmaIII and EcoRI sites for cloning into pDM21. The β TM PCR product was digested with BstXI and EcoRI, gel-purified and ligated into BstXI/EcoRI digested pDM21, to give the pI$A^d$β/OVA vector, pVW229. The Ova peptide oligonucleotide was swapped with the HEL peptide oligonucleotide described in Example 1 above to generate the pI$A^d$β/HEL vector. These vectors were digested with XmaI and EcoRI to generate the full-length peptide linked β chain gene fragments for cloning between the CMV promoter and SV40 poly-A sites of the PEE6 mammalian expression vector (Celltech). These fragments also carry the Kozak consensus sequence for efficient translational initiation (FIG. 18B). The resulting vectors PEE-I$A^d$β/OVA and PEE-I$A^d$β/HEL were digested with Bg/II and BamHI. The CKMB promoter/peptide-β chain fragments were gel-purified and ligated into BamHI digested PEE-I$A^d$α, to generate the final PEE-I$A^d$/OVA and PEE-I$A^d$/HEL expression vectors. A vector without any peptide oligonucleotide, PEE-I$A^d$, was also constructed and used as a control.

In order to clone the B7-1 and B7-2 genes, cDNAs can be generated from total RNA isolated from activated mouse spleen cells or from mouse lymphoma cell lines. These cDNAs serve as templates for PCR amplification using either B7-1 or B7-2 specific primers. The PCR products generated carry 5' and 3' NotI sites for cloning between the CMV promoter and SV40 poly-A sites of pCMVβ mammalian expression vector (Clonetech). These fragments also carry the Kozak consensus sequence for efficient translational initiation.

EXAMPLE 4–11

Assays and Methods of the Invention

General Comments

One or more of several assay systems are suitably employed to test the ability of the soluble MHC fusion complexes of the invention to modulate the activity of T cells and are exemplified in the examples which follow. In a first exemplary assay a mouse MHC class II I-$A^d$/Ig fusion molecule is linked to an antigenic peptide from hen egg lysozyme (HEL 74-86), chicken ovalbumin (Ova 323-339) or one of two single-substitution analogues of the Ova peptide—Ova H331 R or Ova A332Y. The HEL 74-86, Ova 323-339 and Ova H331R peptides are known to bind I-$A^d$ whereas the Ova A332Y analogue will serve as a non-binding control [Buus, S. et al. (1987) Science 235: 1353–1358; Sette, A. et al. (1987) Nature 328: 395–399]. The $His_{331}$ is believed to not be important for MHC binding but it is critical for T cell stimulation and the Ova H331R/I-$A^d$/Ig complex will serve as a TcR antagonist for T cell stimulation. The mouse D0 11.10 T-cell hybridoma specifically recognizes the Ova 323-339/I-$A^d$ complex and is stimulated to produce IL-2. The assay, outlined in Example 4 below, uses the soluble Ova 323-339/I-$A^d$/Ig to suppress T-cell stimulation by APCs loaded with the Ova peptide. Further effects of the soluble peptide-linked MHC/Ig molecules on Ova-specific T-cell proliferation are examined in Example 5. In addition, the effects of the soluble Ova 323-339/I-$A^d$/Ig and soluble HEL 74-86/I-$A^d$/Ig on T cell function in vivo can be examined as described in Examples 6 and 7. Mice are injected with the antigenic HEL and Ova peptides (linked to KLH carrier) and either the soluble Ova 323-339/I-$A^d$/Ig or soluble HEL 74-86/I-$A^d$/Ig molecules. Inhibition of in vivo T cell-dependent antibody responses and proliferation of Ova-specific T cells and HEL-specific T cells will be characterized as described in Examples 6 and 7.

A further model is exemplified by an assay that involves linking a peptide from the influenza nucleoprotein (NP 404-415) to the human class II HLA-DR1/Ig molecules (see Example 5). The soluble NP 404-415/DR1/Ig molecules are analyzed for their ability to inhibit APC/NP 404-415-dependent proliferation of a human T cell line, K68-36. Soluble DR1/Ig molecules linked to a different HLA-DR1 binding peptide (HA 307-319) is used as a negative control.

In an additional model system, the ability of soluble peptide-linked MHC/Ig molecules to suppress autoimmunity is examined. As an animal model for multiple sclerosis, SJL mice can be induce to develop experimental allergic encephalomyelitis (EAE) following immunization with encephalitogenic proteins or peptides or following adoptive transfer of $T_H$ cells specific to these antigens. As described below, the encephalitogenic regions of myelin basic protein (MBP 91-103) and of proteolipoprotein (PLP 139-151) are each linked to the mouse class II I-$A^s$/Ig molecule. The non-binding MBP 1-14 peptide serves as a negative control. The soluble peptide-linked I-$A^s$/Ig molecules is administered to EAE-induced mice. The ability to reduce the incidence and severity of EAE is determined as described in Example 8 which follows. In addition, the immuno-suppressive effects of TcR antagonistic PLP analogs linked to full length I-$A^s$ molecules in EAE-induced mice can be examined in this system. The peptide/MHC complexes will be produced in the muscle following injection with DNA carrying the appropriate gene constructs, as described in Example 11 which follows.

EXAMPLE 4

Effects of the Soluble Peptide-linked MHC/Ig Molecules in an Ovalbumin Specific T Cell Hybridoma System One assay in accordance with the invention involves use of a murine T cell hybridoma, D0 11.10 [Shimonkevitz, R. et al. (1983) J Exp. Med. 158:303] which expresses on its surface a T cell receptor specific for a 21 amino acid peptide fragment (aa 323-339) derived from chicken egg ovalbumin (Ova). This peptide can be presented to D 011.10 only by antigen presenting cells (APC) expressing the murine class II MHC molecule I-$A^d$. When the peptide is presented by the appropriate APC, D0 11.10 cells respond by producing IL-2, which can then be assayed as a measure of T cell activation. The cell line to employ to present the antigen is A20.1-11 [Kim, K. et al. (1979) J. Immunol. 122: 549], which expresses I-$A^d$ on its surface. Briefly, the A20.1-11 cells are incubated in the presence of the peptide fragment until their I-$A^d$ molecules are saturated (approximately 3 hours) with peptide and then washed to remove unbound peptide. D0 11.10 cells are incubated with or without the soluble peptide-linked MHC/Ig molecules for 3 hours (or more) and then washed extensively to remove unbound protein. As described in Example 1 above, the peptides linked to the I-$A^d$β chain include Ova 323-339, one of two single-substitution analogs of the Ova peptide—Ova H331R or Ova A332Y, or a peptide from hen egg lysozyme (HEL 74-86). The Ova 323-339, Ova H331R, HEL 74-86 peptides are known to bind I-A$^d$ whereas the Ova A332Y analog will serve as a non-binding control [Buus, S. et al. (1987) Science 235: 1353–1358; Sette, A. et al. (1987) Nature 328: 395–399]. The HEL 74-86 peptide serves as a non-specific negative control. Antigen-pulsed APC are then incubated with the treated D0 11.10 T cell hybridoma (2×10$^5$/well) for 24 hours at 37° C. in an atmosphere of 5% $CO_2$. Cultures are carried out in complete culture medium (RPMI 1640 supplemented with 10% FBS, penicillin/streptomycin, L-glutamine and 5×10$^{-5}$ M 2-mercaptoethanol) in 96 well flat bottom microtiter plates. After 24 hours, culture supernatant is assayed for the presence of IL-2 using the IL-2 dependent murine T cell line CTLL-2.

Serial twofold dilutions of each culture supernatant is prepared in completed medium in flat bottomed microtiter plates and 1×10$^4$ CTLL-2 cells is added to each well. After 16 to 20 hours the negative control wells (CTLL-2 cultured with medium alone) and positive control wells (CTLL-2 cells cultured with rIL-2) is examined microscopically and at the point at which negative control cells are 90% dead, while positive control cells are still actively proliferating, MTT (2 mg/ml; 25 µl/well) is added and the plates returned to the incubator for an additional 4 hours. At this time, blue crystals formed by MTT in actively metabolizing cells will be dissolved by addition of 150 µl per well of 0.4N HCl in isopropanol per well. After careful mixing, the O.D. at 562 nm is determined using a ELISA plate reader (Ceres-UV900HI). The concentration of IL-2 in experimental wells can be determined by extrapolation from an IL-2 standard curve and then comparison of IL-2 from cultures containing no recombinant protein molecules can be compared to those containing the molecules to be tested and an index of inhibition calculated.

It is believed that use of antigen dose and APC numbers giving slightly submaximal responses of peptide antigen and antigen presenting cells for activation of D0 11.10 is preferred to detect inhibition of the system by recombinant protein molecules. In view thereof, experiments preferably are at least initially conducted with peptide antigen pulse conditions of 100 µg/ml and 10 µg/ml and with APC concentrations of 0.5×10$^5$/well and 0.1×10$^5$/well.

Soluble peptide-linked MHC/Ig molecules are tested for their ability to block this system over a range of concentrations from 10$^{-12}$–10$^{-6}$ M. Testing is suitably performed with approximately a 10:1 to 1:1 molar ratio between the soluble peptide-linked MHC/Ig molecules and the MHC Class II expressed on either 0.5×10$^5$ or 0.1×10$^5$ A20.1-11 cells. Concentrations are adjusted as necessary depending on results of preliminary experiments. A decrease in D0 11.10 IL-2 production following preincubation with the soluble Ova 323-339/I-A$^d$/Ig or Ova H331R/I-A$^d$/Ig molecules compared to preincubation with Ova A332Y/I-A$^d$/Ig or HEL 74-86/I-A$^d$ molecules or no preincubation will indicate that the soluble peptide-linked MHC molecules can suppress immune responses in a peptide-specific manner.

This same assay also can be used to identify peptides that function as TcR antagonist or partial agonists as discussed above.

EXAMPLE 5

Effects of Soluble Peptide-linked MHC/Ig Molecules on Antigen Stimulated T Cell Proliferation A further assay in accordance with the invention examines whether the soluble peptide-linked MHC/Ig molecules are able to suppress immune responses in T cells isolated from mice or humans (rather than the T cell hybridoma described in Example 4 above).

The D0 11.10 T cell hybridoma is partially activated and does not require co-stimulatory signals for complete activation. On the other hand, non-transformed $T_H$ cells isolated from immunized mice require both a peptide/MHC signal as well as co-stimulatory signals in order to proliferate in culture. This system will be used as a sensitive measure of the effects of the soluble peptide-linked MHC/Ig molecules on $T_H$ cell responses. Ova-primed T cells will be obtained from BALB/c mice (MHC Class II: I-A$^d$) by immunizing with 50 µg of Ova 323-339-KLH in complete Freund's adjuvant, subcutaneously at the base of the tail. Two immunizations will be performed at 7 day intervals and, one week after the second injection, mice will be sacrificed and inguinal and paraaortic lymph nodes removed and rendered into a single cell suspension.

The suspension is depleted of antigen presenting cells by incubation on nylon wool and Sephadex G-10 columns, and the resulting purified T cell populations incubated either with Click's medium alone, or with soluble peptide-linked MHC/Ig molecules dissolved in Click's medium. T cells are cultured with the soluble peptide-linked MHC/Ig molecules (as described in Example 4 above) for 3 hours prior to washing and initiation of proliferation assay, however this time period may be increased up to 24 hours if necessary.

Activated B cells from BALB/c mice are used as antigen presenting cells in the proliferation assay. B cells are prepared by culturing spleen cells with 50 µg/ml of LPS for 48 to 72 hours at which time activated cells will be isolated by density gradient centrifugation on Lymphoprep. Activated B cells are then pulsed with ovalbumin peptide for 3 hours, washed extensively, fixed with paraformaldehyde to inhibit proliferation of B cells, and added to purified T cells.

The proliferation assay is carried out in 96 well round bottom microtiter plates at 37° C., 5% $CO_2$ for 3–5 days. Wells are pulsed with 1 µCi of $^3$H-thymidine for 18 hours prior to termination of cultures and harvested using a Skatron cell harvester. Incorporation of $^3$H-thymidine into DNA as a measure of T cell proliferation are determined using an LKB liquid scintillation spectrometer. A decrease in T cell proliferation following preincubation with the soluble Ova 323-339/I-A$^d$/Ig molecules, as compared to preincubation with Ova A332Y/I-A$^d$/Ig or HEL 74-86/I-A$^d$/Ig molecules or no preincubation, indicates the soluble peptide-linked MHC/Ig molecules can suppress immune responses in a peptide-specific manner.

Measurement of IL-2 concentrations in wells containing proliferating T cells at 24 and 48 hours may be a good alternative to carrying out the 3 to 5 day assay of proliferation. Initial experiments involve comparison of these two systems to determine which would be more sensitive to detection of inhibition. Because the detection of IL-2 measures an earlier activation event it may prove to be more useful in this situation.

Initial experiments carried out prior to testing of soluble peptide-linked MHC molecules will determine the optimum parameters for these systems, i.e., supramaximal, maximal and submaximal concentrations of peptide antigen for pulsing of antigen presenting cells, optimal and suboptimal dosages of APC/well, and optimum length of proliferation assay (3–5 days) or IL-2 production assay. As discussed above, it is believed that the system will be most sensitive to inhibition with recombinant proteins at a suboptimal level of T cell activation, so such conditions preferably are chosen for initial experiments.

The effects of soluble peptide-linked human class II MHC/Ig molecules on antigen-stimulated human T cell proliferation will also be examined. Soluble HLA-DR1/Ig molecules covalently attached to either the influenza nuclear protein—NP 404-415 or the influenza hemagglutinin protein HA 307-318 can be produced as described in Examples 1 and 2 above. Both peptides are known to bind the HLA-DR1 molecules. An NP 404-415/DR1 specific human T cell clone, K68-36, will be used to test the effects of preincubation of the soluble peptide-linked MHC/Ig molecules on $^3$H-thymidine incorporation stimulated by NP 404-415 loaded APCs (BLCL-K68 cells; EBV-transformed B cells from the same donor), as described above. Again, a decrease in T cell proliferation following preincubation with the soluble NP 404-415/DR1/Ig molecules compared to preincubation with HA 307-318/DR1/Ig molecules or no preincubation will indicate that the soluble peptide-linked MHC/Ig molecules can suppress human immune responses in a peptide-specific manner.

These assays also can be employed to determine indicate whether a peptide can function as a TcR antagonist or partial agonists as discussed above.

EXAMPLE 6

In vivo Effects of the Soluble Peptide-linked MHC Molecules on Antibody Responses As discussed above, it has been shown that peptide-MHC complexes on the surface of APCs will only induce the clonal expansion of a reactive T cell line specific for the MHC bound peptide if the APCs also deliver co-stimulatory signals. In the absence of co-stimulatory signals delivered by APCs, these particular reactive $T_H$ cells will be induced to a state of anergy.

To test whether the soluble peptide-linked MHC/Ig molecules can induce $T_H$ cell anergy in vivo, the effects of such molecules on $T_H$ cell-dependent immunoglobulin class switching (i.e. IgM to IgG) and on clonal expansion of peptide-specific T cell lines (Example 7 which follows) can be examined.

In order to examine Ig class switching, three test groups are set up as follows:

(a) 15 BALB/c mice are injected intraperitoneally (IP) with 10–100 µg of Ova 323-339-KLH conjugate, in Complete Freund's adjuvant, in order to induce an immune response to the Ova 323-339 peptide. On the day before and the day of immunization with Ova-KLH, 5 of the mice are injected IP with 10–100 µg of the soluble Ova 323-339/MHC I-A$^d$/Ig in PBS. This soluble Ova fusion protein binds to the T cell receptor (TCR) displayed on the Ova 323-339 specific $T_H$ cells. Due to the absence of the co-stimulatory signal, these $T_H$ cells are induced to a state of anergy. The remaining 10 mice serve as control. 5 of them receive PBS and other 5 receive MHC I-A$^d$/Ig intraperitoneally.

(b) Identical experiments are performed with HEL-KLH conjugate and HEL 74-86/MHC I-A$^d$/Ig.

(c) 25 BALB/c mice are injected as described above with both Ova-KLH and HEL-KLH conjugates. 5 of these mice are injected intraperitoneally with Ova 323-339/MHC I-A$^d$/Ig and 5 of them will receive HEL 74-86/MHC I-A$^d$/Ig intraperitoneally. The other mice receive either PBS or MHC I-A$^d$/Ig as controls.

Ten days after the immunization, blood is collected from each mouse by tail bleeding. Mice are anesthetized with metafane in the following manner: cotton or gauze moistened with 20 to 25 drops of metafane and placed in a glass container with a metal or glass cover. The mouse is placed on top of a grate that is over the moistened cotton or gauze. When breathing slows down, the mouse is removed from the chamber and the toes pinched to check reflexes. Once the mouse is sufficiently anesthetized, the tail is held under a heat lamp to increase blood flow. After disinfecting the tail with isopropyl or ethyl alcohol, the tip is clipped off with sharp scissors. Blood is collected in an eppendorf tube. Bleeding can be enhanced by "milking" the tail. After collecting the blood, pressure is applied to the tip of the tail with a gauze pad. The blood is centrifuged at approximately 14,000 G for 3–5 minutes and the serum collected.

Assays are performed in 96-well microtiter plates (Maxisorp F8; Nunc, Inc.) coated at 1–50 µg/ml with OVA-KLH or whole Ovalbumin using a Tris-HC coating buffer, pH 8.5. A second set of plates are coated at 1–50 µg/ml of HEL-KLH or whole HEL. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 µl/well of a 3% BSA solution. Following incubation on a plate rotator at room temperature for 30 minutes, the plates are washed five times with Wash solution. Mouse sera is diluted 1:500 in Sample/conjugate diluent (2% gelatin+0.1% Tween-20 in TBS) and then, in duplicate, serially diluted on the plate. Two identical plates are set up for each coating protein, one for determination of IgM titer and the other for IgG. Following incubation on a plate rotator at room temperature for 30 minutes, the plates are washed five times with Wash solution. Goat anti mouse IgM-HRP and goat anti mouse IgG-HRP conjugates (Boehringer Mannheim, Indianapolis, Ind., 1:100 dilution in Sample/conjugate diluent) are added to the appropriate plates. Following incubation on a plate rotator at room temperature for 30 minutes, the plates are washed five times with Wash solution and then incubated with 100 µl/well of ABTS developing substrate (Kirkgaard & Perry Laboratories, Inc., Gaithersburg, Md.) for 10 minutes on a plate rotator at room temperature. The reactions are stopped with 100 µl/well of Quench buffer (Kirkgaard & Perry Laboratories, Inc., Gaithersburg, Md.) and the absorbance value is read at 405 nm using an automated microtiter plate ELISA reader (Ceres UV900HI, Bioteck, Winooski, Vt.). The titer is determined by plotting the absorbance reading versus the log of the dilutions of the samples and determining the dilution at the mid-point (50% of the absorbance). The titers for IgM versus IgG are then compared. The sera is also checked for cross-reactivity.

EXAMPLE 7

$T_H$ Cell Stimulation in Mice Treated With Soluble Peptide-linked MHC/Ig Molecules The effects of soluble peptide-linked MHC/Ig molecules on clonal expansion of peptide-specific T cell lines in vivo can be suitably examined in accordance with the following assay.

The treatment groups (4 mice per group) are identical to those described in Example 6 above. The immunization protocol is as follows: mice are injected intraperitoneally with 10–100 µg of the soluble Ova 323-339/MHC I-A$^d$/Ig in PBS and 24 hours later injected subcutaneously at the base of the tail with 50 µg of Ova 323-339-KLH. These two injections are repeated 6 and 7 days later. Seven days after completion of the second set of injections, the mice are sacrificed. The inguinal and paraaortic lymph nodes are removed and rendered into a single cell suspension.

The suspension is depleted of antigen presenting cells by incubation on nylon wool and Sephadex G-10 columns, and the resulting purified T cell populations incubated with APCs pulsed with either the Ova 323-339 peptide or the HEL 74-86 peptide.

Activated B cells from BALB/c mice are used at antigen presenting cells in the proliferation assay. B cells are prepared by culturing spleen cells with 50 µg/ml of LPS for 48 to 72 hours at which time activated cells are isolated by density gradient centrifugation on Lymphoprep. Activated B cells are then pulsed with the Ova 323-339 peptide or the HEL 74-86 peptide for 3 hours, washed extensively, fixed with paraformaldehyde to inhibit proliferation of B cells, and added to purified T cells from each panel of mice.

The proliferation assay is carried out in 96 well round bottom microtiter plates at 37° C., 5% $CO_2$ for 3–5 days. Wells are pulsed with 1 µCi of $^3$H-thymidine for 18 hours prior to termination of cultures and harvested using a Skatron cell harvester. Incorporation of $^3$H-thymidine into DNA as a measure of T cell proliferation is determined using an LKB liquid scintillation spectrometer. The degree of peptide-reactive T cell proliferation is indicative of the $T_H$ cell responses (i.e. of clonal expansion) that took place in the mice following immunization.

EXAMPLE 8

Soluble Peptide-linked MHC/Ig-mediated Inhibition of EAE Induction in SJL Mice

Experimental allergic encephalomyelitis (EAE) is an autoimmune disease in mice and serves as an animal model for multiple sclerosis. Encephalitogenic regions of two proteins, myelin basic protein (MBP 91-103) and proteolipoprotein (PLP 139-151), have been defined. In the susceptible SJL mouse strain, EAE can be induced to develop following immunization with the encephalitogenic peptide or adoptive transfer of MBP-reactive T cells. To determine whether treatment with soluble MHC fusion complexes of the invention such as MBP 91-103/MHC I-A$^s$/Ig and PLP 139-151/MHC I-A$^s$/Ig complex will prevent EAE development after T-cell activation, SJL mice can be injected with the examined MHC fusion complex e.g. MBP 91-103 and PLP 139-151 reactive T-cell blasts in vivo.

To induce EAE in SJL mice with MBP 91-103, mice are immunized with 400 µg of MBP 91-103 in complete Freund's adjuvant on the dorsum. Ten to 14 days later, regional draining lymph node cells are harvested as described above and cultured in 24-well plates at a concentration of 6×10$^6$ cells per well in 1.5 ml of RPMI 1640 medium/10% fetal bovine serum/1% penicillin/streptomycin with the addition of MBP at 50 µg/ml. After a 4-day in vitro stimulation, MBP 91-103-reactive T cell blasts are harvested via Ficoll/Hypaque density gradient, washed twice in PBS, and 1.3×10$^7$ cells are injected into each mouse. Mice receiving encephalitogenic MBP 91-103-reactive T cells then receive either 100 µg of soluble MBP 91-103/I-A$^s$/Ig, 100 µg of MBP 1-14/I-A$^s$/Ig (the negative control), or normal saline on days 0, 3, and 7 i.v. (total dose 300 µg). Clinical and histological evaluations are performed to confirm that the MBP 91-103/I-A$^s$/Ig inhibited the development of EAE in these mice.

To induce EAE in SJL mice with PLP peptide 139-151, mice are immunized with PLP peptide 139-151 dissolved in PBS and mixed with complete Freund's adjuvant containing Mycobacterium tuberculosis H37Ra at 4 mg/ml in 1:1 ratio. Mice are injected with 150 µg of peptide adjuvant mixture. On the same day and 48 hours later, all animals are given 400 ng of pertussis toxin. Adoptive transfer of EAE are then performed as described above. PLP 139-151/I-A$^s$/Ig rather than MBP 91-103/I-A$^s$/Ig is then used to prevent the development of EAE.

EXAMPLE 9

Antibody Response in Mice Vaccinated with the Peptide-linked MHC Expression Vectors of the Invention The following assay (illustrated with PEE-IA$^d$/OVA) shows how an immune response can be induced in a mammal in accordance with the invention by administration (e.g., IM) with one or more presenting peptide-linked MHC expression vectors of the invention, and that co-administration of DNA coding for co-stimulatory factor such as B7-1 (or B7-2) expression vector can be employed to further augment the immune response as discussed above. This system will provide a unique method for inducing immune responses (including to provide a vaccination against a targeted disorder) that bypasses the complexities of antigen uptake and processing.

BALB/c mice (five per group) are injected intramuscular (IM) in both hind legs with 100 µg of: (1) PEE-IA$^d$/OVA carrying the coding regions of Ova 323-339/I-A$^d$ under the control of the CMV promoter, (b) pCMV/B7-1 or pCMV/B7-2 containing the coding regions of B7-1 or B7-2 gene under the control of the CMV promoter, (c) PEE-IA$^d$/OVA and either pCMV/B7-1 or pCMV/B7-2, (d) PEE-IA$^d$/HEL bearing the coding region HEL 74-86/I-A$^d$ under the control of the CMV promoter, (e) PEE-IA$^d$/HEL and either pCMV/B7-1 or pCMV/B7-2 or (f) PEE-IA$^d$ containing the coding region of I-A$^d$ under the control of the CMV promoter. Injections are given at 0, 3, and 6 weeks.

At 0, 2, 5, and 8 weeks post initial injection, blood is collected from each mouse by tail bleeding as described in Example 6. The blood is centrifuged at approximately 14,000 G for 3–5 minutes and the serum collected.

Assays are performed in 96-well microtiter plates (Maxisorp F8; Nunc, Inc.) that have been coated at 1–50 µg/ml with OVA-KLH and HEL-KLH using a Tris-HCl coating buffer, pH 8.5. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 µl/well of a 3% BSA solution. Following incubation on a plate rotator at room temperature for 30 minutes, the plates are washed five times with Wash solution. Mouse sera is diluted 1:500 in Sample/conjugate diluent (2% gelatin+0.1% Tween-20 in TBS) and then, in duplicate, serially diluted on the plate. Samples of mouse sera is run on both the OVA-KLH and HEL-KLH coated plates to test for cross-reactivity. Following incubation on a plate rotator at room temperature for 30 minutes, the plates are washed five times with Wash solution and then 100 µl of the goat anti-mouse IgG-HRP conjugates (Boehringer Mannheim, Indianapolis, Ind., 1:100 dilution in Sample/conjugate diluent) are added to the appropriate plates. Following incubation on a plate rotator at room temperature for 30 minutes, the plates are washed five times with Wash solution and then incubated with 100 µl/well of ABTS developing substrate (Kirkgaard & Perry Laboratories, Inc., Gaithersburg, Md.) for 10 minutes on a plate rotator at room temperature. The reactions are stopped with 100 µl/well of Quench buffer (Kirkgaard & Perry Laboratories, Inc., Gaithersburg, Md.) and the absorbance value at 405 nm read using an automated microtiter plate ELISA reader (Ceres UV900HI, Bioteck, Winooski, Vt.). The titer can be determined by plotting the absorbance reading versus the log of the dilutions of the samples and determining the dilution at the mid-point (50% of the absorbance).

EXAMPLE 10

Detection of Peptide Specific T Cells Following Induction of Immune Response with Peptide-linked MHC Expression Vectors In order to determine whether intramuscular injection of DNA has successfully immunized mice to mount a T helper cell response to ovalbumin, an ovalbumin specific T cell proliferation assay can be employed. Mice are immunized by the protocol described in Example 9 and T cells are prepared from the inguinal and paraaortic lymph nodes 7 days after the second immunization.

The suspension is depleted of antigen presenting cells by incubation on nylon wool and Sephadex G-10 columns, and the resulting purified T cell populations incubated with APCs pulsed with either the Ova 323-339 peptide or the HEL 74-86 peptide. Activated B cells from BALB/c mice are used as antigen presenting cells in the proliferation assay. B cells are prepared by culturing spleen cells with 50 µg/ml of LPS for 48 to 72 hours at which time activated cells are isolated by density gradient centrifugation on Lymphoprep. Activated B cells are then pulsed with either the Ova 323-339 peptide or the HEL 74-86 peptide for 3 hours, washed extensively, fixed with paraformaldehyde to inhibit proliferation of B cells, and added to purified T cells.

The proliferation assay is carried out in 96 well round bottom microtiter plates at 37° C., 5% $CO_2$ for 3–5 days. Wells are pulsed with 1 µCi of $^3$H-thymidine for 18 hours prior to termination of cultures and harvested using a Skatorn cell harvester. Incorporation of $^3$H-thymidine into DNA as a measure of T cell proliferation is determined using an LKB liquid scintillation spectrometer. The degree of peptide-reactive T cell proliferation is indicative of the $T_H$ cell responses (i.e. of clonal expansion) that took place in the mice following immunization.

EXAMPLE 11

Suppression of Autoimmune Disease in Mice Injected with TcR Antagonistic Peptide-linked MHC Expression Vectors Examples 3 and 9–10 above show methodologies to be used for stimulating immune responses via MHC fusion complexes of the invention. As discussed above, similar procedures can be employed to inhibit immune responses by using TcR antagonistic peptides linked to the MHC molecules, i.e. the presenting peptide covalently linked to the MHC peptide is a TcR antagonist or partial agonist. As described in Example 1, the PLP peptide 139-151 is capable of inducing EAE in SJL mice. Analogs of this peptide have been characterized for TcR antagonistic activity against a panel of I-$A^s$-restricted, PLP 139-151-specific T cell clones. Two different analogs, PLP-W144Y (HSLGKYLGHPDKF) (SEQ ID NO: 22) and PLP-W144L (HSLGKLLGHPDKF) (SEQ ID NO: 23), were found to be particularly useful for inhibiting in vitro T cell proliferation in most of the T cell clones tested [Franco, A. et al. (1994) Eur. J. Immunol. 24: 940–946]. As a model system, vectors capable of co-expressing the PLP peptide analog-linked I-$A^s$ β chain and the full-length I-$A^s$ α chain molecules can be constructed. Vector construction is suitably similar to that outlined in Example 3 above. The native PLP 139-151 linked-MHC construct serves as a positive (antigenic) control. These vector DNAs (with and without the B7 or B7-2 expression vectors) are suitably injected IM into SJL mice (see Example 9 for injection procedures) prior to and during the induction of EAE. EAE can be induced by the adoptive-transfer of PLP 139-151 reactive $T_H$ cells by procedures as described in Example 8 above. Clinical and histological evaluations are performed to confirm that the PLP antagonist/I-$A^s$ expression vector injection inhibited the development of EAE in the mice.

EXAMPLE 12

Construction of Full-length Peptide-linked I-$A^d$ MHC Expression Vectors

Figure 19:
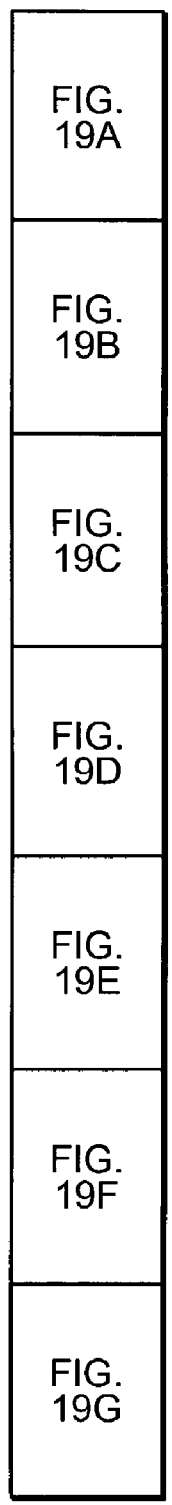
FIG. 19 (total of 7 sheets) shows the cloning scheme carried out in Example 12 which follows.
Figure 19A:
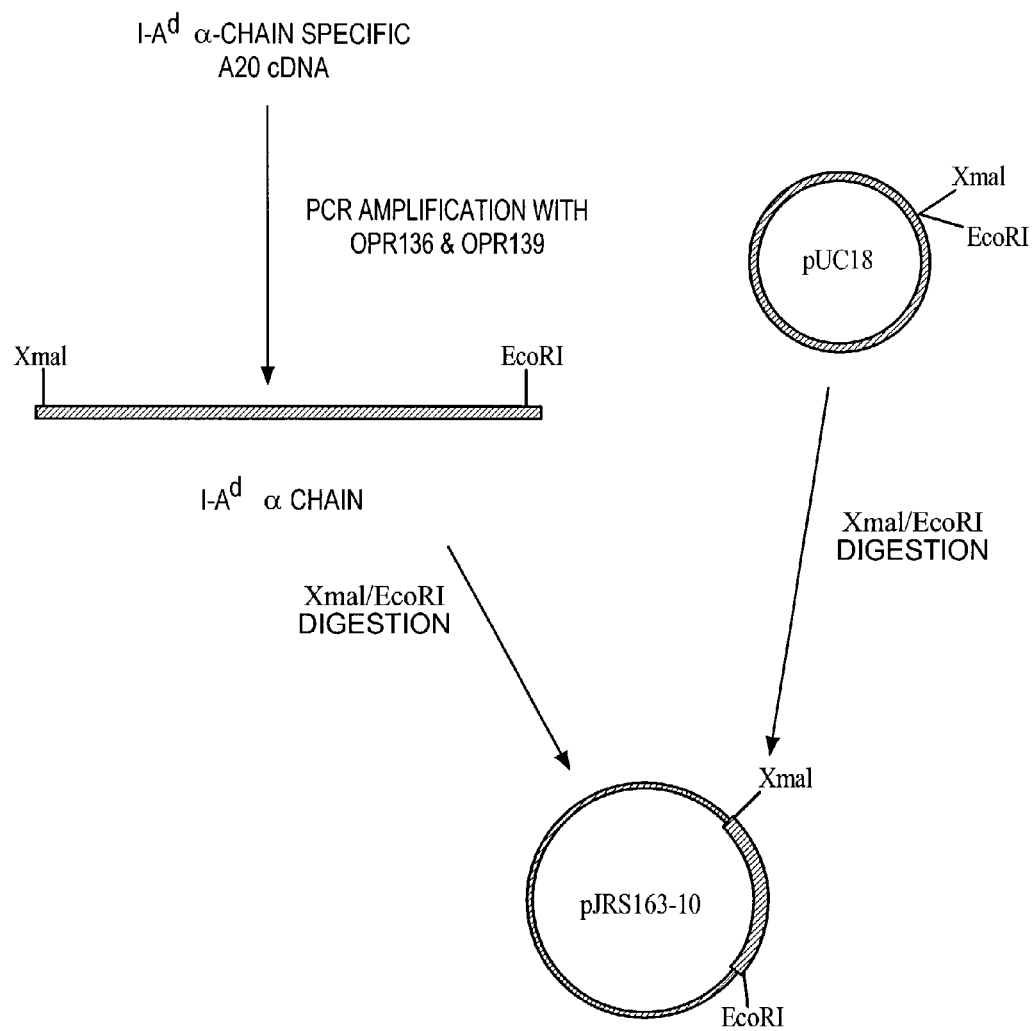
Figure 19B:
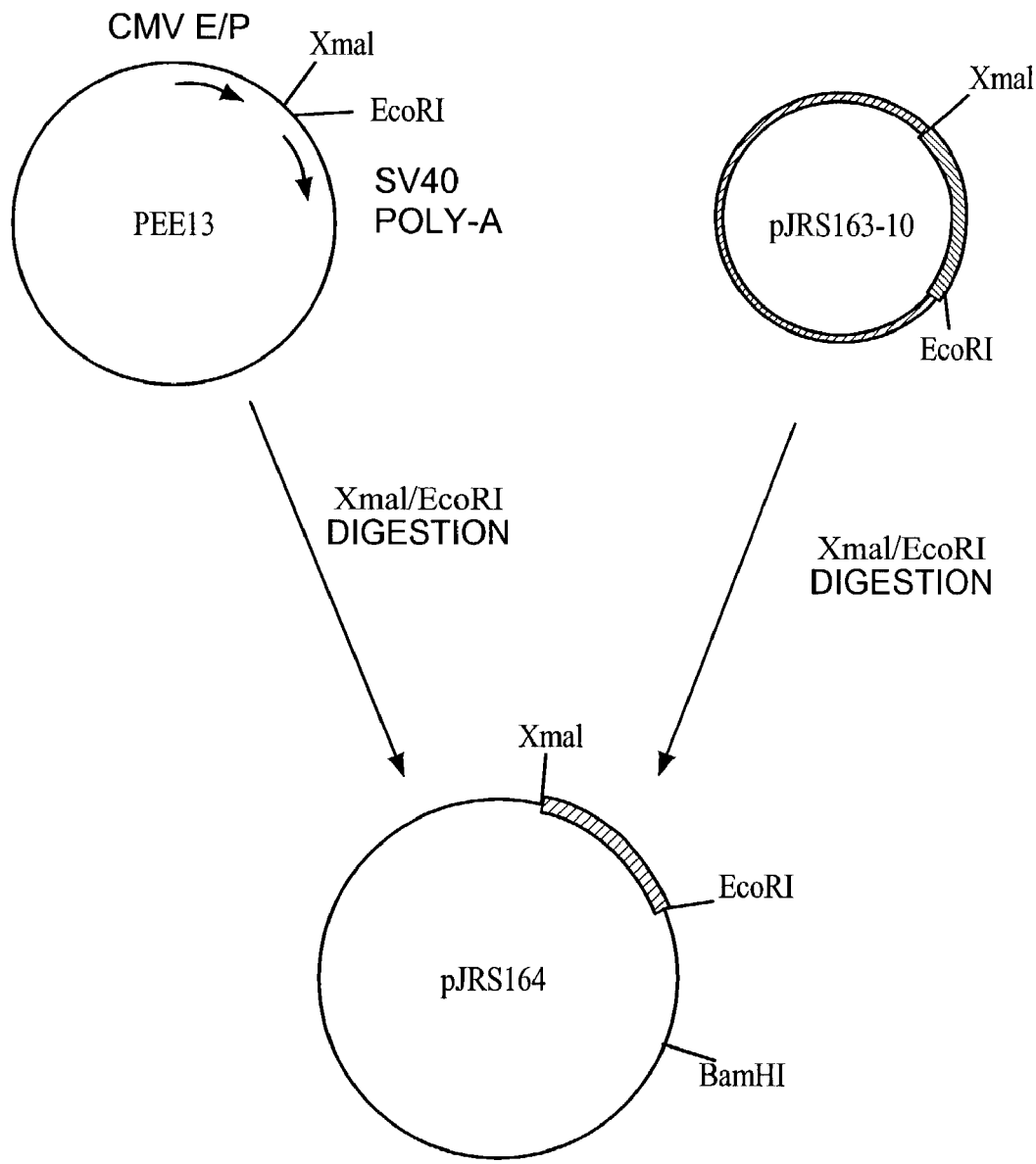
Figure 19C:
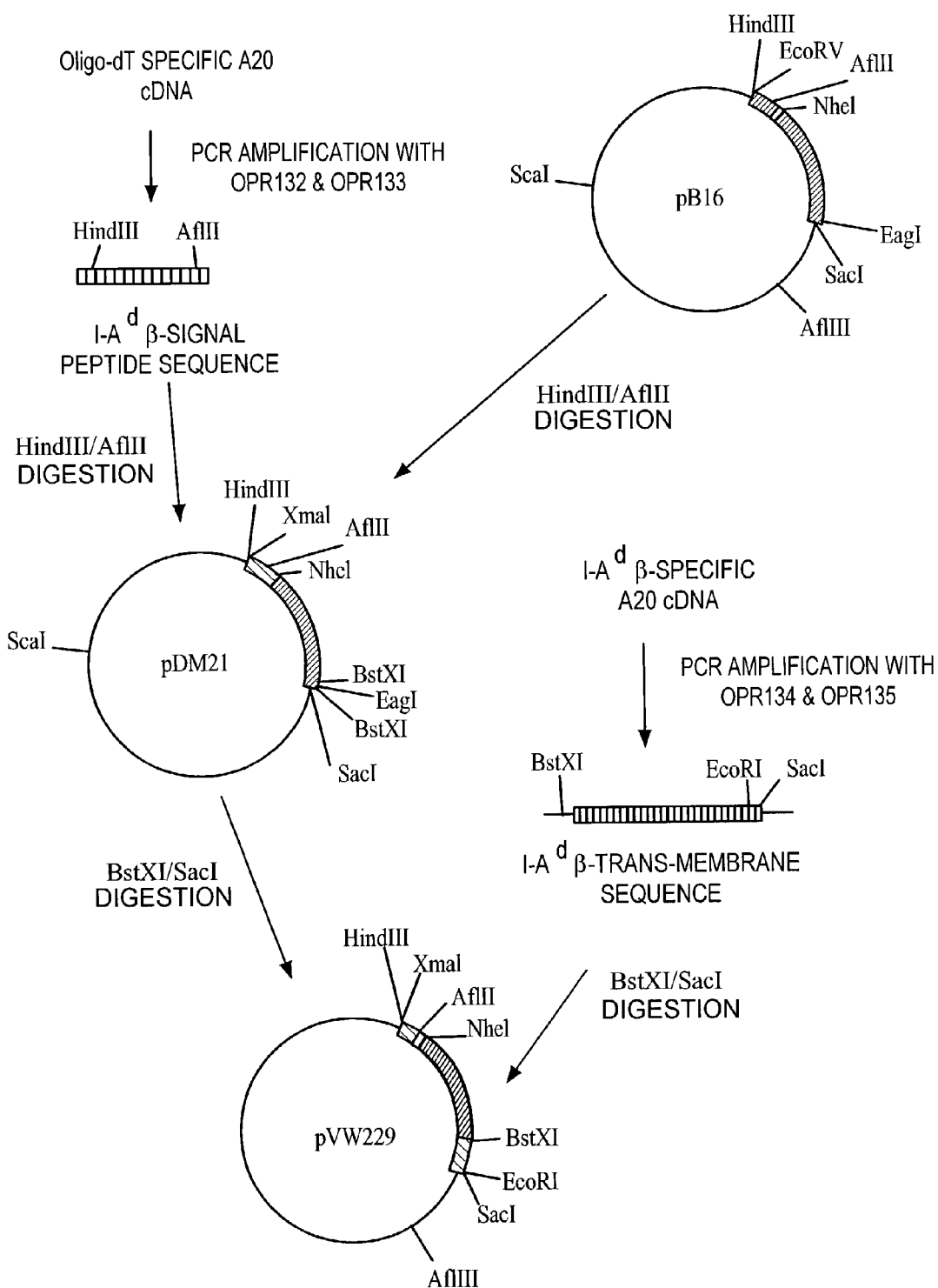
Figure 19D:
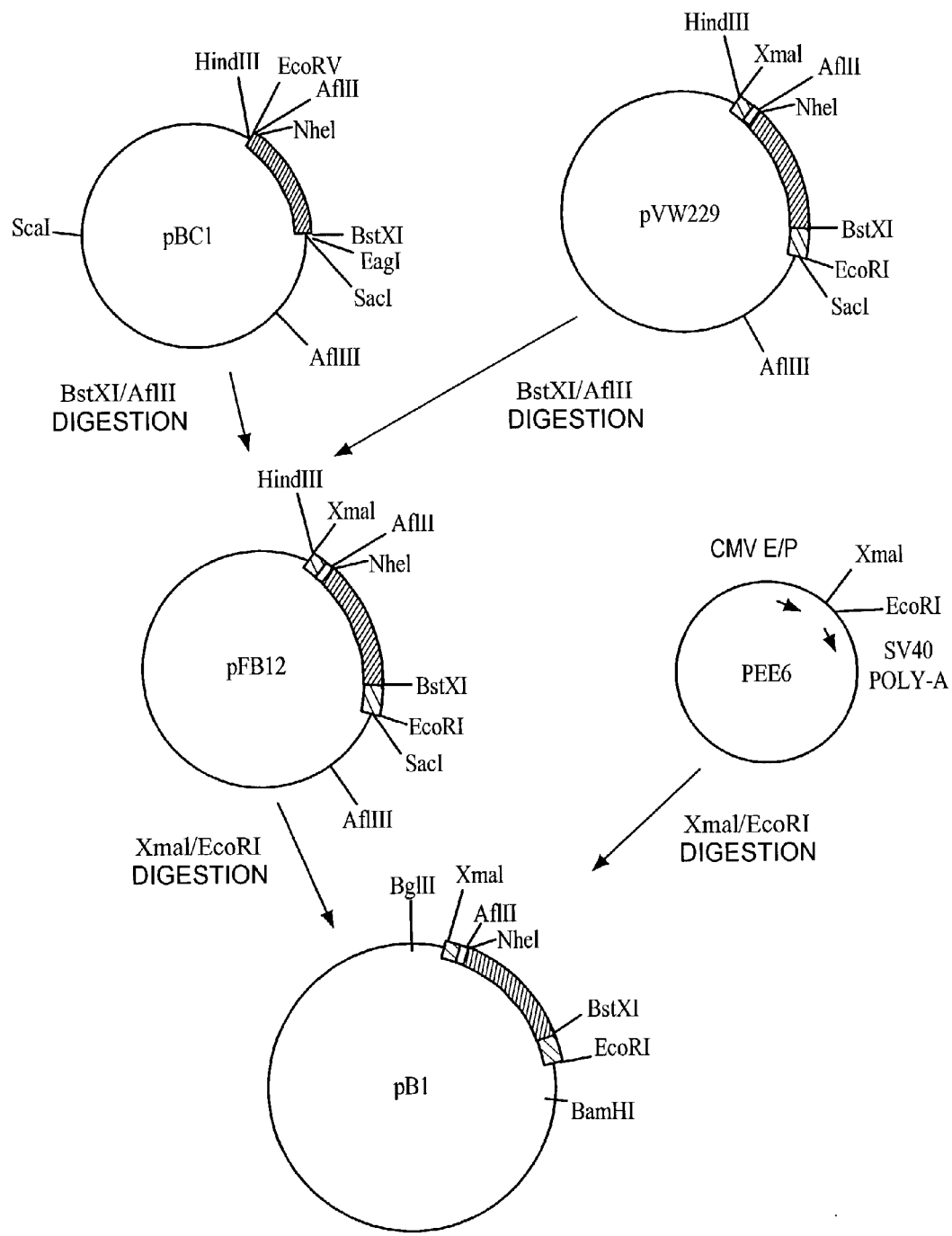
Figure 19E:
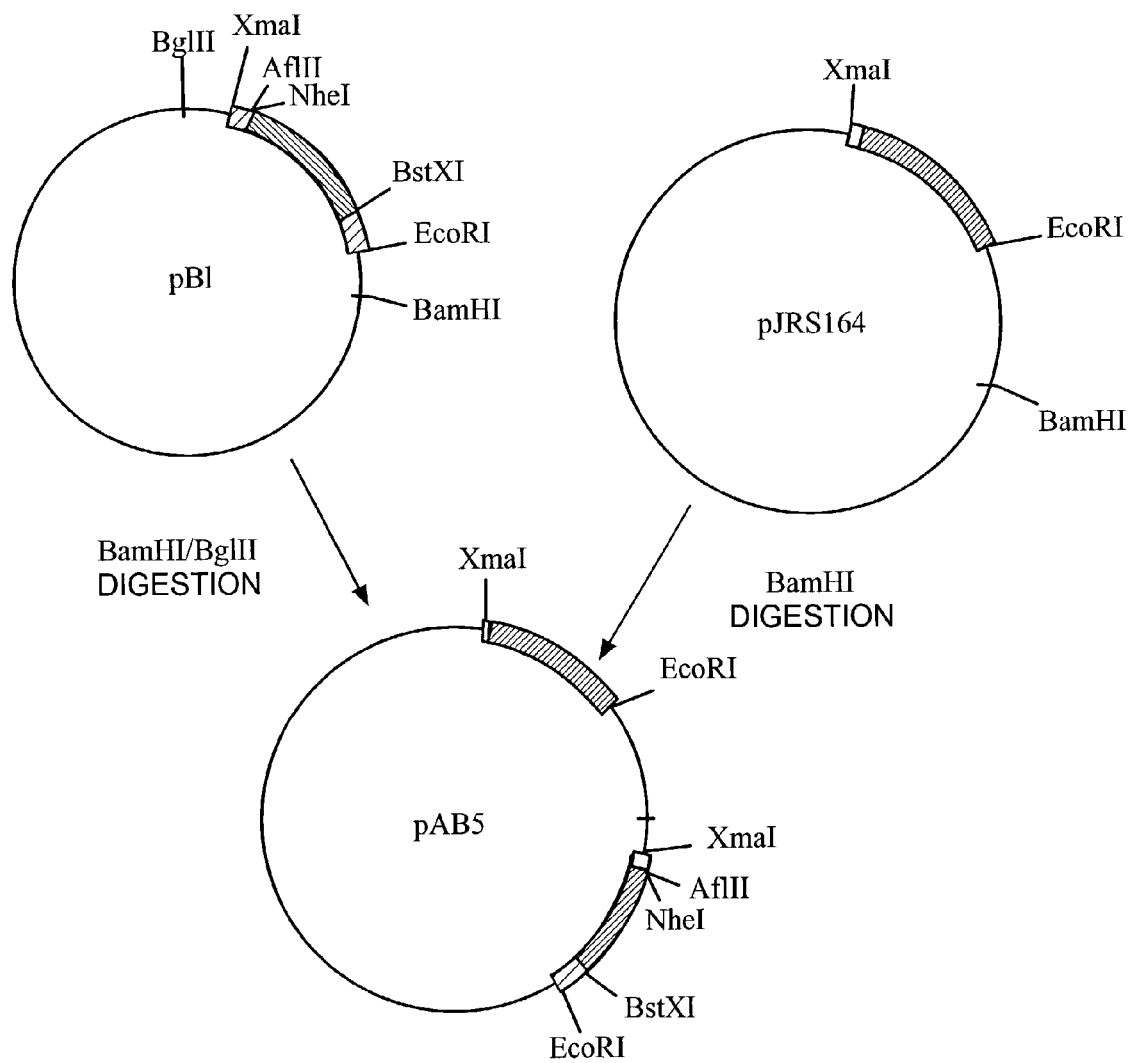
Figure 19F:
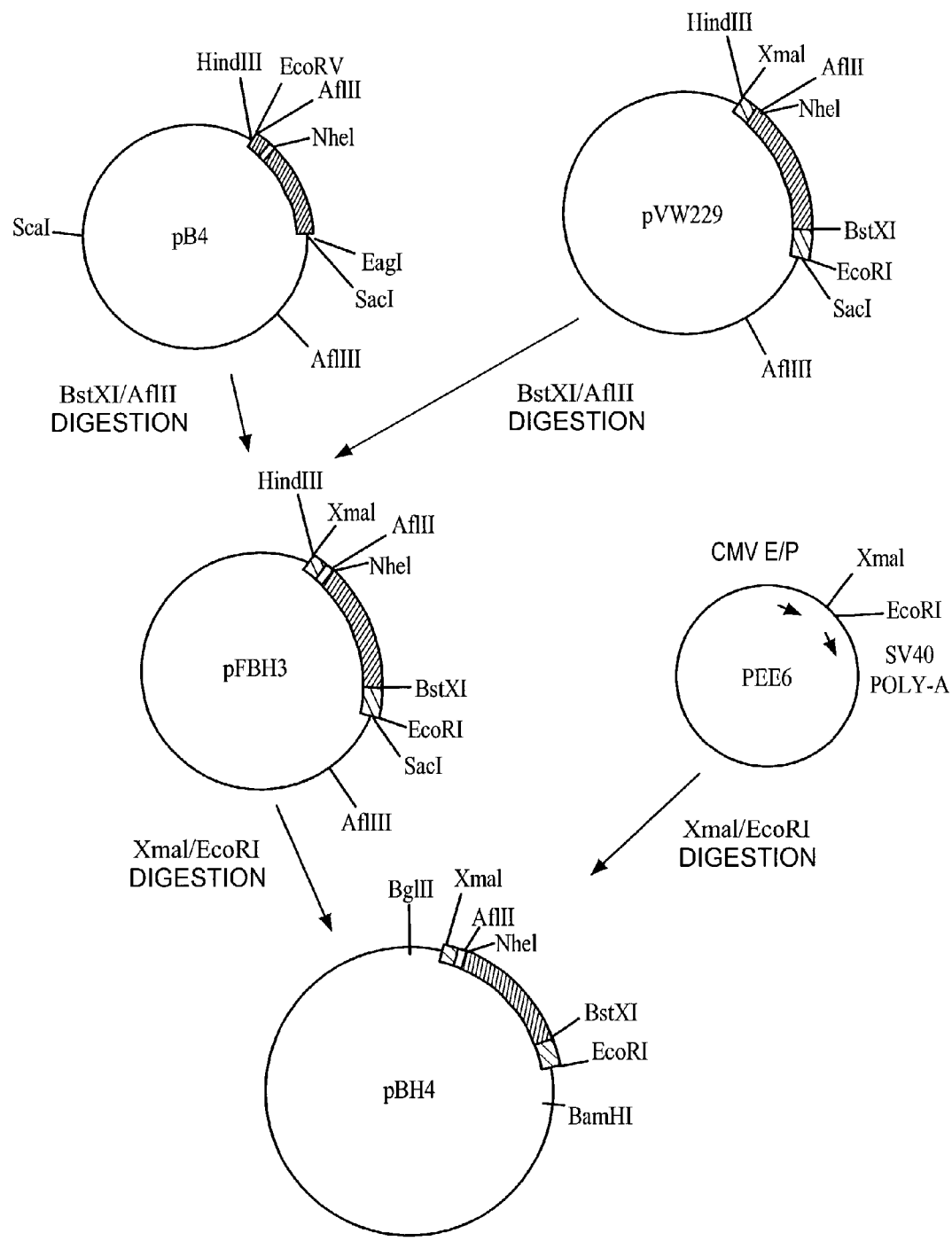
Figure 19G:
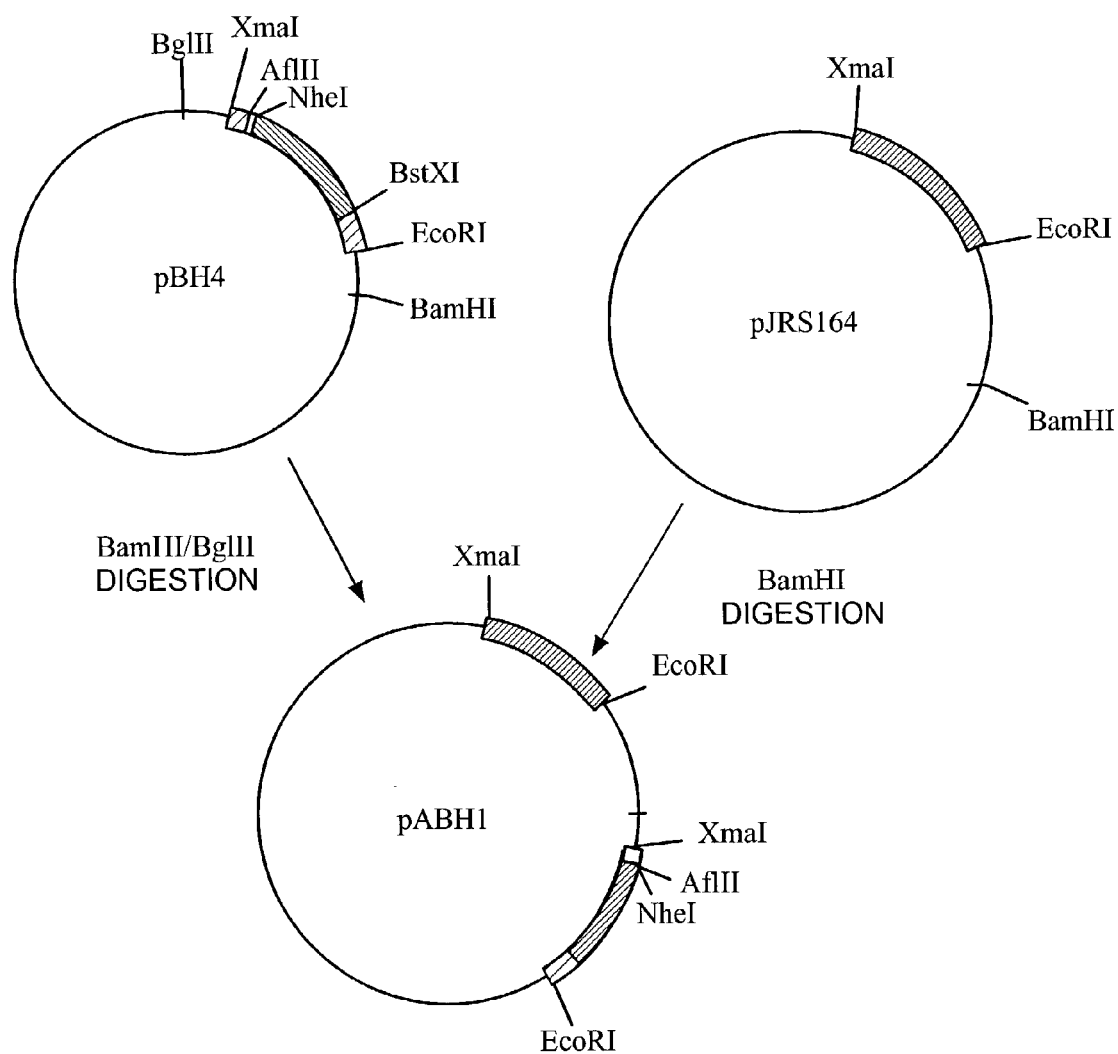

Vectors capable of co-expressing the full-length I-$A^d$ α chain and peptide-linked I-$A^d$ β chain molecules were constructed as outlined in FIG. 19 of the Drawings and by the same or similar procedures as disclosed in Example 3 above. For the I-$A^d$ genes, total RNA was isolated from the mouse B cell lymphoma A20 cell line. Briefly, $1 \times 10^8$ A20 cells (American Type Collection Culture Accession No. TIB 208) were homogenized in 6 ml of ice cold 4 M guanidinium thiocyanate, 0.1 M Tris-HCl, pH 7.5 using a Tissue Tearer homogenizer for 5 minutes. Following homogenization, sodium sarcosyl was added to a final concentration of 0.5% and the solution was mixed thoroughly. The homogenate was centrifuged at 5000 g for 10 minutes and the supernatant was brought up to 10 ml with 4 M guanidinium thiocyanate, 0.1 M Tris-HCl, pH 7.5, 0.5% sodium sarcosyl buffer. The supernatant was gently layered on top of a 3.5 ml cushion of 5.7 M CsCl, 0.01 M EDTA, pH 7.5 in an SW41 clear ultracentrifuge tube. The samples were centrifuged in an SW41 rotor at 32,000 rpm for 24 hours at 20° C. Following centrifugation, the supernatant was carefully removed and the RNA pellet was washed with 70% ethanol. The RNA was dissolved in 350 µl of 3 M sodium acetate and 970 µl of ethanol. This procedure yielded approximately 370 µg of total RNA. The RNA was resuspended to 5 µg/µl with DEPC-treated water and was used for RT-PCR cloning of the I-$A^d$ genes.

To isolate the full-length I-$A^d$ α chain, A20 total RNA (5 µg) was converted to cDNA by using M-MLV Reverse Transcriptase (GIBCO-BRL) and α chain TM-specific priming (oligonucleotide OPR139) according to manufacturer's recommended procedures. This cDNA was used as the template for PCR amplification using an α chain leader-specific primer (OPR136) and an α chain TM-specific primer (OPR139). See FIG. 20 of the Drawings where the sequences of those OPR136 and OPR 139 primers are disclosed. Typical PCR amplification reactions (100 µl) contained template DNA, 10 pmoles of the appropriate primers, 2.5 units of Taq polymerase, 100 µM dNTP, 50 mM KCl, 10 mM Tris-HCl, pH 8.3, 1.5 mM $MgCl_2$, 0.01% gelatin. The template was denatured by an initial incubation at 96° C. for 5 min during which the Taq polymerase was added to hot-start the reaction. The desired products were amplified by 10 thermal cycles of 58° C. for 30 sec, 72° C. for 1 minute, then 96° C. for 1 minute followed by 20 step cycles of 70° C. for 1.5 minute, then 96° C. for 1 minute. The resulting PCR product (~800 bp) contains a 5' XmaI site and a 3' EcoRI site for cloning. In addition, this fragment carries a Kozak consensus sequence for efficient translational initiation (see FIG. 18A of the Drawings where the sequence of the PCR product is disclosed). The PCR product was digested with XmaI and EcoRI, gel-purified and ligated into XamI/EcoRI digested pUC18, to give the vector pJRS163-10. Following sequence verification, the XmaI/EcoRI fragment was excised, purified and subcloned between the CMV promoter and SV40 poly-A-sites of the PEE13 mammalian expression vector (Celltech), resulting in the pJRS164 vector.

The full-length peptide-linked β chain fragment was constructed by inserting the leader and TM sequences into the OVA 323-339 peptide (SISQAVHAAHAEINEAGR) (SEQ ID NO: 24) linked β1-β2 vector (pB16) as described in Example 1 above. A20 total RNA (5 µg) was converted to cDNA by using Superscript-MLV or M-MLV Reverse Transcriptase (GIBCO-BRL) and either oligo dT-specific or β chain TM-specific priming (with OPR135, sequence thereof shown in FIG. 20) according to manufacturer's recommended procedures. These cDNAs were used as the template for PCR amplifications using either a pair of β chain leader-specific primers (OPR132/OPR133; sequences of those primers disclosed in FIG. 20 of the Drawings) and a pair of β chain TM-specific primers (OPR134/OPR135; sequences of those primers disclosed in FIG. 20 of the Drawings). PCR amplification conditions were similar to those described above in this example. Specifically, thermal cycling conditions for amplifying the leader sequence were 10 thermal cycles of 60° C. for 1 minute, 70° C. for 1 minute, and 96° C. for 1 minute followed by 30 step cycles of 70° C. for 1 minute and 96° C. for 1 minute, whereas conditions for amplifying the TM domain were 5 thermal cycles of 60° C. for 30 seconds, 72° C. for 30 seconds, and 96° C. for 1 minute followed by 25 step cycles of 70° C. for 1 minute and 96° C. for 1 minute. The 110 bp β leader PCR product contains 5' HindIII and XmaI sites and a 3' Afni site for cloning into the pB16 OVA peptide-linker-β1-β2 vector. The inclusion of the Af/II site changes the last two amino acids of the I-A$^d$ β chain leader to those found in the IgG leader (see FIG. 18B of the Drawings). The β leader PCR product was digested with HindIII and XmaI, gel-purified and ligated into HindIII/Af/II digested pB16, to give pDM21. The 180 bp β TM PCR product contains a 5' BstXI and sites and 3' XmaIII and EcoRI sites for cloning into the pDM21 vector. The β TM PCR product was digested with BstXI and EcoRI, gel-purified and ligated into BstXI/EcoRI digested pDM21, to give the pVW229 vector. This vector was digested with XmaI and EcoRI to generate the full-length peptide linked β chain gene fragments for cloning between the CMV promoter and SV40 poly-A sites of the PEE6 mammalian expression vector (Celltech). These fragments also carry the Kozak consensus sequence (CCACCATG) (SEQ ID NO: 2) for efficient translational initiation (see FIG. 18A of the Drawings). The resulting pVW231 was digested with Bg/II and BamHI. The CMV promoter/peptide-β chain fragments was gel-purified and ligated into BamHI digested pJRS164, to generate the final pJRS165.1 expression vector containing full length I-A$^d$ α and OVA-linked β chain genes.

Additional plasmids containing the full length I-A$^d$ α chain gene and either the βchain gene without a linked peptide or with the HEL 74-86 peptide (NLCNIPSCALLSS) (SEQ ID NO: 25) were constructed as shown in the scheme of FIG. 19 of the Drawings and served as controls in the induction studies. The Af/II/BstXI fragments of pBC1 and pB4 (as disclosed in Example 1 above) containing the linker-β1-β2 region and the HEL peptide-linker-β1-β2 region, respectively were excised, gel purified, and ligated into Af/II/BstXI digested pVW229. The resulting vectors, pFB12 and pFBH3, have XmaI/EcoRI fragments contain the full length β chain gene linked either to no peptide or the HEL peptide, respectively. These fragments were excised, gel purified and ligated between the CMV promoter and SV40 poly-A sites of XmaI/EcoRI digested PEE6, resulting in pB1 and pBH4. These vectors were digested with Bg/II and BamHI and the CMV promoter/β chain fragments were gel purified and ligated into BamHI digested pJRS164, to generate pAB5, the expression vector containing full length I-A$^d$ α and β chain genes without a linked peptide, and pABH1, the expression vector containing full length I-A$^d$ and HEL-linked β chain genes. Samples of aforesaid plasmids pJRS165.1, pAB5 and pABH1 (Accession Nos. 97301, 97032 and 97033 respectively) have been deposited with the American Type Culture Collection, Rockville, Md.

The murine B7-1 gene was amplified from a plasmid MB7-PCR2 template carrying the B7 gene (provided by E. Podack, Univ. of Miami). These reactions were carried out with Ultima polymerase (Perkin-Elmer) according to manufacturer's recommended procedures using the B7 specific primers B7-1-2F and B7-1-2B (sequences of those primers disclosed in FIG. 20 of the Drawings). Thermal cycling conditions were 20 thermal cycles of 60° C. for 30 seconds, 72° C. for 1.5 minute, and 96° C. for 1 minute followed by 10 step cycles of 72° C. for 1.5 minute and 96° C. for 1 minute. The PCR product generated carries 5' and 3' NotI sites for cloning. This fragment also carries the Kozak consensus sequence (CCACCATG) (SEQ ID NO: 2) for efficient translational initiation. The product was digested with NotI, gel purified and ligated between the CMV promoter and SV40 poly-A sites of NotI-digested pCMVβ mammalian expression vector (Clonetech). The resulting vector was designated pUB719.

EXAMPLE 13

Development of a Cell Line Expressing a Functional Fusion Complex of the Invention on the Cell Surface As further detailed below, a murine B cell tumor (NSO; H-2$^d$ background) has been transfected with the pJRS165.1 construct (murine I-A$^d$/OVA 323-339 described in Example 12 above) and has been shown by flow cytometric analysis of the cell surface to express the MHC portion of the fusion complex. In addition, the fusion complex expressed on these cells was shown to be capable of modulating the activity of the appropriate T cell receptor (TcR) by inducing IL-2 production in the I-A$^d$ restricted, OVA peptide 323-339 specific T cell hybridoma, DO11.10. The results demonstrate, inter alia, that (1) the covalently linked fusion peptide can be loaded into the binding cleft of the MHC with preservation of the conformation of the MHC, (2) the peptide/MHC fusion preserves the functional integrity of the MHC molecule (i.e. it is able to bind the TcR and activate peptide specific T cells) and (3) the ordinary physiologic mechanisms for peptide loading of MHC molecules and subsequent antigen presentation can be bypassed through the present invention.

A. Generation of Transfected Lymphocytes

The NSO murine B cell tumor line was transfected according to the Celitech Glutamine Synthestase Gene Amplification System Manual with minor modifications. This method uses electroporation to transfect mammalian cells with a vector (PEE-13) containing the coding region for the glutamine synthetase. Transfected cells have the ability to synthesize glutamine, thereby surviving without an exogenous supply. Selection of transformed clones was accomplished by isolating the cells that grow in glutamine-free medium. Briefly, 1×10⁷ NSO cells were washed twice in ice cold PBS and resuspended in 760 µl of cold PBS. Forty µg (40 µl at 1 µg/µl) of Sal I digested pJRS165.1 (See Example 12 above) plasmid DNA was added to the cells in an electroporation cuvette (0.4 cm). The cell/DNA mix was placed on ice for 5 minutes and the cells then electroporated using a Gene Pulser (Biorad) to deliver one pulse of 250 volts, 960 µFd. The pulsed cells were placed on ice for 2–5 minutes, removed from the cuvette, and added to 30 ml of non-selective medium (IMDM, 10% FBS, 2 mM L-glutamine, penicillin/streptomycin). Cells were plated in 96-well flat bottomed microtiter plates at 50 µl/well (4 plates, cell suspension in 30 ml of medium as above; 5 plates, cell suspension diluted 1:4; 5 plates, cell suspension diluted 1:20) and then incubated with 5% $CO_2$ at 37C. For the negative control, the same procedure of electroporation and plating was followed except that the DNA was omitted. The next day, 150 µl of selective medium [IMDM, 10% dialyzed FBS, penicillin/streptomycin, nucleosides (6 µg/ml A, G, C and U; 2 µg/ml T), 60 µg/ml glutamate and asparagine] was added to each well. The plates were fed with selective medium on a weekly basis by removing 100 µl/well of used medium and adding 100 µl/well of fresh medium, allowing the cells to gradually deplete the medium of all residual glutamine. Only those cells that have been transformed will survive, colonies becoming evident in 14–21 days. The colonies, or clones, were expanded and screened for expression of conformationally correct surface MHC Class II fusion complex of the invention, as detailed below.

B. Conformation of MHC/peptide Fusion Construct

Clones generated in the above transfection were analyzed for expression of Class II MHC fusion complex at levels significantly higher than the parent cell, NSO. NSO/$IA^d$/OVA clones (1×10⁵) or control cells, NSO or A20.1-11 [Kim, K. et al. (1979) J.Immunol. 122:549], were incubated with FITC-conjugated anti-$IA^d$ antibody (Pharmingen, 1:100 dilution) in staining buffer (PBS/1% FBS) for 45 minutes at 4° C. in the dark. After washing three times in staining buffer, fluorescence was examined on a Beckton Dickinson FACScan flow cytometer. An isotype matched irrelevant antibody (FITC-conjugated anti-$IA^k$, Pharmingen 1:100) was used as negative control. $IA^d$ fluorescence intensity was compared to $IA^k$ expression to determine specific fluorescence (see results set forth in Table 1 below). In that Table, data are reported as peak channel green fluorescence which is a measure of fluorescence intensity and therefore the density of $IA^d$ molecules expressed on the cell surface. The negative control cell line (NSO) peaks at channel 67 and the positive control (A20.1-11) at channel 1322. Clones exhibiting peak fluorescence greater than channel 100 were chosen for further analysis of functionality of the fusion protein. The clones listed in Table 1 have been grown in bulk, frozen and banked for future use. Since the antibody recognize the conformational MHC molecule, this ability to detect the MHC fusion complex on the cell surface using antibody demonstrates the conformation of the MHC class II has been preserved in the recombinant fusion complex.

TABLE 1

$IA^d$ Expression on NSO/$IA^d$/OVA clones (in peak channel fluorescence)

| CLONE | $IA^d$ | $IA^k$ |
|---|---|---|
| A20.1 (+ control) | 1322 | 5 |
| NSO (− control) | 67 | 5 |
| NSO/$IA^d$/OVA.B2 | 528 | 14 |
| NSO/$IA^d$/OVA.B5 | 209 | 10 |
| NSO/$IA^d$/OVA.B4 | 271 | 11 |
| NSO/$IA^d$/OVA.A4 | 153 | 34 |

C. Demonstration of Functional Activity of MHC Fusion Complex

To verify the biologically relevant activity of these recombinant protein molecules, the molecules' ability to interact with the appropriate T cell receptor in vitro in an antigen specific manner and cause activation of the T cell was evaluated.

A murine T cell hybridoma, DO1 1.10 [Shimonkevitz, R. et al. (1983) J. Exp. Med. 158: 303], was utilized which expresses on its surface a T cell receptor specific for a 21 amino acid peptide fragment (aa 323-339) derived from chicken egg ovalbumin (OVA). This peptide can be presented to DO11.10 only by antigen presenting cells (APC) expressing the murine Class II MHC molecule I-$A^d$. When the peptide is presented by the appropriate APC, DO11.10 cells will respond by producing IL-2, which can then be assayed as a measure of T cell activation. The cell line which served as a positive control was A20.1-11, which expresses I-$A^d$ on its surface. Briefly, the A20.1-11 cells (1×10⁵/well) were incubated together with peptide (1 µg/well) and DO11.10 cells (2×10⁵/well), for 24 hours at 37C in an atmosphere of 5% $CO_2$. NSO cells (as negative control) and NSO/$IA^d$/OVA clones (1×10⁵) were incubated with DO11.10 cells in the absence of peptide. Cultures were carried out in complete culture medium (RPMI 1640, 10% FBS, penicillin/streptomycin, 2 mM L-glutamine and 5×10⁻⁵M 2-mercaptoethanol) in 96 well flat bottom microtiter plates. After 24 hours, culture supernatants were assayed for the presence of DO11.10 derived IL-2 using the IL-2 dependent murine T cell line CTLL-2, as described below.

Figure 21:
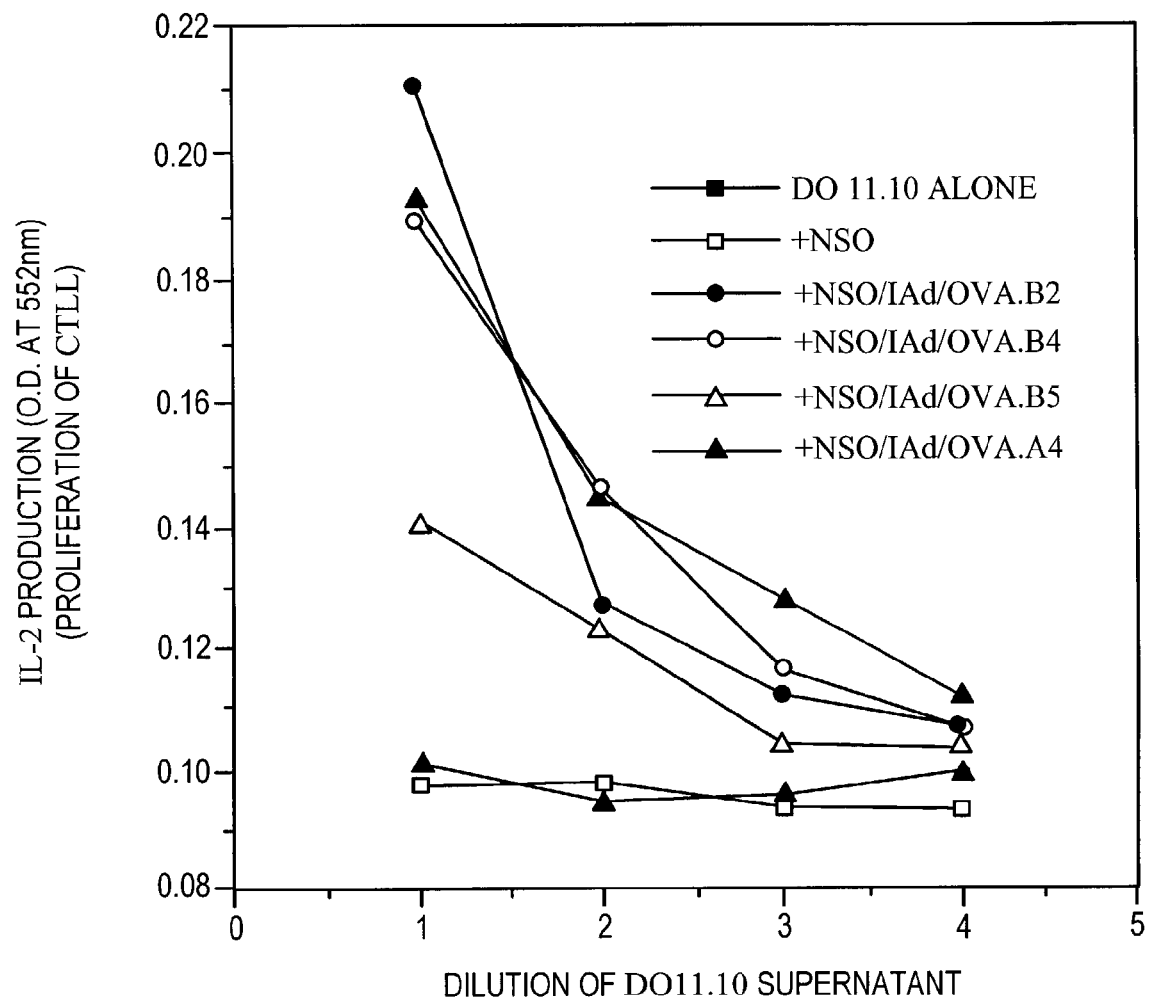
FIG. 21 shows graphically the functional activity of the four clones of Example 13 which follows along with negative control (NSO) and positive control (A20), where the O.D. value of the first four dilutions of DO11.10 culture supernatant is displayed.

Briefly, serial twofold dilutions of each culture supernatant were prepared in complete medium in flat bottomed microtiter plates and 1×10⁴ CTLL-2 cells were added to each well. After 16–20 hours the negative control wells (CTLL-2 cultured with medium alone) and positive control wells (CTLL-2 cells cultured with rIL-2) were examined microscopically and at the point at which negative control cells were approximately 90% dead, while positive control cells were still actively proliferating, MTT (2 mg/ml in PBS; 25 µl/well) was added and the plates returned to the incubator for an additional 4 hours. At this time, blue crystals of formazan formed in actively metabolizing cells were dissolved by addition of 150 µl of 0.4N HCl in isopropanol per well. After careful mixing, the O.D. at 562 nm was determined using a Ceres-UV90HI plate reader. Data demonstrating the functional activity of the four clones discussed above along with appropriate negative (NSO) controls is shown in FIG. 21 of the Drawings and is represented in a graph displaying the O.D. value of the first four dilutions of DO11.10 culture supernatant, as a measure of T cell activation.

These results establish the MHC/peptide complex expressed on these transfected cells is biologically functional, in that it can engage the TcR on DO11.10 and trigger the production of IL-2. These results indicate that such engineered cells expressing unique MHC/peptide constructs in the absence of co-stimulatory signals, can be of clinical importance in disease states in which an inappropriate immune response to a peptide has pathological consequences for the host, such as in allergy or in certain autoimmune disorders. This technique also has the potential, through further manipulation of the engineered cells, to serve as a vector to deliver a positive signal for immunization.

EXAMPLE 14

Assay for Immune Induction or Suppression by Cells Expressing MHC Fusion Complex of the Invention The following assay can be employed to evaluate the capability of MHC fusion complex cell lines of the invention (i.e., cells that have introduced therein DNA coding for an MHC fusion complex of the invention) for inducing or suppressing an immune response in a host to which the cells have been administered.

The following exemplification of the assay utilizes an animal model of immunization with ovalbumin peptide 323-339 and manipulation of the response to the peptide using the engineered fusion complex expressing cells described in Example 13 above. The methodology of this example can be applied to a wide variety of MHC fusion complexes of the invention that contain a presenting peptide which can modulate (i.e., suppress or induce) an immune response in mammals and which can be linked to an MHC molecule of the invention such as by a flexible linker as disclosed above.

The cells that can be utilized in this assay (NSO/IA$^d$/OVA.B2, NSO/IA$^d$/OVA.B4, NSO/IA$^d$/OVA.B5 and NSO/IA$^d$/OVA.A4) are transfected with the MHC/OVA 323-339 fusion complex DNA, pJRS165.1 (see Examples 12 and 13 above). These cells express only low levels of costimulatory molecules (i.e., a non-effective T cell proliferation amount) and therefore are not capable of initiating the initial priming event for induction of immunity to the peptide (as is known in the art, B cells are capable of activating memory T cells, but, unlike "professional APC" are unable to deliver the signal required for induction of immunity). Injection of these cells into a histocompatible host can result in interaction with T cells in the absence of co-stimulatory molecules, and therefore induction of antigen specific unresponsiveness or T cell tolerance.

The assay can be specifically conducted as follows. BALB/c (IA$^d$) mice (3-4 per group) are injected i.v. in the tail or s.c. in the base of the tail with the cells or reagents listed in Table 2 below. Cells are washed in PBS, resuspended to 1×10$^8$/ml in PBS and injected into the tail vein (0.1 ml; 1×10$^7$ cells/mouse). Ovalbumin peptide (2 mg/ml in PBS) is mixed with complete Freund's adjuvant containing Mycobacterium tuberculosis H37Ra in a 1:1 v/v ratio. Fifty microliters are injected s.c. into each side of the base of the tail. Seven days after the last injection, lymph nodes (inguinal, paraaortic, cervical, axillary, brachial) are removed and homogenized to obtain a single cell suspension. Lymph nodes from individual mice within a group are processed separately. T cells are purified from lymph node populations by passage of cell suspensions over G-10 and nylon wool to remove accessory cells. Antigen presenting cells are prepared from the spleens of naive BALB/c mice by homogenizing spleens to obtain a single cell suspension, lysis of erythrocytes using Gey's solution, treatment with mitomycin C (100 µg/ml in RPMI 1640/1% FBS for 1 hour at 37° C.) to inhibit APC proliferation, and 3 washes to remove residual mitomycin C. Assays for induction of a T cell response are carried out in 96 well round bottom microtiter plates. Two to 4×10$^5$ T cells are mixed with 2–4×10$^5$ APC. Each T cell/APC combination is incubated, in triplicate, with and without OVA peptide (range 10–200 ng/well) for 3–5 days. Approximately 18 hr before termination of the culture 0.4 uCi of $^3$H-thymidine is added to each well. The wells are harvested using a Skatron cell harvester and $^3$H-thymidine incorporation (a measure of DNA synthesis and, therefore, T cell proliferation) is determined using a LKB liquid scintillation spectrometer.

A positive response is evident if the wells containing peptide incorporate significantly more DNA than those without peptide. Typically mice are considered positive where proliferation (in mean cpm) in response to peptide is more than about 3 standard deviations greater than the background proliferation without peptide. For each group, mean peptide specific proliferation is calculated by averaging values for each of the 3 mice. Suppression of immunization will typically be considered as having occurred when the experimental group mean is greater than about 3 standard deviations less than the positive control group mean.

Referring to Table 2 below, groups 1 (uninjected) and 4 (injection of NSO alone) serve as negative controls and should not respond to in vitro challenge with peptide. Group 2 receives 2 injections of peptide, the classical immunization protocol, and should respond optimally to in vitro peptide presentation. Group 3 receives one injection of peptide and can be expected to respond suboptimally in vitro. Group 5 receives NSO cells first and then peptide one week later. Injection of NSO cells should not interfere with priming by peptide, therefore results from this group should be similar to group 3 and serve as a negative control for tolerance induction (Group 7). Group 6 receives the cells expressing the fusion complex. Due to lack of expression of co-stimulatory molecules necessary for stimulation of naive T cells, this group serves as a negative control for Group 7. No response from this group could potentially mean either "no response" or "specific unresponsiveness". Group 7, which receives an initial injection of NSO/IA$^d$/OVA cells and then an injection of peptide, will differentiate between these two outcomes. A lack of response to in vitro challenge with peptide from this group will demonstrate the induction of specific unresponsiveness, or tolerance.

TABLE 2

| Group Number | Injection #1 (Day - 14) | Injection #2 (Day - 7) | in vitro challenge (Day - 0) |
|---|---|---|---|
| 1 (neg control-a) | — | — | peptide |
| 2 (pos control-a) | peptide (s.c.) | peptide (s.c.) | peptide |
| 3 (pos control-a) | — | peptide (s.c.) | peptide |
| 4 (neg control-b) | NSO (i.v.) | — | peptide |
| 5 (pos control-c) (neg control-c) | NSO (i.v.) | peptide (s.c.) | peptide |
| 6 (experimental) (& neg cont-d) | NSO/IA$^d$/OVA (i.v.) | — | peptide |
| 7 (experimental) | NSO/IA$^d$/OVA (i.v.) | peptide (s.c.) | peptide |

EXAMPLE 15

T-cell Activation After Intramuscular (i.m.) Injection of DNA Coding for MHC Fusion Complex of the Invention Alone or in Combination with DNA Coding for Costimulatory Molecules The skeletal muscle can play a role as an immunological microenvironment. Previous work has shown that foreign genes can be expressed in muscle cells (Wolff J. A. et al. *Science* (1990) 247: 1465) and that an immune response is elicited against these antigens (Ulmer J. B. et al. *Science* (1993) 259: 1745). It also has been reported that stimulation of cultured human muscle cells (myoblasts) with interferon-γ (IFN-γ) leads to the expression of MHC class II complexes on these cells (Goebels N. et al. *J. Immunol.* (1992) 149: 661–667).

Mouse muscle cells were injected with DNA coding for a specific murine OVA 323-339/IA$^d$MHCII fusion complex (pJRS165.1) and the costimulatory signal B7-1 (pUB719) to generate local antigen presenting cells (APCs) that express the fusion complex containing the ovalbumin peptide 323-339. These APCs will eventually activate T-cells. As detailed below, DNA coding for an MHC fusion complex of the invention and co-stimulatory molecule was injected (i.m.) into BALB/c mice in order to elicit a specific T-cell proliferation response to the peptide encoded by the DNA (illustrated with pJRS165.1 and pUB719).

Three groups of BALB/c mice (3 mice per group) were injected i.m. in both hind leg quadriceps with 50 μL sterile PBS containing the plasmids 1) pJRS165.1 carrying the encoding region of the murine OVA 323-339/I-A$^d$ MHCII under the control of the CMV promoter alone or 2) pJRS165.1 and pUB719 containing the coding region of the murine B7-1 gene under the control of the CMV promoter or 3) pUB719 alone. The mice were previously anesthetized in a chamber saturated with Metophane® (Pitman-Moor, Mundelein, Ill.) according to the method disclosed in Example 6 above.

Within every group, 3 mice were injected with 100 μg DNA in 100 μL PBS at week 0 and a boost injection with the same DNA was performed at week 3. Ten days after the last injection, the inguinal and paraaortic lymph nodes were collected. Lymph node cells were isolated and submitted to an OVA specific T-cell proliferation assay as follows. The cells were washed 3 times in complete medium (RPMI-1640, 10% FBS, 2 mM L-glutamine, penicillin, streptomycin, and 5×10$^{-5}$ 2-mercaptoethanol) and resuspended at 5×10$^6$ cells/mL. One hundred microliters of the cell suspension were added to wells of a 96-well round bottomed microtiter plate. Dilutions of the OVA (323-339) peptide were prepared ranging from 0.8 μg/mL to 10 μg/mL and 100 μL/well was added to the cells in triplicate. Background proliferation was determined by omitting the peptide. The plates were incubated with 5% CO$_2$ at 37° C., for 3–5 days. Wells were pulsed with 0.4 μCi of $^3$H-thymidine for 18 hours prior to termination of cultures and harvested using a Skatron Cell Harvester. Incorporation of $^3$H-thymidine into DNA as a measure of T-cell proliferation was determined using an LKB liquid scintillation spectrometer. The degree of peptide reactive T-cell proliferation was indicative of the T$_H$-cell responses (i.e. of clonal expansion) that took place in the mice following immunization.

Figure 22:
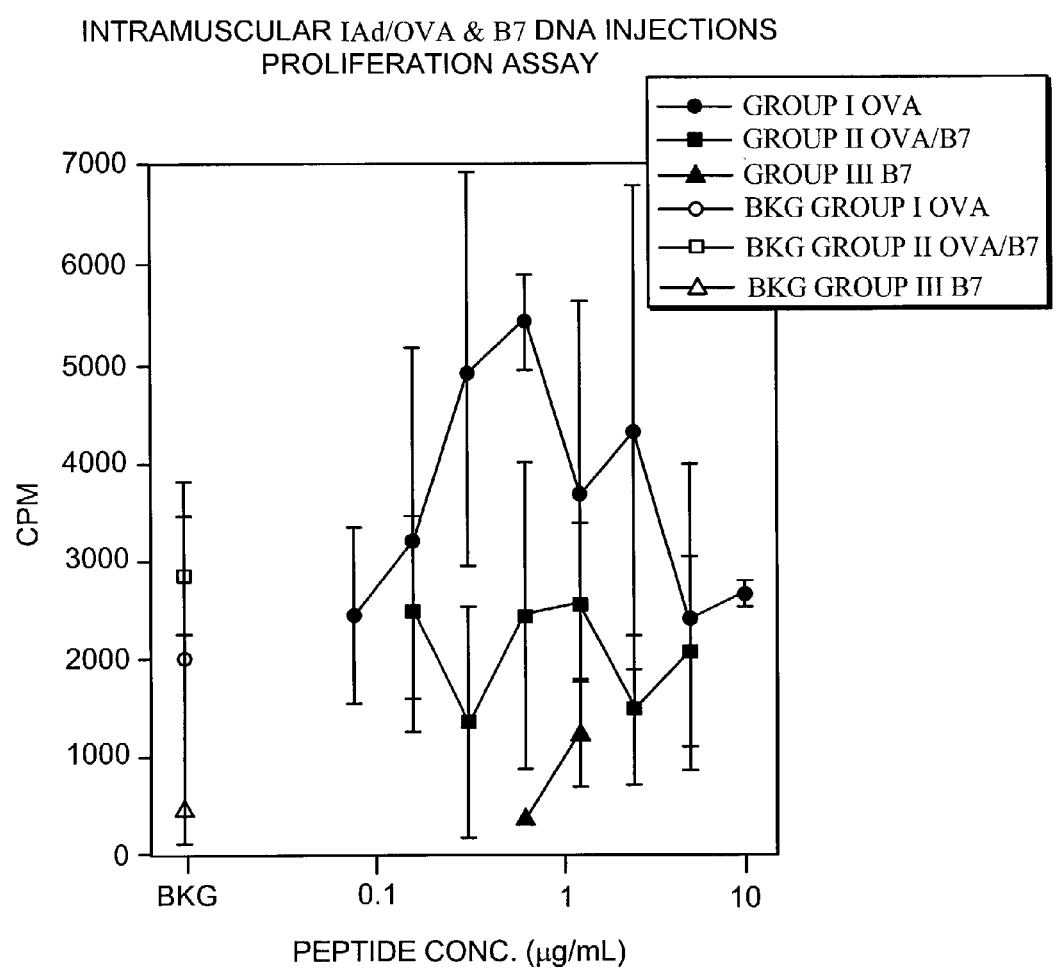
FIG. 22 shows graphically the results of the T cell proliferation assay of Example 15 which follows.

The results of the proliferation assay are shown in FIG. 22 of the Drawings. Specifically, injection of 100 μg DNA showed no significant OVA specific T-cell proliferation neither in the case of pJRS165.1 injection nor if pUB719 was coinjected. These results indicate that in this case administering DNA coding for OVA 323-339/MCHII fusion complexes alone or in combination with costimulatory molecule DNA intramuscularly does not induce an immune response against the OVA peptide. The limited proliferative response observed at high doses of injected pJRS165.1 DNA (i.e. 100 μg) may be the result of transforming intradermal dendritic cells (intradermal APCs) during the injection (see Example 16 below).

EXAMPLE 16

In vivo T Cell Activation After Intradermal (i.d.) Injection of DNA Coding for MHC Fusion Complex of the Invention Dendritic cells are professional, intradermal antigen presenting cells (APCs). The transformation of these cells (illustrated in this example) or other cells (such as exemplified in Example 13 above) with specific MHC class II fusion complexes of the invention can induce a peptide specific T-cell response. These APCs already bear the costimulatory molecules (i.e. B7-1) which provide the second activation signal to T-cells.

Two groups of BALB/c mice (9 mice per group) were injected i.d. on the shaved back with 100 μl PBS containing 10 μg of 1) pJRS165.1 carrying the encoding region of the murine OVA 323-339/I-A$^d$ MHC class II fusion gene under the control of the CMV promoter or 2) pABH1 carrying the encoding region of the murine HEL 74-86/I-A$^d$ MHCII fusion complex under the control of the CMV promoter as a control group. Four, 7 and 14 days after the injection the inguinal and paraaortic lymph nodes were collected. Lymph node cells were isolated and submitted to an OVA specific T-cell proliferation assay as follows. Cells were washed 3 times in complete medium (RPMI-1640, 10% FBS, 2 mM L-glutamine, penicillin, streptomycin, and 5×10$^{-5}$ M 2-mercaptoethanol) and resuspended at 5×10$^6$ cells/mL. One hundred microliters of the cell suspension were added to wells of a 96-well round bottomed microtiter plate. Dilutions of the OVA (323-339) peptide were prepared ranging from 0.08 μg/mL to 10 μg/ml and 100 μl/well was added to the cells in triplicate. Background proliferation was determined by omitting the peptide. Plates were incubated with 5% CO$_2$ at 37° C., for 3–5 days. Wells were pulsed with 0.4 μCi of $^3$H-thymidine for 18 hours prior to termination of cultures and harvested using a Skatron Cell Harvester. Incorporation of $^3$H-thymidine into DNA as a measure of T-cell proliferation was determined using an LKB liquid scintillation spectrometer. The degree of peptide reactive T-cell proliferation was indicative of the T$_H$-cell responses (i.e. of clonal expansion) that took place in the mice following immunization.

Figure 23:
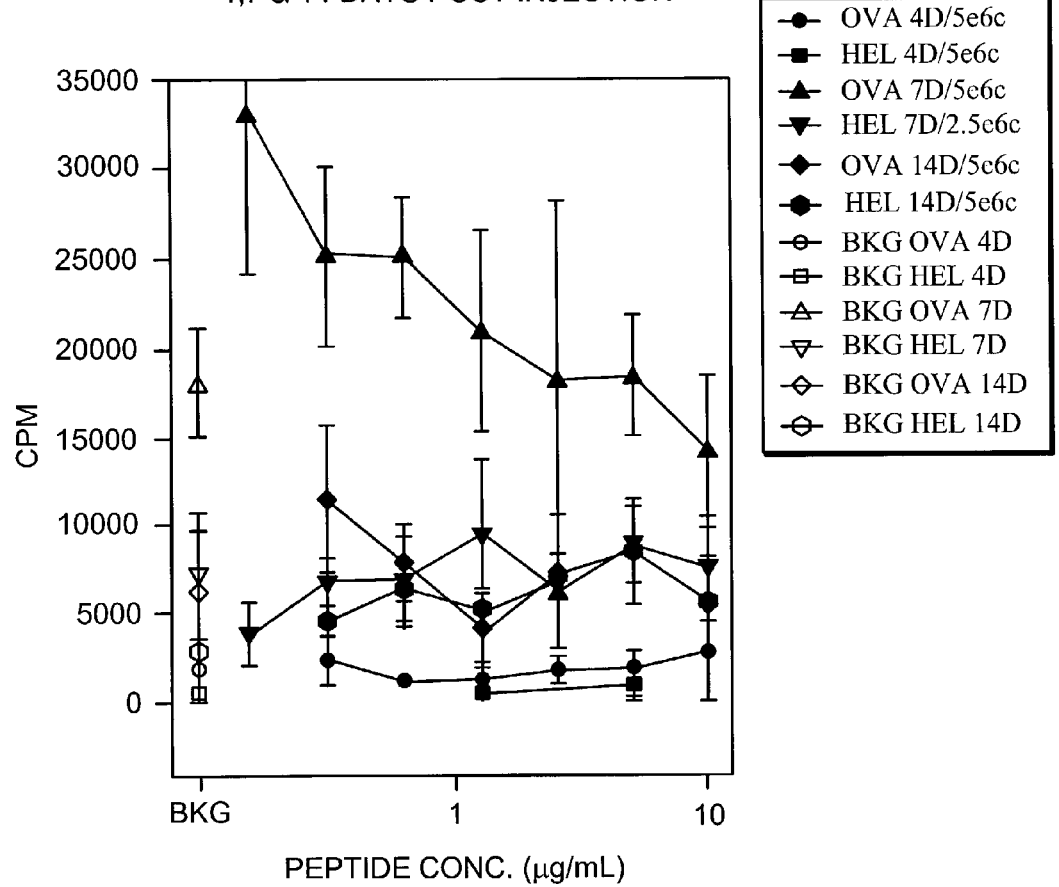
FIG. 23 shows graphically the results of the T cell proliferation assay of Example 16 which follows.

The results of the proliferation assays are shown in FIG. 23 of the Drawings. No significant specific T-cell proliferation is detected (approx. 2,500 cpm) 4 days post injection either in pJRS165.1 or pABH1 injected mice. Seven days after the injection, lymph node cells from pJRS165.1 injected mice show a 12 times higher proliferation at a stimulating peptide concentration of 0.31 μg/mL compared to day 4. Higher peptide concentrations reduced the proliferative response to approx 15,000 cpm. Cells, however, from pABH1 injected mice showed no significant increase in proliferation (approx. 7,000 cpm) at all 3 time points. The specific (OVA) proliferative response at 14 days post injection is 3 times lower than at day 7 indicating that the maximal stimulation period has elapsed. These results indicated that intradermal APCs have been transformed with functional OVA 323-339/MHCII fusion complex and that OVA specific T-cells have been primed and expanded. Because of the absence of stimulus (HEL-peptide) the HEL specific T-cells (activated by pABH1 transformed APCs) do not proliferate in the test. A lag period of 4 days is observed prior to any T-cell activation.

EXAMPLE 17

Construction of Vectors for Expressing Soluble and Membrane-bound Single-chain MHC Class II Molecules with Specific Presenting Peptides The MHC class II genes used for these constructs were originally isolated by PCR amplification of cDNA generated from the appropriate APC as described in the above examples (see in particular Example 1 above). Fragments of the I-A$^d$ α and β chain genes were generated by PCR amplification using cloned genes as template DNA and were assembled in the cloning scheme shown in FIG. 25 of the Drawings resulting in a chimeric gene encoding the antigenic peptide, OVA 323-339, linked to a single-chain I-A$^d$ molecule. Briefly, the α1-α2 gene fragment cloned into 39AD2 served as the template for PCR amplification using primers JLA007 and JLA010 (all of the oligoriucleotides used in cloning are listed in FIG. 26 of the Drawings), resulting in the addition of a 5' XhoI and a 3' XmaI restriction site. The α1-α2 PCR product was digested with XhoI and XmaI, gel-purified and subcloned into the pLL101 vector resulting in the pJAα9 construct. This vector adds sequence encoding a 6×His tag to the end of the α1-α2 protein to aid in protein to aid in protein purification.

The strategy for isolating the I-A$^d$ β1-β2 gene fragment and attaching the linker sequence has been described in the above examples. The 10 aa linker-β1-β2 gene fragment in pBC1 served as the template for PCR amplification using JLA005 and JLA009 primers to add NcoI and SpeI restriction sites necessary for subsequent cloning. The PCR products were digested with NcoI/SpeI digested pJAα9 resulting in the pJAα9β20 construct. In order to generate a single chain class II molecule, it was determined by computer modeling of the HLA-DR1 crystal structure that a flexible linker could be inserted between the carboxyl terminus of the β2 domain and the amino terminus of the α1 domain. Based on that the distance between these residues was 47 angstroms, a 24 amino acid linker primarily comprised of the (GGGGS) motif repeated four times was modeled and used. To insert sequences encoding this flexible peptide between the cloned β and α chain gene fragments, oligonucleotides, JA301 and JA302, were annealed and ligated into SpeI/XhoI digested pJAα9β20. The resulting construct was called pJALNK. pJALNK was digested with NheI and EcoRI and the β1β2-α1α2 single chain gene fragment was gel purified. This fragment was inserted into the pVW229 vector carrying the β chain leader sequence and the regions encoding the OVA 323-339 peptide as described in the above examples. The resulting construct SSC1 contains a chimeric gene encoding the β leader/OVA peptide/10 aa linker/β1-β2/20 aa linker/α1-α2/6×His tag. The sequence of this gene is shown in FIG. 27 of the Drawings.

To construct a vector for expression of soluble singlechain (sc) class II molecules in an insect cell expression system, the chimeric gene was removed from SSC1 by digestion with NcoI and EcoRI and gel purified. The fragment was ligated into NcoI/EcoRI-digested p2Bac vector (In Vitrogen—part number V1908-10) to created pMBSC1.2.

Figure 28:
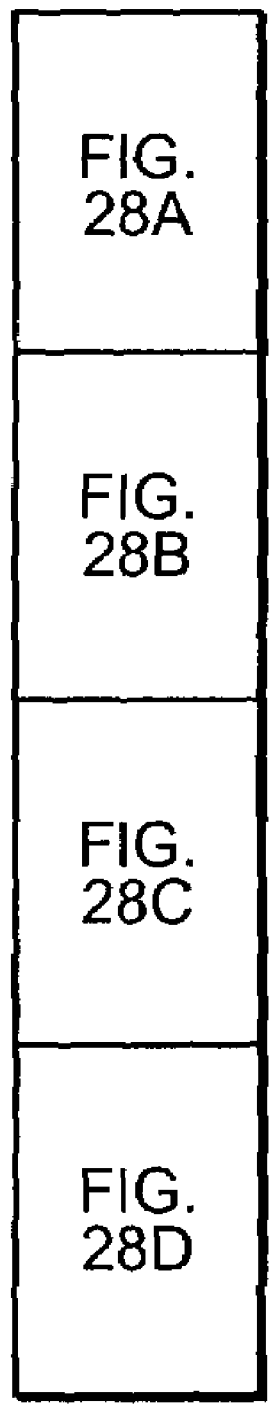
FIG. 28 (SEQ ID NO: 122) shows the DNA and amino acid sequences of the SCT1 single-chain gene.

To generate a vector capable of expressing membrane bound sc class II molecules in mammalian cells, the Bc/I-EcoRI fragment of pJRS163-10 that encodes the α chain transmembrane TM domain was subcloned into Bc/I-EcoRI digested SSCI vector. The resulting vector, SCTM1, was digested with XmaI and EcoRI and the single-chain I-A$^d$-OVA cassette was inserted into the PEE13 mammalian expression vector, giving the SCT1 construct. The sequence of the chimeric gene is shown in FIG. 28 of the Drawings.

Figure 29:
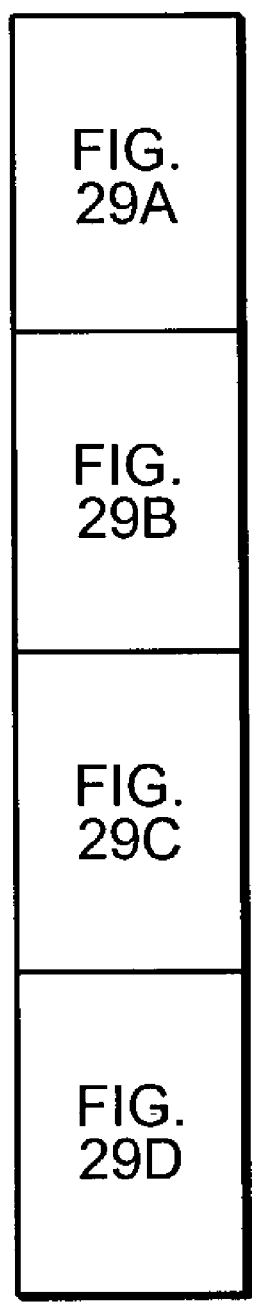
FIG. 29 (SEQ ID NO: 123) shows the DNA and amino acid sequences of the SCE1 single-chain gene.

To generate a vector capable of expressing soluble sc-MHC molecules in mammalian cells, the α chain template DNA was amplified by PCR from pJRS163-10 using primers JS305 and OPR142, thereby adding sequence encoding the EE antibody tag to the 3' end of the gene fragment. The PCR product was digested with Bcn and EcoRI and cloned into digested SSC1 vector. The resulting vector, SCEE1, was digested with Bc/I-EcoRI and the single-chain I-A$^d$-OVA cassette was inserted into the PEE13 mammalian expression vector, giving the SCE1 construct. The sequence of the chimeric gene is shown in FIG. 29 of the Drawings. Samples of the above single chain plasmids pMBSC1.2, SCT1 and SCE1 have been deposited with the American Type Culture Collection, Rockville, Md.

EXAMPLE 18

Production of Soluble Single Chain MHC Molecules of the Invention (MHC II (I-A$^d$) in Insect Cells)

The purified pMBSC1.2 plasmid was used in a cotransfection and recombinant virus was enriched from wild type AcMNPV by limiting dilution (see D. R. O'Reilly et al., Baculovirus Expression Vectors: A Laboratory Manual. WH Freeman & Co. New York (1992)). SF9 cells were used throughout.

Supernatant from wells was tested by ELISA to identify virus producing recombinant product (sc I-A$^d$-OVA). The ELISA assay involves coating 100 ngs of M5/114 (ATCC TIB 120) anti-IA$^d$ onto wells of 96 well microtiter plates in 50 microliters of 0.1M carbonate buffer pH 8.2. Blocking was done with 200 μl of PBS 10% FBS (fetal bovine serum from Biowhittaker part number 14-901F) for at least 1 hour and plates were washed three times with 200 μls of wash buffer (PBS with 0.5 ml Tween 20/1.) Samples were added at 100 μl/well and incubated 15 minutes at 37° C. Plates were washed four times with 200 μl wash buffer. Biotinylated AMS-32.1 anti-IA$^d$ (part number 06032D from Pharmingen) was added at 100 ng/well in 100 μl PBS 10% FBS. Following incubation for 15 minutes at 37° C., the plates were washed four times with wash buffer. Avidin peroxidase (Sigma) was added at 250 ng/well in 100 μl/well PBS 10% FBS and incubated for 15 minutes at 37° C. Plates were then washed eight times with 200 μl wash buffer and 100 μl of ABTS substrate (Kirkegaard and Perry part numbers 5060-00 or 50-60-01) was added per well. Absorbance was measured at 405 nm.

The cotransfection mix supernatant was tested for I-A$^d$ reactivity by the above ELISA. Mean absorbance of duplicate wells are shown in Table 3 below. The specificity of the signal observed shown to be due to secretion of sc I-A$^d$-OVA into culture supernatant by SF9 cells.

Limiting dilution subcloning was done on the cotransfection mix by diluting virus in complete media (TNMFH part number 51942 from JRH Biosciences supplemented with 10% FBS) and incubating virus dilutions with 2×10$^4$ SF9 cells/well in 96 well plates. Supernatant from wells that showed visible signs of infection but no polyhedra were tested in the $IA^d$ ELISA. Clones C6 (1.557), and F8 (1.446) are strongly positive. C12 is clearly negative (0.124).

Five hundred microliters of positive clone C6 was added to each of three one liter flasks containing SF9 cells at $1 \times 10^6$ cells/ml. Approximately 2200 mls of infection supernatant was used in the purification of sc I-$A^d$-OVA as described in Example 19 below. The thus purified single chain MHC II complex was assayed for ability to modulate the activity of DO11.10 T cell hybridoma as described in Example 20 below.

TABLE 3

I-$A^d$ ELISA of insect cell culture supernatants from cotransfections

| Sample dilution | Absorbance |
| --- | --- |
| Undiluted | 0.857 |
| 1:2 | 0.524 |
| 1:4 | 0.305 |
| 1:8 | 0.165 |

Negative controls including sample diluent (0.064) and supernatant from an infection done with a recombinant Baculovirus containing the gene for Neuron Specific Enolase (NSE) in SF9 cells showed negligible binding (0.098).

EXAMPLE 19

Purification of Single Chain MHC Molecules of the Invention (MHC II (I-Ad) Expressed in Insect Cells)

The following steps were carried out in the preparation of soluble single-chain I-$A^d$-OVA from insect cell culture supernatants.

Ammonium Sulfate Fractionation: At 0–4° C., solid ammonium sulfate (0.436 g/ml) was slowly added into insect cell culture medium (2200 ml) while stirring the sample. Following the addition of ammonium sulfate, stirring of the sample was continued for 30 minutes. The mixture was then centrifuged at 26000 g and 4° C. for 30 minutes, the supernatant discarded, and the pellet resuspended in 100 ml of phosphate-buffered saline (PBS). The resuspended sample was dialyzed against 4000 ml of PBS at 4° C. for about 20 hours, with one change of fresh PBS after first 4.5–5 hours of dialysis. The volume of the dialyzed sample was measured and solid NaCl and 20% (v/v) Tween 20 was added to 0.5 NaOH, followed by filtration through a 0.8 micron filter.

Metal Chelate Affinity and Immunoaffinity Chromatography: All the following steps were done at room temperature.

Ni-IDA Sepharose: The sample provided by the above fractionation step was loaded onto a Ni-IDA Sepharose Fast Flow column (2.6×7.2 cm, 38.0 ml) that had been equilibrated with at least 5 bed volumes of PBS, 0.5 M NaCl, 0.2% (v/v) Tween 20, pH 8.0. The flow rate for loading sample was 3 ml/minute. Then the column was washed with at least 7–8 bed volumes of the above equilibration buffer, followed by 2.5–3 bed volumes of 20 mM $Na_2HPO_4$, pH 7.0, 0.2 M NaCl. The flow rate for washing was 5 ml/minute. I-$A^d$ protein was eluted with stepwise pH decreases effected by mixing different portions of Buffer A (20 mM $Na_2HPO_4$, pH 7.0, 0.2 M NaCl) and Buffer B (20 mM $Na_2HPO_4$, pH 3.0, 0.2 M NaCl) programmed in a FPLC controller. An ELISA assay using anti-I-$A^d$ monoclonal antibody (which recognize conformational epitopes of I-Ad molecules) indicated that I-Ad is present in fractions eluted by 90% and 100% Buffer B. Those $A_{280\ nm}$ peaks eluted by 90% and 100% Buffer B were pooled, immediately adjusting to pH 7.0 with 1 M Tris. The sample was concentrated and buffer-exchanged into 20 mM Tris-HCl, pH 8.0 by ultrafiltration.

Immunoaffinity Chromatography: The sample from the above step was first passed through a Protein A Sepharose Fast Flow column (1.6×5 cm, 10 ml) and then applied onto a column (1.6×3.4 cm, 6.8 ml) of Protein A Sepharose Fast Flow crosslinked with MKD 6, an anti-I-$A^d$ monoclonal antibody. The two columns had been previously equilibrated with 20 mM Tris-HC1, pH 8.0. Following sample application, the immunoaffinity column was washed with 20 mM Tris-HC1, pH 8.0 until $A_{280}$nm baseline was reached. The antibody column was then washed with the same buffer containing 1 M NaClas above to remove nonspecific bound proteins. The 1-$A^d$ protein was then eluted with 50 mM glycine-NaOH, pH 11.0. The eluted protein peak (monitored by $A_{280\ nm}$) from the antibody column was immediately adjusted to pH 8.0 with 2M glycine, pH 2.0, concentrated and buffer-exchanged into 20 mM Tris-HCl, pH 8.0 by ultrafiltration. The purified sample was stored at 4–8° C. The purity and functionality of I-$A^d$ sample were tested by sodium dodecyl sulfate-polyacrylamide gel electrophoresis and T-cell activation assay (see below), respectively. Purified single-chain I-$A^d$-OVA from this preparation showed no contaminating bands on a Coommassie stained polyacrylamide gel and total protein was 125 µg/ml by total protein assay.

EXAMPLE 20

Activity of Single-chain MHC Complexes of the Invention

It was determined whether purified single-chain I-$A^d$/OVA MHC complexes of the invention could activate the OVA- specific DO11.10 T cell hybridoma as measured by IL-2 and IL-4 production. This method involves coating single-chain I-$a^d$/OVA onto IMMULON II plates (Dynatech) in PBS overnight at 4° C. Wells were emptied, washed once with PBS and $1 \times 10^5$ DO11.10 cells were added per well in 200 µl RPMI 10% FBS. Following incubation overnight at 37° C. in a humid incubator with 10% $CO_2$, culture supernatants were harvested, cells were removed by centrifugation and IL-2 and IL-4 levels were determined by ELISA as follows.

The rat anti-mouse IL-2 ELISA capture antibody (Pharmingen part number 18161 D) was coated at 100 ng/well in 50 µl 0.1M carbonate pH 8.2. Blocking was done with 200 µl of PBS 10% FBS for at least 1 hour and the plates were washed three times with 200 µl of wash buffer (PBS with 0.5 ml Tween 20 per 1). Samples were added at 100 µl/well and incubated for 4 hours at room temperature or overnight at 4° C. Plates were washed four times with 200 µl wash buffer and biotinylated rat anti-mouse IL-2 (Pharmingen) was added at 100 ng/well in 100 µl PBS 10% FBS. Following incubation for 45 minutes at room temperature, the plates were washed four times with wash buffer. Avidin peroxidase (Sigma part number A-3151) was added at 250 ng/well in 100 µl/ well PBS 10% FBS and incubated for 30 minutes at room temperature. Plates were then washed eight times with 200 µl wash buffer and 100 µl of ABTS substrate (Kirkegaard and Perry part number 5060-00 or 50-66-01) was added per well. Absorbance was measured at 405 nm. The IL-4 ELISA protocol was identical except for the use of IL-4 specific capture and probe antibodies (Pharmingen). The results of one activation assay is shown in Table 4 below. Neither DI11.10 cells alone nor DO11.10+A20 (I-A$^d$ positive) cells secreted any IL-2 or II-4. The sc I-A$^d$-OVA resulted in the secretion of IL-2 and IL-4 by the DO11.10 T cell hybridoma. A second activation was done with lower doses of immobilized sc I-A$^d$-OVA. Secretion levels of IL-2 and IL-4 both titered down to zero, as shown in Table 5 below. In both experiments, IL-2 and IL-4 were secreted by DO11.10 cells in a dose dependent manner with regard to exposure to immobilized sc I-A$^d$-OVA.

TABLE 4

DO11.10 activation assay using immobilized purified sc I-A$^d$-OVA

| sc IA$^d$-OVA (ng/well) | IL-2 concentration in DO11 super (U/ml) | IL-4 concentration in DO11 super(U/ml) |
| --- | --- | --- |
| 2500 | 143 | 23 |
| 1250 | 126 | 20 |
| 625 | 116 | 15 |
| 312 | 109 | 16 |
| 156 | 100 | 10 |
| 78 | 45 | 7 |
| 0 (DO11.10 only) | 0 | 0 |

TABLE 5

DO11.10 activation assay using immobilized purified sc I-A$^d$-OVA-extended dilution

| scIA$^d$-OVA (ng/well) | IL-2 concentration in DO11 super (U/ml) | IL-r concentration in DO11 super (U/ml) |
| --- | --- | --- |
| 625 | 38 | 2.0 |
| 312 | 35 | 1.5 |
| 156 | 24 | 0.9 |
| 78 | 17 | 0.8 |
| 39 | 0 | 0 |
| 0 (DO11.10 only) | 0 | 0 |

EXAMPLE 21

Production of Single-chain MHC Molecules (class II) in Mammalian Cells

Transfection and selection of mammalian cell lines was carried out as follows: 1×10$^7$ NSO cells were washed twice in ice cold PBS, resuspended in 760 μl of cold PBS, and mixed with 40 μg (1 μg/μl) of Sa/I linearized plasmic SCE1 or SCT1 DNA. After 5 minutes incubation on ice, the cells were electroporated using a Gene Pulser (Biorad) to deliver one pulse of 250 volts, 960 μFd. The pulsed cells were placed on ice for 2–5 minutes and added to 30 ml of non-selective medium (IMDM, 10% FBS, 2 mM glutamine, 5000 units/ml penicillin, 5000 μg/ml streptomycin). Cells were plated in 96-well flat bottom tissue culture plates and 24 h later, 150 μl of selective medium (IMDM, 10% dialyzed FBS, 5000 units/ml penicillin, 5000 μg/ml streptomycin, 1× nucleosides, 1× glutamate+asparagine) was added to each well. The plates were fed with selective medium on a weekly basis by removing 100 μl/well used medium and adding 100 μl/well of fresh selective medium, allowing the cells to gradually deplete the medium of all residual glutamine. The glutamine synthetase gene carried on the SCE1 and SCT1 plasmids allows selective growth of the transfected cells in glutamine-free media. Colonies of the cells transfected with the plasmic became evident after 14–21 days. The transfectants carrying the SCT1 vector (i.e. membrane-bound form of the sc I-A$^d$-OVA molecules) were expanded and screened for expression of the MHC molecules by flow cytometry as described below.

Clones generated from the transfection/selection protocol were analyzed for surface expression of class II MHC molecules at levels significantly higher than the parental cell line. The cells were incubated with FITC-conjugated anti-I-A$^d$ antibody, AMS 32.1 (PharMingen, 1:100 dilution) in cold staining buffer (PBS, 1% FCS) for 45 minutes in the dark. After washing three times in staining buffer, fluorescence was examined of a FACScan flow cytometer (Beckton Dickinson). An isotype matched FITC-conjugated anti-I-A$^k$ antibody, 10–3.6 (PharMingen, 1:100 dilution) was used as a negative control. The results of such an assay, shown in Table 6 below for three independent SCT1 transfected cell lines, indicate that the transfected cells express the sc I-A$^d$-OVA on their cell surface.

The transfectants carrying the SCE1 vector (i.e. soluble form of the sc I-A$^d$ OVA molecules) were expanded and screened for expression and secretion of the MHC molecules by the I-Ad specific ELISA assays described in Example 18 above. The results of such an assay of the culture supernatant from two SCE1 transfected cell lines are shown in Table 7 below. These results indicate that the transfected cells produce and secrete the sc I-A$^d$-OVA molecule. This system could be used to generate large amounts of soluble peptide-linked single-chain MHC molecules.

TABLE 6

Surface expression of I-A$^d$ molecules on transfected cell lines

| | Mean Fluorescence | |
| --- | --- | --- |
| Cell line | I-A$^d$-specific | I-A$^k$-specific |
| NSO (parental) | 280.4 | 32.1 |
| T2 (SCT1-transfectant) | 612.8 | 22.0 |
| T6 (SCT1-transfectant) | 417.9 | 45.1 |
| T12 (SCT1-transfectant) | 911.1 | 45.9 |

TABLE 7

I-A$^d$ ELISA assay on SCE1 transfectant cell culture supernatants

| Culture Supernatant undiluted) | Absorbance |
| --- | --- |
| NSO (parental cell line) | 0.444 |
| E10 (SCE1 transfectant) | 0.781 |
| E11 (SCE1 transfectant) | 0.960 |
| sc I-A$^d$-OVA from insect cell culture (positive control) | 2.44 |

EXAMPLE 22

Activity of the Single-chain I-A$_d$ Molecules Expressed on Mammalian Cells

Stimulation of IL-2 release from the OVA 323-339 specific I-A$^d$ restricted DO11.10 T cell hybridoma was carried out as described in Example 20 above. Briefly, 1×10$^5$ SCT1 transfectant cells or A20.11 were incubated together with (varying amounts) OVA peptide and 2×10$^5$/well DO11.10 cells at 37° C. in an atmosphere of 5% CO$_2$. Cultures were carried out in complete medium (RPMI 1640 supplemented with 10% FBS, penicillin/streptomycin, L-glutamine and 50 μM 2-mercaptoethanol) in 96 well flat bottom microtiter plates. After 24 hours, culture supernatants were assayed for the presence of DO11.10 derived IL-2 using the IL-2 ELISA assay described in Example 20 above or by measuring the growth of the IL-2 dependent murine T-cell line CTLL-2. In the latter test, serial twofold dilutions of each culture supernatant were prepared in complete medium in flat bottomed microtiter plates and 1×10$^4$ CTLL-2 cells were added to each well. A standard curve of (amounts) rIL-2 was run in parallel. After 16 to 20 h, MTT (2 mg/ml, 27 µl/well) was added and the plates incubated for 4 h. At this time, blue crystals formed by MTT in actively metabolizing cells were dissolved by addition of 150 µl of 0.4 N HCl in isopropanol. After mixing, the O.D. at 562 was determined using a Ceres-UV900HI plate reader. The absorbance corresponds to the level of CTLL cell growth supported by the IL-2 in the culture media.

The results of two such activation assay are shown in Tables 8 and 9 below. Similar results were obtained using the CTLL assay.

TABLE 8

DO11.10 T cell hybridoma activation by SCT1 transfected cell lines

| Antigen presenting cell assayed | IL-2 ELISA result (Absorbance) |
|---|---|
| NSO (parental cell line) | 0.047 |
| T2 (SCT1 transfectant) | 0.758 |
| T6 (SCT1 transfectant) | 0.307 |
| A20 + OVA 323–339 peptide (positive control) | 1.33 |

TABLE 9

DO11.10 T cell hybridoma activation by SCT1 transfected T12 cells

| Antigen presenting cell assayed | IL-2 ELISA result (Absorbance) |
|---|---|
| NSO (parental cell line) | 0.078 |
| T12 (SCT1 transfectant) | 1.03 |
| A20 + OVA 323–339 peptide (positive control) | 1.45 |

EXAMPLE 23

Immunosuppression Using Soluble Peptide-linked Single-chain MHC Class II Molecules of the Invention To test whether the soluble peptide-linked single-chain class II molecules can induce $T_H$ cell anergy in an animal model system, the effects of the molecules on $T_H$ cell-dependent immunoglobulin class switching (i.e. IgM to IgG) and on clonal expansion of peptide-specific T cell lines can be examined.

In order to examine Ig class switching, two test groups are set up as follows: (a) 10 BALB/c mice are injected with 100 µg of OVA 323-339 in Complete Freund's adjuvant H37Ra at the base of the tail and boosted again 7 days later, in order to induce an immune response to the OVA 323-339 peptide. On the day before the day of each immunization with OVA, 5 of the mice are injected IV with 10–100 µg of the soluble single-chain I-A$^d$OVA in PBS. This soluble fusion protein will bind to the T cell receptor (TCR) displayed on the OVA 323-339 specific THE cells. Due to the absence of the co-stimulatory signal, these $T_H$ cells are induced to a state of anergy. Since the immunoglobulin class switching is a $T_H$ cell dependent process, it is expected that the induction of anti-OVA 323-339 IgG antibody will be reduced in the single-chain I-A$^d$-OVA treated mice. The remaining 5 mice serve as control and receive PBS.

Ten days after the second immunization, blood is collected from each mouse by tail bleeding. The blood is centrifuged at approximately 14,000 G for 3–5 minutes and the serum collected. Assays are performed in 96-well microtiter plates (Maxisorp F8; Nunc, Inc.) coated at 1–50 µg/ml with ovalbumin using a Tris-HCl coating buffer, pH 8.5. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 µl/well of a 3% BSA solution. Following incubation on a plate rotator at room temperature for 30 minutes, the plates are washed five times with Wash solution. Mouse sera diluted 1:500 in sample/conjugate diluent (2% gelatin+0.1% Tween-20 in TBS) and then, in duplicate, serially diluted on the plate. Two identical plates are set up for each coating protein, one for determination of IgM titer and the other for IgG. following incubation at room temperature for 30 minutes, the plates are washed five times with Wash solution. Goat anti mouse IgM-HRP and goat anti mouse IgG-HRP conjugates (Boehringer Mannheim, Indianapolis, Ind., 1:100 dilution in Sample/conjugate diluent) are added to the appropriate plates. Following incubation at room temperature for 30 minutes, the plates are washed five times with Wash solution and then incubated with 100 µl/well of ABTS developing substrate (Kirkgaard & Perry Laboratories, Inc., Gaithersburg, Md.) for 10 minutes at room temperature. The reactions are stopped with 100 µl/well of Quench buffer (Kirkgaard & Perry laboratories, Inc., Gaithersburg, Md.) and the absorbance values are read at 405 nm using an automated microtiter plate ELISA reader (Ceres UV900HI, Bioteck, Winooski, Vt.). The titer is determined by plotting the absorbance reading versus the log of the dilutions of the samples. The titers for IgM is versus are then compared. As detailed above, the soluble peptide-linked single-chain MHC class II molecules are expected to inhibit the IgG class switching in a peptide specific manner due to the anergy induced in the corresponding peptide-reactive $T_H$ cells.

The effects of soluble peptide-linked single-chain MHC molecules on clonal expansion of peptide-specific T cell lines in vivo can be examined as follows. Treatment groups (4 mice per group) are suitably the same as described above. The immunization protocol is suitably as follows: mice are injected IV with 10–100 µg of the soluble single-chain I-A$^d$-OVA fusion protein in PBS and 24 hours later injected subcutaneously at the base of the tail with 50 µg of OVA 323-339 in complete Freunds Adjuvant H37Ra. These two injections are repeated 6 and 7 days later. Seven days after completion of the second set of injections, the mice are sacrificed. The inguinal and paraaortic lymph nodes are removed and rendered into a single cell suspension.

The suspension is depleted of antigen presenting cells by incubation on nylon wool and Sephadex G-10 columns, and the resulting purified T cell populations incubated with APCs pulsed with the OVA 323-339 peptide. Spleenic B cells serve as antigen presenting cells. These cells are fixed with mitomycin C (50 to 100 µg/ml in a suspension of 4×10$^6$ spleenocytes/ml) to inhibit proliferation of the B cells, washed extensively and added to purified T cells with various concentrations of the OVA 323-339 peptide. The proliferation assay is carried out in 96 well round bottom microtiter plates at 37° C., 5% CO$_2$ for 3–5 days. Wells are pulsed with 1 µCi of $^3$H-thymidine 18 hrs prior to termination of cultures and harvested using a Skatron cell harvester. Incorporation of $^3$H-thymidine into DNA as a measure of T cell proliferation is determined using an LKB liquid scintillation spectrometer. The degree of peptide-reactive T cell proliferation is indicative of the $T_H$ cell responses (i.e. of clonal expansion) that took place in the mice following immunization.

EXAMPLE 24

Immunosuppressive Approach by DNA Inoculation with Vectors Expressing Peptide-linked Single-chain MHC Molecules of the Invention An example of a model system for testing the effects of the DNA inoculation approach (particularly intramuscular or intradermal) is outlined as follows. Three groups of BALB/c mice are injected intramuscular (IM) in both hind legs with 100 μg of: (1) SCE1, (b) SCT1, or (c) saline. Injections will be given at 0, 2, and 4 weeks. At 4 and 5 weeks after the initial DNA injection, OVA peptide 323-339 (100 μg/mouse in complete Freunds H37Ra adjuvant) is injected subcutaneously at the base of the tail. Two weeks later (week 8), blood is collected from each mouse by tail bleeding and serum obtained following centrifugation at approximately 14,000 G for 3–5 minutes. Titers of OVA-specific IgG and IgM antibodies is determined as described above. The degree of OVA-specific IgG antibody is indicative of the $T_H$ cell directed immunoglobulin class switching that took place in the mice following immunization with the peptide. Therefore, DNA inoculation with the peptide-linked single-chain MHC expression vectors will cause a reduction in the level of peptide-specific IgG antibodies without effecting IgM antibody levels.

An alternative assay is to measure OVA-specific $T_H$ cell clonal expansion or proliferation. Briefly, a cell suspension will be prepared from the inguinal and paraaortic lymph notes 7 days after the second OVA immunization. The suspension is depleted of antigen presenting cells by incubation on nylon wool and Sephadex G-10 columns, and the resulting purified T cell populations incubated with APCs pulsed with the OVA 323-339 peptide. Spleenic B cells serve as antigen presenting cells. These cells are fixed with mitomycin C (50 to 100 μg/ml in a suspension of $4 \times 10^6$ spleenocytes/ml) to inhibit proliferation of the B cells, washed extensively and added to purified T cells with various concentrations of the OVA 323-339 peptide. The OVA-specific T cell proliferation assay is carried out as described above. The degree of peptide-reactive T cell proliferation is indicative of the $T_H$ cell responses (i.e. of clonal expansion) that took place in the mice following immunization with the peptide. Therefore, DNA inoculation with the peptide-linked single-chain MHC expression vectors may cause a reduction in the level of peptide-specific $T_H$ cell proliferation.

The invention has been described with reference to preferred embodiments thereof. However, it will be appreciated that those skilled in the art, upon consideration of this disclosure, may make modifications and improvements within the spirit and scope of the invention.

---

What is claimed is:

1. A multivalent MHC fusion complex comprising two or more linked MHC fusion complexes,
wherein each MHC fusion complex comprises a MHC class II molecule that contains a peptide-biding groove, an antigenic or antagonistic presenting peptide covalently linked to an N-terminus of the MHC molecule and effectively positioned in the peptide-binding groove, and a linker sequence interposed between the presenting peptide and the MHC molecule, the fusion complex being capable of increasing or decreasing T cell proliferation or activity, wherein the MHC fusion complex are genetically modified to include a terminal amino acid residue(s) with chemically reactive side chains and the reactive side chains are used to chemically cross-link the MHC fusion complexes.

2. The multivalent MHC fusion complex of claim 1, wherein the MHC fusion complex does not contain the transmembrane and cytoplasmic domains of the MHC molecule and is linked to an immunoglobulin.

3. The multivalent MHC fusion complex of claim 2, wherein the immunoglobulin is IgG, IgM or Fab'$_2$.

4. The multivalent MHC fusion complex of claim 1, wherein two or more of the MHC fusion complexes are chemically cross-linked together or to a suitable particle.

5. The multivalent MHC fusion complex of claim 1 wherein the C terminus of the β chain of MHC fusion complex is genetically modified to include amino acid residue(s) with chemically reactive side chains.

6. The multivalent MHC fusion complex of claim 1 wherein two or more of the MHC fusion complexes are chemically cross-linked to a dendrimer particle.

7. The multivalent MHC fusion complex of claim 1, wherein each MHC fusion complex therein is the same.

8. A multivalent MHC fusion complex comprising two or more linked MHC fusion complexes,
wherein each MHC fusion complex comprises a MHC class II molecule that contains a peptide-biding groove, an antigenic or antagonistic presenting peptide covalently linked to an N-terminus of the MHC molecule and effectively positioned in the peptide-binding groove, and a linker sequence interposed between the presenting peptide and the MHC molecule, the fusion complex being capable of increasing or decreasing T cell proliferation or activity, wherein the MHC fusion complex are genetically modified to include a terminal amino acid residue(s) with chemically reactive side chains and the reactive side chains are used to chemically cross-link the MHC fusion complexes and further wherein each MHC fusion complex therein is the same.

9. A multivalent MHC fusion complex comprising two or more linked MHC fusion complexes,
wherein each MHC fusion complex comprises a MHC class II molecule that contains a peptide-biding groove, an antigenic or antagonistic presenting peptide covalently linked to an N-terminus of the MHC molecule and effectively positioned in the peptide-binding groove, and a linker sequence interposed between the presenting peptide and the MHC molecule, the fusion complex being capable of increasing or decreasing T cell proliferation or activity, wherein the MHC fusion complex are genetically modified to include a terminal amino acid residue(s) with chemically reactive side chains and the reactive side chains are used to chemically cross-link the MHC fusion complexes and further wherein the amino acid is a Cys or His residue.

10. A multivalent MHC fusion complex comprising two or more linked MHC fusion complexes,
wherein each MHC fusion complex comprises a MHC class II molecule that contains a peptide-biding groove, an antigenic or antagonistic presenting peptide covalently linked to an N-terminus of the MHC molecule and effectively positioned in the peptide-binding groove, and a linker sequence interposed between the presenting peptide and the MHC molecule, the fusion complex being capable of increasing or decreasing T cell proliferation or activity, wherein the MHC fusion complex are genetically modified to include a terminal amino acid residue(s) with chemically reactive side chains and the reactive side chains are used to chemically cross-link the MHC fusion complexes and further wherein wherein the C terminus of the β chain of MHC fusion complex is genetically modified to include amino acid residue(s) with chemically reactive side chains and the amino acid is a Cys or His residue.

* * * * *

SEQUENCE LISTING (1) GENERAL INFORMATION:

(iii) NUMBER OF SEQUENCES: 123

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: unknown
      (D) TOPOLOGY: unknown (xi) SEQUENCE DESCRIPTION: SEQ ID NO: 1:

Ala Ser Gly Gly Gly Gly Ser Gly Gly Gly
1               5                   10

(2) INFORMATION FOR SEQ ID NO: 2:

(i) SEQUENCE CHARACTERISTICS:
      (A) LENGTH: 8 base pairs
      (B) TYPE: nucleic acid
      (C) STRANDEDNESS: unknown
      (D) TOPOLOGY: unknown (xi) SEQUENCE DESCRIPTION: SEQ ID NO: 2:

CCACCATG                                                                8

(2) INFORMATION FOR SEQ ID NO: 3:

(i) SEQUENCE CHARACTERISTICS:
      (A) LENGTH: 18 amino acids
      (B) TYPE: amino acid
      (C) STRANDEDNESS: unknown
      (D) TOPOLOGY: unknown (xi) SEQUENCE DESCRIPTION: SEQ ID NO: 3:

Ser Ile Ser Gln Ala Val His Ala Ala His Ala Glu Ile Asn Glu Ala
1               5                  10                  15

Gly Arg (2) INFORMATION FOR SEQ ID NO: 4:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 4:

Ser Ile Ser Gln Ala Val His Ala Ala Arg Ala Glu Ile Asn Glu Ala
1               5                  10                  15

Gly Arg (2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 5:

Ser Ile Ser Gln Ala Val His Ala Ala His Tyr Glu Ile Asn Glu Ala
1               5                  10                  15

Gly Arg (2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 6:

Asn Leu Cys Asn Ile Pro Cys Ser Ala Leu Leu Ser Ser
1               5                  10

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 7:

Gln Ile Ser Val Gln Pro Ala Phe Ser Val Gln
1               5                  10

(2) INFORMATION FOR SEQ ID NO: 8:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown -continued (xi) SEQUENCE DESCRIPTION: SEQ ID NO: 8:

Pro Lys Tyr Val Lys Gln Asn Thr Leu Lys Leu Ala Thr
1               5                   10

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 9:

His Tyr Gly Ser Leu Pro Gln Lys Ser Gln His Gly Arg
1               5                   10

(2) INFORMATION FOR SEQ ID NO: 10:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 10:

His Ser Leu Gly Lys Trp Leu Gly His Pro Asp Lys Phe
1               5                   10

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (xi) SEQUENCE DESCRIPTION: SEQ ID NO: 11:

Met Ala Ser Gln Lys Arg Pro Ser Gln Arg Ser Lys Tyr Leu
1               5                   10

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (xi) SEQUENCE DESCRIPTION: SEQ ID NO: 12:

GCAGAAGAAT TCGAGCTCGG CCCCCAG                                              27

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 13:

GATGATATCA GAGAGAAATA CATACTAACA CAC                                       33

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 14:

```
CGGAAGAAAG AGACTTCGGC CGCTACTTAC                                    30
```

(2) INFORMATION FOR SEQ ID NO: 15:

(i) SEQUENCE CHARACTERISTICS:
        (A) LENGTH: 47 base pairs
        (B) TYPE: nucleic acid
        (C) STRANDEDNESS: unknown
        (D) TOPOLOGY: unknown (xi) SEQUENCE DESCRIPTION: SEQ ID NO: 15:

```
GTGTGTTAGT ATGTATTTCT CTCTGATATC TTCAGCTTCC AGCAGTG                 47
```

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO: 16:

```
TCTTCTAGAA GACCACGCTA C                                             21
```

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 17:

```
GATGATATCC GGCCGAAGTC TCTTTCTTCC GTTGTC                             36
```

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO: 18:

```
CAGGGTTATC AACACCCTGA AAAC                                          24
```

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO: 19:

```
GTCACAGTTA TCCACTCTGT C                                             21
```

(2) INFORMATION FOR SEQ ID NO: 20:

(i) SEQUENCE CHARACTERISTICS:
        (A) LENGTH: 38 base pairs
        (B) TYPE: nucleic acid
        (C) STRANDEDNESS: unknown
        (D) TOPOLOGY: unknown (xi) SEQUENCE DESCRIPTION: SEQ ID NO: 20:

CCGTCTCCTC AGGTACGGCC GGCCTCTCCA GGTCTTCG                        38

(2) INFORMATION FOR SEQ ID NO: 21:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 21:

CACAGTTATC CACTCTGTCT TTGATATCAC AGGTGTCCT                        39

(2) INFORMATION FOR SEQ ID NO: 22:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 22:

His Ser Leu Gly Lys Tyr Leu Gly His Pro Asp Lys Phe
1            5                  10

(2) INFORMATION FOR SEQ ID NO: 23:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 23:

His Ser Leu Gly Lys Leu Leu Gly His Pro Asp Lys Phe
1            5                  10

(2) INFORMATION FOR SEQ ID NO: 24:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 24:

Ser Ile Ser Gln Ala Val His Ala Ala His Ala Glu Ile Asn Glu Arg Gly
1            5                  10                15

Arg (2) INFORMATION FOR SEQ ID NO: 25:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 25:

Asn Leu Cys Asn Ile Pro Ser Cys Ala Leu Leu Ser Ser
 1               5                  10

(2) INFORMATION FOR SEQ ID NO: 26:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 26:

GGGGGGGCCA TGGCCGAAGA CGACATTGAG GCCGAC                  36

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 27:

GCGGCGACTA GTCCAGTGTT TCAGAACCGG CTC                     33

(2) INFORMATION FOR SEQ ID NO: 28:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 28:

CCCCCCGATA TCTCAGCTTC CAGCAGTGGA GACGACATTG AG            42

(2) INFORMATION FOR SEQ ID NO: 29:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 29:

CCCCCCCGGC CGCTACTTAC GTTTCCAGTG TTTCAGAACC GG            42

(2) INFORMATION FOR SEQ ID NO: 30:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO: 30:

GGGGGGGCCA TGGCCGGAAA CTCCGAAAGG CATTTCG                 37

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (xi) SEQUENCE DESCRIPTION: SEQ ID NO: 31:

GCGGCGACTA GTCCACTCCA CAGTGATGGG GC                                           32

(2) INFORMATION FOR SEQ ID NO: 32:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 32:

CCCCCCCGGC CGTACCTGAG GACCACTCCA CAGTGATGG                                    39

(2) INFORMATION FOR SEQ ID NO: 33:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (xi) SEQUENCE DESCRIPTION: SEQ ID NO: 33:

CCCCCCGATA TCACAGGTGT CTTAAGTGCT AGCGGAGGGG GCGGAAGCGG CGGAGGGGGA             60

AACTCCGAAA GGCATTTC                                                          78

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 34:

AGCTTGATAT CACAGGTGTC TTAAGTGGAG                                              30

(2) INFORMATION FOR SEQ ID NO: 35:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 35:

CTAGCTCCAC TTAAGACACC TGTGATATCA                                              30

(2) INFORMATION FOR SEQ ID NO: 36:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (xi) SEQUENCE DESCRIPTION: SEQ ID NO: 36:

TCCGGAGGCG GCGGAGACTC CGAAAGGCAT TTCG                                         34

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 37:

CGATCGCTAG CGGCGGTGGT GGTTCCGGTG GCGGCGGAG                                    39

(2) INFORMATION FOR SEQ ID NO: 38:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 38:

CCCCCCAGGC TTCCCGGGCC ACCATGCCGT GCAGCAGAGC TC                                42

(2) INFORMATION FOR SEQ ID NO: 39:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 39:

CCCCCCGAGC TCGAATTCTC ATAAAGGCCC TGGGTGTCTG                                   40

(2) INFORMATION FOR SEQ ID NO: 40:

(i) SEQUENCE CHARACTERISTICS:
        (A) LENGTH: 44 base pairs
        (B) TYPE: nucleic acid
        (C) STRANDEDNESS: unknown
        (D) TOPOLOGY: unknown (xi) SEQUENCE DESCRIPTION: SEQ ID NO: 40:

CCCCCCAAGC TTCCCGGGCC ACCATGGCTC TGCAGATCCC CAGC                              44

(2) INFORMATION FOR SEQ ID NO: 41:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (xi) SEQUENCE DESCRIPTION: SEQ ID NO: 41:

CCCCCCACTT AAGGTCCTTG GGCTGCTCAG CACC                                         34

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (xi) SEQUENCE DESCRIPTION: SEQ ID NO: 42:

CCCCCCCCAT CACTGTGGAG TGGAGGG                                                 27

(2) INFORMATION FOR SEQ ID NO: 43:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 43:

CCCCCCGAGC TCGAATTCTC ACTGCAGGAG CCCTGCTGG                    39

(2) INFORMATION FOR SEQ ID NO: 44:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 44:

GGGGGGAAGC TTATGATCAA AGAAGAACAT GTGATCATC                    39

(2) INFORMATION FOR SEQ ID NO: 45:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 45:

GCGGCGGGAT CCGTTCTCTG TAGTCTCTGG GAGAGG                       36

(2) INFORMATION FOR SEQ ID NO: 46:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 46:

GGGGGGAAGC TTATGGGGGA CACCCGACCA CGTTTCTTGT GGCAGC            46

(2) INFORMATION FOR SEQ ID NO: 47:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 47:

GGGGGGGCCA TGGCCATCAA AGAAGAACAT GTGATCATC                    39

(2) INFORMATION FOR SEQ ID NO: 48:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 48:

GCGGCGACTA GTGTTCTCTG TAGTCTCTGG GAGAGG                       36

(2) INFORMATION FOR SEQ ID NO: 49:

(i) SEQUENCE CHARACTERISTICS:
        (A) LENGTH: 57 base pairs
        (B) TYPE: nucleic acid
        (C) STRANDEDNESS: unknown
        (D) TOPOLOGY: unknown (xi) SEQUENCE DESCRIPTION: SEQ ID NO: 49:

GGGGGGAAGC TTGATATCTC AGCTTCCAGC AGTAGTATCA AAGAAGAACA TGTGATC　　　57

(2) INFORMATION FOR SEQ ID NO: 50:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 50:

GGGGGGCGGC CGCTACTTAC GTTTCTCTGG GAGAGGGCTT GGAGC　　　45

(2) INFORMATION FOR SEQ ID NO: 51:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (xi) SEQUENCE DESCRIPTION: SEQ ID NO: 51:

GCGGCGGGAT CCCTTGCTCT GTGCAGATTC AGACC　　　35

(2) INFORMATION FOR SEQ ID NO: 52:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (xi) SEQUENCE DESCRIPTION: SEQ ID NO: 52:

GGGGGGGCCA TGGCCGGATC CGCTAGCGGG GACACCCGAC CACGTTTCTT G　　　51

(2) INFORMATION FOR SEQ ID NO: 53:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 53:

GCGGCGACTA GTCTTGCTCT GTGCAGATTC AGACCG　　　36

(2) INFORMATION FOR SEQ ID NO: 54:

(i) SEQUENCE CHARACTERISTICS:
        (A) LENGTH: 56 base pairs
        (B) TYPE: nucleic acid
        (C) STRANDEDNESS: unknown
        (D) TOPOLOGY: unknown (xi) SEQUENCE DESCRIPTION: SEQ ID NO: 54:

GTTGTCTTAA GTGGAGCTAG CGGAGGGGGC GGGTCCGGAG GTGGTGGGA CACCCG　　　56

(2) INFORMATION FOR SEQ ID NO: 55:

(i) SEQUENCE CHARACTERISTICS:
        (A) LENGTH: 57 base pairs
        (B) TYPE: nucleic acid
        (C) STRANDEDNESS: unknown
        (D) TOPOLOGY: unknown (xi) SEQUENCE DESCRIPTION: SEQ ID NO: 55:

GAAATGACAT TCAAACTTCA GCTGCCACAA GAAACGTGGT CGGGTGTCCC CACCACC      57

(2) INFORMATION FOR SEQ ID NO: 56:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 56:

GGGGGGCGGC CGTACCTGAG GACTTGCTCT GTGCAGATTC AG      42

(2) INFORMATION FOR SEQ ID NO: 57:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 57:

TTAAGTATCT CTCAGGCTGT TCACGCTGCT CACGCTGAAA TCAACGAAGC TGGTCGTG      58

(2) INFORMATION FOR SEQ ID NO: 58:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 58:

CTAGCACGAC CAGCTTCGTT GATTTCAGCC TGAGCAGCGT GAACAGCCTG AGAGATAC      58

(2) INFORMATION FOR SEQ ID NO: 59:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 59:

TTAAGTATCT CTCAGGCTGT TCACGCTGCT CGGGCTGAAA TCAACGAAGC TGGTCGTG      58

(2) INFORMATION FOR SEQ ID NO: 60:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 60:

CTAGCACGAC CAGCTTCGTT GATTTCAGCC CGAGCAGCGT GAACAGCCTG AGAGATAC      58

(2) INFORMATION FOR SEQ ID NO: 61:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 61:

TTAAGTATCT CTCAGGCTGT TCACGCTGCT CACTACGAAA TCAACGAAGC TGGTCGTG        58

(2) INFORMATION FOR SEQ ID NO: 62:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 62:

CTAGCACGAC CAGCTTCGTT GATTTCATAG TGAGCAGCGT GAACAGCCTG AGAGATAC        58

(2) INFORMATION FOR SEQ ID NO: 63:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 63:

TTAAGTAACC TGTGCAACAT CCCCTGCAGC GCCCTGCTGA GCTCCG        46

(2) INFORMATION FOR SEQ ID NO: 64:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 64:

CTAGCGGAGC TCAGCAGGGC GCTGCAGGGG ATGTTGCACA GGTTAC        46

(2) INFORMATION FOR SEQ ID NO: 65:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 65:

TTAAGTCAGA TCAGCGTGCA GCCCGCCTTC AGCGTGCAGG        40

(2) INFORMATION FOR SEQ ID NO: 66:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 66:

CTAGCCTGCA CGCTGAAGGC GGGCTGAACG CTGATCTGAC        40

(2) INFORMATION FOR SEQ ID NO: 67:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 67:

TTAAGTCCCA AGTACGTGAA GCAGAACACC CTGAAGCTGG CCACCG                46

(2) INFORMATION FOR SEQ ID NO: 68:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 68:

CTAGCGGTGG CCAGCTTCAG GGTGTTCTGC TTCACGTACT TGGGAC                46

(2) INFORMATION FOR SEQ ID NO: 69:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 69:

TTAAGTCACT ATGGCTCCCT GCCGCAGAAG TCCCAGCACG GGCGCG                46

(2) INFORMATION FOR SEQ ID NO: 70:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 70:

CTAGCGCGCC CGTGCTGGGA CTTCTGCGGC AGGGAGCCAT AGTGAC                46

(2) INFORMATION FOR SEQ ID NO: 71:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 71:

TTACATCACT CCCTGGGCAA GTGGCTGGGC CACCCGGACA AGTTCG                46

(2) INFORMATION FOR SEQ ID NO: 72:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 72:

CTAGCGAACT TGTTCGGGTG GCCCAGCCAC TTGCCCAGGG AGTGAC                46

(2) INFORMATION FOR SEQ ID NO: 73:

(i) SEQUENCE CHARACTERISTICS:
        (A) LENGTH: 49 base pairs
        (B) TYPE: nucleic acid
        (C) STRANDEDNESS: unknown
        (D) TOPOLOGY: unknown (xi) SEQUENCE DESCRIPTION: SEQ ID NO: 73:

TTAAGTATGG CATCCCAGAA GCGCCCGTCC CAGCGCTCCA AGTACCTGG                    49

(2) INFORMATION FOR SEQ ID NO: 74:

(i) SEQUENCE CHARACTERISTICS:
            (A) LENGTH: 49 base pairs
            (B) TYPE: nucleic acid
            (C) STRANDEDNESS: unknown
            (D) TOPOLOGY: unknown (xi) SEQUENCE DESCRIPTION: SEQ ID NO: 74:

CTAGCCAGGT ACTTGGAGCG CTGGGACGGG CGCTTCTGGG ATGCCATAC                    49

(2) INFORMATION FOR SEQ ID NO: 75:

(i) SEQUENCE CHARACTERISTICS:
            (A) LENGTH: 45 base pairs
            (B) TYPE: nucleic acid
            (C) STRANDEDNESS: unknown
            (D) TOPOLOGY: unknown (xi) SEQUENCE DESCRIPTION: SEQ ID NO: 75:

GATATCTCAG CTTCCAGCAG TGAAGACGAC ATTGAGGCCG ACCAC                        45

(2) INFORMATION FOR SEQ ID NO: 76:

(i) SEQUENCE CHARACTERISTICS:
            (A) LENGTH: 36 base pairs
            (B) TYPE: nucleic acid
            (C) STRANDEDNESS: unknown
            (D) TOPOLOGY: unknown (xi) SEQUENCE DESCRIPTION: SEQ ID NO: 76:

CCGGTTCTGA AACACTGGAA ACGTAAGTAG CGGCCG                                  36

(2) INFORMATION FOR SEQ ID NO: 77:

(i) SEQUENCE CHARACTERISTICS:
            (A) LENGTH: 11 amino acids
            (B) TYPE: amino acid
            (C) STRANDEDNESS: unknown
            (D) TOPOLOGY: unknown (xi) SEQUENCE DESCRIPTION: SEQ ID NO: 77:

Ser Ser Ser Glu Asp Asp Ile Glu Ala Asp His
1               5                   10

(2) INFORMATION FOR SEQ ID NO: 78:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (xi) SEQUENCE DESCRIPTION: SEQ ID NO: 78:

Pro Val Leu Lys His Trp Lys Arg
1               5

(2) INFORMATION FOR SEQ ID NO: 79:

(i) SEQUENCE CHARACTERISTICS:
            (A) LENGTH: 72 base pairs
            (B) TYPE: nucleic acid
            (C) STRANDEDNESS: unknown
            (D) TOPOLOGY: unknown -continued (xi) SEQUENCE DESCRIPTION: SEQ ID NO: 79:

GATATCACAG GTGTCTTAAG TGGAGCTAGC GGAGGGGGCG GAAGCGGCGG AGGGGGAAAC    60

TCCGAAAGGC AT    72

(2) INFORMATION FOR SEQ ID NO: 80:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 80:

ATCACTGTGG AGTGGTCCTC AGGTACGGCC GCC    33

(2) INFORMATION FOR SEQ ID NO: 81:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (xi) SEQUENCE DESCRIPTION: SEQ ID NO: 81:

Val Leu Ser Gly Ala Ser Gly Gly Gly Ser Gly Gly Gly Gly Asn
1               5                   10                  15

Ser Glu Arg His
            20

(2) INFORMATION FOR SEQ ID NO: 82:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (xi) SEQUENCE DESCRIPTION: SEQ ID NO: 82:

Ile Thr Val Glu Trp Ser Ser
1               5

(2) INFORMATION FOR SEQ ID NO: 83:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 83:

GATATCTCAG CTTCCAGCAG TGAAGACGAC ATTGAGGCCG ACCAC    45

(2) INFORMATION FOR SEQ ID NO: 84:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 84:

CCGGTTCTGA AACACTGGAA ACGTAAGTAG CGGCCG    36

(2) INFORMATION FOR SEQ ID NO: 85:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 85:

```
Ser Ser Ser Glu Asp Asp Ile Glu Ala Asp His
1               5                   10
```

(2) INFORMATION FOR SEQ ID NO: 86:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 86:

```
Pro Val Leu Lys His Trp Lys Arg
1               5
```

(2) INFORMATION FOR SEQ ID NO: 87:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (xi) SEQUENCE DESCRIPTION: SEQ ID NO: 87:

```
GATATCACAG GTGTCTTAAG TGGAGCTAGC GGCGGTGGTG GTTCCGGTGG CGGCGGAGAC    60

TCCGAAAGGC AT                                                       72
```

(2) INFORMATION FOR SEQ ID NO: 88:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 88:

```
ATCACTGTGG AGTGGTCCTC AGGTACGGCC GCC                                 33
```

(2) INFORMATION FOR SEQ ID NO: 89:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (xi) SEQUENCE DESCRIPTION: SEQ ID NO: 89:

```
Val Leu Ser Gly Ala Ser Gly Gly Gly Ser Gly Gly Gly Asp
1               5                   10                  15

Ser Glu Arg His
            20
```

(2) INFORMATION FOR SEQ ID NO: 90:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (xi) SEQUENCE DESCRIPTION: SEQ ID NO: 90:

Ile Thr Val Glu Trp Ser Ser
1           5

(2) INFORMATION FOR SEQ ID NO: 91:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 91:

GATATCTCAG CTTCCAGCAG TATCAAAGAA GAACATGTGA TCATC          45

(2) INFORMATION FOR SEQ ID NO: 92:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 92:

CCAGAGACTA CAGAGAACAA ACGTAAGTAG CGGCCG          36

(2) INFORMATION FOR SEQ ID NO: 93:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 93:

Ser Ser Ser Ile Lys Glu Glu His Val Ile Ile
1           5                 10

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 94:

Pro Glu Thr Thr Glu Asn Lys Arg
1           5

(2) INFORMATION FOR SEQ ID NO: 95:

(i) SEQUENCE CHARACTERISTICS:
        (A) LENGTH: 90 base pairs
        (B) TYPE: nucleic acid
        (C) STRANDEDNESS: unknown
        (D) TOPOLOGY: unknown (xi) SEQUENCE DESCRIPTION: SEQ ID NO: 95:

GATATCACAG GTGTCTTAAG TGGAGCTAGC GGAGGGGGCG GGTTCGGAGG TGGTGGGGAC        60

ACCCGACCAC GTTTCTTGTG GCAGCTGAAG        90

(2) INFORMATION FOR SEQ ID NO: 96:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO: 96:

TCTGAATCTG CACAGAGCAA GTCCTCAGGT ACGGCCG        37

(2) INFORMATION FOR SEQ ID NO: 97:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (xi) SEQUENCE DESCRIPTION: SEQ ID NO: 97:

Val Leu Ser Gly Ala Ser Gly Gly Gly Ser Gly Gly Gly Gly Asp
1               5                   10                  15

Thr Arg Pro Arg Phe Leu Trp Gln Leu Lys
            20                  25

(2) INFORMATION FOR SEQ ID NO: 98:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO: 98:

Ser Glu Ser Ala Gln Ser Lys Ser Ser
1               5

(2) INFORMATION FOR SEQ ID NO: 99:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (xi) SEQUENCE DESCRIPTION: SEQ ID NO: 99:

GTCCAGCTGT CTTGTTTCAG TACTGATC        28

(2) INFORMATION FOR SEQ ID NO: 100:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (xi) SEQUENCE DESCRIPTION: SEQ ID NO: 100:

GTAAGTAGCG GCCG        14

(2) INFORMATION FOR SEQ ID NO: 101:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO: 101:

```
GGTATGTAAA AATAAACATC ACAG                                      24
```

(2) INFORMATION FOR SEQ ID NO: 102:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO: 102:

```
GCTTTGCTTA CGGAGTTACT C                                         21
```

(2) INFORMATION FOR SEQ ID NO: 103:

(i) SEQUENCE CHARACTERISTICS:
        (A) LENGTH: 95 base pairs
        (B) TYPE: nucleic acid
        (C) STRANDEDNESS: unknown
        (D) TOPOLOGY: unknown (xi) SEQUENCE DESCRIPTION: SEQ ID NO: 103:

```
CCCGGGCCAC CATGCCGTGC AGCAGAGCTC TGATTCTGGG GGTCCTCGCC CTGAACACCA    60

TGCTCAGCCT CTGCGGAGGT GAAGACGACA TTGAG                               95
```

(2) INFORMATION FOR SEQ ID NO: 104:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 104:

```
CGATCAGGTG GCACCTCCAG ACACCCAGGG CCTTTATGAG AATTC                45
```

(2) INFORMATION FOR SEQ ID NO: 105:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (xi) SEQUENCE DESCRIPTION: SEQ ID NO: 105:

```
Met Pro Cys Ser Arg Ala Leu Ile Leu Gly Val Leu Ala Leu Asn Thr
1               5                   10                  15

Met Leu Ser Leu Cys Gly Gly Glu Asp Asp Ile Glu
            20                  25
```

(2) INFORMATION FOR SEQ ID NO: 106:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (xi) SEQUENCE DESCRIPTION: SEQ ID NO: 106:

Arg Ser Gly Gly Thr Ser Arg His Pro Gly Pro Leu
1               5                  10

(2) INFORMATION FOR SEQ ID NO: 107:

(i) SEQUENCE CHARACTERISTICS:
        (A) LENGTH: 194 base pairs
        (B) TYPE: nucleic acid
        (C) STRANDEDNESS: unknown
        (D) TOPOLOGY: unknown (xi) SEQUENCE DESCRIPTION: SEQ ID NO: 107:

```
AAGCTTCCCG GGCCACCATG GCTCTGCAGA TCCCCAGCCT CCTCCTCTCA GCTGCTGTGG      60

TGGTGCTGAT GGTGCTGAGC AGCCCAAGGA CCTTAAGTAT CTCTCAGGCT GTTCACGCTG     120

CTCACGCTGA AATCAACGAA GCTGGTCGTG CTAGCGGAGG GGGCGGAAGC GGCGGAGGGG     180

GAAACTCCGA AAGG                                                       194
```

(2) INFORMATION FOR SEQ ID NO: 108:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 108:

```
CCTCCTCCAG CAGGGCTCCT GCAGTGAGAA TTCGAGCTC                             39
```

(2) INFORMATION FOR SEQ ID NO: 109:

(i) SEQUENCE CHARACTERISTICS:
        (A) LENGTH: 59 amino acids
        (B) TYPE: amino acid
        (C) STRANDEDNESS: unknown
        (D) TOPOLOGY: unknown (xi) SEQUENCE DESCRIPTION: SEQ ID NO: 109:

Met Ala Leu Gln Ile Pro Ser Leu Leu Leu Ser Ala Ala Val Val
1               5                  10                  15

Leu Met Val Leu Ser Ser Pro Arg Thr Leu Ser Ile Ser Gln Ala Val
            20                  25                  30

His Ala Ala His Ala Glu Ile Asn Glu Ala Gly Arg Ala Ser Gly Gly
        35                  40                  45

Gly Gly Ser Gly Gly Gly Gly Asn Ser Glu Arg
    50                  55

(2) INFORMATION FOR SEQ ID NO: 110:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 110:

Pro Pro Pro Ala Gly Leu Leu Gln
1               5

(2) INFORMATION FOR SEQ ID NO: 111:

(i) SEQUENCE CHARACTERISTICS:
        (A) LENGTH: 43 base pairs
        (B) TYPE: nucleic acid
        (C) STRANDEDNESS: unknown
        (D) TOPOLOGY: unknown (xi) SEQUENCE DESCRIPTION: SEQ ID NO: 111:

```
CCCCCCCCGC GGCCGCCCCA CCATGGGACT GAGTAACATT CTC          43
```

(2) INFORMATION FOR SEQ ID NO: 112:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 112:

```
CCCCCCGCGG CCGCTTTAAA AACATGTATC ACTTTT                   36
```

(2) INFORMATION FOR SEQ ID NO: 113:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 113:

```
CCCCCCGCCA TGGCCGCTAG CGGAGGGGGC GGAAGC                   36
```

(2) INFORMATION FOR SEQ ID NO: 114:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 114:

```
CCCGGGGCCT CGAGTGAAGA CGACATTGAG GCCGAC                   36
```

(2) INFORMATION FOR SEQ ID NO: 115:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 115:

```
CCCCCCACTA GTCCACTCCA CAGTGATGGG GCT                      33
```

(2) INFORMATION FOR SEQ ID NO: 116:

(i) SEQUENCE CHARACTERISTICS:
        (A) LENGTH: 37 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO: 116:

CCCCCCCCCG GGACCAGTGT TTCAGAACCG GCTCCTC                                37

(2) INFORMATION FOR SEQ ID NO: 117:

(i) SEQUENCE CHARACTERISTICS:
        (A) LENGTH: 65 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 117:

TCGAGGAACC GCCACCGCCA GAACCGCCGC CACCGGAACC ACCACCGCCG CTGCCACCGC        60

CACCA                                                                   65

(2) INFORMATION FOR SEQ ID NO: 118:

(i) SEQUENCE CHARACTERISTICS:
        (A) LENGTH: 65 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 118:

CTAGTGGTGG CGGTGGCAGC GGCGGTGGTG GTTCCGGTGG CGGCGGTTCT GGCGGTGGCG        60

GTTCC                                                                   65

(2) INFORMATION FOR SEQ ID NO: 119:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 119:

CTTGGGAATC TTGACTAAGA GG                                                22

(2) INFORMATION FOR SEQ ID NO: 120:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 120:

CAGGTCGAAT TCTCATTCCA TCGGCATGTA CTCTTCTTCC TCCCAGTGTT TCAGAACCGG        60

(2) INFORMATION FOR SEQ ID NO: 121:

(i) SEQUENCE CHARACTERISTICS:
        (A) LENGTH: 1385 base pairs
        (B) TYPE: nucleic acid
        (C) STRANDEDNESS: unknown
        (D) TOPOLOGY: unknown
```

(ii) MOLECULE TYPE: DNA (genomic)

(ix) FEATURE:
    (A) NAME/KEY: CDS
    (B) LOCATION: 6..1382

(xi) SEQUENCE DESCRIPTION: SEQ ID NO: 121:

```
CCACC ATG GCT CTG CAG ATC CCC AGC CTC CTC CTC TCA GCT GCT GTG          47
      Met Ala Leu Gln Ile Pro Ser Leu Leu Leu Ser Ala Ala Val
       1               5                  10

GTG GTG CTG ATG GTG CTG AGC AGC CCA AGG ACC TTA AGT ATC TCT CAG        95
Val Val Leu Met Val Leu Ser Ser Pro Arg Thr Leu Ser Ile Ser Gln
 15              20                  25                  30

GCT GTT CAC GCT GCT CAC GCT GAA ATC AAC GAA GCT GGT CGT GCT AGC       143
Ala Val His Ala Ala His Ala Glu Ile Asn Glu Ala Gly Arg Ala Ser
                 35                  40                  45

GGA GGG GGC GGA AGC GGC GGA GGG GGA AAC TCC GAA AGG CAT TTC GTG       191
Gly Gly Gly Gly Ser Gly Gly Gly Gly Asn Ser Glu Arg His Phe Val
                 50                  55                  60

GTC CAG TTC AAG GGC GAG TGC TAC TAC ACC AAC GGG ACG CAG CGC ATA       239
Val Gln Phe Lys Gly Glu Cys Tyr Tyr Thr Asn Gly Thr Gln Arg Ile
             65                  70                  75

CGG CTC GTG ACC AGA TAC ATC TAC AAC CGG GAG GAG TAC GTG CGC TAC       287
Arg Leu Val Thr Arg Tyr Ile Tyr Asn Arg Glu Glu Tyr Val Arg Tyr
         80                  85                  90

GAC AGC GAC GTG GGC GAG TAC CGC GCG GTG ACC GAG CTG GGG CGG CCA       335
Asp Ser Asp Val Gly Glu Tyr Arg Ala Val Thr Glu Leu Gly Arg Pro
 95                 100                 105                 110

GAC GCC GAG TAC TGG AAC AGC CAG CCG GAG ATC CTG GAG CGA ACG CGG       383
Asp Ala Glu Tyr Trp Asn Ser Gln Pro Glu Ile Leu Glu Arg Thr Arg
                115                 120                 125

GCC GAG GTG GAC ACG GCG TGC AGA CAC AAC TAC GAG GGG CCG GAG ACC       431
Ala Glu Val Asp Thr Ala Cys Arg His Asn Tyr Glu Gly Pro Glu Thr
                130                 135                 140

AGC ACC TCC CTG CGG CGG CTT GAA CAG CCC AAT GTC GCC ATC TCC CTG       479
Ser Thr Ser Leu Arg Arg Leu Glu Gln Pro Asn Val Ala Ile Ser Leu
            145                 150                 155

TCC AGG ACA GAG GCC CTC AAC CAC CAC AAC ACT CTG GTC TGT TCG GTG       527
Ser Arg Thr Glu Ala Leu Asn His His Asn Thr Leu Val Cys Ser Val
        160                 165                 170

ACA GAT TTC TAC CCA GCC AAG ATC AAA GTG CGC TGG TTC AGG AAT GGC       575
Thr Asp Phe Tyr Pro Ala Lys Ile Lys Val Arg Trp Phe Arg Asn Gly
175                 180                 185                 190

CAG GAG GAG ACA GTG GGG GTC TCA TCC ACA CAG CTT ATT AGG AAT GGG       623
Gln Glu Glu Thr Val Gly Val Ser Ser Thr Gln Leu Ile Arg Asn Gly
                195                 200                 205

GAC TGG ACC TTC CAG GTC CTG GTC ATG CTG GAG ATG ACC CCT CAT CAG       671
Asp Trp Thr Phe Gln Val Leu Val Met Leu Glu Met Thr Pro His Gln
                210                 215                 220

GGA GAG GTC TAC ACC TGC CAT GTG GAG CAT CCC AGC CTG AAG AGC CCC       719
Gly Glu Val Tyr Thr Cys His Val Glu His Pro Ser Leu Lys Ser Pro
            225                 230                 235

ATC ACT GTG GAG TGG ACT AGT GGT GGC GGT GGC AGC GGC GGT GGT GGT       767
Ile Thr Val Glu Trp Thr Ser Gly Gly Gly Gly Ser Gly Gly Gly Gly
        240                 245                 250

TCC GGT GGC GGC GGT TCT GGC GGT GGC GGT TCC TCG AGT GAA GAC GAC       815
Ser Gly Gly Gly Gly Ser Gly Gly Gly Ser Ser Ser Glu Asp Asp
255                 260                 265                 270

ATT GAG GCC GAC CAC GTA GGC TTC TAT GGT ACA ACT GTT TAT CAG TCT       863
Ile Glu Ala Asp His Val Gly Phe Tyr Gly Thr Thr Val Tyr Gln Ser
                275                 280                 285
```

```
CCT GGA GAC ATT GGC CAG TAC ACA CAT GAA TTT GAT GGT GAT GAG TTG      911
Pro Gly Asp Ile Gly Gln Tyr Thr His Glu Phe Asp Gly Asp Glu Leu
            290                 295                 300

TTC TAT GTG GAC TTG GAT AAG AAG AAA ACT GTC TGG AGG CTT CCT GAG      959
Phe Tyr Val Asp Leu Asp Lys Lys Lys Thr Val Trp Arg Leu Pro Glu
        305                 310                 315

TTT GGC CAA TTG ATA CTC TTT GAG CCC CAA GGT GGA CTG CAA AAC ATA     1007
Phe Gly Gln Leu Ile Leu Phe Glu Pro Gln Gly Gly Leu Gln Asn Ile
320                 325                 330

GCT GCA GAA AAA CAC AAC TTG GGA ATC TTG ACT AAG AGG TCA AAT TTC     1055
Ala Ala Glu Lys His Asn Leu Gly Ile Leu Thr Lys Arg Ser Asn Phe
335                 340                 345                 350

ACC CCA GCT ACC AAT GAG GCT CCT CAA GCG ACT GTG TTC CCC AAG TCC     1103
Thr Pro Ala Thr Asn Glu Ala Pro Gln Ala Thr Val Phe Pro Lys Ser
            355                 360                 365

CCT GTG CTG CTG GGT CAG CCC AAC ACC CTT ATC TGC TTT GTG GAC AAC     1151
Pro Val Leu Leu Gly Gln Pro Asn Thr Leu Ile Cys Phe Val Asp Asn
        370                 375                 380

ATC TTC CCA CCT GTG ATC AAC ATC ACA TGG CTC AGA AAT AGC AAG TCA     1199
Ile Phe Pro Pro Val Ile Asn Ile Thr Trp Leu Arg Asn Ser Lys Ser
385                 390                 395

GTC ACA GAC GGC GTT TAT GAG ACC AGC TTC CTC GTC AAC CGT GAC CAT     1247
Val Thr Asp Gly Val Tyr Glu Thr Ser Phe Leu Val Asn Arg Asp His
400                 405                 410

TCC TTC CAC AAG CTG TCT TAT CTC ACC TTC ATC CCT TCT GAT GAT GAC     1295
Ser Phe His Lys Leu Ser Tyr Leu Thr Phe Ile Pro Ser Asp Asp Asp
415                 420                 425                 430

ATT TAT GAC TGC AAG GTG GAG CAC TGG GGC CTG GAG GAG CCG GTT CTG     1343
Ile Tyr Asp Cys Lys Val Glu His Trp Gly Leu Glu Glu Pro Val Leu
                435                 440                 445

AAA CAC TGG TCC CGG GCT AGT CAC CAT CAC CAT CAC CAC TAG             1385
Lys His Trp Ser Arg Ala Ser His His His His His His
            450                 455

(2) INFORMATION FOR SEQ ID NO: 122:

(i) SEQUENCE CHARACTERISTICS:
        (A) LENGTH: 1508 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 6..1505

(xi) SEQUENCE DESCRIPTION: SEQ ID NO: 122:

CCACC ATG GCT CTG CAG ATC CCC AGC CTC CTC CTC TCA GCT GCT GTG        47
      Met Ala Leu Gln Ile Pro Ser Leu Leu Leu Ser Ala Ala Val
          460                 465                 470

GTG GTG CTG ATG GTG CTG AGC AGC CCA AGG ACC TTA AGT ATC TCT CAG      95
Val Val Leu Met Val Leu Ser Ser Pro Arg Thr Leu Ser Ile Ser Gln
475                 480                 485

GCT GTT CAC GCT GCT CAC GCT GAA ATC AAC GAA GCT GGT CGT GCT AGC     143
Ala Val His Ala Ala His Ala Glu Ile Asn Glu Ala Gly Arg Ala Ser
490                 495                 500                 505

GGA GGG GGC GGA AGC GGC GGA GGG GGA AAC TCC GAA AGG CAT TTC GTG     191
Gly Gly Gly Gly Ser Gly Gly Gly Gly Asn Ser Glu Arg His Phe Val
                510                 515                 520
```

-continued

```
GTC CAG TTC AAG GGC GAG TGC TAC TAC ACC AAC GGG ACG CAG CGC ATA     239
Val Gln Phe Lys Gly Glu Cys Tyr Tyr Thr Asn Gly Thr Gln Arg Ile
        525                 530                 535

CGG CTC GTG ACC AGA TAC ATC TAC AAC CGG GAG GAG TAC GTG CGC TAC     287
Arg Leu Val Thr Arg Tyr Ile Tyr Asn Arg Glu Glu Tyr Val Arg Tyr
        540                 545                 550

GAC AGC GAC GTG GGC GAG TAC CGC GCG GTG ACC GAG CTG GGG CGG CCA     335
Asp Ser Asp Val Gly Glu Tyr Arg Ala Val Thr Glu Leu Gly Arg Pro
555                 560                 565

GAC GCC GAG TAC TGG AAC AGC CAG CCG GAG ATC CTG GAG CGA ACG CGG     383
Asp Ala Glu Tyr Trp Asn Ser Gln Pro Glu Ile Leu Glu Arg Thr Arg
570                 575                 580                 585

GCC GAG GTG GAC ACG GCG TGC AGA CAC AAC TAC GAG GGG CCG GAG ACC     431
Ala Glu Val Asp Thr Ala Cys Arg His Asn Tyr Glu Gly Pro Glu Thr
                590                 595                 600

AGC ACC TCC CTG CGG CGG CTT GAA CAG CCC AAT GTC GCC ATC TCC CTG     479
Ser Thr Ser Leu Arg Arg Leu Glu Gln Pro Asn Val Ala Ile Ser Leu
                605                 610                 615

TCC AGG ACA GAG GCC CTC AAC CAC CAC AAC ACT CTG GTC TGT TCG GTG     527
Ser Arg Thr Glu Ala Leu Asn His His Asn Thr Leu Val Cys Ser Val
                620                 625                 630

ACA GAT TTC TAC CCA GCC AAG ATC AAA GTG CGC TGG TTC AGG AAT GGC     575
Thr Asp Phe Tyr Pro Ala Lys Ile Lys Val Arg Trp Phe Arg Asn Gly
        635                 640                 645

CAG GAG GAG ACA GTG GGG GTC TCA TCC ACA CAG CTT ATT AGG AAT GGG     623
Gln Glu Glu Thr Val Gly Val Ser Ser Thr Gln Leu Ile Arg Asn Gly
650                 655                 660                 665

GAC TGG ACC TTC CAG GTC CTG GTC ATG CTG GAG ATG ACC CCT CAT CAG     671
Asp Trp Thr Phe Gln Val Leu Val Met Leu Glu Met Thr Pro His Gln
                670                 675                 680

GGA GAG GTC TAC ACC TGC CAT GTG GAG CAT CCC AGC CTG AAG AGC CCC     719
Gly Glu Val Tyr Thr Cys His Val Glu His Pro Ser Leu Lys Ser Pro
                685                 690                 695

ATC ACT GTG GAG TGG ACT AGT GGT GGC GGT GGC AGC GGC GGT GGT GGT     767
Ile Thr Val Glu Trp Thr Ser Gly Gly Gly Gly Ser Gly Gly Gly Gly
                700                 705                 710

TCC GGT GGC GGC GGT TCT GGC GGT GGC GGT TCC TCG AGT GAA GAC GAC     815
Ser Gly Gly Gly Gly Ser Gly Gly Gly Gly Ser Ser Ser Glu Asp Asp
        715                 720                 725

ATT GAG GCC GAC CAC GTA GGC TTC TAT GGT ACA ACT GTT TAT CAG TCT     863
Ile Glu Ala Asp His Val Gly Phe Tyr Gly Thr Thr Val Tyr Gln Ser
730                 735                 740                 745

CCT GGA GAC ATT GGC CAG TAC ACA CAT GAA TTT GAT GGT GAT GAG TTG     911
Pro Gly Asp Ile Gly Gln Tyr Thr His Glu Phe Asp Gly Asp Glu Leu
                750                 755                 760

TTC TAT GTG GAC TTG GAT AAG AAG AAA ACT GTC TGG AGG CTT CCT GAG     959
Phe Tyr Val Asp Leu Asp Lys Lys Lys Thr Val Trp Arg Leu Pro Glu
                765                 770                 775

TTT GGC CAA TTG ATA CTC TTT GAG CCC CAA GGT GGA CTG CAA AAC ATA    1007
Phe Gly Gln Leu Ile Leu Phe Glu Pro Gln Gly Gly Leu Gln Asn Ile
                780                 785                 790

GCT GCA GAA AAA CAC AAC TTG GGA ATC TTG ACT AAG AGG TCA AAT TTC    1055
Ala Ala Glu Lys His Asn Leu Gly Ile Leu Thr Lys Arg Ser Asn Phe
795                 800                 805

ACC CCA GCT ACC AAT GAG GCT CCT CAA GCG ACT GTG TTC CCC AAG TCC    1103
Thr Pro Ala Thr Asn Glu Ala Pro Gln Ala Thr Val Phe Pro Lys Ser
810                 815                 820                 825

CCT GTG CTG CTG GGT CAG CCC AAC ACC CTT ATC TGC TTT GTG GAC AAC    1151
Pro Val Leu Leu Gly Gln Pro Asn Thr Leu Ile Cys Phe Val Asp Asn
                830                 835                 840
```

```
ATC TTC CCA CCT GTG ATC AAC ATC ACA TGG CTC AGA AAT AGC AAG TCA    1199
Ile Phe Pro Pro Val Ile Asn Ile Thr Trp Leu Arg Asn Ser Lys Ser
        845                 850                 855

GTC ACA GAC GGC GTT TAT GAG ACC AGC TTC CTC GTC AAC CGT GAC CAT    1247
Val Thr Asp Gly Val Tyr Glu Thr Ser Phe Leu Val Asn Arg Asp His
            860                 865                 870

TCC TTC CAC AAG CTG TCT TAT CTC ACC TTC ATC CCT TCT GAT GAT GAC    1295
Ser Phe His Lys Leu Ser Tyr Leu Thr Phe Ile Pro Ser Asp Asp Asp
    875                 880                 885

ATT TAT GAC TGC AAG GTG GAG CAC TGG GGC CTG GAG GAG CCG GTT CTG    1343
Ile Tyr Asp Cys Lys Val Glu His Trp Gly Leu Glu Glu Pro Val Leu
890                 895                 900                 905

AAA CAC TGG GAA CCT GAG ATT CCA GCC CCC ATG TCA GAG CTG ACA GAA    1391
Lys His Trp Glu Pro Glu Ile Pro Ala Pro Met Ser Glu Leu Thr Glu
                910                 915                 920

ACT GTG GTG TGT GCC CTG GGG TTG TCT GTG GGC CTT GTG GGC ATC GTG    1439
Thr Val Val Cys Ala Leu Gly Leu Ser Val Gly Leu Val Gly Ile Val
            925                 930                 935

GTG GGC ACC ATC TTC ATC ATT CAA GGC CTG CGA TCA GGT GGC ACC TCC    1487
Val Gly Thr Ile Phe Ile Ile Gln Gly Leu Arg Ser Gly Gly Thr Ser
        940                 945                 950

AGA CAC CCA GGG CCT TTA TGA                                        1508
Arg His Pro Gly Pro Leu
    955
```

(2) INFORMATION FOR SEQ ID NO: 123:

(i) SEQUENCE CHARACTERISTICS:
        (A) LENGTH: 1382 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 6..1382

(xi) SEQUENCE DESCRIPTION: SEQ ID NO: 123:

```
CCACC ATG GCT CTG CAG ATC CCC AGC CTC CTC CTC TCA GCT GCT GTG        47
      Met Ala Leu Gln Ile Pro Ser Leu Leu Leu Ser Ala Ala Val
                                505                 510

GTG GTG CTG ATG GTG CTG AGC AGC CCA AGG ACC TTA AGT ATC TCT CAG      95
Val Val Leu Met Val Leu Ser Ser Pro Arg Thr Leu Ser Ile Ser Gln
515                 520                 525                 530

GCT GTT CAC GCT GCT CAC GCT GAA ATC AAC GAA GCT GGT CGT GCT AGC     143
Ala Val His Ala Ala His Ala Glu Ile Asn Glu Ala Gly Arg Ala Ser
            535                 540                 545

GGA GGG GGC GGA AGC GGC GGA GGG GGA AAC TCC GAA AGG CAT TTC GTG     191
Gly Gly Gly Gly Ser Gly Gly Gly Gly Asn Ser Glu Arg His Phe Val
        550                 555                 560

GTC CAG TTC AAG GGC GAG TGC TAC TAC ACC AAC GGG ACG CAG CGC ATA     239
Val Gln Phe Lys Gly Glu Cys Tyr Tyr Thr Asn Gly Thr Gln Arg Ile
    565                 570                 575

CGG CTC GTG ACC AGA TAC ATC TAC AAC CGG GAG GAG TAC GTG CGC TAC     287
Arg Leu Val Thr Arg Tyr Ile Tyr Asn Arg Glu Glu Tyr Val Arg Tyr
580                 585                 590

GAC AGC GAC GTG GGC GAG TAC CGC GCG GTG ACC GAG CTG GGG CGG CCA     335
Asp Ser Asp Val Gly Glu Tyr Arg Ala Val Thr Glu Leu Gly Arg Pro
595                 600                 605                 610
```

-continued

| | | |
|---|---|---|
| GAC GCC GAG TAC TGG AAC AGC CAG CCG GAG ATC CTG GAG CGA ACG CGG<br>Asp Ala Glu Tyr Trp Asn Ser Gln Pro Glu Ile Leu Glu Arg Thr Arg<br>              615                      620                    625 | 383 |
| GCC GAG GTG GAC ACG GCG TGC AGA CAC AAC TAC GAG GGG CCG GAG ACC<br>Ala Glu Val Asp Thr Ala Cys Arg His Asn Tyr Glu Gly Pro Glu Thr<br>           630                      635                    640 | 431 |
| AGC ACC TCC CTG CGG CGG CTT GAA CAG CCC AAT GTC GCC ATC TCC CTG<br>Ser Thr Ser Leu Arg Arg Leu Glu Gln Pro Asn Val Ala Ile Ser Leu<br>              645                      650                655 | 479 |
| TCC AGG ACA GAG GCC CTC AAC CAC CAC AAC ACT CTG GTC TGT TCG GTG<br>Ser Arg Thr Glu Ala Leu Asn His His Asn Thr Leu Val Cys Ser Val<br>660                      665                      670 | 527 |
| ACA GAT TTC TAC CCA GCC AAG ATC AAA GTG CGC TGG TTC AGG AAT GGC<br>Thr Asp Phe Tyr Pro Ala Lys Ile Lys Val Arg Trp Phe Arg Asn Gly<br>675                      680                      685                690 | 575 |
| CAG GAG GAG ACA GTG GGG GTC TCA TCC ACA CAG CTT ATT AGG AAT GGG<br>Gln Glu Glu Thr Val Gly Val Ser Ser Thr Gln Leu Ile Arg Asn Gly<br>              695                      700                705 | 623 |
| GAC TGG ACC TTC CAG GTC CTG GTC ATG CTG GAG ATG ACC CCT CAT CAG<br>Asp Trp Thr Phe Gln Val Leu Val Met Leu Glu Met Thr Pro His Gln<br>              710                      715                    720 | 671 |
| GGA GAG GTC TAC ACC TGC CAT GTG GAG CAT CCC AGC CTG AAG AGC CCC<br>Gly Glu Val Tyr Thr Cys His Val Glu His Pro Ser Leu Lys Ser Pro<br>           725                      730                    735 | 719 |
| ATC ACT GTG GAG TGG ACT AGT GGT GGC GGT GGC AGC GGC GGT GGT GGT<br>Ile Thr Val Glu Trp Thr Ser Gly Gly Gly Gly Ser Gly Gly Gly Gly<br>              740                      745                750 | 767 |
| TCC GGT GGC GGC GGT TCT GGC GGT GGC GGT TCC TCG AGT GAA GAC GAC<br>Ser Gly Gly Gly Gly Ser Gly Gly Gly Gly Ser Ser Ser Glu Asp Asp<br>755                      760                      765                770 | 815 |
| ATT GAG GCC GAC CAC GTA GGC TTC TAT GGT ACA ACT GTT TAT CAG TCT<br>Ile Glu Ala Asp His Val Gly Phe Tyr Gly Thr Thr Val Tyr Gln Ser<br>              775                      780                785 | 863 |
| CCT GGA GAC ATT GGC CAG TAC ACA CAT GAA TTT GAT GGT GAT GAG TTG<br>Pro Gly Asp Ile Gly Gln Tyr Thr His Glu Phe Asp Gly Asp Glu Leu<br>           790                      795                    800 | 911 |
| TTC TAT GTG GAC TTG GAT AAG AAG AAA ACT GTC TGG AGG CTT CCT GAG<br>Phe Tyr Val Asp Leu Asp Lys Lys Lys Thr Val Trp Arg Leu Pro Glu<br>              805                      810                815 | 959 |
| TTT GGC CAA TTG ATA CTC TTT GAG CCC CAA GGT GGA CTG CAA AAC ATA<br>Phe Gly Gln Leu Ile Leu Phe Glu Pro Gln Gly Gly Leu Gln Asn Ile<br>           820                      825                    830 | 1007 |
| GCT GCA GAA AAA CAC AAC TTG GGA ATC TTG ACT AAG AGG TCA AAT TTC<br>Ala Ala Glu Lys His Asn Leu Gly Ile Leu Thr Lys Arg Ser Asn Phe<br>835                      840                      845                850 | 1055 |
| ACC CCA GCT ACC AAT GAG GCT CCT CAA GCG ACT GTG TTC CCC AAG TCC<br>Thr Pro Ala Thr Asn Glu Ala Pro Gln Ala Thr Val Phe Pro Lys Ser<br>              855                      860                865 | 1103 |
| CCT GTG CTG CTG GGT CAG CCC AAC ACC CTT ATC TGC TTT GTG GAC AAC<br>Pro Val Leu Leu Gly Gln Pro Asn Thr Leu Ile Cys Phe Val Asp Asn<br>           870                      875                    880 | 1151 |
| ATC TTC CCA CCT GTG ATC AAC ATC ACA TGG CTC AGA AAT AGC AAG TCA<br>Ile Phe Pro Pro Val Ile Asn Ile Thr Trp Leu Arg Asn Ser Lys Ser<br>              885                      890                895 | 1199 |
| GTC ACA GAC GGC GTT TAT GAG ACC AGC TTC CTC GTC AAC CGT GAC CAT<br>Val Thr Asp Gly Val Tyr Glu Thr Ser Phe Leu Val Asn Arg Asp His<br>           900                      905                    910 | 1247 |
| TCC TTC CAC AAG CTG TCT TAT CTC ACC TTC ATC CCT TCT GAT GAT GAC<br>Ser Phe His Lys Leu Ser Tyr Leu Thr Phe Ile Pro Ser Asp Asp Asp<br>915                      920                      925                930 | 1295 |

-continued

| ATT | TAT | GAC | TGC | AAG | GTG | GAG | CAC | TGG | GGC | CTG | GAG | GAG | CCG | GTT | CTG | 1343 |
| Ile | Tyr | Asp | Cys | Lys | Val | Glu | His | Trp | Gly | Leu | Glu | Glu | Pro | Val | Leu | |
| | | | | 935 | | | | | 940 | | | | | 945 | | |

| AAA | CAC | TGG | GAG | GAA | GAA | GAG | TAC | ATG | CCG | ATG | GAA | TGA | 1382 |
| Lys | His | Trp | Glu | Glu | Glu | Glu | Tyr | Met | Pro | Met | Glu | * | |
| | | | 950 | | | | | 955 | | | | | |